US009409915B2

(12) United States Patent
Player et al.

(10) Patent No.: US 9,409,915 B2
(45) Date of Patent: *Aug. 9, 2016

(54) SUBSTITUTED AZA-BICYCLIC IMIDAZOLE DERIVATIVES USEFUL AS TRPM8 RECEPTOR MODULATORS

(71) Applicant: Janssen Pharmaceutica NV, Beerse (BE)

(72) Inventors: Mark R. Player, Phoenixville, PA (US); Raul Calvo, Royersford, PA (US); Jinsheng Chen, Exton, PA (US); Sanath Meegalla, Garnet Valley, PA (US); Daniel J. Parks, Downingtown, PA (US); William J. Parsons, Belle Mead, NJ (US); Scott Ballentine, Lansdale, PA (US); Shawn Branum, Easton, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/623,671

(22) Filed: Feb. 17, 2015

(65) Prior Publication Data

US 2015/0158875 A1 Jun. 11, 2015

Related U.S. Application Data

(62) Division of application No. 14/172,395, filed on Feb. 4, 2014, now Pat. No. 9,023,846, which is a division of application No. 13/034,922, filed on Feb. 25, 2011, now Pat. No. 8,680,098.

(60) Provisional application No. 61/310,870, filed on Mar. 5, 2010.

(51) Int. Cl.
*C07D 471/04* (2006.01)
*C07D 487/04* (2006.01)
*A61K 31/5377* (2006.01)
*A61K 31/437* (2006.01)
*A61K 31/52* (2006.01)
*A61K 31/4985* (2006.01)
*C07D 473/00* (2006.01)

(52) U.S. Cl.
CPC ............ *C07D 487/04* (2013.01); *C07D 471/04* (2013.01); *C07D 473/00* (2013.01)

(58) Field of Classification Search
CPC ............... C07D 471/04; C07D 487/04; A61K 31/5377; A61K 31/437; A61K 31/52; A61K 31/4985
USPC ............ 546/118; 514/234.2, 303, 236.2, 249; 544/277, 127, 350
See application file for complete search history.

(56) References Cited

U.S. PATENT DOCUMENTS

| 6,943,199 | B2 | 9/2005 | De Lombaert et al. |
| 7,622,479 | B2 | 11/2009 | Oda et al. |
| 8,680,098 | B2 * | 3/2014 | Player .................... 514/234.2 |
| 2008/0139608 | A1 | 6/2008 | Chang et al. |

FOREIGN PATENT DOCUMENTS

| EP | 0168500 A1 | 1/1986 |
| JP | 2007-513105 A | 5/2007 |
| JP | 2008-539185 A | 11/2008 |
| WO | WO 85/03077 A | 7/1985 |
| WO | WO 2004/035549 A1 | 4/2004 |
| WO | WO 2005/054188 A1 | 6/2005 |
| WO | WO 2006/027365 A1 | 3/2006 |
| WO | WO 2006/114313 A1 | 11/2006 |
| WO | WO 2006/134318 A1 | 12/2006 |
| WO | WO 2007/107470 A2 | 9/2007 |
| WO | WO 2008/141731 A2 | 11/2008 |
| WO | WO 2009/098448 A1 | 8/2009 |
| WO | WO 2009/134750 A1 | 11/2009 |

OTHER PUBLICATIONS

International Search Report relating to International Patent Application No. PCT/US2011/026974. Date of Mailing of International Search Report: Jun. 16, 2011.
Written Opinion of the International Searching Authority relating to International Patent Applications No. PCT/US2011/026974. Date of Mailing of Written Opinion: Jun. 16, 2011.
Abe, J., et al. "Ca2+-dependent PKC activation mediates menthol-induced desensitization of transient receptor potential M8.", *Neurosci. Lett.*, 2006, pp. 140-144, vol. 397(1-2).
Behrendt, H-J., et al., "Characterization of the mouse cold menthol receptor TRPM8 and vanilloid receptor type-1 VR1 using a fluorometric imaging plate reader (FLIPR) assay.", *Brit J Pharmacol*, 2004, pp. 737-745, vol. 141(4).
Bennett, G.J., et al., "A peripheral mononeuropathy in rat that produces disorder of pain sensation like those seen in man.", *Pain*, 1988, pp. 87-107, vol. 33(1).
Gilman, H., et al., "Orientation in the Furan Series. X. Anomalous Friedel-Crafts Reactions.", *J. Am. Chem. Soc.*, May 1935, pp. 909-912, vol. 57.
Gilman, H., et al., "Orientation in the Furan Series. XI. Cleavage-Rearrangements in the Friedel-Crafts Reactions.", *J. Am. Chem. Soc.*, Feb. 1939, pp. 473-478, vol. 61.
Kobayashi, K., et al. "Distinct expression of TRPM8, TRPA1 and TRPV1 mRNAs in rat primary afferent neurons with a c-fibers and colocalization with trk receptors.", *J. Comp. Neurol.*, 2005, pp. 596-606, vol. 493(4).

(Continued)

*Primary Examiner* — Niloofar Rahmani

(57) ABSTRACT

The present invention is directed to substituted aza-bicyclic imidazole derivatives, pharmaceutical compositions containing them and their use in the treatment of disorders and conditions modulated by TRP M8, including for example, inflammatory pain, inflammatory hyperalgesia, inflammatory hypersensitivity condition, neuropathic pain, neuropathic cold allodynia, inflammatory somatic hyperalgesia, inflammatory visceral hyperalgesia, cardiovascular disease aggravated by cold and pulmonary disease aggravated by cold.

14 Claims, 1 Drawing Sheet

(56) References Cited

OTHER PUBLICATIONS

McKemy, D.D., et al "Identification of a cold receptor reveals a general role for TRP channels in thermosensation.", *Nature*, 2002, pp. 52-58, vol. 416(6876).
Molander, G.A., et al., "Intramolecular Nucleophilic Acyl Substitution Reactions of Halo-Substituted Esters and Lactones. New Applications of Organosamarium Reagants." *J. Org. Chem.*, 1993, pp. 7216-7227, vol. 58.
Premkumar, L.S., et al. "Downregulation of Transient Receptor Potential Melastatin 8 by Protein Kinase C-Mediated Dephosphorylation.", *J. Neurosci.*, 2005, pp. 11322-11329, vol. 25(49).
Roza, C. et al., "Cold sensitivity in axotomized fibers of experimental neuromas in mice.", *Pain*, 2006, pp. 24-36, vol. 120(1-2).
Stanetty, P. et al., "Herbizide Thienylharnstoffe, II.", *Monatshefte für Chemie*, 1989, pp. 65-72, vol. 120(1).
Wei, E.T., et al., "AG-3-5: a chemical producing sensations of cold.", *J Pharm Pharmacol.*, 1983, pp. 110-112, vol. 35.
Xing, H., et al., "Chemical and Cold Sensitivity of Two Distinct populations of TRPM8-Expressing Somatosensory Neurons.", *J. Neurophysiol.*, 2006, pp. 1221-1230, vol. 95(2).

\* cited by examiner

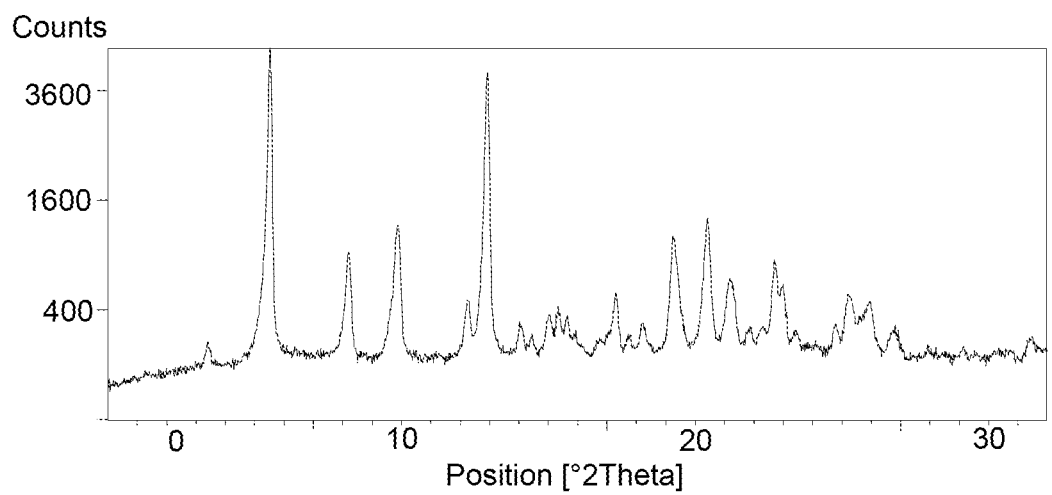
Measured pXRD for compound for fomrula (I-S), prepared as described in Example 35, STEP H

SUBSTITUTED AZA-BICYCLIC IMIDAZOLE DERIVATIVES USEFUL AS TRPM8 RECEPTOR MODULATORS

CROSS-REFERENCE TO RELATED APPLICATIONS

The present application is a divisional of U.S. application Ser. No. 14/172,395, filed on Feb. 4, 2014, which is a divisional of U.S. application Ser. No. 13/034,922, filed on Feb. 25, 2011, now granted as U.S. Pat. No. 8,680,098, and claims the benefits of the filing of U.S. Provisional Application No. 61/310,870, filed on Mar. 5, 2010. The complete disclosures of the aforementioned related patent applications are hereby incorporated herein by reference for all purposes.

FIELD OF THE INVENTION

The present invention is directed to substituted aza-bicyclic imidazole derivatives, pharmaceutical compositions containing them and their use in the treatment of disorders and conditions modulated by the TRPM8 (transient receptor potential, melastatin subfamily, type 8) channel. More particularly, the compounds of the present invention are useful in the treatment of inflammatory pain, inflammatory hyperalgesia, inflammatory hypersensitivity condition, neuropathic pain, neuropathic cold allodynia, inflammatory somatic hyperalgesia, inflammatory visceral hyperalgesia, cardiovascular disease aggravated by cold and pulmonary disease aggravated by cold.

BACKGROUND OF THE INVENTION

Transient receptor potential (TRP) channels are non-selective cation channels that are activated by a variety of stimuli. Numerous members of the ion channel family have been identified to date, including the cold-menthol receptor, also called TRPM8 (MCKEMY, D. D., et al "Identification of a cold receptor reveals a general role for TRP channels in thermosensation", *Nature*, 2002, pp 52-58, vol. 416 (6876)). Collectively, the thermosensitive TRP channels and related TRP-like receptors, such as TRPV1/2/3 and TRPM8, connote sensory responsivity to the entire continuum of thermal exposure, selectively responding to threshold temperatures ranging from noxious hot through noxious cold as well as to certain chemicals that mimic these sensations. Specifically, TRPM8 is known to be stimulated by cool to cold temperatures as well as by chemical agents, such as menthol and icilin, which may be responsible for the therapeutic cooling sensation that these agents provoke.

TRPM8 is located on primary nociceptive neurons (Aδ- and C-fibers) and is also modulated by inflammation-mediated second messenger signals (ABE, J., et al. "Ca2+-dependent PKC activation mediates menthol-induced desensitization of transient receptor potential M8", *Neurosci. Lett.*, 2006, pp 140-144, Vol. 397(1-2); PREMKUMAR, L. S., et al. "Downregulation of Transient Receptor Potential Melastatin 8 by Protein Kinase C-Mediated Dephosphorylation", *J. Neurosci.*, 2005, pp 11322-11329, Vol. 25(49)). The localization of TRPM8 on both A Aδ- and C-fibers may provide a basis for abnormal cold sensitivity in pathologic conditions wherein these neurons are altered, resulting in pain, often of a burning nature (KOBAYASHI, K., et al. "Distinct expression of TRPM8, TRPA1 and TRPV1 mRNAs in rat primary afferent neurons with a c-fibers and colocalization with trk receptors" *J. Comp. Neurol.*, 2005, pp 596-606, Vol. 493(4), 596-606; ROZA, C. et al., "Cold sensitivity in axotomized fibers of experimental neuromas in mice", *Pain* 2006, pp 24-36, Vol 120(1-2); and XING, H., et al., "Chemical and Cold Sensitivity of Two Distinct populations of TRPM8-Expressing Somatosensory Neurons", *J. Neurophysiol.*, 2006, pp 1221-1230, Vol. 95(2)). Cold intolerance and paradoxical burning sensations induced by chemical or thermal cooling closely parallel symptoms seen in a wide range of clinical disorders and thus provide a strong rationale for the development of TRPM8 modulators as novel antihyperalgesic or antiallodynic agents. TRPM8 is also known to be expressed in the brain, lung, bladder, gastrointestinal tract, blood vessels, prostate and immune cells, thereby providing the possibility for therapeutic modulation in a wide range of maladies.

There remains a need in the art for TRPM8 antagonists that can be used to treat a disease or condition in a mammal in which the disease or condition is affected by the modulation of TRPM8 receptors, such as chronic or acute pain, or the diseases that lead to such pain, as well as pulmonary or vascular dysfunction.

SUMMARY OF THE INVENTION

The present invention is directed to compounds of formula (I)

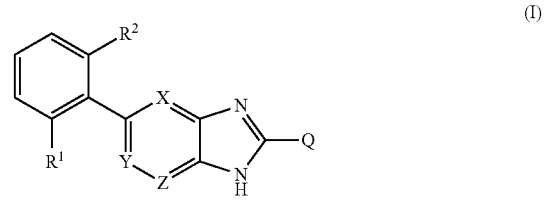

wherein $R^1$ is selected from the group consisting of hydrogen, fluoro, chloro, fluorinated $C_{1-4}$alkyl and fluorinated $C_{1-4}$alkoxy;

$R^2$ is selected from the group consisting of hydrogen, chloro, bromo, $C_{1-4}$alkyl, fluorinated $C_{1-4}$alkyl and fluorinated $C_{1-4}$alkoxy; provided that when $R^2$ is other than hydrogen, then

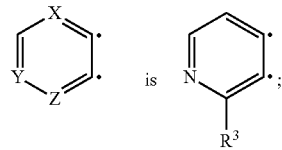

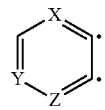

is selected from the group consisting of

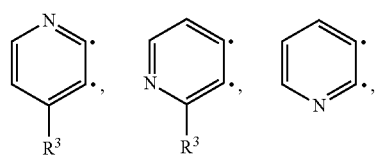

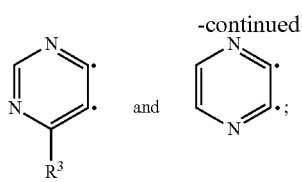 and wherein $R^3$ is selected from the group consisting of hydrogen, chloro, cyano, $C_{1-4}$alkyl, fluorinated $C_{1-4}$alkyl, $C_{1-4}$alkoxy, fluorinated $C_{1-4}$alkoxy, —O—$(CH_2)_2$—OH, —O—$CH_2$—$CO_2$H, —O—$(CH_2)_2$—O—$(C_{1-4}$alkyl), —O—$CH_2$-(fluorinated $C_{1-2}$alkyl), —O—$(CH_2)_2$—$NR^A R^B$ and —$NR^A R^B$;

wherein $R^A$ and $R^B$ are each independently selected from the group consisting of hydrogen and $C_{1-4}$alkyl;

alternatively $R^A$ and $R^B$ are taken together with the nitrogen atom to which they are bound to form a ring structure selected form the group consisting of pyrrolidin-1-yl, piperidin-1-yl, piperazin-1-yl, 4-methyl-piperidin-1-yl, 4-methyl-piperazin-1-yl and morpholin-4-yl;

Q is an optionally substituted ring structure selected from the group consisting of formulas (a) through (h)

(a)

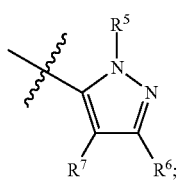

(an optionally substituted 5-pyrazolyl)

(b)

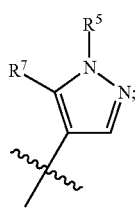

(an optionally substituted 4-pyrazolyl)

wherein $R^5$ is $C_{1-4}$alkyl; $R^6$ is selected from the group consisting of $C_{1-4}$alkyl and fluorinated $C_{1-4}$alkyl; and $R^7$ is selected from the group consisting of hydrogen, chloro, fluoro, cyano, $C_{1-4}$alkyl and $C_{1-4}$alkoxy;

(c)

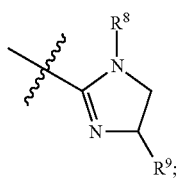

(an optionally substituted 2-imidazolyl)

wherein $R^8$ and $R^9$ are each independently selected from the group consisting of $C_{1-4}$alkyl;

(d)

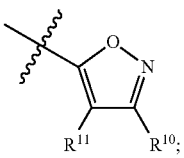

(an optionally substituted 5-isoxazolyl)

wherein $R^{10}$ is $C_{1-4}$alkyl; and $R^{11}$ is selected from the group consisting of hydrogen and cyano;

(e)

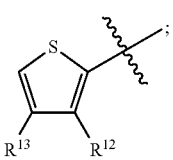

(an optionally substituted 2-thienyl)

wherein $R^{12}$ and $R^{13}$ are each independently selected from the group consisting of hydrogen and $C_{1-4}$alkyl;

(f)

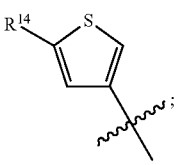

(an optionally substituted 3-thienyl)

wherein $R^{14}$ is $C_{1-4}$alkyl;

(g)

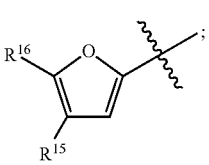

(an optionally substituted 2-furyl)

wherein $R^{15}$ is $C_{1-4}$alkyl; and $R^{16}$ is selected from the group consisting of hydrogen, chloro and bromo; and (h)

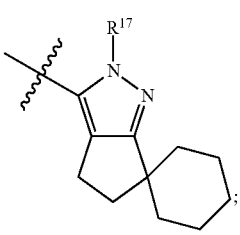

(an optionally substituted spiro-tricyclic group)

wherein $R^{17}$ is $C_{1-4}$alkyl;

and solvates, hydrates, tautomers and pharmaceutically acceptable salts thereof.

The present invention is further directed to processes for the preparation of the compounds of formula (I). The present invention is further directed to a product prepared according to the process described herein.

The present invention is further directed to a compound of formula (I-S)

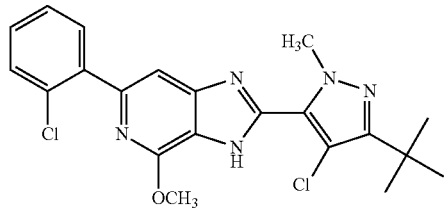

(I-S)

and solvates, hydrates, tautomers and pharmaceutically acceptable salts thereof. The present invention is further directed to a process for the preparation of a compound of formula (I-S) or pharmaceutically acceptable salt thereof. The present invention is further directed to a crystalline form of the compound of formula (I-S), as herein described in more details.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder modulated by TRPM8 (selected from the group consisting of inflammatory pain, including visceral pain, neuropathic pain, including neuropathic cold allodynia, cardiovascular disease aggravated by cold and pulmonary disease aggravated by cold, in a subject in need thereof, comprising administering to the subject a therapeutically effective amount of any of the compounds or pharmaceutical compositions described above.

Another example of the invention is the use of any of the compounds described herein in the preparation of a medicament wherein the medicament is prepared for treating: (a) inflammatory pain, (b) neuropathic pain, (c) cardiovascular disease aggravated by cold, or (d) pulmonary disease aggravated by cold, in a subject in need thereof.

BRIEF DESCRIPTION OF THE DRAWINGS

FIG. 1 illustrates a representative pXRD spectra from the compound of formula (I-S), prepared as described in Example 35, STEP H.

DETAILED DESCRIPTION OF THE INVENTION

The present invention is directed to compounds of formula (I)

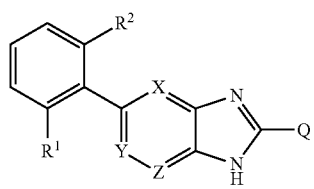

(I)

wherein $R^1$, $R^2$,

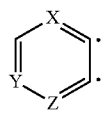

and Q are as herein defined, and solvates, hydrates, tautomers and pharmaceutically acceptable salts thereof. The compounds of the present invention are useful in the treatment of disorders mediated by TRPM8, including inflammatory pain (including visceral pain), inflammatory hyperalgesia, neuropathic pain (including neuropathic cold allodynia), inflammatory somatic hyperalgesia, inflammatory visceral hyperalgesia, cardiovascular disease aggravated by cold and pulmonary disease aggravated by cold.

In an embodiment, the present invention is directed to compounds of formula (I-A)

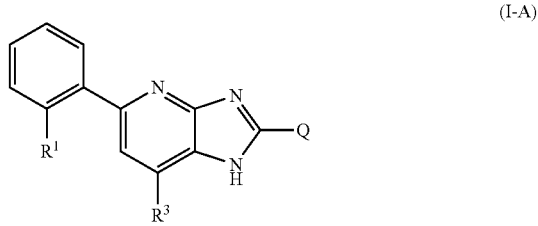

(I-A)

wherein all variables are as herein defined, and pharmaceutically acceptable salts thereof. In another embodiment, the present invention is directed to compounds of formula (I-B)

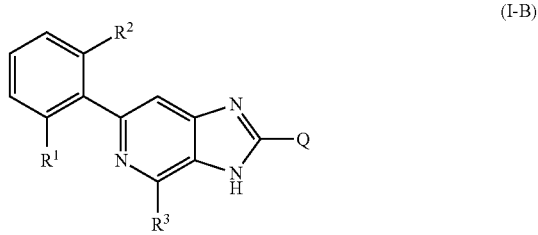

(I-B)

wherein all variables are as herein defined, and pharmaceutically acceptable salts thereof. In another embodiment, the present invention is directed to compounds of formula (I-C)

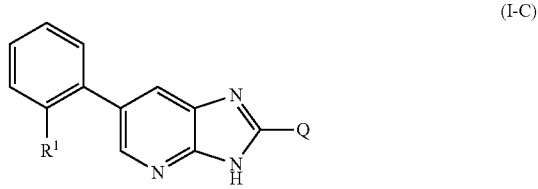

(I-C)

wherein all variables are as herein defined, and pharmaceutically acceptable salts thereof. In another embodiment, the present invention is directed to compounds of formula (I-D)

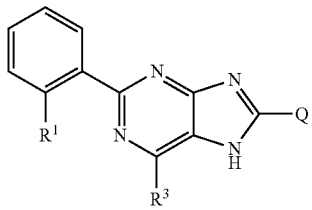

(I-D)

wherein all variables are as herein defined, and pharmaceutically acceptable salts thereof. In another embodiment, the present invention is directed to compounds of formula (I-E)

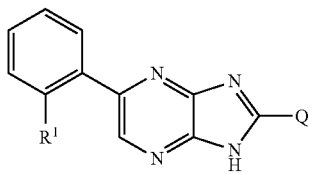

(I-E)

wherein all variables are as herein defined, and pharmaceutically acceptable salts thereof.

In an embodiment, the present invention is directed to a compound of formula (I-S)

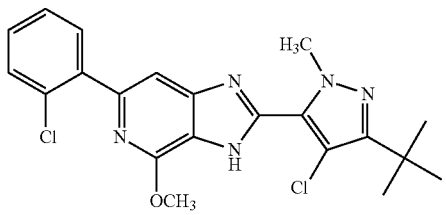

(I-S)

and solvates, hydrates, tautomers or pharmaceutically acceptable salts thereof. In another embodiment, the present invention is directed to a compound of formula (I-S) or a pharmaceutically acceptable salt thereof. In another embodiment, the present invention is directed to a compound of formula (I-S) or a pharmaceutically acceptable salt thereof, wherein the pharmaceutically acceptable salt thereof is selected from the group consisting of sodium salt, potassium salt, hydrochloride salt, trifluoroacetic acid salt and methanesulfonic acid salt thereof, preferably, the sodium salt thereof.

In an embodiment of the present invention, $R^1$ is selected from the group consisting of hydrogen, fluoro, chloro, fluorinated $C_{1-2}$alkyl and fluorinated $C_{1-2}$alkoxy. In another embodiment of the present invention, $R^1$ is selected from the group consisting of hydrogen, chloro, fluoro, trifluoromethyl and trifluoromethoxy. In another embodiment of the present invention, $R^1$ is selected from the group consisting of chloro, fluoro, trifluoromethyl and trifluoromethoxy. In another embodiment of the present invention, $R^1$ is selected from the group consisting of chloro and trifluoromethyl.

In an embodiment of the present invention, $R^2$ is selected from the group consisting of hydrogen, chloro, trifluoromethyl and trifluoromethoxy; provided that when $R^2$ is other than hydrogen, then

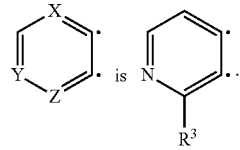

In another embodiment of the present invention, $R^2$ is selected from the group consisting of hydrogen and chloro; provided that when $R^2$ is chloro, then

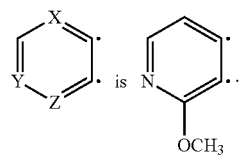

In another embodiment of the present invention, $R^2$ is hydrogen.

In an embodiment of the present invention,

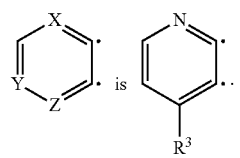

In another embodiment of the present invention,

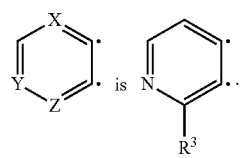

In another embodiment of the present invention,

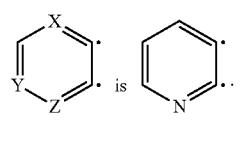

In another embodiment of the present invention,

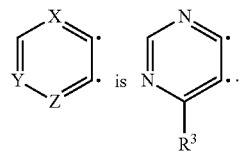

In another embodiment of the present invention,

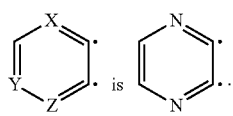 is

One skilled in the art will recognize that in the definition of the

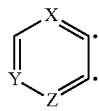

group, the variables X, Y and Z are bivalent and are selected to yield the desired ring structures. More particularly, X is selected from the group consisting of CH and N; Y is selected from the group consisting of CH and N; and Z is selected from the group consisting of CH—$R^3$ and N, wherein $R^3$ is as herein defined.

In an embodiment of the present invention,

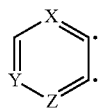

is selected from the group consisting of

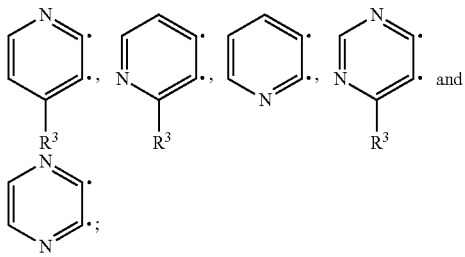

wherein $R^3$ is selected from the group consisting of hydrogen, chloro, cyano, $C_{1-2}$alkyl, fluorinated $C_{1-2}$alkyl, $C_{1-4}$alkoxy, fluorinated $C_{1-2}$alkoxy, —O—$(CH_2)_2$—OH, —O—$CH_2$—$CO_2H$, —O—$(CH_2)_2$—O—$(C_{1-4}$alkyl), —O—$CH_2$-(fluorinated $C_{1-2}$alkyl), —O—$(CH_2)_2$—$NR^A R^B$ and —$NR^A R^B$; wherein $R^A$ and $R^B$ are each independently selected from the group consisting of hydrogen and $C_{1-2}$alkyl; alternatively $R^A$ and $R^B$ are taken together with the nitrogen atom to which they are bound to form a ring structure selected from the group consisting of pyrrolidin-1-yl, piperidin-1-yl, piperazin-1-yl, 4-methyl-piperazin-1-yl and morpholin-4-yl.

In another embodiment of the present invention,

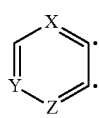

is selected from the group consisting of

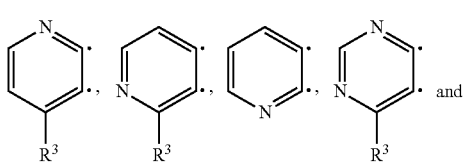

-continued

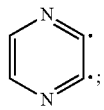

wherein $R^3$ is selected form the group consisting of hydrogen, chloro, cyano, $C_{1-2}$alkyl, trifluoromethyl, $C_{1-4}$alkoxy, —O—$(CH_2)_2$—OH, —O—$CH_2$—$CO_2H$, —O—$(CH_2)_2$—O—$(C_{1-2}$alkyl), O—$CH_2$-(fluorinated $C_{1-2}$alkyl), —O—$(CH_2)_2$—$NR^A R^B$, pyrrolidin-1-yl, piperidin-1-yl, piperazin-1-yl, 4-methyl-piperazin-1-yl and morpholin-4-yl; and wherein $R^A$ and $R^B$ are each an independently selected $C_{1-2}$alkyl; alternatively $R^A$ and $R^B$ are taken together with the nitrogen atom to which they are bound to form a ring structure selected from the group consisting of pyrrolidin-1-yl, piperidin-1-yl, piperazin-1-yl, 4-methyl-piperazin-1-yl and morpholin-4-yl.

In another embodiment of the present invention,

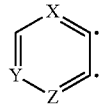

is selected from the group consisting of

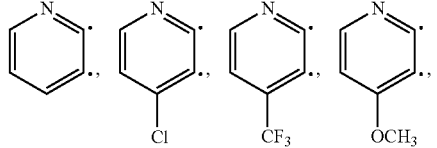

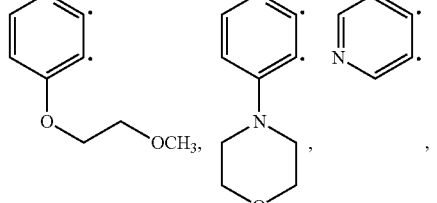

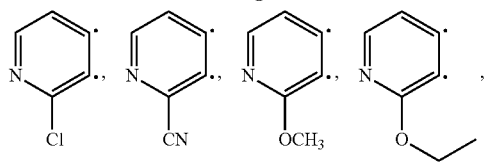

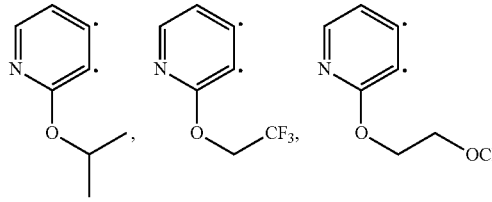

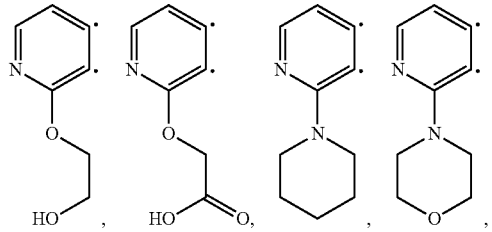

-continued
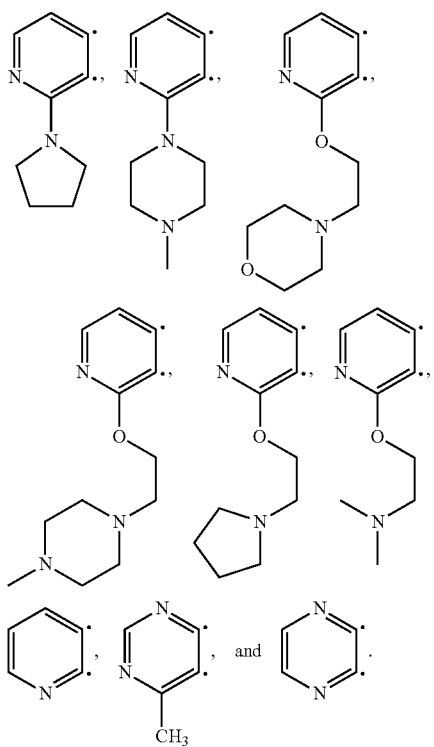
In another embodiment of the present invention,
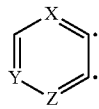
is selected from the group consisting of
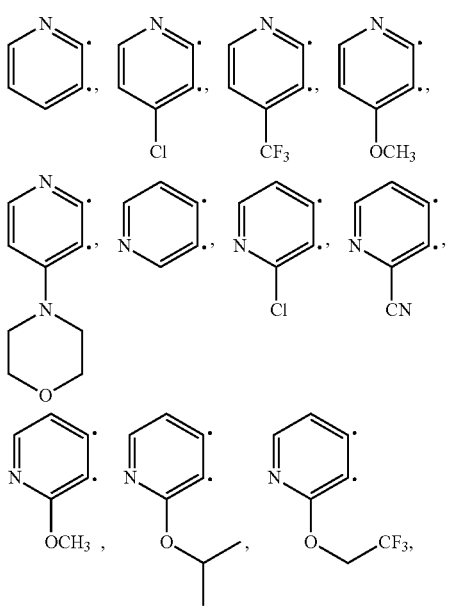
-continued
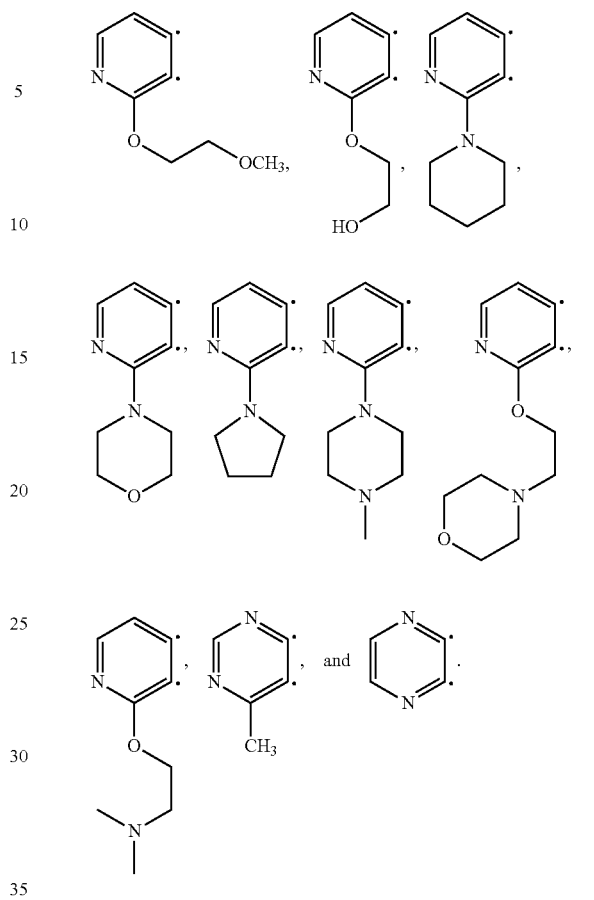
In another embodiment of the present invention,
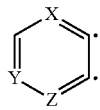
is selected from the group consisting of
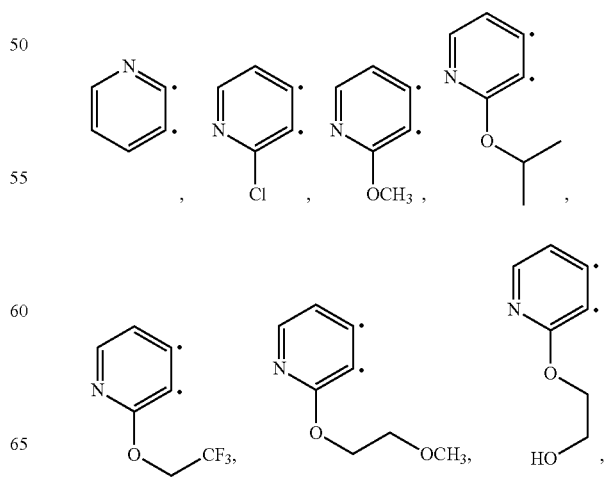

-continued

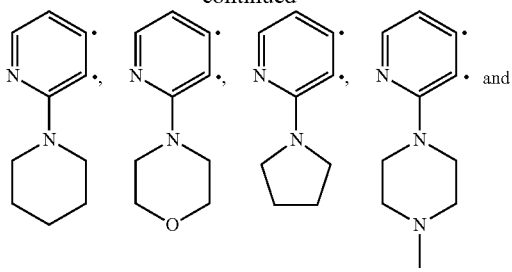 and 

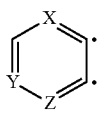

In another embodiment of the present invention,

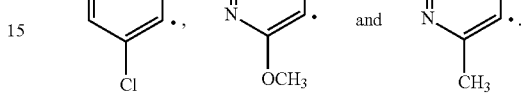

is selected from the group consisting of

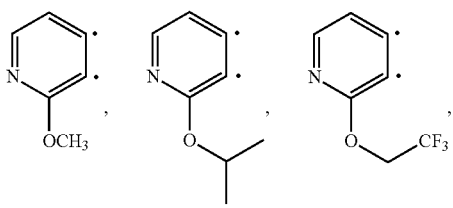

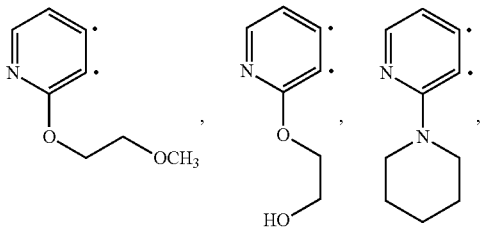

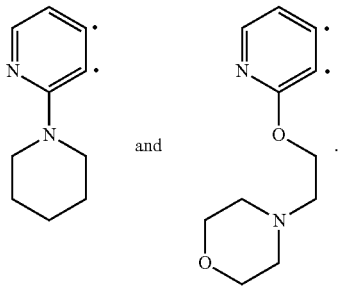 and

In another embodiment of the present invention,

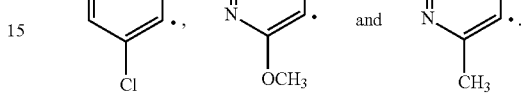

is selected from the group consisting of

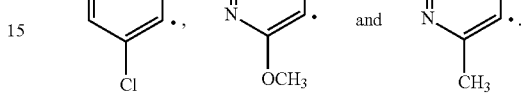

In an embodiment of the present invention, $R^3$ is selected from the group consisting of hydrogen, chloro, cyano, $C_{1-2}$alkyl, fluorinated $C_{1-2}$alkyl, $C_{1-4}$alkoxy, fluorinated $C_{1-2}$alkoxy, —O—$(CH_2)_2$—OH, —O—$CH_2$—$CO_2H$, —O—$(CH_2)_2$—O—$(C_{1-4}$alkyl), —O—$CH_2$-(fluorinated $C_{1-2}$alkyl), —O—$(CH_2)_2$—$NR^AR^B$ and —$NR^AR^B$. In another embodiment of the present invention, $R^3$ is selected form the group consisting of hydrogen, chloro, cyano, $C_{1-2}$alkyl, trifluoromethyl, $C_{1-4}$alkoxy, —O—$(CH_2)_2$—OH, —O—$CH_2$—$CO_2H$, —O—$(CH_2)_2$—O—$(C_{1-2}$alkyl), —O—$CH_2$-(fluorinated $C_{1-2}$alkyl), —O—$(CH_2)_2$—$NR^AR^B$, pyrrolidin-1-yl, piperidin-1-yl, piperazin-1-yl, 4-methyl-piperazin-1-yl and morpholin-4-yl. In another embodiment of the present invention, $R^3$ is selected from the group consisting of hydrogen, chloro, cyano, methyl, trifluoromethyl, trifluoromethoxy, methoxy, ethoxy, isopropoxy, —O—$(CH_2)_2$—OH, —O—$CH_2$—$CO_2H$, —O—$(CH_2)_2$—$OCH_3$, —O—$CH_2$—$CF_3$, Pyrrolidin-1-yl, piperidin-1-yl, 4-methyl-piperazin-1-yl, morpholin-4-yl, —O—$(CH_2)_2$—$N(CH_3)_2$, —O—$(CH_2)_2$-(pyrrolidin-1-yl), —O—$(CH_2)_2$-(4-methyl-piperazin-1-yl) and —O—$(CH_2)_2$-(morpholin-4-yl).

In another embodiment of the present invention, $R^3$ is selected from the group consisting of hydrogen, chloro, cyano, methyl, trifluoromethyl, trifluoromethoxy, methoxy, isopropoxy, —O—$(CH_2)_2$—OH, —O—$(CH_2)_2$—$OCH_3$, —O—$CH_2$—$CF_3$, Pyrrolidin-1-yl, piperidin-1-yl, 4-methyl-piperazin-1-yl, morpholin-4-yl, —O—$(CH_2)_2$—$N(CH_3)_2$, and —O—$(CH_2)_2$-(morpholin-4-yl). In another embodiment of the present invention, $R^3$ is selected from the group consisting of hydrogen, chloro, cyano, methyl, trifluoromethyl, trifluoromethoxy, methoxy, isopropoxy, —O—$(CH_2)_2$—OH, —O—$(CH_2)_2$—$OCH_3$, —O—$CH_2$—$CF_3$, Pyrrolidin-1-yl, piperidin-1-yl, 4-methyl-piperazin-1-yl, morpholin-4-yl and —O—$(CH_2)_2$-(morpholin-4-yl). In another embodiment of the present invention, $R^3$ is selected from the group consisting of methoxy, isopropoxy, —O—$(CH_2)_2$—OH, —O—$(CH_2)_2$—$OCH_3$, —O—$CH_2$—$CF_3$, piperidin-1-yl, morpholin-4-yl and —O—$(CH_2)_2$-(morpholin-4-yl). In another embodiment of the present invention, $R^3$ is selected from the group consisting of chloro, methyl and methoxy.

In an embodiment of the present invention, $R^A$ and $R^B$ are each independently selected from the group consisting of hydrogen and $C_{1-2}$alkyl; alternatively $R^A$ and $R^B$ are taken together with the nitrogen atom to which they are bound to form a ring structure selected from the group consisting of pyrrolidin-1-yl, piperidin-1-yl, piperazin-1-yl, 4-methyl-piperazin-1-yl and morpholin-4-yl. In another embodiment of the present invention, $R^A$ and $R^B$ are each an independently selected $C_{1-2}$alkyl; alternatively $R^A$ and $R^B$ are taken together with the nitrogen atom to which they are bound to form a ring structure selected from the group consisting of pyrrolidin-1-yl, piperidin-1-yl, piperazin-1-yl, 4-methyl-piperazin-1-yl and morpholin-4-yl. In another embodiment of the present invention $R^A$ and $R^B$ are each ethyl. In another embodiment of the present invention $R^A$ and $R^B$ are taken together with the nitrogen atom to which they are bound to form a ring structure selected from the group consisting of pyrrolidin-1-yl, piperidin-1-yl, piperazin-1-yl, 4-methyl-piperazin-1-yl and morpholin-4-yl.

In an embodiment of the present invention, Q is one or more ring structures selected from the group consisting of formulas (a) through (h), as herein defined.

In an embodiment of the present invention, Q is (a)

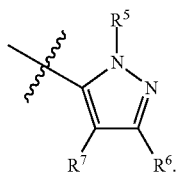

In another embodiment of the present invention, Q is (b)

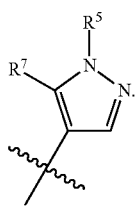

In an embodiment of the present invention, $R^5$ is $C_{1-4}$alkyl. In another embodiment of the present invention, $R^5$ is $C_{1-2}$alkyl. In another embodiment of the present invention, $R^5$ is selected from the group consisting of tert-butyl and methyl. In another embodiment of the present invention, $R^5$ is methyl.

In an embodiment of the present invention, $R^6$ is selected from the group consisting of $C_{1-4}$alkyl and fluorinated $C_{1-4}$alkyl. In another embodiment of the present invention, $R^6$ is selected from the group consisting of tert-butyl, trifluoromethyl and 1,1-dimethyl-2-fluoro-ethyl. In another embodiment of the present invention, $R^6$ is selected from the group consisting of tert-butyl and 1,1-dimethyl-2-fluoro-ethyl. In another embodiment of the present invention, $R^6$ is tert-butyl.

In an embodiment of the present invention, $R^7$ is selected from the group consisting of hydrogen, chloro, fluoro, cyano, $C_{1-4}$alkyl and $C_{1-4}$alkoxy. In another embodiment of the present invention, $R^7$ is selected from the group consisting of hydrogen, chloro, fluoro, cyano, $C_{1-2}$alkyl and $C_{1-2}$alkoxy. In another embodiment of the present invention, $R^7$ is selected from the group consisting of hydrogen, chloro, fluoro, cyano, methyl and methoxy. In another embodiment of the present invention, $R^7$ is selected from the group consisting of hydrogen, chloro, fluoro, cyano and methoxy. In another embodiment of the present invention, $R^7$ is selected from the group consisting of chloro and cyano.

In another embodiment of the present invention, Q is (c)

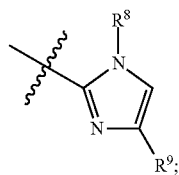

wherein $R^8$ and $R^9$ are each independently selected from the group consisting of $C_{1-4}$alkyl. In another embodiment of the present invention, $R^8$ and $R^9$ are each independently selected from the group consisting of methyl and tert-butyl. In another embodiment of the present invention, $R^8$ is methyl and $R^9$ is tert-butyl.

In another embodiment of the present invention, Q is (d)

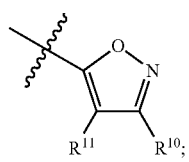

wherein $R^{10}$ is $C_{1-4}$alkyl; and $R^{11}$ is selected from the group consisting of hydrogen and cyano. In another embodiment of the present invention, $R^{10}$ is $C_{1-4}$alkyl. In another embodiment of the present invention, $R^{10}$ is tert-butyl. In another embodiment of the present invention, $R^{11}$ is selected from the group consisting of hydrogen and cyano. In another embodiment of the present invention, $R^{11}$ is hydrogen.

In another embodiment of the present invention, Q is (e)

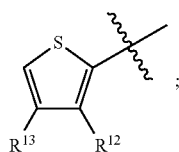

wherein $R^{12}$ and $R^{13}$ are each independently selected from the group consisting of hydrogen and $C_{1-4}$alkyl. In an embodiment of the present invention, $R^{12}$ is hydrogen. In another embodiment of the present invention $R^{13}$ is $C_{1-4}$alkyl. In another embodiment of the present invention, $R^{13}$ is tert-butyl and isopropyl. In another embodiment of the present invention, $R^{13}$ is isopropyl.

In another embodiment of the present invention, Q is (f)

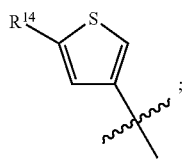

wherein $R^{14}$ is $C_{1-4}$alkyl. In another embodiment of the present invention, $R^{14}$ is tert-butyl and isopropyl. In another embodiment of the present invention, $R^{14}$ is isopropyl.

In another embodiment of the present invention, Q is (g)

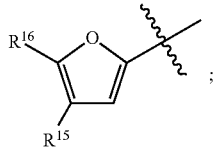

wherein $R^{15}$ is $C_{1-4}$alkyl; and $R^{16}$ is selected from the group consisting of hydrogen, chloro and bromo. In another embodiment of the present invention, $R^{15}$ is $C_{1-4}$alkyl. In another embodiment of the present invention, $R^{15}$ is tert-butyl. In another embodiment of the present invention, $R^{16}$ is selected from the group consisting of hydrogen, chloro and bromo. In another embodiment of the present invention, $R^{16}$ is selected from the group consisting of hydrogen and bromo.

In another embodiment of the present invention, Q is (h)

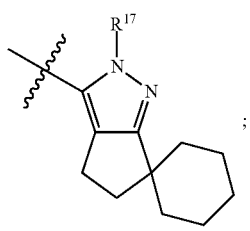

wherein $R^{17}$ is $C_{1-4}$alkyl. In another embodiment of the present invention, $R^{17}$ is $C_{1-2}$alkyl. In another embodiment of the present invention, $R^{17}$ is methyl.

In an embodiment of the present invention, Q is an optionally substituted ring structure selected from the group consisting of formulas (a) through (h)

(a)

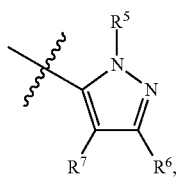

(b)

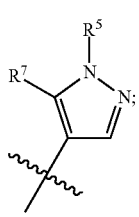

wherein $R^5$ is $C_{1-4}$alkyl; $R^6$ is selected from the group consisting of $C_{1-4}$alkyl and fluorinated $C_{1-4}$alkyl; and $R^7$ is selected from the group consisting of hydrogen, chloro, fluoro, cyano, $C_{1-2}$alkyl and $C_{1-2}$alkoxy;

(c)

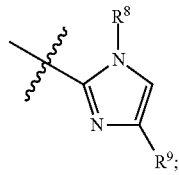

wherein $R^8$ and $R^9$ are each independently selected from the group consisting of $C_{1-4}$alkyl;

(d)

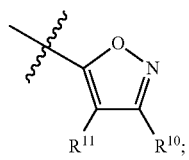

wherein $R^{10}$ is $C_{1-4}$alkyl; and $R^{11}$ is selected from the group consisting of hydrogen and cyano;

(e)

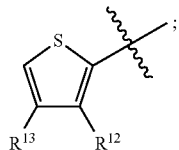

wherein $R^{12}$ and $R^{13}$ are each independently selected from the group consisting of hydrogen and $C_{1-4}$alkyl;

(f)

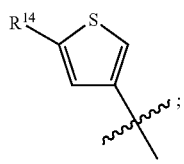

wherein $R^{14}$ is selected from the group consisting of $C_{1-4}$alkyl;

(g)

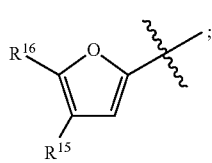

wherein $R^{15}$ is $C_{1-4}$alkyl; and $R^{16}$ is selected from the group consisting of hydrogen, chloro and bromo; and (h)

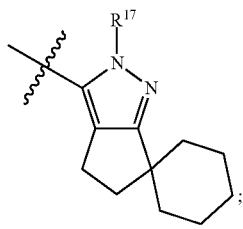

wherein $R^{17}$ is $C_{1-2}$alkyl.

In another embodiment of the present invention, Q is an optionally substituted ring structure selected from the group consisting of formulas (a) through (h)

(a)

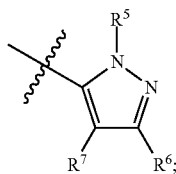

(b)

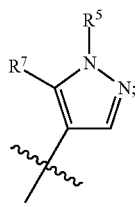

wherein $R^5$ is $C_{1-4}$alkyl; $R^6$ is selected from the group consisting of $C_{1-4}$alkyl and fluorinated $C_{1-4}$alkyl; and $R^7$ is selected from the group consisting of hydrogen, chloro, fluoro, cyano, $C_{1-2}$alkyl and $C_{1-2}$alkoxy;

(c)

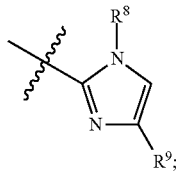

wherein $R^8$ and $R^9$ are each independently selected from the group consisting of $C_{1-4}$alkyl;

(d)

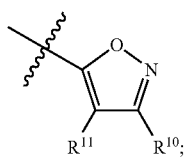

wherein $R^{10}$ is $C_{1-4}$alkyl; and $R^{11}$ is selected from the group consisting of hydrogen and cyano;

(e)

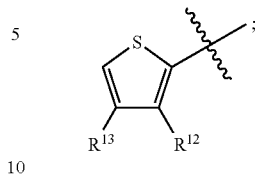

wherein $R^{12}$ is hydrogen and $R^{13}$ is selected from the group consisting of $C_{1-4}$alkyl;

(f)

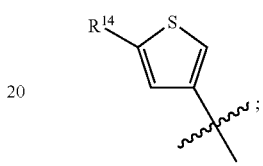

wherein $R^{14}$ is selected from the group consisting of $C_{1-4}$alkyl;

(g)

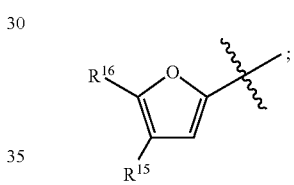

wherein $R^{15}$ is $C_{1-4}$alkyl; and $R^{16}$ is selected from the group consisting of hydrogen and bromo; and (h)

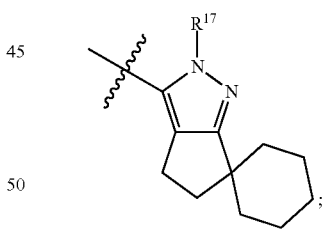

wherein $R^{17}$ is $C_{1-2}$alkyl.

In another embodiment of the present invention, Q is selected from the group consisting of 1-methyl-3-tert-butyl-pyrazol-5-yl, 1-methyl-3-tert-butyl-4-chloro-pyrazol-5-yl, 1-methyl-3-tert-butyl-4-fluoro-pyrazol-5-yl, 1-methyl-3-tert-butyl-4-cyano-pyrazol-5-yl, 1-methyl-3-trifluoromethyl-4-chloro-pyrazol-5-yl, 1-methyl-3-tert-butyl-4-methoxy-pyrazol-5-yl, 1-methyl-3-(1,1-dimethyl-2-fluoro-ethyl)-4-chloro-pyrazol-5-yl, 1-tert-butyl-pyrazol-4-yl, 1-tert-butyl-5-methyl-pyrazol-4-yl, 1-methyl-3-tert-butyl-imidazol-2-yl, 3-tert-butyl-isoxazol-5-yl, 3-tert-butyl-4-cyano-isoxazol-5-yl, 4-isopropyl-thien-2-yl, 5-isopropyl-thien-3-yl, 4-tert-butyl-fur-2-yl, 4-tert-butyl-5-bromo-fur-2-yl, and

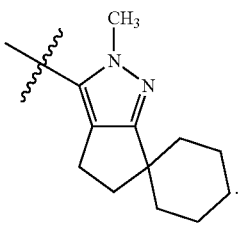 [SMILES: *c1c2c(nn1C)C1(CCCCC1)CC2]

In another embodiment of the present invention, Q is selected from the group consisting of 1-methyl-3-tert-butyl-pyrazol-5-yl, 1-methyl-3-tert-butyl-4-chloro-pyrazol-5-yl, 1-methyl-3-tert-butyl-4-fluoro-pyrazol-5-yl, 1-methyl-3-tert-butyl-4-cyano-pyrazol-5-yl, 1-methyl-3-tert-butyl-4-methoxy-pyrazol-5-yl, 1-methyl-3-(1,1-dimethyl-2-fluoro-ethyl)-4-chloro-pyrazol-5-yl, 3-tert-butyl-isoxazol-5-yl, 3-tert-butyl-4-cyano-isoxazol-5-yl, 4-isopropyl-thien-2-yl, 5-isopropyl-thien-3-yl, 4-tert-butyl-fur-2-yl, 4-tert-butyl-5-bromo-fur-2-yl and

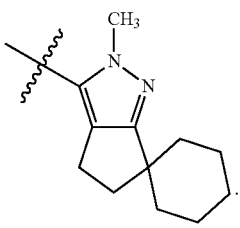 [SMILES: *c1c2c(nn1C)C1(CCCCC1)CC2]

In another embodiment of the present invention, Q is selected from the group consisting of 1-methyl-3-tert-butyl-4-chloro-pyrazol-5-yl, 1-methyl-3-tert-butyl-4-cyano-pyrazol-5-yl, 1-methyl-3-(1,1-dimethyl-2-fluoro-ethyl)-4-chloro-pyrazol-5-yl, 3-tert-butyl-isoxazol-5-yl and

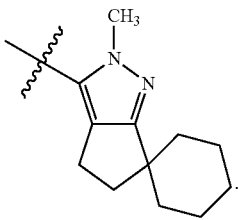 [SMILES: *c1c2c(nn1C)C1(CCCCC1)CC2]

In another embodiment of the present invention, Q is selected from the group consisting of 1-methyl-3-tert-butyl-4-chloro-pyrazol-5-yl, 1-methyl-3-tert-butyl-4-cyano-pyrazol-5-yl and 1-methyl-3-(1,1-dimethyl-2-fluoro-ethyl)-4-chloro-pyrazol-5-y. In another embodiment of the present invention, Q is selected from the group consisting of 1-methyl-3-tert-butyl-4-chloro-pyrazol-5-yl and 1-methyl-3-tert-butyl-4-cyano-pyrazol-5-yl.

In an embodiment, the present invention is directed to compounds of formula (I-B)

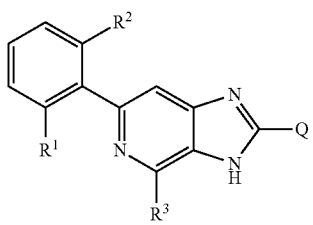

(I-B)

wherein $R^1$, $R^2$ and $R^3$ are as herein defined, and solvates, hydrates, tautomers and pharmaceutically acceptable salts thereof.

In an embodiment, the present invention is directed to compounds of formula (I-B) wherein $R^1$ is selected from the group consisting of hydrogen, fluoro, chloro, fluorinated $C_{1-2}$alkyl and fluorinated $C_{1-2}$alkoxy. In another embodiment, the present invention is directed to compounds of formula (I-B) wherein $R^1$ is selected from the group consisting of hydrogen, chloro, fluoro, trifluoromethyl and trifluoromethoxy. In another embodiment, the present invention is directed to compounds of formula (I-B) wherein $R^1$ is selected from the group consisting of chloro, fluoro, trifluoromethyl and trifluoromethoxy. In another embodiment, the present invention is directed to compounds of formula (I-B) wherein $R^1$ is selected from the group consisting of chloro and trifluoromethyl.

In an embodiment, the present invention is directed to compounds of formula (I-B) wherein $R^2$ is selected from the group consisting of hydrogen, chloro, trifluoromethyl and trifluoromethoxy. In another embodiment, the present invention is directed to compounds of formula (I-B) wherein $R^2$ is selected from the group consisting of hydrogen and chloro. In another embodiment, the present invention is directed to compounds of formula (I-B) wherein $R^2$ is hydrogen.

In an embodiment, the present invention is directed to compounds of formula (I-B) wherein $R^3$ is selected from the group consisting of hydrogen, chloro, cyano, $C_{1-2}$alkyl, fluorinated $C_{1-2}$alkyl, $C_{1-4}$alkoxy, fluorinated $C_{1-2}$alkoxy, —O—$(CH_2)_2$—OH, —O—$CH_2$—$CO_2H$, —O—$(CH_2)_2$—O—($C_{1-4}$alkyl), —O—$CH_2$-(fluorinated $C_{1-2}$alkyl), —O—$(CH_2)_2$—$NR^AR^B$ and —$NR^AR^B$; wherein $R^A$ and $R^B$ are each independently selected from the group consisting of hydrogen and $C_{1-2}$alkyl; alternatively $R^A$ and $R^B$ are taken together with the nitrogen atom to which they are bound to form a ring structure selected from the group consisting of pyrrolidin-1-yl, piperidin-1-yl, piperazin-1-yl, 4-methyl-piperazin-1-yl and morpholin-4-yl. In another embodiment, the present invention is directed to compounds of formula (I-B) wherein $R^3$ is selected form the group consisting of hydrogen, chloro, cyano, $C_{1-4}$alkoxy, —O—$(CH_2)_2$—OH, —O—$CH_2$—$CO_2H$, —O—$(CH_2)_2$—O—($C_{1-2}$alkyl), —O—$CH_2$-(fluorinated $C_{1-2}$alkyl), —O—$(CH_2)_2$—$NR^AR^B$, pyrrolidin-1-yl, piperidin-1-yl, piperazin-1-yl, 4-methyl-piperazin-1-yl and morpholin-4-yl; wherein $R^A$ and $R^B$ are each an independently selected $C_{1-2}$alkyl; alternatively $R^A$ and $R^B$ are taken together with the nitrogen atom to which they are bound to form a ring structure selected from the group consisting of pyrrolidin-1-yl, piperidin-1-yl, 4-methyl-piperazin-1-yl and morpholin-4-yl.

In another embodiment, the present invention is directed to compounds of formula (I-B) wherein $R^3$ is selected from the group consisting of hydrogen, chloro, cyano, methoxy, ethoxy, isopropoxy, —O—$CH_2$—$CF_3$, —O—$(CH_2)_2$—$OCH_3$, —O—$(CH_2)_2$—OH, —O—$(CH_2)_2$—$CO_2H$, pyrrolidin-1-yl, morpholin-4-yl, piperidin-1-yl, 4-methyl-piperazin-1-yl, —O—$(CH_2)_2$—$N(CH_3)_2$, —O—$(CH_2)_2$-(morpholin-4-yl), —O—$(CH_2)_2$-(pyrrolidin-1-yl) and —O—$(CH_2)_2$-(4-methyl-piperazin-1-yl). In another embodiment, the present invention is directed to compounds of formula (I-B) wherein $R^3$ is selected from the group consisting of hydrogen, chloro, cyano, methoxy, isopropoxy, —O—$CH_2$—$CF_3$, —O—$(CH_2)_2$—$OCH_3$, —O—$(CH_2)_2$—OH, pyrrolidin-1-yl, morpholin-4-yl, piperidin-1-yl, 4-methyl-piperazin-1-yl, —O—$(CH_2)_2$—$N(CH_3)_2$ and —O—$(CH_2)_2$-(morpholin-4-yl). In another embodiment, the present invention is directed to compounds of formula (I-B) wherein $R^3$ is selected from the group consisting of chloro, methoxy, isopropoxy, —O—$CH_2$—$CF_3$, —O—$(CH_2)_2$—$OCH_3$, —O—$(CH_2)_2$—OH, pyrrolidin-1-yl, morpholin-4-yl, piperidin-1-yl, 4-methyl-piperazin-1-yl and —O—(CH$_2$)$_2$-(morpholin-4-yl). In another embodiment, the present invention is directed to compounds of formula (I-B) wherein R$^3$ is selected from the group consisting of chloro, methoxy, isopropoxy, —O—CH$_2$—CF$_3$, —O—(CH$_2$)$_2$—OCH$_3$, —O—(CH$_2$)$_2$—OH, morpholin-4-yl, piperidin-1-yl and —O—(CH$_2$)$_2$-(morpholin-4-yl). In another embodiment, the present invention is directed to compounds of formula (I-B) wherein R$^3$ is —OCH$_3$.

In an embodiment, the present invention is directed to compounds of formula (I-B) wherein Q is an optionally substituted ring structure selected from the group consisting of formulas (a) through (h)

(a)

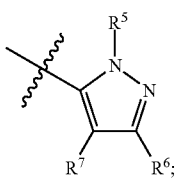

(b)

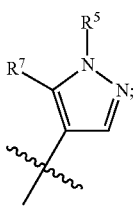

wherein R$^5$ is C$_{1-4}$alkyl; R$^6$ is selected from the group consisting of C$_{1-4}$alkyl and fluorinated C$_{1-4}$alkyl; and R$^7$ is selected from the group consisting of hydrogen, chloro, fluoro, cyano, C$_{1-2}$alkyl and C$_{1-2}$alkoxy;

(c)

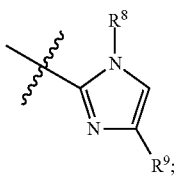

wherein R$^8$ and R$^9$ are each independently selected from the group consisting of C$_{1-4}$alkyl;

(d)

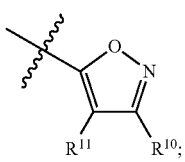

wherein R$^{10}$ is C$_{1-4}$alkyl; and R$^{11}$ is selected from the group consisting of hydrogen and cyano;

(e)

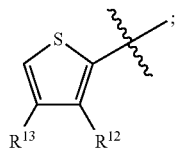

wherein R$^{12}$ is hydrogen and R$^{13}$ is selected from the group consisting of C$_{1-4}$alkyl;

(f)

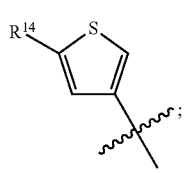

wherein R$^{14}$ is selected from the group consisting of C$_{1-4}$alkyl;

(g)

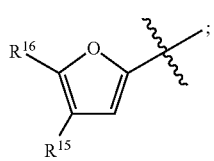

wherein R$^{15}$ is C$_{1-4}$alkyl; and R$^{16}$ is selected from the group consisting of hydrogen and bromo; and (h)

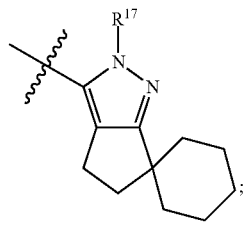

wherein R$^{17}$ is C$_{1-2}$alkyl.

In another embodiment, the present invention is directed to compounds of formula (I-B) wherein Q is selected from the group consisting of 1-methyl-3-tert-butyl-pyrazol-5-yl, 1-methyl-3-tert-butyl-4-chloro-pyrazol-5-yl, 1-methyl-3-tert-butyl-4-fluoro-pyrazol-5-yl, 1-methyl-3-tert-butyl-4-cyano-pyrazol-5-yl, 1-methyl-3-trifluoromethyl-4-chloro-pyrazol-5-yl, 1-methyl-3-tert-butyl-4-methoxy-pyrazol-5-yl, 1-methyl-3-(1,1-dimethyl-2-fluoro-ethyl)-4-chloro-pyrazol-5-yl, 1-tert-butyl-pyrazol-4-yl, 1-tert-butyl-5-methyl-pyrazol-4-yl, 1-methyl-3-tert-butyl-imidazol-2-yl, 3-tert-butyl-isoxazol-5-yl, 3-tert-butyl-4-cyano-isoxazol-5-yl, 4-isopropyl-thien-2-yl, 5-isopropyl-thien-3-yl, 4-tert-butyl-fur-2-yl, 4-tert-butyl-5-bromo-fur-2-yl, and

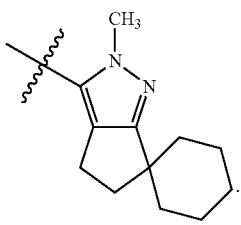 [SMILES: *c1c2c(nn1C)C1(CCCCC1)CC2]

In another embodiment, the present invention is directed to compounds of formula (I-B) wherein Q is selected from the group consisting of 1-methyl-3-tert-butyl-pyrazol-5-yl, 1-methyl-3-tert-butyl-4-chloro-pyrazol-5-yl, 1-methyl-3-tert-butyl-4-fluoro-pyrazol-5-yl, 1-methyl-3-tert-butyl-4-cyano-pyrazol-5-yl, 1-methyl-3-tert-butyl-4-methoxy-pyrazol-5-yl, 1-methyl-3-(1,1-dimethyl-2-fluoro-ethyl)-4-chloro-pyrazol-5-yl, 3-tert-butyl-isoxazol-5-yl, 3-tert-butyl-4-cyano-isoxazol-5-yl, 4-isopropyl-thien-2-yl, 5-isopropyl-thien-3-yl, 4-tert-butyl-fur-2-yl, 4-tert-butyl-5-bromo-fur-2-yl and

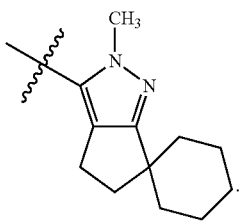 [SMILES: *c1c2c(nn1C)C1(CCCCC1)CC2]

In another embodiment, the present invention is directed to compounds of formula (I-B) wherein Q is selected from the group consisting of 1-methyl-3-tert-butyl-4-chloro-pyrazol-5-yl, 1-methyl-3-tert-butyl-4-cyano-pyrazol-5-yl, 1-methyl-3-(1,1-dimethyl-2-fluoro-ethyl)-4-chloro-pyrazol-5-yl, 3-tert-butyl-isoxazol-5-yl, and

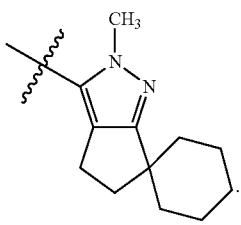 [SMILES: *c1c2c(nn1C)C1(CCCCC1)CC2]

In another embodiment, the present invention is directed to compounds of formula (I-B) wherein Q is selected from the group consisting of 1-methyl-3-tert-butyl-4-chloro-pyrazol-5-yl, 1-methyl-3-tert-butyl-4-cyano-pyrazol-5-yl and 1-methyl-3-(1,1-dimethyl-2-fluoro-ethyl)-4-chloro-pyrazol-5-yl. In another embodiment, the present invention is directed to compounds of formula (I-B) wherein Q is selected from the group consisting of 1-methyl-3-tert-butyl-4-chloro-pyrazol-5-yl and 1-methyl-3-tert-butyl-4-cyano-pyrazol-5-yl.

Additional embodiments of the present invention, include those wherein the substituents for one or more of the variables defined herein (i.e. $R^1$, $R^2$, Q, etc.) are independently selected to be any individual substituent or any subset of substituents selected from the complete list as defined herein.

Representative compounds of formula (I) are listed in Table 1, below. In another embodiment, the present invention is directed to any single compound or subset of compounds selected from the representative compounds listed in Table 1, below.

TABLE 1

Representative Compounds of Formula (I)

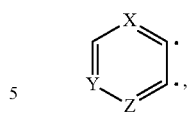

| Cmpd No. | $R^1$ | ![ring] | Q |
|---|---|---|---|
| 1 | CF$_3$ | pyridyl-CF$_3$ | 1-methyl-3-tert-butyl-4-chloro-pyrazol-5-yl |
| 2 | OCF$_3$ | pyridyl-OCH$_3$ | 1-methyl-3-tert-butyl-4-chloro-pyrazol-5-yl |
| 3 | CF$_3$ | pyrazinyl-CH$_3$ | 1-methyl-3-tert-butyl-4-chloro-pyrazol-5-yl |
| 4 | CF$_3$ | pyrazinyl-CH$_3$ | 3-tert-butyl-isoxazol-5-yl |
| 5 | CF$_3$ | pyridyl-Cl | 1-methyl-3-tert-butyl-4-chloro-pyrazol-5-yl |

TABLE 1-continued

Representative Compounds of Formula (I)

| # | | | |
|---|---|---|---|
| 6 | CF₃ | 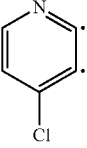 | 1-methyl-3-tert-butyl-pyrazol-5-yl |
| 7 | CF₃ | 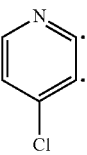 | 3-tert-butyl-isoxazol-5-yl |
| 8 | CF₃ | 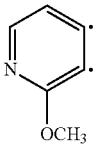 | 3-tert-butyl-isoxazol-5-yl |
| 9 | CF₃ | 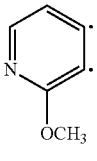 | 1-methyl-3-tert-butyl-4-chloro-pyrazol-5-yl |
| 10 | CF₃ | 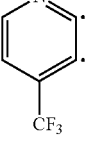 | 3-tert-butyl-isoxazol-5-yl |
| 11 | Cl | 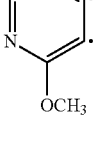 | 1-methyl-3-tert-butyl-4-chloro-pyrazol-5-yl |
| 12 | Cl | 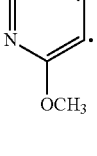 | 1-methyl-3-tert-butyl-pyrazol-5-yl |
| 13 | CF₃ | 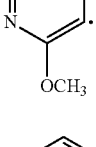 | 3-tert-butyl-4-cyano-isoxazol-5-yl |
| 14 | CF₃ | 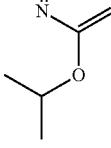 | 1-methyl-3-tert-butyl-4-cyano-pyrazol-5-yl |
| 15 | CF₃ | 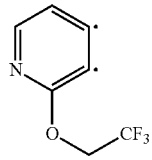 | 1-methyl-3-tert-butyl-4-cyano-pyrazol-5-yl |
| 16 | CF₃ | 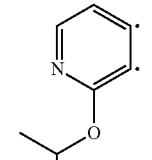 | 1-methyl-3-tert-butyl-4-chloro-pyrazol-5-yl |
| 17 | Cl | 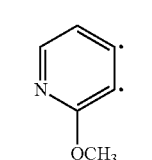 | 1-methyl-3-tert-butyl-4-cyano-pyrazol-5-yl |
| 18 | Cl | 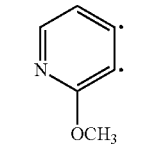 | 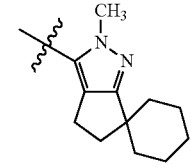 |
| 19 | CF₃ | 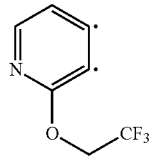 | 1-methyl-3-tert-butyl-4-chloro-pyrazol-5-yl |
| 20 | CF₃ | 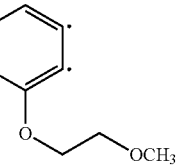 | 1-methyl-3-tert-butyl-4-chloro-pyrazol-5-yl |
| 21 | CF₃ | 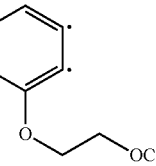 | 1-methyl-3-tert-butyl-4-cyano-pyrazol-5-yl |
| 22 | CF₃ | 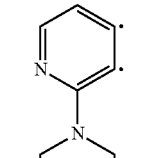 | 1-methyl-3-tert-butyl-4-cyano-pyrazol-5-yl |
| 23 | Cl | 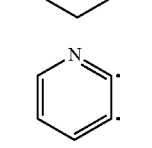 | 1-methyl-3-tert-butyl-4-chloro-pyrazol-5-yl |

TABLE 1-continued

Representative Compounds of Formula (I)

| # | R | Ar | Het |
|---|---|---|---|
| 24 | CF$_3$ | 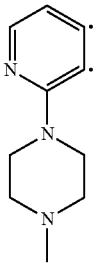 | 1-methyl-5-tert-butyl-4-cyano-pyrazol-5-yl |
| 25 | OCF$_3$ |  | 1-methyl-3-tert-butyl-4-chloro-pyrazol-5-yl |
| 26 | Cl |  | 3-tert-butyl-isoxazol-5-yl |
| 27 | Cl |  | 1-methyl-3-tert-butyl-pyrazol-5-yl |
| 28 | CF$_3$ | 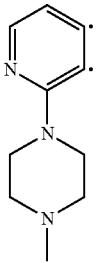 | 1-methyl-3-tert-butyl-4-chloro-pyrazol-5-yl |
| 29 | OCF$_3$ |  | 3-tert-butyl-isoxazol-5-yl |
| 30 | F |  | 3-tert-butyl-isoxazol-5-yl |
| 31 | CF$_3$ |  | 3-tert-butyl-isoxazol-5-yl |
| 32 | CF$_3$ |  | 1-methyl-3-tert-butyl-4-chloro-pyrazol-5-yl |
| 33 | F |  | 1-methyl-3-tert-butyl-4-chloro-pyrazol-5-yl |
| 34 | CF$_3$ |  | 1-methyl-3-tert-butyl-pyrazol-5-yl |
| 35 | CF$_3$ | 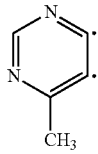 | 1-methyl-3-tert-butyl-pyrazol-5-yl |
| 36 | F |  | 1-methyl-3-tert-butyl-pyrazol-5-yl |
| 37 | OCF$_3$ |  | 1-methyl-3-tert-butyl-pyrazol-5-yl |
| 39 | OCF$_3$ |  | 1-methyl-3-tert-butyl-pyrazol-5-yl |
| 40 | CF$_3$ |  | 1-methyl-3-tert-butyl-pyrazol-5-yl |
| 41 | Cl |  | 1-methyl-3-tert-butyl-pyrazol-5-yl |
| 42 | F |  | 1-methyl-3-tert-butyl-pyrazol-5-yl |
| 43 | F |  | 1-methyl-3-tert-butyl-4-chloro-pyrazol-5-yl |
| 44 | F |  | 1-methyl-3-tert-butyl-4-cyano-pyrazol-5-yl |
| 45 | CF$_3$ |  | 1-methyl-3-tert-butyl-4-cyano-pyrazol-5-yl |
| 46 | CF$_3$ |  | 1-methyl-3-tert-butyl-4-chloro-pyrazol-5-yl |
| 47 | H |  | 1-methyl-3-tert-butyl-4-cyano-pyrazol-5-yl |
| 48 | F |  | 1-methyl-3-trifluoromethyl-4-chloro-pyrazol-5-yl |

TABLE 1-continued

Representative Compounds of Formula (I)

| | | | |
|---|---|---|---|
| 49 | CF$_3$ | 2-(morpholin-4-yl)ethoxy-pyridin-2-yl | 1-methyl-3-tert-butyl-4-chloro-pyrazol-5-yl |
| 50 | CF$_3$ | 2-(4-methylpiperazin-1-yl)ethoxy-pyridin-2-yl | 1-methyl-3-tert-butyl-4-chloro-pyrazol-5-yl |
| 51 | Cl | 2-(pyrrolidin-1-yl)ethoxy-pyridin-2-yl | 1-methyl-3-tert-butyl-4-chloro-pyrazol-5-yl |
| 52 | CF$_3$ | 2-(pyrrolidin-1-yl)ethoxy-pyridin-2-yl | 1-methyl-3-tert-butyl-4-chloro-pyrazol-5-yl |
| 53 | CF$_3$ | 2-(dimethylamino)ethoxy-pyridin-2-yl | 1-methyl-3-tert-butyl-4-chloro-pyrazol-5-yl |
| 54 | Cl | 2-(morpholin-4-yl)ethoxy-pyridin-2-yl | 1-methyl-3-tert-butyl-4-chloro-pyrazol-5-yl |
| 55 | Cl | 2-(4-methylpiperazin-1-yl)ethoxy-pyridin-2-yl | 1-methyl-3-tert-butyl-4-chloro-pyrazol-5-yl |
| 56 | Cl | 2-(dimethylamino)ethoxy-pyridin-2-yl | 1-methyl-3-tert-butyl-4-chloro-pyrazol-5-yl |
| 57 | CF$_3$ | 2-hydroxyethoxy-pyridin-2-yl | 1-methyl-3-tert-butyl-4-chloro-pyrazol-5-yl |
| 58 | Cl | 2-hydroxyethoxy-pyridin-2-yl | 1-methyl-3-tert-butyl-4-chloro-pyrazol-5-yl |
| 59 | CF$_3$ | 2-(morpholin-4-yl)-pyridin-2-yl | 1-methyl-3-tert-butyl-4-chloro-pyrazol-5-yl |

TABLE 1-continued

Representative Compounds of Formula (I)

| | | | |
|---|---|---|---|
| 60 | CF$_3$ | 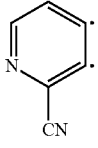 | 1-methyl-3-tert-butyl-4-chloro-pyrazol-5-yl |
| 61 | CF$_3$ | 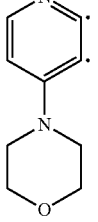 | 1-methyl-3-tert-butyl-4-chloro-pyrazol-5-yl |
| 62 | CF$_3$ | 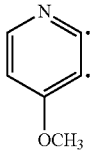 | 1-methyl-3-tert-butyl-4-chloro-pyrazol-5-yl |
| 63 | CF$_3$ | 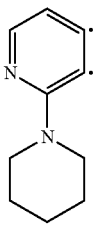 | 1-methyl-3-tert-butyl-4-chloro-pyrazol-5-yl |
| 64 | CF$_3$ | 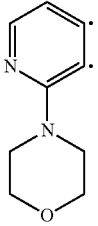 | 3-tert-butyl-4-cyano-isoxazol-5-yl |
| 65 | CF$_3$ | 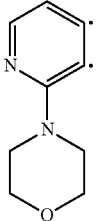 | 1-methyl-3-tert-butyl-4-cyano-pyrazol-5-yl |
| 66 | CF$_3$ | 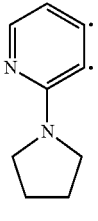 | 1-methyl-3-tert-butyl-4-chloro-pyrazol-5-yl |
| 67 | CF$_3$ | 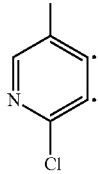 | 1-methyl-3-tert-butyl-4-chloro-pyrazol-5-yl |
| 68 | CF$_3$ | 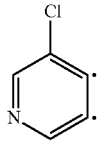 | 1-methyl-3-tert-butyl-4-chloro-pyrazol-5-yl |
| 70 | CF$_3$ | 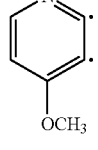 | 3-tert-butyl-4-cyano-isoxazol-5-yl |
| 71 | CF$_3$ | 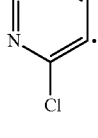 | 1-methyl-3-tert-butyl-4-chloro-pyrazol-5-yl |
| 72 | CF$_3$ | 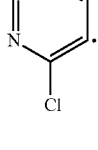 | 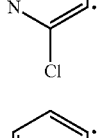 |
| 73 | CF$_3$ | 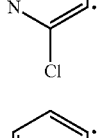 | 3-tert-butyl-isoxazol-5-yl |
| 74 | CF$_3$ | 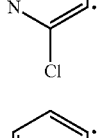 | 1-methyl-3-tert-butyl-pyrazol-5-yl |
| 75 | CF$_3$ | 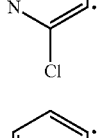 | 1-methyl-3-tert-butyl-4-cyano-pyrazol-5-yl |
| 76 | CF$_3$ | 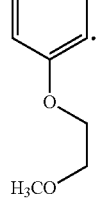 | 1-methyl-3-tert-butyl-4-chloro-pyrazol-5-yl |

TABLE 1-continued

Representative Compounds of Formula (I)

| | | | |
|---|---|---|---|
| 77 | F | 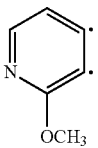 | 1-methyl-3-tert-butyl-4-fluoro-pyrazol-5-yl |
| 78 | CF$_3$ | 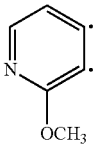 | 1-methyl-3-tert-butyl-4-fluoro-pyrazol-5-yl |
| 79 | CF$_3$ | 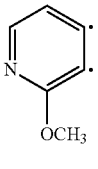 | 1-methyl-3-tert-butyl-4-methoxy-pyrazol-5-yl |
| 80 | CF$_3$ | 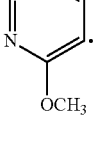 | 1-methyl-3-tert-butyl-pyrazol-5-yl |
| 81 | CF$_3$ | 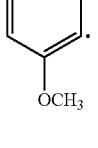 | 1-methyl-3-tert-butyl-pyrazol-5-yl |
| 83 | Cl | 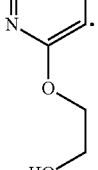 | 1-methyl-3-tert-butyl-4-cyano-pyrazol-5-yl |
| 84 | CF$_3$ | 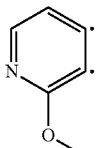 | 1-methyl-3-tert-butyl-4-cyano-pyrazol-5-yl |
| 85 | Cl | 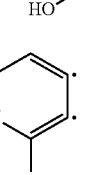 | 1-methyl-3-tert-butyl-4-cyano-pyrazol-5-yl |
| 86 | CF$_3$ | 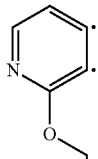 | 1-methyl-3-tert-butyl-4-cyano-pyrazol-5-yl |
| 87 | Cl | 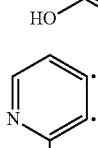 | 1-methyl-3-tert-butyl-4-chloro-pyrazol-5-yl |
| 88 | CF$_3$ | 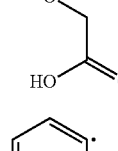 | 1-methyl-3-tert-butyl-4-chloro-pyrazol-5-yl |
| 89 | Cl | 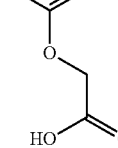 | 1-methyl-3-tert-butyl-4-chloro-pyrazol-5-yl |
| 90 | OCF$_3$ | 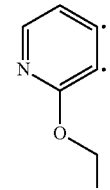 | 1-methyl-3-tert-butyl-4-chloro-pyrazol-5-yl |
| 91 | F | 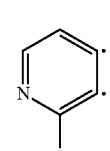 | 1-methyl-3-tert-butyl-4-chloro-pyrazol-5-yl |
| 92 | F | 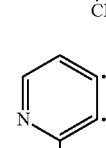 | 1-methyl-3-tert-butyl-4-chloro-pyrazol-5-yl |

TABLE 1-continued

Representative Compounds of Formula (I)

| | | | |
|---|---|---|---|
| 93 | OCF₃ | 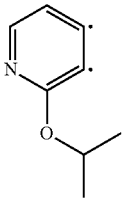 | 1-methyl-3-tert-butyl-4-chloro-pyrazol-5-yl |
| 94 | OCF₃ | 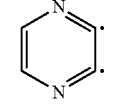 | 1-methyl-3-tert-butyl-4-chloro-pyrazol-5-yl |
| 95 | CF₃ | 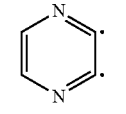 | 1-methyl-3-tert-butyl-4-chloro-pyrazol-5-yl |
| 96 | F | 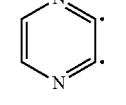 | 1-methyl-3-tert-butyl-4-chloro-pyrazol-5-yl |
| 97 | Cl | 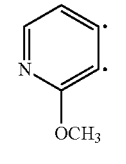 | 1-methyl-3-(1,1-dimethyl-2-fluoro-ethyl)-4-chloro-pyrazol-5-yl |
| 98 | Cl | 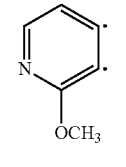 | 5-isopropyl-thien-3-yl |
| 99 | Cl | 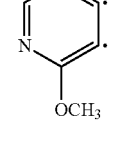 | 4-tert-butyl-fur-2-yl |
| 100 | Cl | 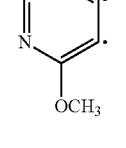 | 1-tert-butyl-5-methyl-pyrazol-4-yl |
| 101 | Cl | 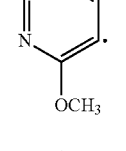 | 4-tert-butyl-5-bromo-fur-2-yl |
| 102 | Cl | 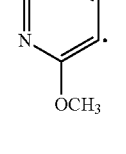 | 1-tert-butyl-pyrazol-4-yl |
| 105 | Cl | 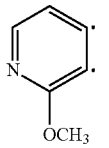 | 4-isopropyl-thien-2-yl |
| 106 | Cl | 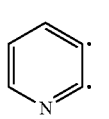 | 4-tert-butyl-5-bromo-fur-2-yl |
| 107 | Cl | 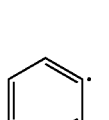 | 1-tert-butyl-5-methyl-pyrazol-4-yl |
| 108 | Cl | 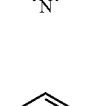 | 1-methyl-3-tert-butyl-4-chloro-pyrazol-5-yl |
| 109 | Cl | 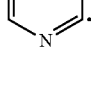 | 1-methyl-3-tert-butyl-4-chloro-pyrazol-5-yl |
| 110 | Cl | 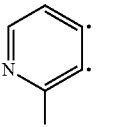 | 1-methyl-3-tert-butyl-4-chloro-pyrazol-5-yl |
| 111 | Cl | 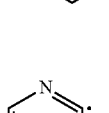 | 1-methyl-3-tert-butyl-imidazol-2-yl |
| 112 | CF₃ | 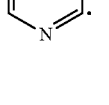 | 1-methyl-3-tert-butyl-pyrazol-5-yl |

TABLE 1-continued

Representative Compounds of Formula (I)

| Cmpd No. | R¹ | R² | Y-Z | Q |
|---|---|---|---|---|
| 103 | Cl | Cl | (pyridine with OCH₃) | 1-methyl-3-tert-butyl-4-chloro-pyrazol-5-yl |

In another embodiment, the present invention is directed to a compound of formula (I) that exhibits a % Inhibition at 0.2 µM of greater than or equal to about 10% (preferably greater than or equal to about 25%, more preferably greater than or equal to about 80%, more preferably greater than or equal to about 80%), also preferred are greater than or equal to 20% at 0.5 µM, and further preferred are greater than or equal to 30% at 1 µM, as measured according to the procedure described in Biological Example 1, which follows herein.

In an embodiment, the present invention is directed to a compound of formula (I) which exhibits an $IC_{50}$ of less than or 0.100 µM, preferably less than or equal to about 0.05 µM, more preferably less than or equal to about 0.025 µM, more preferably less than or equal to about 0.01 µM, more preferably less than or equal to about 0.005 µM, as measured according to the procedure described in Biological Example 1, which follows herein.

As used herein, the term "alkyl" whether used alone or as part of a substituent group, include straight and branched chains. For example, alkyl radicals include methyl, ethyl, propyl, isopropyl, butyl, isobutyl, sec-butyl, tert-butyl, pentyl and the like. Unless otherwise noted, the notation "$C_{X-Y}$alkyl" wherein X and Y are integers shall indicate an alkyl group as herein define containing between X and Y carbon atoms. For example, the term "$C_{1-4}$alkyl" shall include straight and branched alkyl chains containing between one to four carbon atoms.

As used herein, unless otherwise noted, "alkoxy" shall denote an oxygen ether radical of the above described straight or branched chain alkyl groups. For example, methoxy, ethoxy, n-propoxy, sec-butoxy, tert-butoxy, n-hexyloxy and the like. Similarly, the term "$C_{X-Y}$alkoxy" wherein X and Y are integers shall indicate an alkoxy group as herein define containing between X and Y carbon atoms. For example, the term "$C_{1-4}$alkoxy" shall include straight and branched alkoxy groups containing one to four carbon atoms, more particularly, methoxy and ethoxy.

As used herein, unless otherwise noted, the term "fluorinated $C_{1-4}$alkyl" shall mean any $C_{1-4}$alkyl group as defined above substituted with at least one fluoro atom. Suitable examples include but are not limited to —$CF_3$, —$CH_2$—$CF_3$, —$CF_2$—$CF_2$—$CF_2$—$CF_3$, —$CCl_3$, $CH_2CCl_3$, and the like. Similarly, as used herein, unless otherwise noted, the term "fluorinated $C_{1-4}$alkoxy" shall mean any $C_{1-4}$alkyl group as defined above substituted with at least one fluoro atom. Suitable examples include but are not limited to —$OCF_3$, —$OCH_2$—$CF_3$, —$OCF_2$—$CF_2$—$CF_2$—$CF_3$, and the like.

When a particular group is "substituted", that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

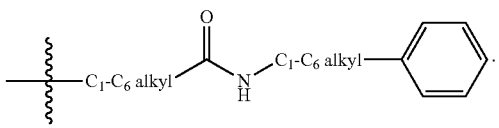

Abbreviations used in the specification, particularly the Schemes and Examples, are as follows:

| | |
|---|---|
| AcOH or HOAc = | Acetic Acid |
| BF₃•OEt₂ = | Boron Trifluoride Etherate |
| tert-BuOH = | tert-Butanol |
| DCM = | Dichloromethane |
| DCE = | 1,2-Dichloroethane |
| DDQ = | 2,3-Dichloro-5,6-dicyanobenzoquinone |

| | |
|---|---|
| Dess-Martin Periodinane = | [1,1,1-Triacetoxy-1,1-dihydro-1,2-benziodoxol-3-3(1H)-one] |
| DIEA or DIPEA = | Diisopropylethylamine |
| DMA = | Dimethylacetamide |
| DME = | 1,2-Dimethoxyethane |
| DMF = | N,N-Dimethylformamide |
| DMFDMA = | N,N-dimethylformamide dimethylacetal |
| DMSO = | Dimethylsulfoxide |
| $Et_2O$ = | Diethyl Ether |
| EtOAc = | Ethyl Acetate |
| EtOH = | Ethanol |
| FBS = | Fetal Bovine Serum |
| HPLC = | High Pressure Liquid Chromatography |
| IPA = | Isopropanol |
| KOMe = | Potassium Methoxide |
| MeOH = | Methanol |
| MsOH = | Methanesulfonic acid |
| MTBE = | Methyl tert-butyl Ether |
| NaOMe = | Sodium Methoxide |
| NaOEt = | Sodium Ethoxide |
| NMP = | N-Methyl-2-pyrrolidone |
| Pd/C = | Palladium on Carbon Catalyst |
| $Pd(OAc)_2$ = | Palladium (II) acetate |
| $PdCl_2$dppf or (dppf)$PdCl_2$ = | [1,1'-Bis(diphenylphosphino)ferrocene]dichloropalladium(II). |
| $PdCl_2$dPPf•DCM or (dppf)$PdCl_2$•DCM = | (1,1'-Bis(diphenylphosphino ferrocene) dichloropalladium(II) dichloromethane (1:1) adduct (or complex) |
| $Pd_2(dba)_3$ = | Tris(dibenzylidene acetone)dipalladium(0) |
| $Pd(PPh_3)_4$ = | Tetrakis(triphenylphosphine) palladium (0) |
| Pt(Sulfided)/C = | Sulfided Platinum on Carbon Catalyst |
| TEA = | Triethylamine |
| TFA = | Trifluoroacetic Acid |
| THF = | Tetrahydrofuran |
| TLC = | Thin Layer Chromatography |
| TRPM8 = | Transient Receptor Potential M8 channel |

As used herein, unless otherwise noted, the terms "treating", "treatment" and the like, shall include the management and care of a subject or patient (preferably mammal, more preferably human) for the purpose of combating a disease, condition or disorder and includes the administration of a compound of the present invention to prevent the onset of the symptoms or complications, alleviate the symptoms or complications or eliminate the disease, condition or disorder.

As used herein, unless otherwise noted, the term "prevention" shall include (a) reduction in the frequency of one or more symptoms; (b) reduction in the severity of one or more symptoms; (c) delay or avoidance of the development of additional symptoms; and/or (d) delay or avoidance of the development of the disorder or condition.

One skilled in the art will recognize that wherein the present invention is directed to methods of prevention, a subject in need thereof (i.e., a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical professional to be at risk of developing said disorder, disease or condition. For example, the subject may be deemed at risk of developing a disorder, disease or condition (and therefore in need of prevention or preventive treatment) as a consequence of the subject's medical history, including but not limited to family history, pre-disposition, co-existing (comorbid) disorders or conditions, genetic testing and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For the purposes of the present invention, the term "antagonist" is used to refer to a compound capable of producing, depending on the circumstance, a functional antagonism of an ion channel, including but not limited to competitive antagonists, non-competitive antagonists, desensitizing agonists and partial agonists.

For purposes of the present invention, the term "TRPM8-modulated" is used to refer to the condition of being affected by the modulation of the TRPM8 channel, including but not limited to the state of being mediated by the TRPM8 channel.

As antagonists of the TRPM8 channel, the compounds of formula (I) are useful in methods for treating and preventing a disease, a syndrome, a condition or a disorder in a subject, including an animal, a mammal and a human in which the disease, the syndrome, the condition or the disorder is affected by the modulation of TRPM8 channels. Such methods comprise, consist of and consist essentially of administering to a subject, including an animal, a mammal and a human in need of such treatment or prevention, a therapeutically effective amount of a compound, salt or solvate of formula (I). In particular, the compounds of formula (I) are useful for preventing or treating pain or diseases, syndromes, conditions or disorders causing such pain or pulmonary or vascular dysfunction. More particularly, the compounds of formula (I) are useful for preventing or treating inflammatory pain, inflammatory hypersensitivity conditions, neuropathic pain, anxiety, depression, and cardiovascular disease aggravated by cold, including peripheral vascular disease, vascular hypertension, pulmonary hypertension, Raynaud's disease, and coronary artery disease, by administering to a subject in need thereof a therapeutically effective amount of a compound of formula (I).

Examples of inflammatory pain include pain due to a disease, condition, syndrome or disorder, including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis.

One type of inflammatory pain is inflammatory hyperalgesia, which can be further distinguished as inflammatory somatic hyperalgesia or inflammatory visceral hyperalgesia. Inflammatory somatic hyperalgesia can be characterized by the presence of an inflammatory hyperalgesic state in which a hypersensitivity to thermal, mechanical and/or chemical stimuli exists. Inflammatory visceral hyperalgesia can also be characterized by the presence of an inflammatory hyperalgesic state, in which an enhanced visceral irritability exists. Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease or ulcerative colitis.

One embodiment of the present invention is directed to a method for treating inflammatory somatic hyperalgesia in which a hypersensitivity to thermal, mechanical and/or chemical stimuli exists, comprising the step of administering to a mammal in need of such treatment a therapeutically effective amount of a compound, salt or solvate of formula (I).

A further embodiment of the present invention is directed to a method for treating inflammatory visceral hyperalgesia in which an enhanced visceral irritability exists, comprising, consisting of, and/or consisting essentially of the step of administering to a subject in need of such treatment a therapeutically effective amount of a compound, salt or solvate of formula (I).

A further embodiment of the present invention is directed to a method for treating neuropathic cold allodynia in which a hypersensitivity to a cooling stimuli exists, comprising, consisting of, and/or consisting essentially of the step of administering to a subject in need of such treatment a therapeutically effective amount of a compound, salt or solvate of formula (I).

Examples of a neuropathic pain include pain due to a disease, syndrome, condition or disorder, including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (e.g., trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

As used herein, unless otherwise noted, the term "cardiovascular disease aggravated by cold" shall include peripheral vascular disease, vascular hypertension, pulmonary hypertension, Raynaud's disease and coronary artery disease.

In an embodiment, the present invention is directed to methods for the treatment of inflammatory pain, inflammatory hypersensitivity condition or neuropathic pain, comprising administering to a subject in need thereof a therapeutically effective amount of a compound of formula (I).

In an embodiment of the present invention, the inflammatory pain is pain due to inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis. Preferably, the inflammatory pain is inflammatory hyperalgesia.

In another embodiment of the present invention, the inflammatory hyperalgesia is inflammatory somatic hyperalgesia or inflammatory visceral hyperalgesia.

In another embodiment, the present invention is directed to methods for the treatment of inflammatory hyperplasia, wherein the inflammatory hyperalgesia is due to inflammation, osteoarthritis, rheumatoid arthritis, back pain, joint pain, abdominal pain, musculoskeletal diseases, skin diseases, post operative pain, headaches, fibromyalgia, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, Crohn's Disease, or ulcerative colitis.

In another embodiment, the present invention is directed to methods of treating inflammatory hypersensitivity conditions, wherein the inflammatory hypersensitivity condition is urinary incontinence, benign prostatic hypertrophy, cough, asthma, rhinitis, nasal hypersensitivity, itch, contact dermatitis, dermal allergy, or chronic obstructive pulmonary disease.

In another embodiment, the present invention is directed to methods for the treatment of neuropathic pain, wherein the neuropathic pain is due to cancer, a neurological disorder, spine or peripheral nerve surgery, a brain tumor, traumatic brain injury (TBI), spinal cord trauma, a chronic pain syndrome, fibromyalgia, chronic fatigue syndrome, a neuralgia, lupus, sarcoidosis, peripheral neuropathy, bilateral peripheral neuropathy, diabetic neuropathy, central pain, neuropathies associated with spinal cord injury, stroke, ALS, Parkinson's disease, multiple sclerosis, sciatic neuritis, mandibular joint neuralgia, peripheral neuritis, polyneuritis, stump pain, phantom limb pain, a bony fracture, oral neuropathic pain, Charcot's pain, complex regional pain syndrome I and II (CRPS I/II), radiculopathy, Guillain-barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia or vidian neuralgia. Preferably, the neuropathic pain is neuropathic cold allodynia or neuralgia. Preferably, the neuralgia is trigeminal neuralgia, glossopharyngeal neuralgia, postherpetic neuralgia, or causalgia.

In another embodiment, the present invention is directed to methods for the treatment of neuropathic cold allodynia, wherein the neuropathic cold allodynia is pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II), or radiculopathy.

In another embodiment, the present invention is directed to methods for the treatment of anxiety, wherein the anxiety is social anxiety, post traumatic stress disorder, phobias, social phobia, special phobias, panic disorder, obsessive compulsive disorder, acute stress disorder, separation anxiety disorder, or generalized anxiety disorder.

In another embodiment, the present invention is directed to methods for the treatment of depression wherein the depression is major depression, bipolar disorder, seasonal affective disorder, post natal depression, manic depression, or bipolar depression.

In another embodiment, the present invention is directed to a method for the treatment of inflammatory somatic hyperalgesia in which a hypersensitivity to thermal stimuli exists. In another embodiment, the present invention is directed to a method for the treatment of inflammatory visceral hyperalgesia in which an enhanced visceral irritability exists. In another embodiment, the present invention is directed to a method for the treatment of neuropathic cold allodynia in which a hypersensitivity to cooling stimuli exists.

In another embodiment, the present invention is directed to a method for the treatment of cardiovascular disease aggravated by cold, including peripheral vascular disease, vascular hypertension, pulmonary hypertension, Raynaud's disease and coronary artery disease.

In another embodiment, the present invention is directed to methods for the treatment and/or prevention of migraine, post herpetic neuralgia, post traumatic neuralgia, post chemotherapy neuralgia, complex regional pain syndrome I and II (CRPS I/II), fibromyalgia, inflammatory bowel disease, pruritis, asthma, chronic obstructive pulmonary disease, toothache, bone pain or pyresis in a mammal, which method comprises administering to a mammal in need of such treatment or prevention a therapeutically effective amount of a TRPM8 antagonist.

In another embodiment, the present invention is directed to methods for the treatment and/or prevention of hypertension, peripheral vascular disease, Raynaud's disease, reperfusion injury or frostbite in a mammal, which method comprises administering to a mammal in need of such treatment or prevention a therapeutically effective amount of a TRPM8 antagonist.

In yet another embodiment, the present invention is directed to methods for accelerating postert-anesthetic recovery or post hypothermia recovery in a mammal, which method comprises administering to a mammal in need of such treatment a therapeutically effective amount of a TRPM8 antagonist.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same or different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, triflate and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art. As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, tert-butyl, benzyl, phenylethyl, CH$_2$=CH—CH$_2$—, and the like; amides—groups of the formula —C(O)—R' wherein R' is for example methyl, phenyl, trifluoromethyl, and the like; N-sulfonyl derivatives—groups of the formula —SO$_2$+R" wherein R" is for example tolyl, phenyl, trifluoromethyl, 2,2,5,7,8-pentamethylchroman-6-yl-, 2,3,6-trimethyl-4-methoxybenzene, and the like; and benzylic groups such as benzyl, 4-methoxybenzyl, 2,4-dimethoxybenzyl, and the like. Other suitable nitrogen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α−obs]/[α−max])×100.

One embodiment of the present invention is directed to a composition comprising the dextrorotatory enantiomer of a compound of formula (I) wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ dextrorotatory} = \frac{(\text{mass dextrorotatory})}{(\text{mass dextrorotatory}) + (\text{mass levorotatory})} \times 100$$

Another embodiment of the present invention is a composition comprising the levorotatory enantiomer of a compound of formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ levorotatory} = \frac{(\text{mass levorotatory})}{(\text{mass dextrorotatory}) + (\text{mass levorotatory})} \times 100.$$

General Synthetic Methods

Compounds of formula (I) wherein

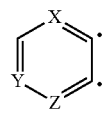

is selected from the group consisting of

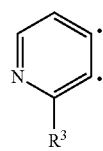 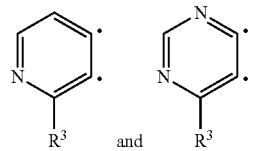

may be prepared as described in Scheme 1, below.

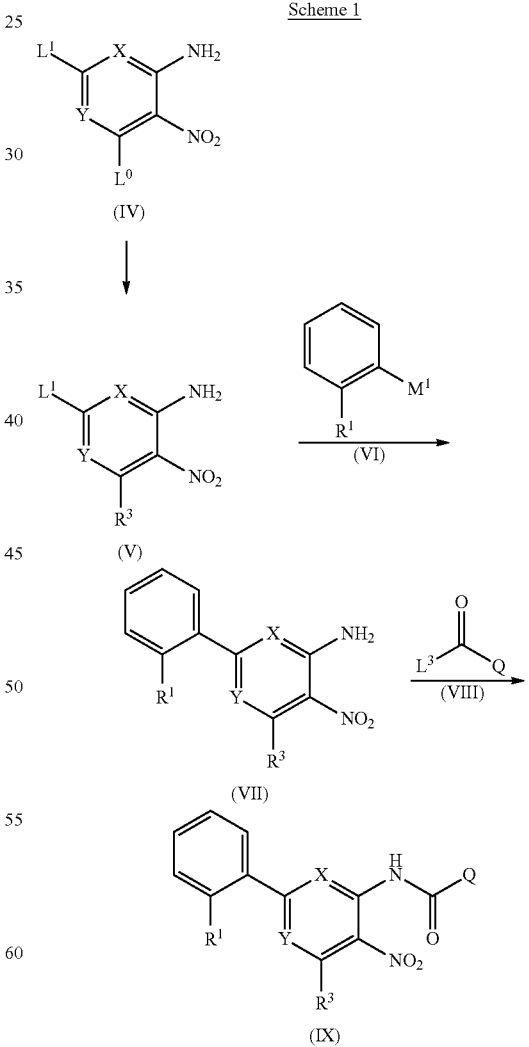

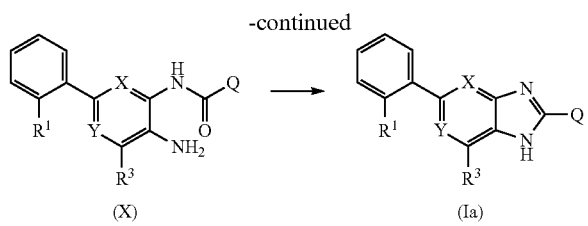

Accordingly, a suitably substituted compound of formula (IV), wherein 12 is a suitably selected leaving group such as chloro, bromo, and the like and wherein $L^1$ is a suitably selected leaving group such as chloro, bromo, triflate, and the like, a known compound or compound prepared by known methods, is reacted with a suitably selected nucleophilic reagent; according to known methods; to yield the corresponding compound of formula (V).

More particularly, for the preparation of a compound of formula (V) wherein $R^3$ is —$NR^A R^B$, the compound of formula (IV) is reacted with a suitably substituted amine of the formula $NHR^A R^B$, a known compound or compound prepared by known methods; in the presence of a suitably selected base such as $K_2CO_3$, $Na_2CO_3$, and the like; in a suitably selected organic solvent such as DMF, NMP, DMA, and the like. For the preparation of a compound of formula (V) wherein $R^3$ is cyano, the compound of formula (IV) is reacted with, for example, NaCN, CuCN, and the like; in a suitably selected organic solvent such as NMP, DMF, and the like. For the preparation of a compound of formula (V) wherein $R^3$ is selected from the group consisting of $C_{1-4}$alkoxy, fluorinated $C_{1-4}$alkoxy, —O—$(CH_2)_2$—OH, —O—$(CH_2)_2$—O—$(C_{1-4}$alkyl), —O—$CH_2$-(fluorinated $C_{1-2}$alkyl) and —O—$(CH_2)_2$—$NR^A R^B$, the compound of formula (IV) is reacted with, for example, the corresponding $R^3$—Na or $R^3$—K reagent, a known compound or compound prepared by known methods, as would be readily recognized by one skilled in the art.

One skilled in the art will recognize that compounds of formula (V) wherein $R^3$ is —O—$CH_2$—C(O)OH may be prepared by further oxidizing a corresponding compound of formula (V) wherein $R^3$ is —O—$(CH_2)_2$—OH, according to known methods, to convert the —O—$CH_2$—$CH_2$—OH to the corresponding aldehyde (i.e. converting —O—$CH_2$—$CH_2$—OH to the corresponding —O—$CH_2$—CHO). For example, a suitably substituted compound of formula (V) wherein $R^3$ is —O—$(CH_2)_2$—OH may be reacted with a suitably selected reagent such as Dess-Martin periodinane, oxalyl chloride/DMSO, and the like, according to known methods. The resulting aldehyde compound may then be further oxidized by, for example, reacting with a suitably selected reagent such as $NaClO_2$, and the like, in the presence of 2-methyl-2-butene, and the like; to yield the corresponding compound of formula (V) wherein the aldehyde is converted to the corresponding carboxyl acid (i.e. converting the —O—$(CH_2)_2$—CHO group to the corresponding —O—$CH_2$—C(O)OH group).

Compounds of formula (V) wherein $R^3$ is selected from the group consisting of hydrogen, chloro, $C_{1-4}$alkyl and fluorinated $C_{1-4}$alkyl are known compounds, commercially available compounds or compounds prepared by known methods and as such are selected as the starting material. (Thus, for said compounds, the transformation from a compound of formula (IV) is not necessary).

The compound of formula (V), is reacted with a suitably substituted compound of formula (VI), wherein $M^1$ is a suitably selected activating group such as (a) boronic acid (—B(OH)$_2$), (b) a suitably selected boronic ester such as pinacolatoboryl, neopentylglycolatoboryl, and the like, (c) a suitably selected trialkylstannyl such as tri(n-butyl)tin, and the like, (d) a suitably selected trialkylsilyl such as triallylsilyl, and the like or (e) a suitably selected aryldialkylsilyl such as 2-(hydroxymethyl)phenyl-dimethylsilyl, and the like, a known compound or compound prepared by known methods, under suitable coupling conditions, to yield the corresponding compound of formula (VII).

For example, wherein compound of formula (VI), where $M^1$ is —B(OH)$_2$ or a suitably selected boronic ester, the compound of formula (V) is reacted with the compound of formula (VI) under Suzuki coupling conditions, more particularly in the presence of a suitably selected palladium catalyst such as palladium (II) acetate, palladium (II) chloride, bis(acetonitrile)-dichloro-palladium(II), allylpalladium (II) chloride dimer, tris(dibenzylidineacetone) dipalladium (0) (Pd$_2$(dba)$_3$), 2-(di-tert-butylphosphino)biphenyl, dichloro-bis(di-tert-butylphenylphosphine)-palladium (II), (1,1'-bis(di-tert-butylphosphino)ferrocene) palladium (II) chloride [1,1'-bis-(diphenylphosphino)-ferrocene]-palladium (II) dichloride dichloromethane adduct ((dppf)PdCl$_2$.DCM), 2-(dicyclohexylphosphino)-2',4',6'-tri-iso-propyl-1,1'-biphenyl, tetrakis(triphenylphosphine) palladium(0) (Pd(PPh$_3$)$_4$), and the like; optionally in the presence of a suitably selected added ligand such as triphenylphosphine, tri-o-tolylphosphine, tri(tert-butyl)-phosphine, tricyclohexylphosphine, 1,1'-bis(diphenylphosphino)-ferrocene, bis[2-(diphenylphosphino)phenyl]ether, 2-dicyclohexylphosphino-2',6'-dimethoxybiphenyl, tris(2-furyl)phosphine, 1-butyl-3-methylimidazolium hexafluorophosphate, and the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, aqueous sodium hydroxide, aqueous sodium bicarbonate; potassium phosphate or preferably aqueous sodium carbonate; in a suitably selected organic solvent such as ethanol, THF, DMF, toluene, benzene, DME, 1,4-dioxane, and the like or a mixture of organic solvents, for example in a mixture of toluene and ethanol; preferably at a suitable temperature in the range of from about room temperature to about 180° C.

The compound of formula (VII) is reacted with a suitably substituted compound of formula (VIII), wherein $L^3$ is a suitably selected leaving group such as chloro, bromo, fluoro, and the like, preferably chloro, a known compound or compound prepared by known methods; in the presence of a suitably selected inorganic base such as sodium hydride, potassium hydride, potassium tert-butoxide, n-butyllithium, and the like, preferably sodium hydride; in a suitably selected organic solvent such as DMF, THF, and the like, to yield the corresponding compound of formula (IX).

The compound of formula (IX) is reacted with a suitably selected reducing agent such as hydrogen in the presence of a catalyst such as palladium on carbon, hydrogen in the presence of a catalyst such as platinum on carbon doped with vanadium, tin (II) chloride, Pt(sulfide)/C, and the like; in a suitably selected organic solvent such as methanol, ethanol, THF, ethyl acetate, and the like, to yield the corresponding compound of formula (X).

The compound of formula (X) is reacted with POCl$_3$ or a suitably selected acid catalyst such as (1S)-(+)-10-camphorsulfonic acid, p-toluenesulfonic acid, acetic acid, and the like; neat or in a suitably selected organic solvent such as 1,4-dioxane, toluene, and the like; to yield the corresponding compound of formula (Ia).

Alternatively, the compound of formula (IX) is reacted with a suitably selected reducing agent such as iron powder, and the like; in the presence of a suitably selected acid catalyst such as acetic acid, p-toluenesulfonic acid, camphorsulfonic acid, and the like; neat or in a suitably selected organic solvent such as acetic acid, 1,4-dioxane, toluene, and the like; preferably at a temperature in the range of from about 80° C. to about 100° C., to yield the corresponding compound of formula (Ia).

Compounds of formula (I) wherein

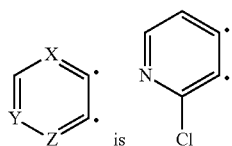

are preferably prepared by reacting a suitably substituted compound of formula (VII) wherein

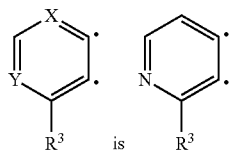

and wherein $R^3$ is hydrogen, with a mixture of $SnCl_2$ and hydrochloric acid; to reduce the nitro group to the corresponding amino group, while simultaneously replacing the $R^3$ hydrogen group with chloro, to yield the corresponding compound of formula (XI)

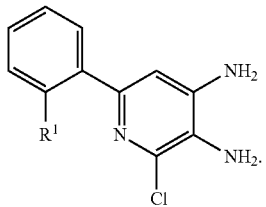

(XI)

Said compound of formula (XI) is then reacted with a suitably substituted compound of formula (VIII), as described above to yield a mixture of the corresponding compounds of formula (XI) and (XII)

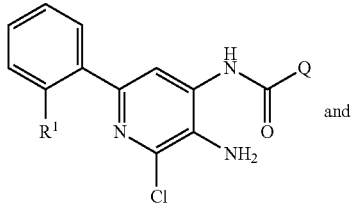

(XI) and

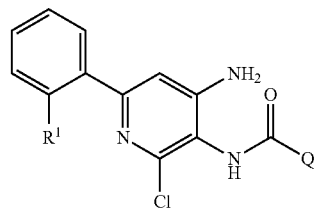

(XII)

which mixture of compounds is then reacted under ring closure conditions, as described above, to yield the corresponding desired compound of formula (I).

Compounds of formula (I) wherein is may be prepared according to the procedure as described in Scheme 2, below.

Scheme 2

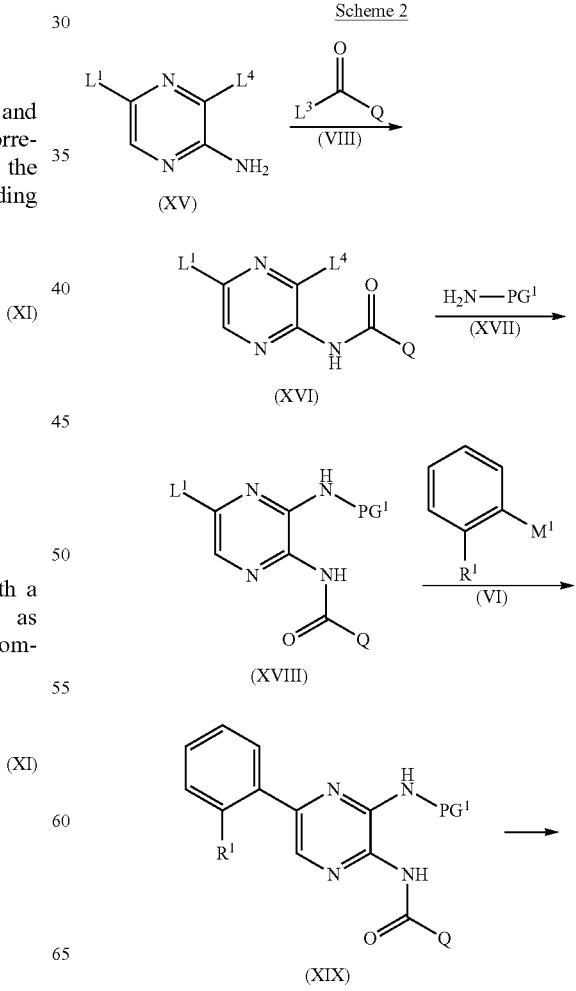

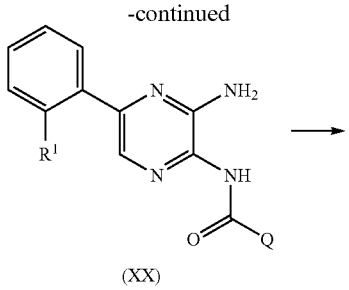

(XX)

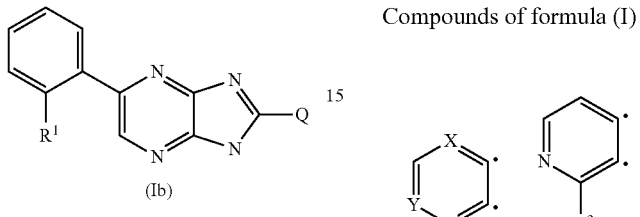

(Ib)

Accordingly, a suitably selected compound of formula (XV), wherein $L^1$ is a suitably selected leaving group such as chloro, bromo, and the like, preferably bromo, and wherein $L^4$ is a suitably selected leaving group such as chloro, bromo, and the like, preferably bromo, wherein $L^1$ and $L^4$ are preferably the same; is reacted with a suitably substituted compound of formula (VIII), wherein $L^3$ is a suitably selected leaving group such as chloro, bromo, fluoro, and the like, preferably chloro, a known compound or compound prepared by known methods; in the presence of a suitably selected inorganic base such as sodium hydride, potassium hydride, potassium tert-butoxide and the like, preferably sodium hydride, in a suitably selected organic solvent such as DMF, THF, and the like; to yield the corresponding compound of formula (XVI).

The compound of formula (XVI) is reacted with a suitably substituted compound of formula (XVII), wherein $PG^1$ is a suitably selected nitrogen protecting group such as 4-methoxybenzyl, 2,4-dimethoxybenzyl, benzyl, tert-butyl, and the like, a known compound or compound prepared by known methods, preferably 4-methoxybenzyl-amine; optionally in the presence of a base such as TEA, DIPEA, and the like; in a suitably selected organic solvent such as THF, DMF, 1,4-dioxane, and the like, preferably 1,4-dioxane; preferably at a temperature in the range of from about room temperature to about 180° C., preferably at about 65° C.; to yield the corresponding compound of formula (XVIII).

The compound of formula (XVIII) is reacted with a suitably substituted compound of formula (VI), wherein M' is a suitably selected activating group such as (a) boronic acid (—B(OH)$_2$), (b) a suitably selected boronic ester such as pinacolatoboryl, neopentylglycolatoboryl, and the like, (c) a suitably selected trialkylstannyl such as tri(n-butyl)tin, and the like, (d) a suitably selected trialkylsilyl such as triallylsilyl, and the like or (e) a suitably selected aryldialkylsilyl such as 2-(hydroxymethyl)phenyl-dimethylsilyl, and the like, a known compound or compound prepared by known methods, under suitable coupling conditions, for example, as described in more detail in Scheme 1, above; to yield the corresponding compound of formula (XIX).

The compound of formula (XIX) is de-protected according to known methods, to yield the corresponding compound of formula (XX). For example, wherein $PG^1$ is 4-methoxybenzyl, the compound of formula (XIX) may be de-protected by reacting with a suitably selected acid such as HCl, TFA, and the like; neat or in a suitably selected organic solvent such as DCE, chloroform, and the like; preferably at a temperature in the range of from about room temperature to about 150° C., preferably at about 65° C.; to yield the corresponding compound of formula (XX).

The compound of formula (XX) is reacted with POCl$_3$ or a suitably selected acid catalyst such as (1S)-(+)-10-camphorsulfonic acid, p-toluenesulfonic acid, acetic acid, and the like; neat or in a suitably selected organic solvent such as 1,4-dioxane, toluene, and the like; to yield the corresponding compound of formula (Ib).

Compounds of formula (I) wherein

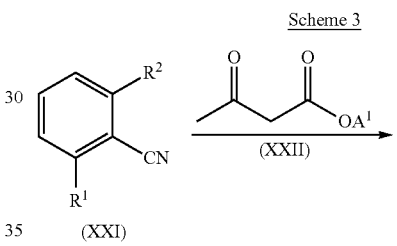

may alternatively be prepared as described in Scheme 3, below.

Scheme 3

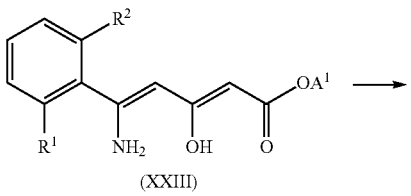

(XXI)           (XXII)

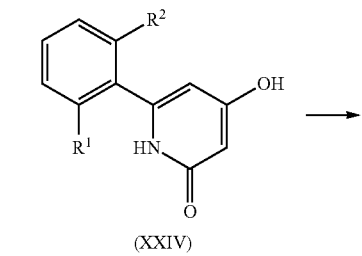

(XXIII)

(XXIV)

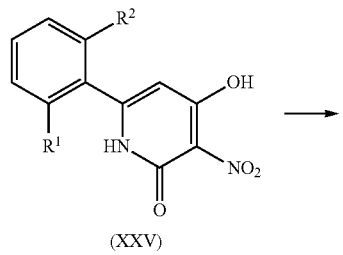

(XXV)

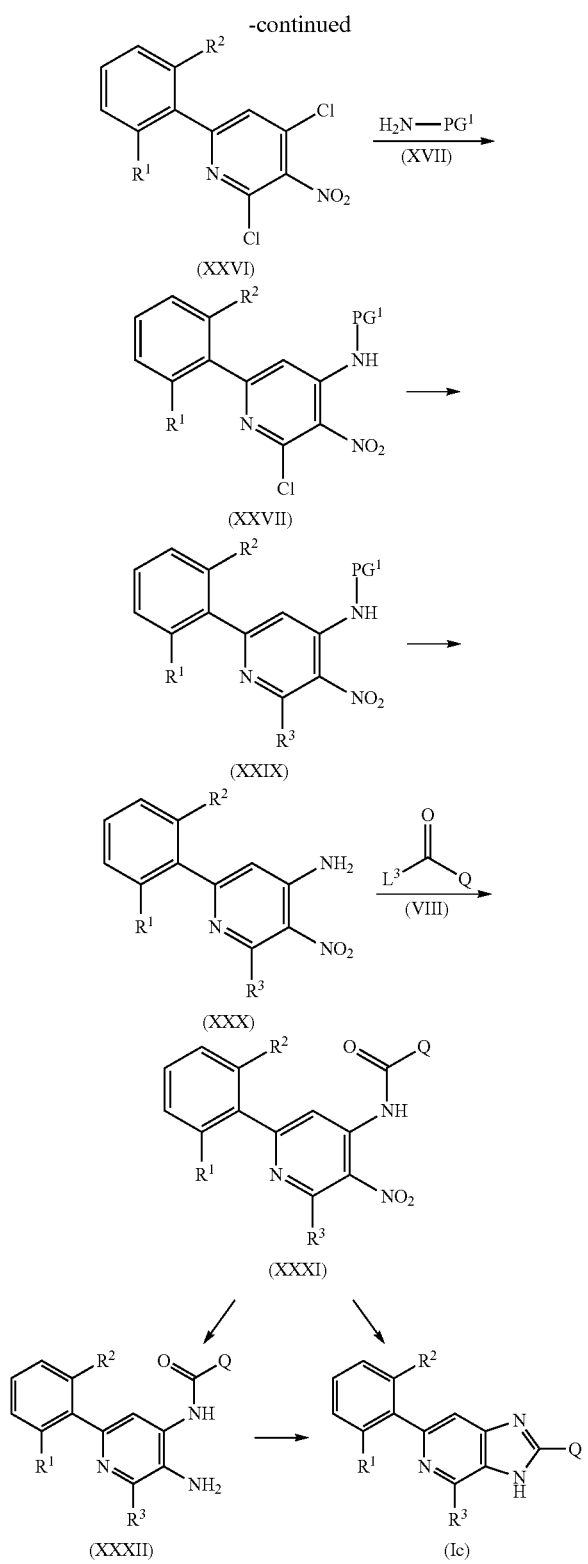

butoxide, n-butyllithium and the like; in a suitably selected organic solvent such as THF, DME, DMF, 1,4-dioxane, and the like; to yield the corresponding compound of formula (XXIII).

The compound of formula (XXIII) is cyclized according to known methods, for example by heating to a temperature in the range of from about 80° C. to about solvent reflux temperature; in a suitably selected organic solvent such as toluene, xylene, chlorobenzene, and the like, preferably toluene; to yield the corresponding compound of formula (XXIV).

The compound of formula (XXIV) is reacted with a suitably selected nitrating agent such as nitric acid, fuming nitric acid, and the like; in a suitably selected organic solvent such as acetic acid, sulfuric acid, and the like, preferably acetic acid; preferably at a temperature in the range of from about room temperature to about 80° C., more preferably at about 60° C.; to yield the corresponding compound of formula (XXV).

The compound of formula (XXV) is reacted with a suitably selected chlorinating agent such as $POCl_3$, $PCl_3$, and the like; neat or in a suitably selected organic solvent such as toluene, and the like; at a temperature in the range of from about 80° C. to about 120° C., preferably at about 100° C.; to yield the corresponding compound of formula (XXVI).

One skilled in the art will recognize that the compound of formula (XXV) may alternatively be reacted with a suitably selected brominating agent such as $POBr_3$, $PBr_3$, and the like; neat or in a suitably selected solvent such as toluene, and the like, to yield the corresponding compound of formula (XXVI) wherein the chloro group on the 4-position of the pyridine is replaced with a bromo. Said compound may then be reacted as hereinafter described, using the bromo rather than the chloro as the leaving group.

The compound of formula (XXVI) is reacted with a suitably substituted compound of formula (XVII), wherein $PG^1$ is a suitably selected nitrogen protecting group such as tert-butyl, benzyl, 4-methyoxybenzyl, and the like, a known compound or compound prepared by known methods; optionally in the presence of a base such as TEA, DIPEA and the like; in a suitably selected organic solvent such as THF, DMF, 1,4-dioxane, ethyl acetate, NMP, and the like, preferably 1,4-dioxane; preferably at a temperature in the range of from about room temperature to about 180° C., preferably at about 65° C.; to yield the corresponding compound of formula (XXVII).

One skilled in the art will recognize that the compound of formula (XXVI) may alternatively be reacted with ammonia or an ammonia equivalent such as ammonium acetate, and the like, in a suitably selected solvent such as methanol, 1,4-dioxane, NMP, THF, and the like; at a temperature in the range of from about 0° C. to about 100° C.; to yield the corresponding compound of formula (XXVII) wherein the $PG^1$ group is replaced with hydrogen.

For the preparation of compounds of formula (I) wherein $R^3$ is other than hydrogen, chloro, $C_{1-4}$alkyl or fluorinated $C_{1-4}$alkyl, the compound of formula (XXVII) wherein $R^3$ is chloro, is reacted with a suitably selected nucleophile, according to known methods, to yield the corresponding compound or formula (XXIX).

More particularly, a compound of formula (XXIX) wherein $R^3$ is $-NR^AR^B$ may be prepared by reacting a compound of formula (XXVII) wherein $R^3$ is chloro with a suitably substituted amine of the formula $NHR^AR^B$, a known compound or compound prepared by known methods; in the presence of a suitably selected base such as $K_2CO_3$, $Na_2CO_3$, and the like; in a suitably selected organic solvent such as DMF, DMA, NMP, and the like. Further, a compound of Accordingly, a suitably substituted compound of formula (XXI), a known compound or compound prepared by known methods, is reacted with a suitably substituted compound of formula (XXII), wherein $A^1$ is $C_{1-4}$alkyl or phenyl, preferably methyl or ethyl, a known compound or compound prepared by known methods; in the presence of a suitably selected base such as sodium hydride, potassium hydride, potassium tertformula (XXIX) wherein R³ is cyano may be prepared by reacting a compound of formula (XXVII) wherein R³ is chloro with, for example, NaCN, CuCN, and the like; in a suitably selected organic solvent such as DMF, NMP, and the like. Further, a compound of formula (XXIX) wherein R³ is selected from the group consisting of $C_{1-4}$alkoxy, fluorinated $C_{1-4}$alkoxy, —O—(CH₂)₂—OH, —O—(CH₂)₂—O—($C_{1-4}$alkyl), —O—CH₂-(fluorinated $C_{1-2}$alkyl) and —O—(CH₂)₂—NR^A R^B may be prepared by reacting a compound of formula (XXVII) with, for example, the corresponding R³—Na or R³—K reagent, a known compound or compound prepared by known methods, as would be readily recognized by one skilled in the art.

One skilled in the art will recognize that compounds of formula (XXIX) wherein R³ is —O—CH₂—C(O)OH may be prepared by further oxidizing the corresponding compound of formula (XXIX) wherein R³ is —O—(CH₂)₂—OH, according to known methods, to convert the —O—CH₂—CH₂—OH to the corresponding aldehyde (i.e. converting —O—CH₂—CH₂—OH to the corresponding —O—CH₂—CHO). For example, a suitably substituted compound of formula (V) wherein R³ is —O—(CH₂)₂—OH may be reacted with a suitably selected reagent such as Dess-Martin periodinane, oxalyl chloride/DMSO, and the like, according to known methods. The resulting aldehyde compound may then be further oxidized by, for example, reacting with a suitably selected reagent such as NaClO₂, and the like, in the presence of 2-methyl-2-butene, and the like; to yield the corresponding compound of formula (XXIX) wherein the aldehyde is converted to the corresponding carboxyl acid (i.e. converting the —O—(CH₂)₂—CHO group to the corresponding —O—CH₂—C(O)OH group).

The compound of formula (XXIX) (or the compound of formula (XXVII) if R³ is hydrogen) is de-protected according to known method, to yield the corresponding compound of formula (XXX). For example, wherein PG¹ is p-methoxybenzyl, the compound of formula (XXIX) may be de-protected by reacting with a suitably selected acid such as HCl, TFA, and the like; neat or in a suitably selected organic solvent such as DCE, chloroform, and the like; preferably at a temperature in the range of from about room temperature to about 150° C., preferably at about 65° C.; to yield the corresponding compound of formula (XXX).

The compound of formula (XXX) is reacted with a suitably substituted compound of formula (VIII), wherein L³ is a suitably selected leaving group such as chloro, bromo, fluoro, and the like, preferably chloro, a known compound or compound prepared by known methods; in the presence of a suitably selected inorganic base such as sodium hydride, potassium hydride, potassium tert-butoxide and the like, preferably sodium hydride, in a suitably selected organic solvent such as DMF, THF, and the like; to yield the corresponding compound of formula (XXXI).

The compound of formula (XXXI) is reacted with a suitably selected reducing agent such as hydrogen in the presence of a catalyst such as palladium on carbon, hydrogen in the presence of a catalyst such as platinum on carbon doped with vanadium, tin (II) chloride, Pt (Sulfided)/C, and the like; in a suitably selected organic solvent such as methanol, ethanol, THF, and the like, to yield the corresponding compound of formula (XXXII).

The compound of formula (XXXII) is reacted with POCl₃ or a suitably selected acid catalyst such as (1S)-(+)-10-camphorsulfonic acid, p-toluenesulfonic acid, acetic acid, and the like; neat or in a suitably selected organic solvent such as 1,4-dioxane, toluene, and the like; to yield the corresponding compound of formula (Ic).

Alternatively, the compound of formula (XXXI) is reacted with a suitably selected reducing agent such as iron powder, and the like; in the presence of a suitably selected acid catalyst such as acetic acid, p-toluenesulfonic acid, camphorsulfonic acid, and the like; neat or in a suitably selected organic solvent such as acetic acid, 1,4-dioxane, toluene, and the like; preferably at a temperature in the range of from about 80° C. to about 100° C., to yield the corresponding compound of formula (Ic).

Compounds of formula (I) wherein

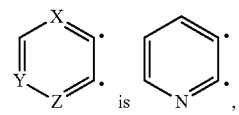

may be prepared as described in Scheme 4, below.

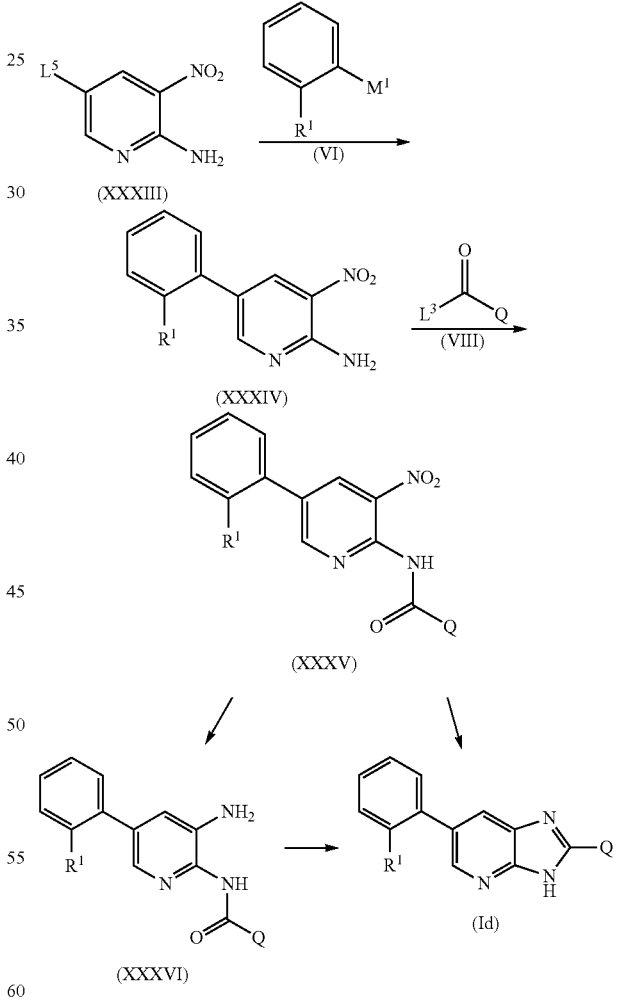

Accordingly, a suitably substituted compound of formula (XXXIII), wherein L⁵ is a suitably selected leaving group such as is a suitably selected leaving group such as chloro, bromo, triflate, and the like, a known compound or compound prepared by known methods, is reacted with a suitably substituted compound of formula (VI), wherein M¹ is a suitably selected activating group such as (a) boronic acid (—B(OH)$_2$), (b) a suitably selected boronic ester such as pinacolatoboryl, neopentylglycolatoboryl, and the like, (c) a suitably selected trialkylstannyl such as tri(n-butyl)tin, and the like, (d) a suitably selected trialkylsilyl such as triallylsilyl, and the like or (e) a suitably selected aryldialkylsilyl such as 2-(hydroxymethyl)phenyl-dimethylsilyl, and the like, a known compound or compound prepared by known methods, under suitable coupling conditions, to yield the corresponding compound of formula (XXXIV).

For example, wherein compound of formula (VI), where M$^1$ is —B(OH)$_2$ or a suitably selected boronic ester, the compound of formula (XXXIII) is reacted with the compound of formula (VI) under Suzuki coupling conditions, more particularly in the presence of a suitably selected palladium catalyst such as palladium (II) acetate, palladium (II) chloride, bis(acetonitrile)-dichloro-palladium(II), allylpalladium (II) chloride dimer, tris(dibenzylidineacetone) dipalladium (0) (Pd$_2$(dba)$_3$), 2-(di-tert-butylphosphino)biphenyl, dichloro-bis(di-tert-butylphenylphosphine)-palladium (II), [1,1'-bis-(diphenylphosphino)-ferrocene]-palladium (II) dichloride dichloromethane adduct ((dppf)PdCl$_2$.DCM), 2-(dicyclohexylphosphino)-2',4',6'-tri-i-propyl-1,1'-biphenyl, tetrakis(triphenylphosphine) palladium(0) (Pd(PPh$_3$)$_4$), (1,1'-bis(di-tert-butylphosphino)ferrocene palladium (II) chloride, and the like; optionally in the presence of a suitably selected added ligand such as triphenylphosphine, tri-o-tolylphosphine, tri(tert-butyl)-phosphine, tricyclohexylphosphine, 1,1'-bis(diphenylphosphino)-ferrocene, bis[2-(diphenyl-phosphino)phenyl]ether, 2-dicyclohexylphosphino-2',6'-dimethoxybiphenyl, tris(2-furyl)phosphine, 1-butyl-3-methylimidazolium hexafluorophosphate, and the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, aqueous sodium hydroxide, aqueous sodium bicarbonate; potassium phosphate or preferably aqueous sodium carbonate; in a suitably selected organic solvent such as ethanol, THF, DMF, toluene, benzene, DME, 1,4-dioxane, and the like; preferably at a suitable temperature in the range of from about room temperature to about 180° C.

The compound of formula (XXXIV) is reacted with a suitably substituted compound of formula (VIII), wherein L$^3$ is a suitably selected leaving group such as chloro, bromo, fluoro, and the like, preferably chloro, a known compound or compound prepared by known methods; in the presence of a suitably selected inorganic base such as sodium hydride, potassium hydride, potassium tert-butoxide, n-butyllithium, and the like, preferably sodium hydride; in a suitably selected organic solvent such as DMF, THF, and the like, to yield the corresponding compound of formula (XXXV).

The compound of formula (XXXV) is reacted with a suitably selected reducing agent such as hydrogen in the presence of a catalyst such as palladium on carbon, hydrogen in the presence of a catalyst such as platinum on carbon doped with vanadium, tin (II) chloride, Pt (Sulfided)/C, and the like; in a suitably selected organic solvent such as methanol, ethanol, THF, and the like, to yield the corresponding compound of formula (XXXVI).

The compound of formula (XXXVI) is reacted with POCl$_3$ or a suitably selected acid catalyst such as (1S)-(+)-10-camphorsulfonic acid, p-toluenesulfonic acid, acetic acid, and the like; neat or in a suitably selected organic solvent such as 1,4-dioxane, toluene, and the like; to yield the corresponding compound of formula (Id).

Alternatively, the compound of formula (XXXV) is reacted with a suitably selected reducing agent such as iron powder, and the like; in the presence of a suitably selected acid catalyst such as acetic acid, p-toluenesulfonic acid, camphorsulfonic acid, and the like; neat or in a suitably selected organic solvent such as acetic acid, 1,4-dioxane, toluene, and the like; preferably at a temperature in the range of from about 80° C. to about 100° C., to yield the corresponding compound of formula (Id).

Compounds of formula (I) wherein

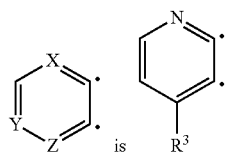

may be prepared according to the process outlined in Scheme 5, below.

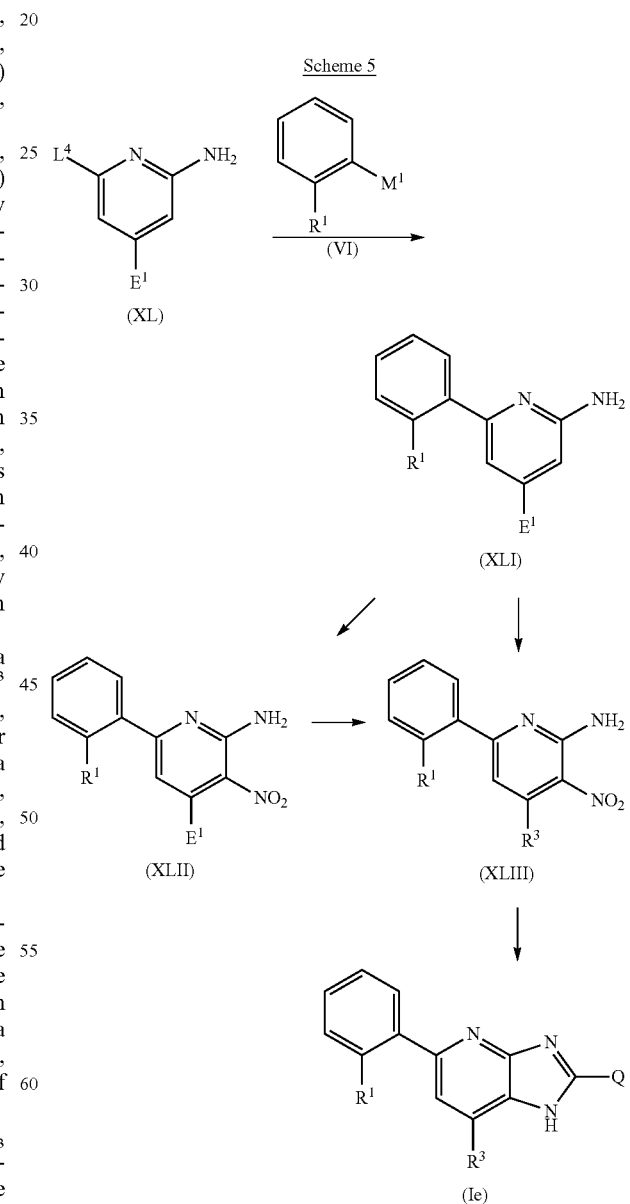

Accordingly, a suitably substituted compound of formula (XL), wherein L$^4$ is a suitably selected leaving group such as chloro, bromo, and the like, and wherein $E^1$ is selected from the group consisting of hydrogen, chloro, $C_{1-4}$alkyl and fluorinated $C_{1-4}$alkyl, a known compound or compound prepared by known methods, is reacted with a suitably substituted compound of formula (VI), wherein $M^1$ is a suitably selected activating group such as (a) boronic acid (—B(OH)$_2$), (b) a suitably selected boronic ester such as pinacolatoboryl, neopentylglycolatoboryl, and the like, (c) a suitably selected trialkylstannyl such as tri(n-butyl)tin, and the like, (d) a suitably selected trialkylsilyl such as triallylsilyl, and the like or (e) a suitably selected aryldialkylsilyl such as 2-(hydroxymethyl)phenyl-dimethylsilyl, and the like, a known compound or compound prepared by known methods, under suitable coupling conditions, to yield the corresponding compound of formula (XLI)).

For example, wherein compound of formula (VI), $M^1$ is —B(OH)$_2$ or a suitably selected boronic ester, the compound of formula (XL) is reacted with the compound of formula (VI) under Suzuki coupling conditions, more particularly in the presence of a suitably selected palladium catalyst such as palladium (II) acetate, palladium (II) chloride, bis(acetonitrile)-dichloro-palladium(II), allylpalladium (II) chloride dimer, tris(dibenzylidineacetone) dipalladium (0) (Pd$_2$(dba)$_3$), 2-(di-tert-butylphosphino)biphenyl, dichloro-bis(di-tert-butylphosphine)-palladium (II), [1,1'-bis-(diphenylphosphino)-ferrocene]-palladium (II) dichloride dichloromethane adduct ((dppf)PdCl$_2$.DCM), 2-(dicyclohexylphosphino)-2',4',6'-tri-iso-propyl-1,1'-biphenyl, tetrakis(triphenylphosphine) palladium(0) (Pd(PPh$_3$)$_4$), (1,1'-bis(di-tert-butylphosphino)ferrocene palladium(II) chloride, and the like; optionally in the presence of a suitably selected added ligand such as triphenylphosphine, tri-o-tolylphosphine, tri(tert-butyl)-phosphine, tricyclohexylphosphine, 1,1'-bis(diphenylphosphino)-ferrocene, bis[2-(diphenyl-phosphino)phenyl]ether, 2-dicyclohexylphosphino-2',6'-dimethoxybiphenyl, tris(2-furyl)phosphine, 1-butyl-3-methylimidazolium hexafluorophosphate, and the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, aqueous sodium hydroxide, aqueous sodium bicarbonate; potassium phosphate or preferably aqueous sodium carbonate; in a suitably selected organic solvent such as ethanol, THF, DMF, toluene, benzene, DME, 1,4-dioxane, and the like; preferably at a suitable temperature in the range of from about room temperature to about 180° C.

The compound of formula (XLI) is reacted with a suitably selected nitrating agent such as nitric acid, potassium nitrate, and the like; in a suitably selected organic solvent such as concentrated sulfuric acid, and the like; to yield the corresponding compound of formula (XLIII), wherein $R^3$ is the corresponding $E^1$ substituent, selected from the group consisting of hydrogen, chloro, $C_{1-4}$alkyl and fluorinated $C_{1-4}$alkyl. One skilled in the art will recognize that the compound of formula (XLI) may be reacted to yield the corresponding compound of formula (XLIII) by reacted with other known nitrating agents, according to known methods (for example, reacting with nitronium tetrafluoroborate in DCM).

Alternatively, wherein the compound of formula (XLI) $E^1$ is chloro, the compound of formula (XLI) may be reacted with a suitably selected nitrating agent such as nitric acid, potassium nitrate, and the like; in a suitably selected organic solvent such as concentrated sulfuric acid, and the like; to yield the corresponding compound of formula (XLII).

The compound of formula (XLII) is then reacted with a suitably selected nucleophile, according to known methods, to yield the corresponding compound of formula (XLIII) wherein $R^3$ is the corresponding substituent selected from the group consisting of —NR$^A$R$^B$, cyano, $C_{1-4}$alkoxy, fluorinated $C_{1-4}$alkoxy, —O—(CH$_2$)$_2$—OH, —O—(CH$_2$)$_2$—O—($C_{1-4}$alkyl), —O—CH$_2$-(fluorinated $C_{1-2}$alkyl) and —O—(CH$_2$)$_2$—NR$^A$R$^B$.

More particularly, for the preparation of a compound of formula (XLV) wherein $R^3$ is —NR$^A$R$^B$, the compound of formula (XLII) is reacted with a suitably substituted amine of the formula NHR$^A$R$^B$, a known compound or compound prepared by known methods; in the presence of a suitably selected base such as K$_2$CO$_3$, Na$_2$CO$_3$, and the like; in a suitably selected organic solvent such as DMF, DMA, NMP, and the like. For the preparation of a compound of formula (XLIII) wherein $R^3$ is cyano, the compound of formula (XLII) is reacted with for example NaCN, CuCN, and the like; in a suitably selected organic solvent such as DMF, NMP, and the like. For the preparation of a compound of formula (XLIII) wherein $R^3$ is selected from the group consisting of $C_{1-4}$alkoxy, fluorinated $C_{1-4}$alkoxy, —O—(CH$_2$)$_2$—OH, —O—(CH$_2$)$_2$—O—($C_{1-4}$alkyl), —O—CH$_2$-(fluorinated $C_{1-2}$alkyl) and —O—(CH$_2$)$_2$—NR$^A$R$^B$, the compound of formula (XLII) is reacted with, for example, the corresponding $R^3$—Na or $R^3$—K reagent, a known compound or compound prepared by known methods, as would be readily recognized by one skilled in the art.

One skilled in the art will recognize that compounds of formula (XLV) wherein $R^3$ is —O—CH$_2$—C(O)OH may be prepared by further oxidizing the corresponding compound of formula (XLV) wherein $R^3$ is —O—(CH$_2$)$_2$—OH, according to known methods, to convert the —O—CH$_2$—CH$_2$—OH to the corresponding aldehyde (i.e. converting —O—CH$_2$—CH$_2$—OH to the corresponding —O—CH$_2$—CHO). For example, a suitably substituted compound of formula (XLV) wherein $R^3$ is —O—(CH$_2$)$_2$—OH may be reacted with a suitably selected reagent such as Dess-Martin periodinane, oxalyl chloride/DMSO, and the like, according to known methods. The resulting aldehyde compound may then be further oxidized by, for example, reacting with a suitably selected reagent such as NaClO$_2$, and the like, in the presence of 2-methyl-2-butene, and the like; to yield the corresponding compound of formula (XLV) wherein the aldehyde is converted to the corresponding carboxyl acid (i.e. converting the —O—(CH$_2$)$_2$—CHO group to the corresponding —O—CH$_2$—C(O)OH group).

The compound of formula (XLIII), is then further reacted as herein described, to yield the corresponding compound of formula (Ie). More particularly, the compound of formula (XLIII) is substituted for the compound of formula (VII), and reacting as described in Scheme 1 above, to yield the corresponding compound of formula (Ie). (More particularly, the compound of formula (XLIII) is reacted with a suitably selected compound of formula (VIII) and then further reacted according to the described one-step or two-step process, to reduce the nitro group to the corresponding amine and ring-close, to yield the corresponding compound of formula (Ie).)

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, esultin, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "*Design of Prodrugs*", ed. H. Bundgaard, Elsevier, 1985.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1000 mg or any amount or range therein, and may be given at a dosage of from about 0.01 to about 300 mg/kg/day, or any amount or range therein, preferably from about 0.1 to about 50 mg/kg/day, or any amount or range therein, more preferably from about 0.1 to about 10 mg/kg/day, or any amount or range therein, more preferably from about 0.1 to about 5 mg/kg/day, or any amount or range therein. The dosages, however, may be varied depending upon the requirement of the patients, the severity of the condition being treated and the compound being employed. The use of either daily administration or postert-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating TRP M8 mediated disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably about 0.1 to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I), as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of the present invention may be administered in any of the foregoing compositions and according to dosage regimens established in the art whenever treatment of disorders mediated by TRP M8 is required.

The daily dosage of the products may be varied over a wide range from about 0.01 to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.1 to about 50.0 mg/kg of body weight per day, or any amount or range therein. More preferably, the range is from about 0.1 to about 10 mg/kg/day, or any amount or range therein. More preferably, the range is from about 0.1 to about 5 mg/kg/day, or any amount or range therein. In an embodiment, the range is from about 0.5 to about 10 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Examples A through O, which follow herein, described the synthesis of intermediates in the synthesis of compounds of formula (I).

Example A 5-tert-Butyl-2-methyl-2H-pyrazole-3-carboxylic acid

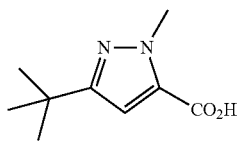

STEP A:
5-tert-Butyl-2-methyl-2H-pyrazole-3-carboxylic acid ethyl ester

Ethyl 5,5-dimethyl-2,4-dioxo-hexanoate (1.02 g, 5.09 mmol) was dissolved in absolute EtOH (20 mL). CH$_3$NHNH$_2$ (0.270 mL, 5.09 mmol) was added dropwise and the resulting mixture was stirred at room temperature for 2 h. The resulting mixture was warmed to 80° C. for 4 h, and then cooled to room temperature. The solvent was removed under reduced pressure, and the resulting residue was chromatographed using a 70-g pre-packed SiO$_2$ column eluting with 1:19 EtOAc-hexanes to yield the title compound as a colorless oil. $^1$H-NMR (400 MHz, CDCl$_3$) δ: 6.68 (s, 1H), 4.33 (q, J=7.2 Hz, 2H), 4.12 (s, 3H), 1.38 (t, J=7.1 Hz, 3H), 1.30 (s, 9H).

STEP B:
5-tert-Butyl-2-methyl-2H-pyrazole-3-carboxylic acid 5-tert-Butyl-2-methyl-2H-pyrazole-3-carboxylic acid ethyl ester (1.08 g, 5.14 mmol, prepared as described in the previous step) was dissolved in MeOH (15 mL), and H$_2$O (15 mL) and 2.5 M aqueous NaOH (5.00 mL, 12.5 mmol) was added. The resulting mixture was stirred at room temperature for 72 h, and then extracted with Et$_2$O (2×10 mL). The aqueous layer was acidified to ca. pH 2 using 3 M aqueous HCl and extracted with DCM (3×20 mL). The combined organic extracts were dried over anhydrous MgSO$_4$ and filtered, and the solvent was removed under reduced pressure to yield the title compound as a white solid. $^1$H-NMR (400 MHz, CDCl$_3$) δ: 6.80 (s, 1H), 4.15 (s, 3H), 1.32 (s, 9H).

Example B 5-tert-Butyl-4-chloro-2-methyl-2H-pyrazole-3-carboxylic acid

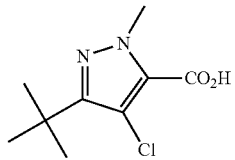

STEP A: 5-tert-Butyl-4-chloro-2-methyl-2H-pyrazole-3-carboxylic acid ethyl ester To a solution of 5-tert-butyl-2-methyl-pyrazole-3-carboxylic acid ethyl ester (2.10 g, 10.0 mmol) in 25 mL of DCM was added sulfuryl chloride (1.05 mL, 13.0 mmol) slowly under Ar. After stirring at room temperature for 3 h under Ar, the resulting mixture was treated with DCM (30 mL), washed with ice H$_2$O, saturated aqueous NaHCO$_3$ and brine, and dried with Na$_2$SO$_4$. Removal of the solvent under reduced pressure yielded the title compound as a white solid. $^1$H-NMR (400 MHz, CDCl$_3$) δ: 4.40 (q, J=7.2 Hz, 2H), 4.07 (s, 3H), 1.42 (t, J=7.2 Hz, 3H), 1.40 (s, 9H). Mass Spectrum (LCMS, ESI pos.) Calculated For C$_{11}$H$_{17}$ClN$_2$O$_2$: 245.1 (M+H). Measured: 245.1.

STEP B: 5-tert-Butyl-4-chloro-2-methyl-2H-pyrazole-3-carboxylic acid

A mixture of 5-tert-butyl-4-chloro-2-methyl-2H-pyrazole-3-carboxylic acid ethyl ester (prepared as described in the previous step, 2.20 g, 9.00 mmol) and 3 N aqueous NaOH (7.50 mL, 22.5 mmol) in MeOH (40 mL) was stirred at room temperature for 4 h. The solvent was removed under reduced pressure, and the residue was treated with H$_2$O (30 mL) and washed with Et$_2$O. The aqueous layer was then acidified to pH 7 by 2 N aqueous HCl and extracted with DCM. The combined organic layers were washed with brine and dried with Na₂SO₄. The solvent was removed in vacuo to yield the title compound as a white solid. ¹H-NMR (400 MHz, CDCl₃) δ: 10.41 (br s, 1H), 4.12 (s, 3H), 1.42 (s, 9H). Mass Spectrum (LCMS, ESI pos.) Calculated for $C_9H_{13}ClN_2O_2$: 217.1 (M+H). Measured: 217.1.

Example C 5-tert-Butyl-4-cyano-2-methyl-2H-pyrazole-3-carboxylic acid

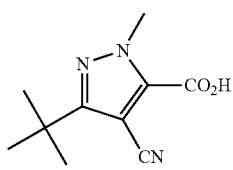

STEP A: 4-Bromo-5-tert-butyl-2-methyl-2H-pyrazole-3-carboxylic acid ethyl ester

To a mixture of 5-tert-butyl-2-methyl-2H-pyrazole-3-carboxylic acid ethyl ester (2.00 g, 9.51 mmol) and K₂CO₃ (3.94 g, 28.5 mmol) in DCM (120 mL), in the dark, was added Br₂ (1.46 mL, 28.5 mmol) slowly under Ar. After stirring at room temperature for 3 h under Ar, the resulting mixture was quenched with saturated aqueous Na₂S₂O₃ (50 mL). The organic layer was separated and washed with H₂O (50 mL) and brine (50 mL), then dried with Na₂SO₄. Removal of the solvent under reduced pressure yielded a white solid. ¹H-NMR (400 MHz, CDCl₃) δ: 4.40 (q, J=7.1 Hz, 2H), 4.08 (s, 3H), 1.43 (t, J=7.1 Hz, 3H), 1.42 (m, 9H). Mass Spectrum (LCMS, ESI pos.) Calculated For $C_{11}H_{17}BrN_2O_2$: 289.1 (M+H). Measured: 289.1.

STEP B: 5-tert-Butyl-4-cyano-2-methyl-2H-pyrazole-3-carboxylic acid ethyl ester

A mixture of 4-bromo-5-tert-butyl-2-methyl-2H-pyrazole-3-carboxylic acid ethyl ester (1.00 g, 3.46 mmol) and CuCN (372 mg, 4.15 mmol) in NMP (10 mL) was stirred at 200° C. under microwave irradiation for 1 h. After cooling to room temperature, the mixture was treated with DCM (100 mL) and filtered through diatomaceous earth. The filtrate was concentrated in vacuo, and the residue was purified by flash chromatography on silica gel (0:100-10:90 EtOAc-hexanes) to yield the title compound as a white solid. ¹H-NMR (400 MHz, CDCl₃) δ: 4.45 (q, J=7.2 Hz, 2H), 4.14 (s, 3H), 1.45 (t, J=7.2 Hz, 3H), 1.43 (s, 9H). Mass Spectrum (LCMS, ESI pos.) Calculated For $C_{12}H_{17}N_3O_2$: 236.1 (M+H). Measured: 236.1.

STEP C: 5-tert-Butyl-4-cyano-2-methyl-2H-pyrazole-3-carboxylic acid

Using the procedure for Example A, Step B above, the title compound was prepared from 5-tert-butyl-4-cyano-2-methyl-2H-pyrazole-3-carboxylic acid ethyl ester (prepared as described in the previous step, 610 mg, 2.59 mmol) and 1.0 N aqueous NaOH (4.00 mL, 4.00 mmol) in MeOH (10 mL). The title compound was obtained as a white solid. ¹H-NMR (400 MHz, CDCl₃) δ: 4.17 (s, 3H), 1.45 (s, 9H).

Example D 5-tert-Butyl-4-fluoro-2-methyl-2H-pyrazole-3-carboxylic acid

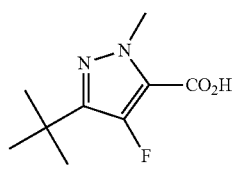

STEP A: 5-tert-Butyl-4-fluoro-2-methyl-2H-pyrazole-3-carboxylic acid ethyl ester 5-tert-Butyl-2-methyl-2H-pyrazole-3-carboxylic acid ethyl ester (210 mg, 1.00 mmol) was added dropwise to a stirred solution of SELECTFLUOR® (531 mg, 1.50 mmol) in anhydrous acetonitrile (4 mL) under an Ar atmosphere. The resulting mixture was then stirred at 80° C. for 12 h, then cooled to room temperature, diluted with EtOAc (2 mL), and filtered. The solvent was removed under reduced pressure and the resulting residue was chromatographed on a 24-g SiO₂ pre-packed column eluting with 0:1-1:4 EtOAc/hexanes to yield 5-tert-Butyl-4-fluoro-2-methyl-2H-pyrazole-3-carboxylic acid ethyl ester. ¹H-NMRH-NMR (400 MHz, CDCl₃) δ: 4.37 (q, J=7.2 Hz, 2H), 4.03 (d, J=1.0 Hz, 3H), 1.39 (t, J=7.1 Hz, 3H), 1.34 (s, 9H).

STEP B: 5-tert-Butyl-4-fluoro-2-methyl-2H-pyrazole-3-carboxylic acid 5-tert-Butyl-4-fluoro-2-methyl-2H-pyrazole-3-carboxylic acid ethyl ester (61.4 mg, 0.269 mmol, prepared as described in the previous step) was dissolved in MeOH (1 mL) then 2 M NaOH (175 µL, 0.350 mmol) was added. The resulting mixture was stirred at room temperature for 18 h and the solvent was removed under reduced pressure. The resulting residue was dissolved in H₂O (10 mL) and acidified to pH ~2 using 3 M HCl. The aqueous layer was extracted with DCM (3×5 mL), the combined organic extracts were dried over MgSO₄ and filtered. The solvent was removed under reduced pressure to yield 5-tert-Butyl-4-fluoro-2-methyl-2H-pyrazole-3-carboxylic acid. ¹H-NMRH-NMR (400 MHz, CDCl₃) δ: 9.89 (br. s., 1H), 4.06 (d, J=1.0 Hz, 3H), 1.36 (s, 9H).

Example E 5-tert-Butyl-4-methoxy-2-methyl-2H-pyrazole-3-carboxylic acid

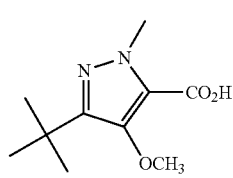

STEP A: 5-tert-Butyl-4-methoxy-2-methyl-2H-pyrazole-3-carboxylic acid ethyl ester

[Bis(trifluoroacetoxy)iodo]benzene (430 mg, 1.00 mmol) was dissolved in anhydrous MeOH (4 mL), the resulting solution was stirred at room temperature for 3 min. $BF_3 \cdot OEt_2$ (0.123 mL, 1.00 mmol) was then added via syringe. Ethyl trimethylacetopyruvate (200 mg, 1.00 mmol) was added dropwise via syringe and the resulting mixture was stirred at room temperature for 12 h. The solvent was removed under reduced pressure and the resulting residue was dissolved in dry EtOH (2 mL). $CH_3NHNH_2$ (52.6 µL, 1.00 mmol) was added via syringe and the resulting mixture was stirred at 80° C. for 8 h. The solvent was removed under reduced pressure and the resulting residue was chromatographed on a 24-g $SiO_2$ pre-packed column eluting with 0:1-3:7 EtOAc/hexanes to yield 5-tert-butyl-4-methoxy-2-methyl-2H-pyrazole-3-carboxylic acid ethyl ester. $^1$H-NMR (400 MHz, $CDCl_3$) δ: 4.39 (q, J=7.1 Hz, 2H), 4.03 (s, 3H), 3.83 (s, 3H), 1.42 (t, J=7.2 Hz, 3H), 1.34 (s, 9H).

STEP B: 5-tert-Butyl-4-methoxy-2-methyl-2H-pyrazole-3-carboxylic acid 5-tert-Butyl-4-methoxy-2-methyl-2H-pyrazole-3-carboxylic acid ethyl ester (52.8 mg, 0.220 mmol, prepared as described in the previous step) was dissolved in MeOH (1 mL) then 2 M NaOH (143 µL, 0.286 mmol) was added. The resulting mixture was stirred at room temperature for 18 h and the solvent was removed under reduced pressure. The residue was dissolved in $H_2O$ (10 mL) and acidified to pH ~2 using 3 M HCl. The aqueous layer was extracted with EtOAc (3×5 mL) and the combined organic extracts were dried over $MgSO_4$ and filtered. The solvent was removed under reduced pressure to yield 5-tert-butyl-4-methoxy-2-methyl-2H-pyrazole-3-carboxylic acid. $^1$H-NMR (400 MHz, $CDCl_3$) δ: 11.65 (br. s., 1H), 4.08 (s, 3H), 3.89 (s, 3H), 1.37 (s, 9H).

NOTE: Later use of this material led to the conclusion that this product was contaminated by a small amount of 5-tert-butyl-2-methyl-2H-pyrazole-3-carboxylic acid. It was suspected to be the result of the presence of a small amount of 5-tert-butyl-2-methyl-2H-pyrazole-3-carboxylic acid ethyl ester from the previous Step A but none of the material was available after use to confirm this suspicion.

Example F

4-Chloro-5-(2-fluoro-1,1-dimethyl-ethyl)-2-methyl-2H-pyrazole-3-carboxylic acid

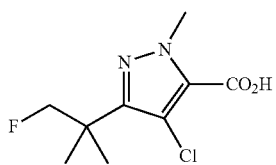

STEP A: 5-(2-fluoro-1,1-dimethyl-ethyl)-2-methyl-2H-pyrazole-3-carboxylic acid ethyl ester NaOEt (3.15 mL of a 21-wt % solution in EtOH, 8.43 mmol) was dissolved in anhydrous toluene (10 mL) and $(CO_2CH_2CH_3)_2$ (0.881 mL, 6.49 mmol) was added. 4,4,4-Trifluoro-3,3-dimethyl-2-butanone (1.00 g, 6.49 mmol) was added and the resulting mixture was stirred at room temperature for 24 h. The resulting mixture was then acidified to pH ~5 using 3 M aqueous HCl and the aqueous phase was extracted with EtOAc (3×40 mL). The combined extracts were dried over $MgSO_4$ and filtered. The solvent was removed under reduced pressure.

The resulting residue was dissolved in absolute EtOH (20 mL) and $CH_3NHNH_2$ (0.342 mL, 6.49 mmol) was added dropwise via syringe to the stirred mixture. The resulting mixture was heated to 80° C. for 16 h, and then cooled to room temperature. The solvent was removed under reduced pressure and the resulting residue was chromatographed using a 70-g $SiO_2$ pre-packed column eluting with 0:1-1:4 EtOAc/hexanes to yield 5-(2-fluoro-1,1-dimethyl-ethyl)-2-methyl-2H-pyrazole-3-carboxylic acid ethyl ester. $^1$H-NMR (400 MHz, $CDCl_3$) δ: 6.74 (s, 1H), 4.38 (d, J=48 Hz, 2H), 4.33 (q, J=7.1 Hz, 2H), 4.13 (s, 3H), 1.38 (t, J=7.1 Hz, 3H), 1.34 (d, J=1.7 Hz, 6H). $^{19}$F NMR (376 MHz, $^1$H-coupled, $CDCl_3$) δ: −221 (t, J=48 Hz, 1F).

NOTE: The $^1$H-NMR spectra of the product indicated the presence of only 1 fluorine, therefore it is believed that the purchased starting ketone was incorrect, and was actually 4-fluoro-3,3-dimethyl-2-butanone, however none of the starting material was available to confirm this suspicion.

STEP B: 4-Chloro-5-(2-fluoro-1,1-dimethyl-ethyl)-2-methyl-2H-pyrazole-3-carboxylic acid ethyl ester 5-(2-fluoro-1,1-dimethyl-ethyl)-2-methyl-2H-pyrazole-3-carboxylic acid ethyl ester (722 mg, 3.16 mmol, prepared as described in the previous step) was dissolved in DCM (5 mL) and $SO_2Cl_2$ (0.256 mL, 3.16 mmol) was added dropwise to the stirred solution. The resulting mixture was stirred at room temperature for 16 h and then the solvent was removed under reduced pressure. The resulting residue was chromatographed on a 40-g $SiO_2$ pre-packed column eluting with 0:1-1:4 EtOAc/heptane to yield 4-chloro-5-(2-fluoro-1,1-dimethyl-ethyl)-2-methyl-2H-pyrazole-3-carboxylic acid ethyl ester. $^1$H-NMR (400 MHz, $CDCl_3$) δ: 4.59 (d, J=47 Hz, 2H), 4.40 (q, J=7.1 Hz, 2H), 4.08 (s, 3H), 1.43 (d, J=1.7 Hz, 6H), 1.41 (t, J=7.2 Hz, 3H).

STEP C: 4-Chloro-5-(2-fluoro-1,1-dimethyl-ethyl)-2-methyl-2H-pyrazole-3-carboxylic acid 4-Chloro-5-(2-fluoro-1,1-dimethyl-ethyl)-2-methyl-2H-pyrazole-3-carboxylic acid ethyl ester (738 mg, 2.81 mmol, prepared as described in the previous step) was dissolved in MeOH (3 mL) and 2 M NaOH (1.83 mL, 3.65 mmol) was added. The resulting mixture was stirred at room temperature for 18 h and then the solvent was removed under reduced pressure. The resulting residue was dissolved in $H_2O$ (10 mL) and then acidified to pH ~2 with concentrated HCl. The product oiled out of solution and solidified on standing. The solid was isolated by filtration, washed with $H_2O$ (2×20 mL), and dried under high vacuum to yield 4-Chloro-5-(2-fluoro-1,1-dimethyl-ethyl)-2-methyl-2H-pyrazole-3-carboxylic acid. $^1$H-NMR (400 MHz, DMSO-$d_6$) δ: 13.89 (br. s., 1H), 4.56 (d, J=48 Hz, 2H), 4.00 (s, 3H), 1.35 (d, J=1.2 Hz, 6H).

Example G

1-tert-Butyl-5-methyl-1H-pyrazole-4-carboxylic acid

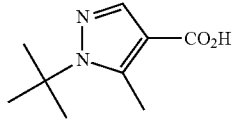

The title compound was prepared according to the procedure as described in Anderson, K. W., et al., PCT Publication, WO 2007/107470, published Sep. 27, 2007, as described in Example 54, Steps 2 and 3, pages 97-98, and substituting triethylamine for the sodium acetate reagent in Step 2) from methyl acetoacetate (1.14 mL, 10.6 mmol), DMFDMA (1.48 mL, 11.1 mmol), tert-butylhydrazine hydrochloride (1.32 g, 10.6 mmol), and TEA (4.43 mL, 31.8 mmol) to yield methyl 1-tert-butyl-5-methyl-1H-pyrazole-4-carboxylate after chromatography using a 80-g SiO$_2$ pre-packed column eluting with 0:1-3:7 EtOAc/heptane. Said product was used directly in the next step without further purification. $^1$H-NMR (400 MHz, CDCl$_3$) δ: 7.78 (s, 1H), 3.80 (s, 3H), 2.75 (s, 3H), 1.66 (s, 9H).

A solution of methyl 1-tert-butyl-5-methyl-1H-pyrazole-4-carboxylate in MeOH (20 mL) was treated with 2 M aqueous NaOH solution (7.95 mL, 15.9 mmol) for 48 h at room temperature. The solvent was removed under reduced pressure and the resulting residue was dissolved in H$_2$O (20 mL). The resulting solution was then acidified to pH-2 using 2 M HCl. The resulting precipitate was isolated by filtration, washed once with H$_2$O (20 mL), and the solid was dried under high vacuum to yield 1-tert-Butyl-5-methyl-1H-pyrazole-4-carboxylic acid. $^1$H-NMR (400 MHz, d$_6$-DMSO) δ: 12.16 (br. s., 1H), 7.67 (s, 1H), 2.69 (s, 3H), 1.59 (s, 9H).

Example H

2-Methyl-6,6-spirocyclohexyl-2,4,5,6-tetrahydro-cyclopentapyrazole-3-carboxylic acid

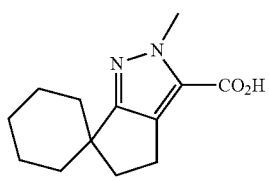 [SMILES: Cn1nc2c(c1C(=O)O)CCC21CCCCC1]

STEP A: 2-Methyl-2H-6,6-spirocyclohexyl-2,4,5,6-tetrahydro-cyclopentapyrazole-3-carboxylic acid ethyl ester To a solution of NaOEt in EtOH (2.5 mL, 6.5 mmol, 21% in EtOH) at −10° C., a mixture of spiro[4.5]decan-1-one (432 mg, 2.83 mmol, prepared as described in Molander, G. A., et al., *J. Org. Chem.*, 1993, Vol. 58, 7216-7227, according to the general procedure described on page 7225) and diethyloxalate (0.85 mL, 6.2 mmol) in EtOH (5 mL) was added. After 15 min the resulting mixture was allowed to warm to room temperature and then stirred for 6 h. The resulting mixture was treated with 1 N aqueous HCl (10 mL), and the product was extracted thrice with 20 mL of DCM. The organic layers were combined, dried (Na$_2$SO$_4$), and concentrated. The residue obtained was dissolved in EtOH (10 mL) and HOAc (2 mL). To this mixture was added, dropwise, anhydrous hydrazine (0.46 mL, 14 mmol). The resulting mixture was stirred at room temperature overnight. Water (20 mL) was added, and the product was extracted twice with 20 mL of EtOAc. The organic layers were combined, dried (Na$_2$SO$_4$), and concentrated. The residue obtained was purified on silica (0:100-100:0 v/v EtOAc-hexanes) to yield 6,6-spirocyclohexyl-2,4,5,6-tetrahydro-cyclopentapyrazole-3-carboxylic acid ethyl ester as a viscous oil. $^1$H-NMR (400 MHz, CDCl$_3$) δ: 4.34 (q, J=7.2 Hz, 2H), 2.72-2.79 (m, 2H), 2.22-2.29 (m, 2H), 1.40-1.80 (m, 13H), 1.35 (t, J=7.2 Hz, 3H).

To a solution of 6,6-spirocyclohexyl-2,4,5,6-tetrahydro-cyclopentapyrazole-3-carboxylic acid ethyl ester (185 mg, 0.747 mmol, as prepared above) in DMF (10 mL) was added K$_2$CO$_3$ (206 mg, 1.49 mmol). The resulting mixture was stirred for 10 min and then treated with CH$_3$I (0.046 mL, 1.49 mmol). The resulting mixture was stirred overnight and then poured into water (10 mL). The product was extracted thrice with EtOAc (20 mL). The organic layers were combined, dried (Na$_2$SO$_4$), and concentrated. The residue obtained was purified on silica gel (0:100-100:0 EtOAc-hexanes) to yield the title compound. $^1$H-NMR (400 MHz; CDCl$_3$) δ: 4.22 (q, J=7.1 Hz, 2H), 4.05 (s, 3H), 2.66 (t, J=7.1 Hz, 2H), 2.12-2.17 (m, 2H), 1.59-1.72 (m, 4H), 1.36-1.48 (m, 6H), 1.27 (t, J=7.1 Hz, 3H).

STEP B: 2-Methyl-2H-6,6-spirocyclohexyl-2,4,5,6-tetrahydro-cyclopentapyrazole-3-carboxylic acid To a solution of 2-methyl-2H-6,6-spirocyclohexyl-2,4,5,6-tetrahydro-cyclopentapyrazole-3-carboxylic acid ethyl ester (prepared as described in the previous step, 124 mg, 0.472 mmol) in MeOH (6 mL) was added LiOH (56.5 mg, 2.36 mmol) followed by water (2 mL). The resulting mixture was stirred at reflux overnight. The resulting mixture was then allowed to cool to room temperature, and MeOH was removed in vacuo. The resulting mixture was acidified with 1 N aqueous HCl, and the product was extracted thrice with DCM (30 mL). The combined organic layers were dried (Na$_2$SO$_4$) and concentrated to yield the title compound as a white solid. $^1$H-NMR (400 MHz, CDCl$_3$) δ: 10.77 (br s, 1H), 4.17 (s, 3H), 2.81 (t, J=7.1 Hz, 2H), 2.13-2.35 (m, 2H), 1.64-1.83 (m, 4H), 1.39-1.62 (m, 6H).

Example I

3-tert-Butylisoxazole-5-carboxylic acid

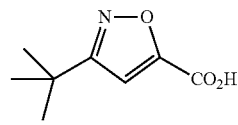

STEP A: 3-tert-Butylisoxazole-5-carboxylic acid methyl ester

Pivaldehyde (1.10 mL, 10.0 mmol) was dissolved in dry DMF (10 mL), and NH$_2$OH.H$_2$O (0.590 mL of 55 wt % aqueous solution, 10.5 mmol) was added via syringe. The resulting mixture was stirred at room temperature for 4 h, NCS (1.40 g, 10.5 mmol) was added in small portions, and the resulting mixture was stirred at room temperature for 1 h. CuSO$_4$.5H$_2$O (75.0 mg, 0.300 mmol), methyl propiolate (1.07 mL, 12.0 mmol), and H$_2$O (5 mL) were added followed by Cu powder (25.0 mg, 0.393 mmol). The resulting mixture was stirred at room temperature for 16 h and quenched with dilute aqueous NH$_4$OH (2 mL). The aqueous solution was extracted with hexanes (3×30 mL), and then the combined organic extracts were dried over MgSO$_4$ and filtered. The solvent was removed under reduced pressure to yield the title compound as a colorless oil. $^1$H-NMR (400 MHz, CDCl$_3$) δ: 6.88 (s, 1H), 3.96 (s, 3H), 1.36 (s, 9H).

STEP B: 3-tert-Butylisoxazole-5-carboxylic acid

Following the procedure described in Example A, STEP B above, the title compound was prepared from 3-tert-butyl-isoxazole-5-carboxylic acid methyl ester (1.68 g, 9.19 mmol, prepared as described in the previous step) and 2.5 M aqueous NaOH (5.00 mL, 12.5 mmol) as a white solid. $^1$H-NMR (400 MHz, CDCl$_3$) δ: 6.99 (s, 1H), 1.38 (s, 9H).

Example J 3-tert-Butyl-4-cyano-isoxazole-5-carboxylic acid

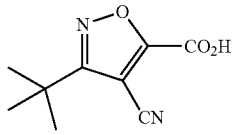

STEP A: 3-tert-Butyl-4-cyano-4,5-dihydro-isoxazole-5-carboxylic acid ethyl ester Pivaldehyde (1.63 mL, 15.0 mmol) was dissolved in anhydrous DMF (15 mL) and H$_2$NOH.xH$_2$O (0.860 mL of a 55% aqueous solution, 15.4 mmol) was added via syringe. The resulting mixture was stirred at room temperature for 1 h and NCS (2.06 g, 15.4 mmol) was added as a solid. The resulting mixture was stirred at room temperature for 1 h and DCM (50 mL) was added. The resulting solution was placed in a dropping funnel and added dropwise over 4 h to a stirred DCM (40 mL) solution of ethyl cis-beta-cyanoacrylate (1.98 mL, 16.5 mmol) and TEA (4.18 mL, 30.0 mmol). After completion of addition, the resulting mixture was stirred for 8 h at room temperature and then concentrated under reduced pressure. The resulting residue was dissolved in DCM (50 mL), washed with H$_2$O (3×30 mL) and brine (30 mL), and dried over anhydrous MgSO$_4$ and filtered. The solvent was removed under reduced pressure. The resulting residue was chromatographed on a 40-g SiO$_2$ pre-packed column eluting with 0:1-3:7 EtOAc/hexanes to yield a mixture (~1:1.6 as measured by $^1$H-NMR) of 3-tert-Butyl-4-cyano-4,5-dihydro-isoxazole-5-carboxylic acid ethyl ester contaminated with ethyl cis-beta-cyanoacrylate. $^1$H-NMR (400 MHz, CDCl$_3$) δ: 5.22 (d, J=5.1 Hz, 1H), 4.55 (d, J=5.1 Hz, 1H), 4.25-4.32 (m, 2H), 1.35 (s, 9H), 1.31-1.36 (t, J=7.1 Hz, 3H).

STEP B: 3-tert-Butyl-4-cyano-isoxazole-5-carboxylic acid ethyl ester 3-tert-Butyl-4-cyano-4,5-dihydro-isoxazole-5-carboxylic acid ethyl ester (1.51 g, 2.56 mmol corrected for the measured purity, prepared as described in the previous step) was dissolved in toluene (10 mL) and DDQ (2.41 g, 10.6 mmol) was added as a solid. The resulting mixture was heated to 110° C. for 16 h and then cooled to room temperature and diluted with hexanes (2 mL). The resulting suspension was filtered and the precipitate was washed once with toluene (4 mL). The filtrates were combined and concentrated under reduced pressure. The resulting residue was chromatographed on a 24-g SiO$_2$ pre-packed column eluting with 0:1-1:4 EtOAc-hexanes to yield 3-tert-butyl-4-cyano-isoxazole-5-carboxylic acid ethyl ester. $^1$H-NMR (400 MHz, CDCl$_3$) δ: 4.52 (q, J=7.1 Hz, 2H), 1.49 (s, 9H), 1.43-1.48 (t, J=7.1 Hz, 3H).

STEP C:
3-tert-Butyl-4-cyano-isoxazole-5-carboxylic acid 3-tert-Butyl-4-cyano-isoxazole-5-carboxylic acid ethyl ester (809 mg, 3.64 mmol, prepared as described in the previous step) was dissolved in MeOH (9 mL) and 1 M LiOH (4.73 mL, 4.73 mmol) was added. The resulting mixture was stirred at room temperature for 3 h and the solvent was removed under reduced pressure. The resulting residue was dissolved in H$_2$O (10 mL) and extracted with DCM (3×10 mL). The aqueous layer was acidified to pH ~2 using 3 M HCl and extracted with EtOAc (3×20 mL). The combined extracts were dried over MgSO$_4$ and filtered. The solvent was removed under reduced pressure to yield 3-tert-butyl-4-cyano-isoxazole-5-carboxylic acid. $^1$H-NMR (400 MHz, CDCl$_3$) δ: 9.90 (br. s., 1H), 1.50 (s, 9H).

Example K 5-bromo-4-tert-butyl-furan-2-carboxylic acid

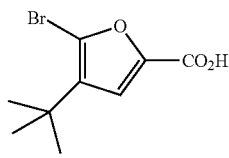

STEP A: Methyl
5-bromo-4-tert-butyl-furan-2-carboxylate

The compound was prepared according to the procedure as described in Gilman, H., et al., J. Am. Chem. Soc., 1939, Vol. 61, pp 473-478, more particular according the general procedure on page 467-477) from methyl 5-bromofuran-2-carboxylate (5.00 g, 24.4 mmol), 1-bromooctadecane (8.13 g, 24.4 mmol), and anhydrous AlCl$_3$ (6.50 g, 48.8 mmol) in CS$_2$ (50 mL) to yield methyl 5-bromo-4-tert-butyl-furan-2-carboxylate. $^1$H-NMR (400 MHz, CDCl$_3$) δ: 7.12 (s, 1H), 3.88 (s, 3H), 1.33 (s, 9H).

STEP B: 5-Bromo-4-tert-butyl-furan-2-carboxylic acid

A solution of methyl 5-bromo-4-tert-butyl-furan-2-carboxylate (1.45 g, 5.57 mmol, prepared as described in the previous step) in a mixture of THF (15 mL), MeOH (10 mL), and H$_2$O (5 mL) was treated with 3 M aqueous NaOH solution (3.00 mL, 9.00 mmol) and the resulting mixture was stirred at room temperature for 16 h. The solvent was removed under reduced pressure and the residue was dissolved in H$_2$O (60 mL) and extracted with Et$_2$O (2×30 mL). The aqueous layer was acidified to pH-2 using 2 M HCl. The precipitate was isolated by filtration, washed with H$_2$O (20 mL), and air-dried to yield 5-bromo-4-tert-butyl-furan-2-carboxylic acid. The filtrate was extracted with EtOAc (3×20 mL) and the combined extracts were dried over MgSO$_4$ and filtered. The solvent was removed under reduced pressure to yield a second crop of 5-bromo-4-tert-butyl-furan-2-carboxylic acid. $^1$H-NMR (400 MHz, CDCl$_3$) δ: 7.25 (s, 1H), 1.35 (s, 9H).

Example L 4-tert-butyl-furan-2-carboxylic acid

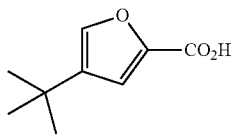

The title compound was prepared according to the procedure as described in Gilman, H., et al., *J. Am. Chem. Soc.*, 1935, Vol. 57, pp 909-912, more particularly, as described on page 910) by treating a dilute aqueous NH$_3$ solution (made by dilution of 1 mL of 29.3% aqueous NH$_3$ with 9 mL of H$_2$O) of 5-bromo-4-tert-butyl-furan-2-carboxylic acid (500 mg, 2.02 mmol, prepared as described in Example K, Step B) with Zn dust (265 mg, 4.05 mmol) to yield the title compound. $^1$H-NMR (400 MHz, CDCl$_3$) δ: 7.40 (d, J=1.0 Hz, 1H), 7.28 (d, J=1.2 Hz, 1H), 1.26 (s, 9H).

Example M 5-isopropylthiophene-3-carboxylic acid

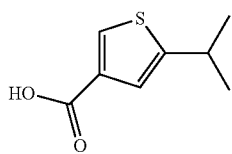

The title compound was prepared by modifying the procedure as described in Stanetty, et al., *Monatshefte für Chemie* (1989), 120(1), 65-72, for the synthesis of compounds (21) and (22), page 70, and substituting pentyl nitrite with tert-butyl nitrite.

Example N

4-Isopropyl-thiophene-2-carboxylic acid

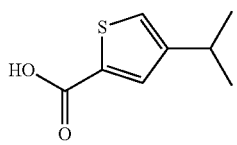

The title compound was prepared according to the procedure described in Alcaraz, L., et al., PCT Publication WO 2009/098448 A1, published Aug. 13, 2009, Example 74, Steps (a) and (b), pages 282-283.

Example O 4-tert-butyl-1-methyl-1H-imidazole-2-carboxylic acid

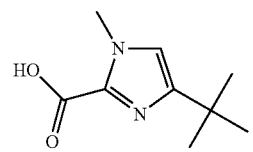

STEP A: 3,3-Dimethyl-1-methylamino-butan-2-one hydrochloride

A solution of 1-bromopinacolone (5.00 g, 27.9 mmol) in acetonitrile (8 mL) was added to a solution of methylamine (6.98 mL, 55.9 mmol, ~8 M in absolute alcohol) at 0° C. over 5 min under Ar. The resulting mixture was stirred at 0° C. for 3 h. Dry diethyl ether (200 mL) was added and the resulting white solid was removed by filtration. The filtrate was concentrated in vacuo and the residue was treated with ethanol (20 mL). To the resulting solution at 0° C. was added 1.0 N HCl in diethyl ether (22.3 mL) over 10 min. The resulting mixture was treated with diethyl ether (150 mL) and the resulting white solid was collected by filtration and dried in vacuo to yield 3,3-dimethyl-1-methylamino-butan-2-one hydrochloride as a white solid. $^1$H-NMR (400 MHz, CD$_3$OD) δ: 4.28 (s, 2H), 2.72 (s, 3H), 1.21 (s, 9H). Mass Spectrum (LCMS, ESI pos.) Calculated For C$_7$H$_{15}$NO: 130.1 (M+H). Measured: 130.1.

STEP B: 4-tert-Butyl-1-methyl-1H-imidazole

A mixture of 3,3-dimethyl-1-methylamino-butan-2-one hydrochloride (1.00 g, 6.04 mmol, prepared as described in the previous step) in formamide (12 mL, 302 mmol) was stirred at 200° C. for 3 h under microwave irradiation. After cooling to room temperature, the resulting mixture was treated with 3N NaOH (30 mL) and extracted with toluene (3×50 mL). The combined organic layers were washed with H$_2$O (30 mL), brine (30 mL) and then dried with Na$_2$SO$_4$. The solvent was evaporated in vacuo and the residue was purified by flash chromatography on silica gel (0:100-10:90 MeOH/DCM) to yield 4-tert-butyl-1-methyl-1H-imidazole as a colorless oil. $^1$H-NMR (400 MHz, CDCl$_3$) δ: 7.32 (s, 1H), 6.55 (s, 1H), 3.59 (s, 3H), 1.25 (s, 9H). Mass Spectrum (LCMS, ESI pos.) Calculated For C$_8$H$_{14}$N$_2$: 139.1 (M+H). Measured: 139.1.

STEP C: 4-tert-Butyl-1-methyl-1H-imidazole-2-carboxylic acid methyl ester

To a mixture of 4-tert-butyl-1-methyl-1H-imidazole (800 mg, 5.79 mmol, prepared as described in the previous step) and triethylamine (2.00 mL, 14.4 mmol) in acetonitrile (10 mL) at −30° C. was added methyl chloroformate (0.890 mL, 11.6 mmol) slowly under Ar. The resulting mixture was warmed to room temperature and continued to stir for 16 h. The resulting mixture was then treated with EtOAc (50 mL)

and washed with H₂O (2×20 mL), brine (20 mL) and then dried with Na₂SO₄. The solvent was evaporated in vacuo and the residue was purified by flash chromatography on silica gel (0:100-10:90 MeOH/DCM) to yield 4-tert-butyl-1-methyl-1H-imidazole-2-carboxylic acid methyl ester as a colorless oil. ¹H-NMR (400 MHz, CDCl₃) δ: 6.78 (s, 1H), 3.95 (s, 3H), 3.92 (s, 3H), 1.30 (s, 9H). Mass Spectrum (LCMS, ESI pos.) Calculated For $C_{10}H_{16}N_2O_2$: 197.1 (M+H). Measured: 197.1.

STEP D:
4-tert-butyl-1-methyl-1H-imidazole-2-carboxylic acid

A mixture of 4-tert-butyl-1-methyl-1H-imidazole-2-carboxylic acid methyl ester (680 mg, 3.46 mmol, prepared as described in the previous step) and 1N NaOH (3.81 mL, 3.81 mmol) in MeOH (10 mL) was stirred at room temperature for 2 h. To the resulting mixture was then added 1.0 N aqueous HCl (3.85 mL). The solvent was removed under reduced pressure and the residue was treated with DCM (50 mL). The solid was filtered off through diatomaceous earth and washed with DCM. The combined organic layers were dried with Na₂SO₄ and concentrated in vacuo to yield 4-tert-butyl-1-methyl-1H-imidazole-2-carboxylic acid as a white solid. ¹H-NMR (400 MHz, CDCl₃) δ: 7.00 (s, 1H), 4.18 (s, 3H), 1.49 (s, 9H). Mass Spectrum (LCMS, ESI pos.) Calculated For $C_9H_{14}N_2O_2$: 183.1 (M+H). Measured: 183.1.

Examples 1 through 35 which follow herein, described the synthesis of representative compounds of formula (I).

Example 1

2-(5-tert-Butyl-4-chloro-2-methyl-2H-pyrazol-3-yl)-7-chloro-5-(2-trifluoromethyl-phenyl-1H-imidazo[4,5-b]pyridine sodium salt (Compound #5)

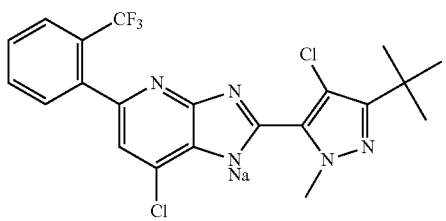

STEP A: 4-Chloro-6-(2-trifluoromethyl-phenyl)-pyridin-2-ylamine

A solution of 4,6-dichloro-pyridin-2-ylamine (1.00 g, 6.14 mmol) in DME (75 mL) and water (50 mL) was treated with Cs₂CO₃ (6.00 g, 18.4 mmol) and 2-(trifluoromethyl)phenylboronic acid (1.52 g, 7.98 mmol). The resulting mixture was degassed by heating under a stream of Ar. Cl₂Pd(dppf).DCM (270 mg, 0.368 mmol) was added, and the mixture was heated to 80° C. for 24 h. The cooled mixture was diluted with EtOAc (70 mL) and washed twice with water (50 mL). The combined aqueous layers were extracted twice with EtOAc (50 mL). The combined organic extracts were dried over MgSO₄ and concentrated in vacuo. The residue was purified on a 115-g SEPRA Si 35 SPE silica column (Flow rate=30 mL/min; Eluent=EtOAc-hexanes, 1:19 for 15 min, 1:19 to 1:3 over 40 min, then 1:3 until product eluted) to yield 4-chloro-6-(2-trifluoromethyl-phenyl)-pyridin-2-ylamine as an off-white solid. ¹H-NMR (400 MHz, CDCl₃) δ: 7.74 (d, J=7.6 Hz, 1H), 7.59 (t, J=7.5 Hz, 1H), 7.50 (t, J=7.7 Hz, 1H), 7.45 (d, J=7.6 Hz, 1H), 6.77 (d, J=1.5 Hz, 1H), 6.53 (d, J=1.5 Hz, 1H), 4.59 (br. s., 2H). Mass Spectrum (LCMS, ESI pos.): Calculated for $C_{12}H_8N_2ClF_3$: 273.0 (M+H). Measured: 273.0.

STEP B: 4-Chloro-3-nitro-6-(2-trifluoromethyl-phenyl)-pyridin-2-ylamine

4-Chloro-6-(2-trifluoromethyl-phenyl)-pyridin-2-ylamine (617.5 mg, 2.27 mmol, prepared as described in STEP A above) was cooled to 0° C. and treated slowly with H₂SO₄ (10 mL). The mixture was stirred at 0° C. for 1 h. Nitric acid (133 μL, 2.94 mmol) was added slowly, and the mixture continued to stir at 0° C. for an additional 1.5 h. Ice (50 mL) was added. A precipitate formed and was filtered, dissolved in DCM (70 mL), and washed with saturated aqueous NaHCO₃ (70 mL). The aqueous layer was extracted with DCM (30 mL). The combined organic extracts were dried over MgSO₄ and concentrated in vacuo. The residue was purified on a 40-g SEPRA Si 35 SPE column (Flow rate=20 mL/min; Eluent=EtOAc-hexanes, 1:19 for 15 min, then 1:19 to 1:3 over 40 min) to yield 4-chloro-3-nitro-6-(2-trifluoromethyl-phenyl)-pyridin-2-ylamine as a yellow solid. The basic mother liquor and acidic filtrate were carefully combined, made basic with 1 N aqueous NaOH, and extracted twice with DCM (100 mL). The combined organic extracts were dried over MgSO₄ and concentrated in vacuo to yield additional product. ¹H-NMR (400 MHz, CDCl₃) δ: 7.76-7.90 (m, 1H), 7.55-7.71 (m, 2H), 7.46 (d, J=7.3 Hz, 1H), 6.93 (s, 1H), 6.11 (br. s., 2H). Mass Spectrum (LCMS, APCI pos.): Calculated for $C_{12}H_7N_3O_2ClF_3$: 318.0 (M+H). Measured: 318.0.

STEP C: 5-tert-Butyl-4-chloro-2-methyl-2H-pyrazole-3-carboxylic acid [4-chloro-3-nitro-6-(2-trifluoromethyl-phenyl)-pyridin-2-yl]-amide A solution of 4-chloro-3-nitro-6-(2-trifluoromethyl-phenyl)-pyridin-2-ylamine (87.5 mg, 0.275 mmol, prepared as described in STEP B above) in THF (10 mL) was treated with NaH (33.1 mg, 0.826 mmol, 60% dispersion in oil), and the mixture was allowed to stir at room temperature for 1 h. Simultaneously, a solution of 5-tert-butyl-4-chloro-2-methyl-2H-pyrazole-3-carboxylic acid (77.6 mg, 0.358 mmol, prepared as described in Example B above) in DCM (10 mL) was treated with oxalyl chloride (31.2 μL, 0.358 mmol), and DMF (2 drops), and the mixture was stirred at room temperature for 1 h. Volatile components were removed in vacuo, to yield 5-tert-butyl-4-chloro-2-methyl-2H-pyrazole-3-carbonyl chloride as a solid. The solid was taken up in anhydrous THF (6 mL) and this acid chloride solution was then added to the sodium anilide solution, as prepared above, and the resulting mixture was stirred at room temperature for 1 h. The mixture was quenched with saturated aqueous NH₄Cl (50 mL) and extracted twice with EtOAc (40 mL and 25 mL). The combined organic extracts were dried over MgSO₄ and concentrated in vacuo. The residue was purified on an 8-g SEPRA Si 35 SPE column (Flow rate=10 mL/min; Eluent=EtOAc-hexanes, 1:19 for 15 min, then 1:19 to 1:3 over 40 min) to yield 5-tert-butyl-4-chloro-2-methyl-2H-pyrazole-3-carboxylic acid [4-chloro-3-nitro-6-(2-trifluoromethyl-phenyl)-pyridin-2-yl]-amide as a colorless glassy solid. Mass Spectrum (LCMS, ESI pos.): Calculated for $C_{21}H_{18}N_5O_3Cl_2F_3$: 516.2 (M+H). Measured: 516.2.

STEP D: 5-tert-Butyl-4-chloro-2-methyl-2H-pyrazole-3-carboxylic acid [3-amino-4-chloro-6-(2-trifluoromethyl-phenyl)-pyridin-2-yl]-amide A solution of 5-tert-butyl-4-chloro-2-methyl-2H-pyrazole-3-carboxylic acid [4-chloro-3-nitro-6-(2-trifluoromethyl-phenyl)-pyridin-2-yl]-amide (109 mg, 0.211 mmol, prepared as described in the previous step) in EtOH (5 mL) and water (2.5 mL) was treated with NH$_4$Cl (113 mg, 2.11 mmol) and iron powder (58.9 mg, 1.06 mmol). The mixture was heated to 60° C. for 5 h, then the EtOH was evaporated in vacuo. The remaining aqueous mixture was diluted with water (30 mL) and extracted twice with EtOAc (25 mL). The combined organic extracts were dried over MgSO$_4$ and concentrated in vacuo. The residue was purified on a 12-g SEPRA Si 35 SPE column (Flow rate=15 mL/min; Eluent=EtOAc-hexanes, 1:99 for 10 min, then 1:99 to 1:4 over 40 min) to yield 5-tert-butyl-4-chloro-2-methyl-2H-pyrazole-3-carboxylic acid [3-amino-4-chloro-6-(2-trifluoromethyl-phenyl)-pyridin-2-yl]-amide as a colorless glassy solid. Mass Spectrum (LCMS, ESI pos.): Calculated for $C_{21}H_{20}N_5OCl_2F_3$: 486.1 (M+H). Measured: 486.2.

STEP E: 2-(5-tert-Butyl-4-chloro-2-methyl-2H-pyrazol-3-yl)-7-chloro-5-(2-trifluoromethyl-phenyl-1H-imidazo[4,5-b]pyridine A solution of 5-tert-butyl-4-chloro-2-methyl-2H-pyrazole-3-carboxylic acid [3-amino-4-chloro-6-(2-trifluoromethyl-phenyl)-pyridin-2-yl]-amide (54.0 mg, 0.111 mmol, prepared as described in STEP D above) in 1,4-dioxane (10 mL) was treated with CSA (51.6 mg, 0.222 mmol), and the mixture was heated to 100° C. under a reflux condenser for 3 h. The cooled resulting mixture was diluted with EtOAc (30 mL) and washed with saturated aqueous NaHCO$_3$ (20 mL). The organic extract was dried over MgSO$_4$ and concentrated in vacuo. The residue was purified on an 8-g SEPRA Si 35 SPE column (Flow rate=10 mL/min; Eluent=EtOAc-hexanes, 1:99 for 10 min, then 1:99 to 1:4 over 40 min) to yield 28.2 mg (54%) of 2-(5-tert-butyl-4-chloro-2-methyl-2H-pyrazol-3-yl)-7-chloro-5-(2-trifluoromethyl-phenyl-1H-imidazo[4,5-b]pyridine. Mass Spectrum (LCMS, ESI pos.): Calculated for $C_{21}H_{18}N_5Cl_2F_3$: 468.1 (M+H). Measured: 468.2.

STEP F: 2-(5-tert-Butyl-4-chloro-2-methyl-2H-pyrazol-3-yl)-7-chloro-5-(2-trifluoromethyl-phenyl-1H-imidazo[4,5-b]pyridine sodium salt 2-(5-tert-Butyl-4-chloro-2-methyl-2H-pyrazol-3-yl)-7-chloro-5-(2-trifluoromethyl-phenyl-1H-imidazo[4,5-b]pyridine (28.2 mg, 0.0602 mmol) was dissolved in anhydrous MeOH (4 mL) and treated with NaOMe (120 µL, 0.060 mmol, 0.5 M in MeOH) at room temperature for 1 h. The resulting mixture was concentrated in vacuo to yield 2-(5-tert-butyl-4-chloro-2-methyl-2H-pyrazol-3-yl)-7-chloro-5-(2-trifluoromethyl-phenyl-1H-imidazo[4,5-b]pyridine sodium salt as a white solid. $^1$H-NMR (400 MHz, CD$_3$OD) δ: 7.69 (d, J=7.6 Hz, 1H), 7.55-7.61 (m, 1H), 7.45-7.52 (m, 2H), 7.01 (s, 1H), 3.81 (s, 3H), 1.34 (s, 9H).

Following the procedures described in Example 1 above, and substituting suitably selected and substituted reagents, starting materials and conditions as would be readily apparent to those skilled in the art, the following representative compounds of the present invention were prepared.

Cmpd 5   2-(5-tert-Butyl-4-chloro-2-methyl-2H-pyrazol-3-yl)-7-chloro-5-(2-trifluoromethyl-phenyl)-1H-imidazo[4,5-b]pyridine hydrochloride $^1$H-NMR (400 MHz, CD$_3$OD) δ: 7.75 (d, J = 7.8 Hz, 1H), 7.64 (t, J = 7.2 Hz, 1H), 7.57 (t, J = 7.5 Hz, 1H), 7.51 (d, J = 7.3 Hz, 1H), 7.42 (s, 1H), 4.51 (s, 1H), 3.97 (s, 3H), 1.35 (s, 9H).
Mass Spectrum (LCMS, APCI pos.): Calculated for $C_{21}H_{18}Cl_2F_3N_5$:
468.1 (M + H); Measured: 468.1.

Cmpd 6   2-(5-tert-butyl-2-methyl-2H-pyrazol-3-yl)-7-chloro-5-(2-trifluoromethyl-phenyl)-1H-imidazo[4,5-b]pyridine sodium salt $^1$H-NMR (400 MHz, CD$_3$OD) δ: 7.79 (d, J = 7.6 Hz, 1H), 7.64-7.71 (m, 1H), 7.54-7.62 (m, 2H), 7.07 (s, 1H), 6.80 (s, 1H), 4.25 (s, 3H), 1.36 (s, 9H).
Mass Spectrum (LCMS, ESI pos.):
Calculated for $C_{21}H_{19}N_5ClF_3$:
434.1 (M + H); Measured: 434.2

Example 2

8-(5-tert-Butyl-4-chloro-2-methyl-2H-pyrazol-3-yl)-6-methyl-2-(2-trifluoromethyl-phenyl)-7H-purine hydrochloride (Compound #3)

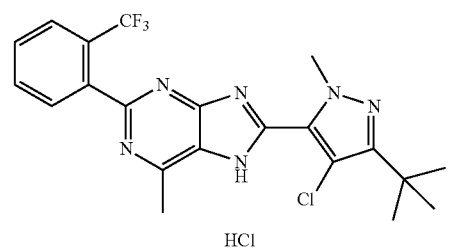 [SMILES: Cc1nc(-c2ccccc2C(F)(F)F)nc2nc(-c3c(Cl)c(C(C)(C)C)nn3C)[nH]c12 ; Cl]

HCl

STEP A: 5-tert-Butyl-4-chloro-2-methyl-2H-[pyrazole-3-carboxylic acid [6-methyl-5-nitro-2-(2-trifluoromethyl-phenyl)-pyrimidin-4-yl]-amide A solution of 6-methyl-5-nitro-2-(2-trifluoromethyl-phenyl)-pyrimidin-4-ylamine (109 mg, 0.365 mmol, prepared as described in Example 1, Step A) in THF (10 mL) was treated with NaH (43.9 mg, 1.10 mmol, 60% dispersion in oil), and the mixture was allowed to stir at room temperature for 1 h. Simultaneously, a solution of 5-tert-butyl-4-chloro-2-methyl-2H-pyrazole-3-carboxylic acid (103 mg, 0.475 mmol, prepared as described in Example B above) in DCM (10 mL) was treated with oxalyl chloride (41.5 µL, 0.475 mmol) and DMF (2 drops), and the mixture was stirred at room temperature for 1 h. Volatile components were removed in vacuo, and the residue was taken up in anhydrous THF (6 mL). The above-prepared acid chloride solution was added to the sodium anilide solution above, and the resulting mixture was stirred at room temperature for 15 min. The resulting mixture was then treated with saturated aqueous NH$_4$Cl (50 mL) and extracted twice with EtOAc (50 mL). The residue was purified on a 24-g SEPRA Si 50 SPE column (Flow rate=20 mL/min; Eluent=EtOAc-hexanes, 1:99 for 15 min, then 1:99 to 3:7 over 40 min) to yield 5-tert-butyl-4-chloro-2-methyl-2H-[pyrazole-3-carboxylic acid [6-methyl-5-nitro-2-(2-trifluoromethyl-phenyl)-pyrimidin-4-yl]-amide as an off-white solid. $^1$H-NMR (400 MHz, CDCl$_3$) δ: 9.59 (s, 1H), 7.81-7.88 (m, 2H), 7.60-7.72 (m, 2H), 4.11 (s, 3H), 2.82 (s, 3H), 1.40 (s, 9H). Mass Spectrum (LCMS, APCI pos.): Calculated for $C_{21}H_{20}N_6O_3ClF_3$: 497.1 (M+H). Measured: 497.2.

STEP B: 8-(5-tert-Butyl-4-chloro-2-methyl-2H-pyrazol-3-yl)-6-methyl-2-(2-trifluoromethyl-phenyl)-7H-purine A solution of 5-tert-butyl-4-chloro-2-methyl-2H-pyrazole-3-carboxylic acid [6-methyl-5-nitro-2-(2-trifluoromethyl-phenyl)-pyrimidin-4-yl]-amide (138 mg, 0.278 mmol, prepared as described in STEP A above) in AcOH (10 mL) was treated with iron powder (77.5 mg, 1.39 mmol), and the mixture was heated to 100° C. for 4 h. The cooled mixture was diluted with EtOAc (50 mL) and washed with saturated aqueous $NaHCO_3$ (50 mL). The aqueous layer was extracted again with EtOAc (50 mL). The combined organic extracts were dried over $MgSO_4$ and concentrated in vacuo. The residue was purified on a 24-g SEPRA Si 50 SPE column (Flow rate=20 mL/min; Eluent=EtOAc-hexanes, 1:9 for 15 min, then 1:9 to 2:3 over 40 min) to yield 8-(5-tert-butyl-4-chloro-2-methyl-2H-pyrazol-3-yl)-6-methyl-2-(2-trifluoromethyl-phenyl)-7H-purine as a white solid. $^1$H-NMR (400 MHz, $CDCl_3$) δ: 10.66 (br. s., 1H), 7.82 (d, J=7.6 Hz, 1H), 7.72-7.77 (m, 1H), 7.66 (t, J=7.5 Hz, 1H), 7.54-7.62 (m, 1H), 4.40 (s, 3H), 2.95 (s, 3H), 1.45 (s, 9H). Mass Spectrum (LCMS, ESI pos.): Calculated for $C_{21}H_{20}N_6ClF_3$: 449.1 (M+H). Measured: 449.1.

STEP C: 8-(5-tert-Butyl-4-chloro-2-methyl-2H-pyrazol-3-yl)-6-methyl-2-(2-trifluoromethyl-phenyl)-7H-purine hydrochloride A solution of 8-(5-tert-Butyl-4-chloro-2-methyl-2H-pyrazol-3-yl)-6-methyl-2-(2-trifluoromethyl-phenyl)-7H-purine (99.7 mg, 0.222 mmol, prepared as in STEP B above) in EtOH (6 mL) was treated with HCl (44.4 μL, 0.222 mmol, 5 M in IPA) at room temperature for 1.5 h and concentrated in vacuo. EtOH (0.5 mL) was added, and the resulting glassy solid was dissolved using sonication and heating. Hexanes (5 mL) were added, and the resulting mixture was concentrated in vacuo. The resulting foamy solid was triturated with hexanes, filtered, and air-dried to yield 8-(5-tert-butyl-4-chloro-2-methyl-2H-pyrazol-3-yl)-6-methyl-2-(2-trifluoromethyl-phenyl)-7H-purine hydrochloride as a white solid. $^1$H-NMR (400 MHz, $CDCl_3$) δ: 7.82-8.03 (m, 2H), 7.65-7.82 (m, 2H), 4.39 (s, 3H), 3.34 (br. s., 3H), 1.45 (s, 9H). Mass Spectrum (LCMS, APCI pos.): Calculated for $C_{21}H_{20}N_6ClF_3$: 449.1 (M+H). Measured: 449.2.

Following the procedures described in Example 2 above, and substituting suitably selected and substituted reagents, starting materials and conditions as would be readily apparent to those skilled in the art, the following representative compounds of the present invention were prepared.

Cmpd 4   8-(3-tert-butyl-isoxazol-5-yl)-6-methyl-2-(2-trifluoromethyl-phenyl)-7H-purine sodium salt
$^1$H-NMR (400 MHz, $CD_3OD$) δ: 7.70 (d, J = 7.8 Hz, 1H), 7.57-7.64 (m, 1H), 7.48-7.57 (m, 2H), 6.95 (s, 1H), 2.72 (s, 3H), 1.32 (s, 9H).
Mass Spectrum (LCMS, APCI pos.) Calculated For $C_{20}H_{18}N_5OF_3$: 402.2 (M + H), Measured: 402.2

Example 3

8-(5-tert-Butyl-4-chloro-2-methyl-2H-pyrazol-3-yl)-6-methyl-2-(2-trifluoromethyl-phenyl)-7H-purine sodium salt (Compound #3)

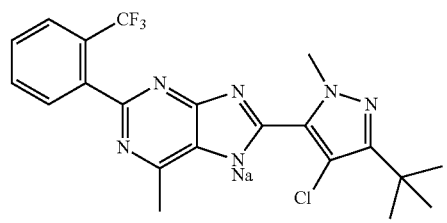

STEP A: 6-Methyl-5-nitro-2-(2-trifluoromethyl-phenyl)-pyrimidin-4-ylamine

To a solution of 2-chloro-6-methyl-5-nitro-pyrimidin-4-ylamine (920 mg, 4.89 mmol) in 1,4-dioxane (50 mL) was treated with (2-trifluoromethylphenyl)boronic acid (1.3 g, 6.8 mmol), $K_3PO_4$ (2.07 g, 9.78 mmol), and (dppf)$PdCl_2$.DCM (318 mg, 0.487 mmol) was heated to 100° C. for 4 h under Ar. The cooled mixture was filtered through a pad of diatomaceous earth, diluted with water, and extracted thrice with EtOAc. The combined organic layers were dried over $MgSO_4$ and concentrated in vacuo. The residue was purified on silica (0:100 v/v to 100:0 v/v EtOAc-hexanes over 20 min) to yield 6-methyl-5-nitro-2-(2-trifluoromethyl-phenyl)-pyrimidin-4-ylamine. $^1$H-NMR (400 MHz, $CDCl_3$) δ: 7.80 (d, J=7.6 Hz, 1H), 7.71-7.75 (m, 1H), 7.65 (t, J=6.9 Hz, 1H), 7.57-7.62 (m, 1H), 2.84 (s, 3H).

STEP B: 8-(5-tert-Butyl-4-chloro-2-methyl-2H-pyrazol-3-yl)-6-methyl-2-(2-trifluoromethyl-phenyl)-7H-purine sodium salt Following the procedure as described in STEPS C, D, E in Example 1, above, the title compound was prepared from 5-tert-butyl-4-chloro-2-methyl-2H-pyrazole-3-carboxylic acid (108 mg, 0.499 mmol, prepared as described in Example B above) and 4-methyl-6-methyl-5-nitro-2-(2-trifluoromethyl-phenyl)-pyrimidin-4-ylamine (149 mg, 0.500 mmol, prepared as in STEP A above) as an off-white solid. $^1$H-NMR (400 MHz; $CD_3OD$) δ: 7.78-7.83 (m, 1H), 7.68-7.74 (m, 1H), 7.60-7.67 (m, 2H), 2.78-2.85 (m, 3H), 1.44 (s, 9H). Mass Spectrum (LCMS, ESI pos.) Calculated for $C_{21}H_{20}ClF_3N_6$: 449.1 (M+H). Measured: 449.2.

Example 4

2-(3-tert-Butyl-isoxazol-5-yl)-7-chloro-5-(2-trifluoromethyl-phenyl)-1H-imidazo[4,5-b]pyridine (Compound #7)

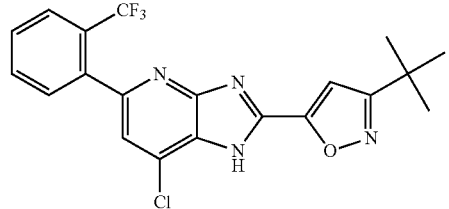 [SMILES: CC(C)(C)c1cc(-c2nc3nc(-c4ccccc4C(F)(F)F)cc(Cl)c3[nH]2)on1]

STEP A: 3-tert-Butyl-isoxazole-5-carboxylic acid [4-chloro-3-nitro-6-(2-trifluoromethyl-phenyl)-pyridin-2-yl]-amide A solution of 4-chloro-3-nitro-6-(2-trifluoromethyl-phenyl)-pyridin-2-ylamine (100 mg, 0.315 mmol, prepared as described in Example 1, Step B above) in THF (10 mL) was treated with NaH (37.8 mg, 0.944 mmol, 60% dispersion in oil), and the mixture was allowed to stir at room temperature for 1 h. Simultaneously, a solution of 3-tert-butyl-isoxazole-5-carboxylic acid (69.2 mg, 0.409 mmol, prepared as described in Example I above) in DCM (10 mL) was treated with oxalyl chloride (35.7 μL, 0.409 mmol) and DMF (2 drops), and the resulting mixture was stirred at room temperature for 1 h. Volatile components were removed in vacuo, and the residue was taken up in anhydrous THF (6 mL). The above-prepared acid chloride solution was added to the sodium anilide solution above, and the resulting mixture was stirred at room temperature for 15 min. The resulting mixture was then quenched with saturated aqueous NH$_4$Cl (20 mL) and extracted twice with EtOAc (30 mL). The combined organic extracts were dried over MgSO$_4$ and concentrated in vacuo. The residue was purified on a 25-g SEPRA Si 50 SPE column (Flow rate=20 mL/min; Eluent=EtOAc-hexanes, 1:99 for 10 min, then 1:99 to 1:3 over 40 min) to yield 3-tert-butyl-isoxazole-5-carboxylic acid [4-chloro-3-nitro-6-(2-trifluoromethyl-phenyl)-pyridin-2-yl]-amide as a yellow solid. Mass Spectrum (LCMS, ESI pos.): Calculated for C$_{21}$H$_{16}$N$_4$O$_4$ClF$_3$: 469.1 (M+H). Measured: 469.1.

STEP B: 3-tert-Butyl-isoxazole-5-carboxylic acid [3-amino-4-chloro-6-(2-trifluoromethyl-phenyl)-pyridin-2-yl]-amide A solution of 3-tert-butyl-isoxazole-5-carboxylic acid [4-chloro-3-nitro-6-(2-trifluoromethyl-phenyl)-pyridin-2-yl]-amide (40.7 mg, 0.0868 mmol, prepared as described in STEP A above) in EtOH (5 mL) and water (2.5 mL) was treated with ammonium chloride (46.4 mg, 0.868 mmol) and iron powder (24.2 mg, 0.434 mmol), and the mixture was stirred at 50° C. for 3 h. The cooled mixture was concentrated in vacuo and partitioned between EtOAc (25 mL) and water (20 mL). The aqueous layer was extracted with EtOAc (20 mL). The combined organic extracts were dried over MgSO$_4$ and concentrated in vacuo. The residue was purified on a 12-g SEPRA Si 50 SPE column (Flow rate=20 mL/min; Eluent=EtOAc-hexanes, 1:99 for 10 min, then 1:99 to 1:3 over 40 min) to yield 3-tert-butyl-isoxazole-5-carboxylic acid [3-amino-4-chloro-6-(2-trifluoromethyl-phenyl)-pyridin-2-yl]-amide as a yellow solid. Mass Spectrum (LCMS, ESI pos.): Calculated for C$_{21}$H$_{18}$N$_4$O$_2$ClF$_3$: 439.1 (M+H). Measured: 439.1.

STEP C: 2-(3-tert-Butyl-isoxazol-5-yl)-7-chloro-5-(2-trifluoromethyl-phenyl)-1H-imidazo[4,5-b]pyridine A solution of 3-tert-butyl-isoxazole-5-carboxylic acid [3-amino-4-chloro-6-(2-trifluoromethyl-phenyl)-pyridin-2-yl]-amide (36.2 mg, 0.0825 mmol, prepared as described in STEP B above) in 1,4-dioxane (10 mL) was treated with (+)-10-camphorsulfonic acid (38.3 mg, 0.165 mmol), and the mixture was heated to 100° C. for 5 h. The cooled mixture was diluted with EtOAc (20 mL) and washed with saturated aqueous NaHCO$_3$ (20 mL). The organic extract was dried over MgSO$_4$ and concentrated in vacuo. The residue was purified on an 8-g SEPRA Si 35 SPE column (Flow rate=15 mL/min; Eluent=EtOAc-hexanes, 1:99 for 10 min, then 1:99 to 1:3 over 40 min) to yield 2-(3-tert-butyl-isoxazol-5-yl)-7-chloro-5-(2-trifluoromethyl-phenyl)-1H-imidazo[4,5-b]pyridine as a white solid. $^1$H-NMR (400 MHz, CDCl$_3$) δ: 7.77 (d, J=7.8 Hz, 1H), 7.58-7.64 (m, 1H), 7.50-7.58 (m, 2H), 7.49 (s, 1H), 7.16 (s, 1H), 1.88 (br. s., 1H), 1.39 (s, 9H). Mass Spectrum (LCMS, APCI pos.): Calculated for C$_{20}$H$_{16}$N$_4$OClF$_3$: 421.1 (M+H). Measured: 421.1.

Example 5

2-(3-tert-Butyl-isoxazol-5-yl)-4-methoxy-6-(2-trifluoromethyl-phenyl)-3H-imidazo[4,5-c]-pyridine sodium salt (Compound #8)

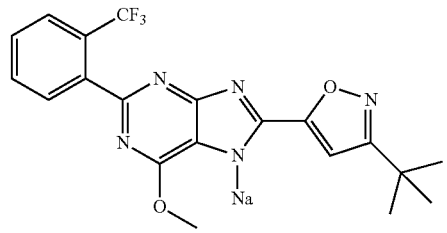

STEP A:
6-Chloro-2-methoxy-3-nitro-pyridin-4-ylamine 2,6-Dichloro-3-nitro-pyridin-4-ylamine (733 mg, 3.52 mmol) was placed in a 48 mL pressure vessel fitted with a magnetic stir bar and treated with NaOMe (7.05 mL, 3.52 mmol, 0.5 M in MeOH). The vessel was sealed and heated to 100° C. for 2 h. The cooled mixture was treated with acetic acid (0.25 mL) in diethyl ether (50 mL). The precipitate was filtered and washed with ether, and the filtrate was concentrated in vacuo. The residue was purified on a 40-g SEPRA Si 35 SPE column (Flow rate=25 mL/min; Eluent=EtOAc-hexanes, 1:19 for 15 min, then 1:19 to 1:4 over 40 min) to yield 6-chloro-2-methoxy-3-nitro-pyridin-4-ylamine as a pale yellow solid. $^1$H-NMR (400 MHz, CDCl$_3$) δ: 6.36 (s, 1H), 6.14 (br. s., 2H), 4.04 (s, 3H).

STEP B: 2-Methoxy-3-nitro-6-(2-trifluoromethyl-phenyl)-4-pyridin-4-ylamine

A solution of 6-chloro-2-methoxy-3-nitro-pyridin-4-ylamine (500 mg, 2.46 mmol, prepared as described in STEP A above) in DME (20 mL) and water (6 mL) was treated with Cs$_2$CO$_3$ (2.40 g, 7.37 mmol) and 2-trifluoromethylphenylboronic acid (560 mg, 2.95 mmol). The resulting mixture was degassed by heating to 80° C. under a stream of Ar. Cl$_2$Pd (dppf).DCM (121 mg, 0.147 mmol) was added, and the mixture was heated to 80° C. for 15 h. The cooled mixture was diluted with water (50 mL) and extracted twice with EtOAc (60 mL). The combined organic extracts were dried over MgSO$_4$ and concentrated in vacuo. The residue was purified on a 24-g SEPRA Si 50 SPE column (Flow rate=20 mL/min; Eluent=EtOAc-hexanes, 1:19 for 5 min, then 1:19 to 1:3 over 40 min) to yield 2-methoxy-3-nitro-6-(2-trifluoromethyl-phenyl)-4-pyridin-4-ylamine as a yellow solid. $^1$H-NMR (400 MHz, CDCl$_3$) δ: 7.77 (d, J=8.3 Hz, 1H), 7.58-7.65 (m, 1H), 7.52-7.58 (m, 1H), 7.48 (d, J=7.6 Hz, 1H), 6.42 (s, 1H), 4.03 (s, 3H). Mass Spectrum (LCMS, APCI pos.): Calculated for $C_{13}H_{10}N_3O_3F_3$: 314.1 (M+H). Measured: 314.1.

STEP C: 3-tert-Butyl-isoxazole-5-carboxylic acid [2-methoxy-3-nitro-6-(2-trifluoromethyl-phenyl)-pyridin-4-yl]-amide A solution of 2-methoxy-3-nitro-6-(2-trifluoromethyl-phenyl)-pyridin-4-ylamine (163 mg, 0.519 mmol, prepared as described in STEP B above) in THF (10 mL) was treated with NaH (62.2 mg, 1.56 mmol, 60% dispersion in oil), and the mixture was allowed to stir at room temperature for 1 h. Simultaneously, a solution of 3-tert-butyl-isoxazole-5-carboxylic acid (114 mg, 0.674 mmol, prepared as described in Example I above) in anhydrous DCM (10 mL) was treated with oxalyl chloride (58.8 µL, 0.674 mmol) and DMF (2 drops), and the mixture was stirred at room temperature for 1 h. Volatile components were removed in vacuo, and the residue was taken up in anhydrous THF (6 mL). The above-prepared acid chloride solution was added to the sodium anilide solution above, and the mixture was stirred at room temperature for 1 h. The mixture was quenched with saturated aqueous $NH_4Cl$ (20 mL) and extracted twice with EtOAc (25 mL). The residue was purified on a 12-g SEPRA Si 50 SPE column (Flow rate=15 mL/min; Eluent=EtOAc-hexanes, 1:99 for 10 min, then 1:99 to 1:4 over 40 min) to yield 3-tert-butyl-isoxazole-5-carboxylic acid [2-methoxy-3-nitro-6-(2-trifluoromethyl-phenyl)-pyridin-4-yl]-amide as a white solid. $^1$H-NMR (400 MHz, $CDCl_3$) δ: 10.62 (s, 1H), 8.39 (s, 1H), 7.82 (d, J=7.3 Hz, 1H), 7.63-7.69 (m, 1H), 7.58-7.63 (m, 1H), 7.56 (d, J=7.6 Hz, 1H), 6.98 (s, 1H), 4.09 (s, 3H), 1.38 (s, 9H). Mass Spectrum (LCMS, APCI pos.): Calculated for $C_{21}H_{19}N_4O_5F_3$: 465.1 (M+H). Measured: 465.1.

STEP D: 2-(3-tert-Butyl-isoxazol-5-yl)-4-methoxy-6-(2-trifluoromethyl-phenyl)-3H-imidazo[4,5-c]-pyridine A solution of 3-tert-butyl-isoxazole-5-carboxylic acid [2-methoxy-3-nitro-6-(2-trifluoromethyl-phenyl)-pyridin-4-yl]-amide (110 mg, 0.237 mmol, prepared as described in STEP C above) in AcOH (5 mL) was treated with iron powder (66.1 mg, 1.18 mmol), and the mixture was heated to 100° C. for 3 h. The AcOH was removed in vacuo. The residue was taken up in saturated aqueous $NaHCO_3$ (50 mL) and extracted twice with EtOAc (50 mL). The combined organic extracts were dried over $MgSO_4$ and concentrated in vacuo. The residue was purified on a 12-g SEPRA Si 50 SPE column (Flow rate=15 mL/min; Eluent=EtOAc-hexanes, 1:99 for 10 min, then 1:99 to 1:3 over 40 min). The chromatography was repeated as above to yield 2-(3-tert-butyl-isoxazol-5-yl)-4-methoxy-6-(2-trifluoromethyl-phenyl)-3H-imidazo[4,5-c]-pyridine as a white solid. Mass Spectrum (LCMS, APCI pos.): Calculated for $C_{21}H_{19}N_4O_2F_3$: 417.1 (M+H). Measured: 417.1.

STEP E: 2-(3-tert-Butyl-isoxazol-5-yl)-4-methoxy-6-(2-trifluoromethyl-phenyl)-3H-imidazo[4,5-c]-pyridine sodium salt A solution of 2-(3-tert-butyl-isoxazol-5-yl)-4-methoxy-6-(2-trifluoromethyl-phenyl)-3H-imidazo[4,5-c]pyridine (67.3 mg, 0.162 mmol, prepared as described in STEP D above) in MeOH (5 mL) was treated with NaOMe (323 µL, 0.162 mmol, 0.5 M in MeOH), and the mixture was stirred at room temperature for 2 h. The solvents were evaporated in vacuo to yield 2-(3-tert-butyl-isoxazol-5-yl)-4-methoxy-6-(2-trifluoromethyl-phenyl)-3H-imidazo[4,5-c]-pyridine sodium salt as an off-white solid. $^1$H-NMR (400 MHz, $CD_3OD$) δ: 7.66 (d, J=7.8 Hz, 1H), 7.49-7.57 (m, 2H), 7.38-7.45 (m, 1H), 7.13 (s, 1H), 6.79 (s, 1H), 3.97 (s, 3H), 1.30 (s, 9H). Mass Spectrum (LCMS, APCI pos.): Calculated for $C_{21}H_{19}N_4O_2F_3$: 417.1 (M+H). Measured: 417.1.

Example 6

2-(5-tert-Butyl-4-chloro-2-methyl-2H-pyrazol-3-yl)-4-methoxy-6-(2-trifluoromethyl-phenyl)-3H-imidazo [4,5-c]pyridine sodium salt (Compound #9)

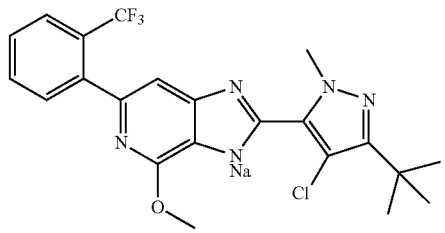

STEP A: 5-tert-Butyl-4-chloro-2-methyl-2H-pyrazole-3-carboxylic acid [2-methoxy-3-nitro-6-(2-trifluoromethyl-phenyl)-pyridin-4-yl]-amide A solution of 2-methoxy-3-nitro-6-(2-trifluoromethyl-phenyl)-pyridin-4-ylamine (162 mg, 0.517 mmol, prepared as described in Example 5, Step B above) in THF (10 mL) was treated with NaH (62.1 mg, 1.55 mmol, 60% dispersion in oil) at room temperature, and the mixture was allowed to stir for 1 h. Simultaneously, a solution of 5-tert-butyl-4-chloro-2-methyl-2H-pyrazole-3-carboxylic acid (168 mg, 0.776 mmol, prepared as described in Example B above) in anhydrous DCM (10 mL) was treated with oxalyl chloride (67.7 µL, 0.776 mmol) and DMF (2 drops), and the mixture was stirred at room temperature for 1 h. Volatile components were removed in vacuo, and the residue was taken up in anhydrous THF (6 mL). The above-prepared acid chloride solution was added to the sodium anilide solution above, and the mixture was stirred at room temperature for 1 h. The mixture was quenched with saturated aqueous $NH_4Cl$ (20 mL) and extracted twice with EtOAc (25 mL). The residue was purified on a 12-g SEPRA Si 50 SPE column (Flow rate=15 mL/min; Eluent=EtOAc-hexanes, 1:99 for 10 min, then 1:99 to 3:17 over 40 min) to yield 5-tert-butyl-4-chloro-2-methyl-2H-pyrazole-3-carboxylic acid [2-methoxy-3-nitro-6-(2-trifluoromethyl-phenyl)-pyridin-4-yl]-amide as a white solid. Mass Spectrum (LCMS, APCI pos.): Calculated for $C_{22}H_{21}N_5O_4ClF_3$: 512.1 (M+H). Measured: 512.1.

STEP B: 2-(5-tert-Butyl-4-chloro-2-methyl-2H-pyrazol-3-yl)-4-methoxy-6-(2-trifluoromethyl-phenyl)-3H-imidazo[4,5-c]pyridine A solution of 5-tert-butyl-4-chloro-2-methyl-2H-pyrazole-3-carboxylic acid [2-methoxy-3-nitro-6-(2-trifluoromethyl-phenyl)-pyridin-4-yl]-amide (149 mg, 0.291 mmol, prepared as described in STEP A above) in AcOH (10 mL) was treated with iron powder (81.3 mg, 1.46 mmol), and the resulting mixture was heated to 100° C. for 1.5 h. The cooled mixture was concentrated in vacuo, taken up in saturated aqueous $NaHCO_3$ (50 mL), and extracted twice with EtOAc (40 mL). The combined organic extracts were dried over $MgSO_4$ and concentrated in vacuo. The residue was purified on a 12-g SEPRA Si 50 SPE column (Flow rate=15 mL/min; Eluent=EtOAc-hexanes, 1:99 for 10 min, then 1:99 to 1:4 over 40 min) to yield 2-(5-tert-butyl-4-chloro-2-methyl-2H- pyrazol-3-yl)-4-methoxy-6-(2-trifluoromethyl-phenyl)-3H-imidazo[4,5-c]pyridine as a white solid. Mass Spectrum (LCMS, ESI pos.): Calculated for $C_{22}H_{21}N_5OClF_3$: 464.1 (M+H). Measured: 464.2.

STEP C: 2-(5-tert-Butyl-4-chloro-2-methyl-2H-pyrazol-3-yl)-4-methoxy-6-(2-trifluoromethyl-phenyl)-3H-imidazo[4,5-c]pyridine sodium salt A solution of 2-(5-tert-butyl-4-chloro-2-methyl-2H-pyrazol-3-yl)-4-methoxy-6-(2-trifluoromethyl-phenyl)-3H-imidazo[4,5-c]pyridine (122 mg, 0.263 mmol, prepared as described in STEP B above) in MeOH (6 mL) was treated with NaOMe (526 µL, 0.263 mmol), and the resulting mixture was stirred at room temperature for 1.5 h. The solvent was removed in vacuo to yield 2-(5-tert-butyl-4-chloro-2-methyl-2H-pyrazol-3-yl)-4-methoxy-6-(2-trifluoromethyl-phenyl)-3H-imidazo[4,5-c]pyridine sodium salt as a white solid. $^1$H-NMR (400 MHz, $CD_3OD$) δ: 7.77 (d, J=7.8 Hz, 1H), 7.60-7.66 (m, 2H), 7.49-7.56 (m, 1H), 7.26 (s, 1H), 4.08 (s, 3H), 3.88 (s, 3H), 1.44 (s, 9H). Mass Spectrum (LCMS, ESI pos.): Calculated for $C_{22}H_{21}N_5OClF_3$: 464.1 (M+H). Measured: 464.2.

Following the procedures described in Example 6 above, and substituting suitably selected and substituted reagents, starting materials and conditions as would be readily apparent to those skilled in the art, the following representative compounds of the present invention were prepared.

| | |
|---|---|
| Cmpd 9 | 2-(5-tert-Butyl-4-chloro-2-methyl-2H-pyrazol-3-yl)-4-methoxy-6-(2-trifluoromethyl-phenyl)-3H-imidazo[4,5-c]pyridine methanesulfonic acid salt<br>$^1$H-NMR (400 MHz, $CD_3OD$) δ: 7.94 (d, J = 7.8 Hz, 1H), 7.75-7.86 (m, 2H), 7.70 (d, J = 7.3 Hz, 1H), 7.55 (d, J = 2.5 Hz, 1H), 4.67-4.75 (m, 3H), 4.16 (s, 3H), 2.70 (s, 3H), 1.46 (s, 9H).<br>Mass Spectrum (LCMS, APCI pos.): Calculated for $C_{22}H_{21}ClF_3N_5O$: 464.1 (M + H); Measured: 464.2. |
| Cmpd 9 | 2-(5-tert-Butyl-4-chloro-2-methyl-2H-pyrazol-3-yl)-4-methoxy-6-(2-trifluoromethyl-phenyl)-3H-imidazo[4,5-c]pyridine hydrochloride<br>$^1$H-NMR (400 MHz, $CD_3OD$) δ: 7.75 (d, J = 7.8 Hz, 1H), 7.64 (t, J = 7.2 Hz, 1H), 7.57 (t, J = 7.5 Hz, 1H), 7.51 (d, J = 7.3 Hz, 1H), 7.42 (s, 1H), 4.51 (s, 1H), 3.97 (s, 3H), 1.35 (s, 9H).<br>Mass Spectrum (LCMS, APCI pos.): Calculated for $C_{21}H_{18}Cl_2F_3N_5$: 468.1 (M + H); Measured: 468.1. |

Example 7

2-(3-tert-Butyl-isoxazol-5-yl)-7-trifluoromethyl-5-(2-trifluoromethyl-phenyl)-1H-imidazo[4,5-b]pyridine (Compound #10)

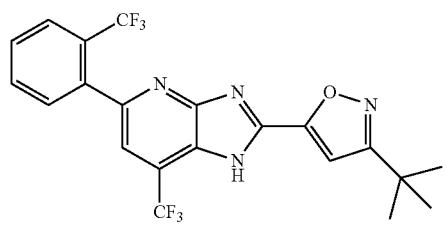 [SMILES: CC(C)(C)c1cc(-c2nc3nc(-c4ccccc4C(F)(F)F)cc(C(F)(F)F)c3[nH]2)on1]

STEP A: (6-Chloro-4-trifluoromethyl-pyridin-2-yl)-(4-methoxy-benzyl)-amine

A solution of 2,6-dichloro-4-trifluoromethyl-pyridine (5.04 g, 23.3 mmol) in pyridine (10 mL) was treated with 4-methoxybenzylamine (9.19 mL, 70.0 mmol) and heated to 110° C. for 26 h. The mixture was cooled, and pyridine (8 mL) was removed in vacuo. The remaining material was diluted with water (50 mL) and extracted twice with EtOAc (75 mL, and 50 mL). The combined organic extracts were dried over $MgSO_4$ and concentrated in vacuo. The residue was purified on a 115-g SEPRA Si 35 SPE column (Flow rate=35 mL/min; Eluent=EtOAc-hexanes, 1:99 for 15 min, then 1:99 to 1:9 over 40 min, 1:9 for 2 min, then 1:9 to 1:4 over 20 min) to yield (6-chloro-4-trifluoromethyl-pyridin-2-yl)-(4-methoxy-benzyl)-amine as a colorless oil, which solidified upon standing. $^1$H-NMR (400 MHz, $CDCl_3$) δ: 7.26 (d, J=8.6 Hz, 2H), 6.88 (d, J=8.6 Hz, 2H), 6.77 (s, 1H), 6.44 (s, 1H), 5.21 (br. s., 1H), 4.44 (d, J=5.6 Hz, 2H), 3.80 (s, 3H). Mass Spectrum (LCMS, ESI pos.): Calculated for $C_{14}H_{12}N_2OClF_3$: 317.1 (M+H). Measured: 317.1.

STEP B: (4-Methoxy-benzyl)-[4-trifluoromethyl-6-(2-trifluoromethyl-phenyl)-pyridin-2-yl]-amine A solution of (6-chloro-4-trifluoromethyl-pyridin-2-yl)-(4-methoxy-benzyl)-amine (7.26 g, 22.9 mmol, prepared as described in STEP A above) in DME (100 mL) and water (50 mL) was treated with 2-trifluoromethylphenylboronic acid (5.66 g, 29.8 mmol), and $Cs_2CO_3$ (11.2 g, 34.4 mmol). The resulting mixture was degassed via heating under a stream of Ar. $Cl_2Pd(dppf).DCM$ (1.13 g, 1.38 mmol) was added, and the mixture was heated to 80° C. for 4 h. The cooled mixture was diluted with water (100 mL) and extracted twice with EtOAc (150 mL). The combined organic extracts were dried over $MgSO_4$ and concentrated in vacuo. The residue was purified on a 115-g SEPRA Si 35 SPE column (Flow rate=30 mL/min; Eluent=EtOAc-hexanes, 1:99 for 10 min, then 1:99 to 1:4 over 40 min) to yield (4-methoxy-benzyl)-[4-trifluoromethyl-6-(2-trifluoromethyl-phenyl)-pyridin-2-yl]-amine as a yellow oil, which solidified upon standing. $^1$H-NMR (400 MHz, $CDCl_3$) δ: 7.76 (d, J=7.8 Hz, 1H), 7.57-7.63 (m, 1H), 7.47-7.55 (m, 2H), 7.27 (d, J=8.6 Hz, 2H), 6.85-6.91 (m, 3H), 6.57 (s, 1H), 5.11 (t, J=5.2 Hz, 1H), 4.48 (d, J=5.6 Hz, 2H), 3.80 (s, 3H). Mass Spectrum (LCMS, APCI pos.): Calculated for $C_{21}H_{16}N_2OF_6$: 427.1 (M+H). Measured: 427.2.

STEP C: 4-Trifluoromethyl-6-(2-trifluoromethyl-phenyl)-pyridin-2-ylamine

A solution of (4-methoxy-benzyl)-[4-trifluoromethyl-6-(2-trifluoromethyl-phenyl)-pyridin-2-yl]-amine (1.00 g, 2.34 mmol, prepared as described in STEP B above) in MeOH (20 mL) was added, the flask was flushed well with Ar, Pd/C (500 mg, 0.235 mmol, 5% on carbon) was added, and the flask was flushed with Ar and fitted with an $H_2$ balloon. The resulting mixture stirred at room temperature for 4 h. The balloon was removed, the flask was flushed again with Ar, the mixture was filtered through diatomaceous earth, and the filter cake was washed well with MeOH. The filtrate was concentrated in vacuo to yield 4-trifluoromethyl-6-(2-trifluoromethyl-phenyl)-pyridin-2-ylamine as a tan solid. $^1$H-NMR (400 MHz, $CDCl_3$) δ: 7.81 (d, J=7.6 Hz, 1H), 7.64-7.76 (m, 2H), 7.59 (d, J=7.1 Hz, 1H), 7.25 (s, 1H), 6.79 (s, 1H), 3.22 (br. s., 4H).

STEP D: 3-Nitro-4-trifluoromethyl-6-(2-trifluoromethyl-phenyl)-pyridin-2-ylamine Sulfuric acid (10 mL) was placed in a 100 mL two-necked round-bottomed flask fitted with a magnetic stir bar and an internal thermometer and cooled to 0° C. 4-Trifluoromethyl-6-(2-trifluoromethyl-phenyl)-pyridin-2-ylamine (720 mg, 2.35 mmol, prepared as described in STEP C above) was added portion wise so that the internal temperature did not exceed 5° C. The resulting mixture was stirred at 0° C. for 1 h. Nitric acid (106 µL, 2.35 mmol) was added slowly, keeping the internal temperature below 10° C. The mixture was stirred an additional 2 h at 0° C., poured over ice water (100 mL), treated with 6 M aqueous NaOH to pH 10, and extracted twice with EtOAc (100 mL). The combined organic extracts were dried over MgSO$_4$ and concentrated in vacuo. The residue was purified on a 24-g SEPRA Si 50 SPE column (Flow rate=20 mL/min; Eluent=EtOAc-hexanes, 1:99 for 10 min, then 1:99 to 1:3 over 40 min) to yield 3-nitro-4-trifluoromethyl-6-(2-trifluoromethyl-phenyl)-pyridin-2-ylamine as a bright yellow solid. Mass Spectrum (LCMS, APCI pos.): Calculated for $C_{13}H_7N_3O_2F_6$: 352.0 (M+H). Measured: 352.0.

STEP E: 3-tert-Butyl-isoxazole-5-carboxylic acid [3-nitro-4-trifluoromethyl-6-(2-trifluoromethyl-phenyl)-pyridin-2-yl]-amide A solution of 3-nitro-4-trifluoromethyl-6-(2-trifluoromethyl-phenyl)-pyridin-2-ylamine (64.0 mg, 0.182 mmol, prepared as described in STEP D above) in THF (10 mL) was treated with NaH (21.9 mg, 0.547 mmol, 60% dispersion in oil), and the resulting mixture was allowed to stir at room temperature for 1 h. Simultaneously, a solution of 3-tert-butyl-isoxazole-5-carboxylic acid (40.1 mg, 0.237 mmol, prepared as described in Example I above) in anhydrous DCM (10 mL) was treated with oxalyl chloride (20.7 µL, 0.237 mmol) and DMF (2 drops), and the resulting mixture was stirred at room temperature for 1 h. Volatile components were removed in vacuo, and the residue was taken up in anhydrous THF (6 mL). The above-prepared acid chloride solution was added to the sodium anilide solution above, and the mixture was stirred at room temperature for 1 h. The mixture was quenched with saturated aqueous NH$_4$Cl (20 mL) and extracted twice with EtOAc (25 mL). The residue was purified on a 12-g SEPRA Si 50 SPE column (Flow rate=15 mL/min; Eluent=EtOAc-hexanes, 1:99 for 10 min, then 1:99 to 1:4 over 40 min) to yield 3-tert-butyl-isoxazole-5-carboxylic acid [3-nitro-4-trifluoromethyl-6-(2-trifluoromethyl-phenyl)-pyridin-2-yl]-amide as an off-white solid. Mass Spectrum (LCMS, APCI pos.): Calculated for $C_{21}H_{16}N_4O_4F_6$: 503.1 (M+H). Measured: 503.2.

STEP F: 2-(3-tert-Butyl-isoxazol-5-yl)-7-trifluoromethyl-5-(2-trifluoromethyl-phenyl)-1H-imidazo[4,5-b]pyridine A solution of 3-tert-butyl-isoxazole-5-carboxylic acid [3-nitro-4-trifluoromethyl-6-(2-trifluoromethyl-phenyl)-pyridin-2-yl]-amide (14.6 mg, 0.029 mmol, prepared as described in STEP E above) in AcOH (3 mL) was treated with iron powder (8.12 mg, 0.145 mmol), and the resulting mixture was stirred at 100° C. for 2 h and concentrated in vacuo. The residue was taken up in saturated aqueous NaHCO$_3$ (30 mL) and extracted twice with EtOAc (25 mL). The combined organic extracts were dried over MgSO$_4$ and concentrated in vacuo. The residue was purified on a 4-g SEPRA Si 50 SPE column (Flow rate=10 mL/min; Eluent=EtOAc-hexanes, 1:99 for 10 min, then 1:99 to 1:4 over 40 min) to yield 2-(3-tert-butyl-isoxazol-5-yl)-7-trifluoromethyl-5-(2-trifluoromethyl-phenyl)-1H-imidazo[4,5-b]pyridine as a white solid. $^1$H-NMR (400 MHz, CD$_3$OD) δ: 7.77 (d, J=7.6 Hz, 1H), 7.63-7.69 (m, 1H), 7.58-7.62 (m, 2H), 7.52-7.58 (m, 1H), 7.26 (s, 1H), 1.33 (s, 9H). Mass Spectrum (LCMS, APCI pos.): Calculated for $C_{21}H_{16}N_4OF_6$: 455.1 (M+H). Measured: 455.1.

Following the procedures described in Example 7 above, and substituting suitably selected and substituted reagents, starting materials and conditions as would be readily apparent to those skilled in the art, the following representative compounds of the present invention were prepared.

Cmpd 1  2-(5-tert-Butyl-4-chloro-2-methyl-2H-pyrazol-3-yl)-7-trifluoromethyl-5-(2-trifluoromethyl-phenyl)-1H-imidazo[4,5-b]pyridine sodium salt
$^1$H-NMR (400 MHz; CD$_3$OD) δ: 7.81 (d, J = 7.6 Hz, 1H), 7.64-7.70 (m, 1H), 7.53-7.64 (m, 3H), 4.16 (s, 3H), 1.42, (s, 9H).
Mass Spectrum (LCMS, ESI pos.) Calculated For $C_{22}H_{18}ClF_6N_5$: 502.1 (M + H), Measured: 502.2.

Example 8

2-(5-tert-butyl-4-chloro-2-methyl-2H-pyrazol-3-yl)-6-(2-trifluoromethyl-phenyl)-1H-imidazo[4,5-b]pyrazine (Compound #95)

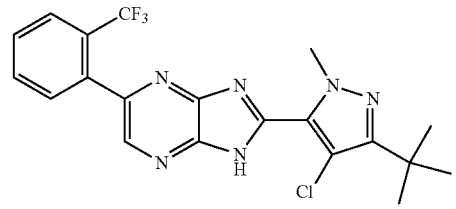 [SMILES: Cn1nc(C(C)(C)C)c(Cl)c1-c1nc2nc(-c3ccccc3C(F)(F)F)cnc2[nH]1]

STEP A: 5-tert-butyl-4-chloro-2-methyl-2H-pyrazole-3-carboxylic acid [5-bromo-3-(4-methoxy-benzylamino)-pyrazin-2-yl]-amide To a solution of 3,5-dibromo-pyrazin-2-ylamine (252 mg, 1.00 mmol) in DME (10 mL) 60% NaH (120 mg, 3.00 mmol) was added portion wise. The resulting mixture was stirred at room temperature for 30 min and then treated with 5-tert-butyl-4-chloro-2-methyl-2H-pyrazole-3-carbonyl chloride (234 mg, 1.00 mmol, prepared as described in Example 1, STEP C). The resulting mixture was stirred at room temperature for 2 h and treated with saturated NH$_4$Cl (20 mL) followed by EtOAc (20 mL). The organic layer was separated, dried (Na$_2$SO$_4$) and concentrated. The resulting residue was dissolved in 1,4-dioxane (10 mL) and treated with 4-methoxybenzylamine (0.650 mL, 5.00 mmol). The resulting mixture was stirred at 65° C. for 2 h. The resulting mixture was allowed to cool to room temperature and then treated with water (10 mL) and EtOAc (20 mL). The organic layer was separated, dried (Na$_2$SO$_4$) and concentrated. The resulting residue was purified on silica (0:100-50:50 EtOAc:hexane) to yield 5-tert-butyl-4-chloro-2-methyl-2H-pyrazole-3-carboxylic acid [5-bromo-3-(4-methoxy-benzylamino)-pyrazin-2-yl]-amide. $^1$H-NMR (400 MHz, CDCl$_3$) δ: 8.77 (br. s., 1H), 7.70 (s, 1H), 7.34 (d, J=8.6 Hz, 2H), 6.88 (d, J=8.6 Hz, 2H), 6.28-6.36 (m, 1H), 4.59 (d, J=5.1 Hz, 2H), 4.08 (s, 3H), 3.80 (s, 3H), 1.40 (s, 9H).

93

STEP B: 5-tert-butyl-4-chloro-2-methyl-2H-pyrazole-3-carboxylic acid [3-(4-methoxy-benzylamino)-5-(2-trifluoromethyl-phenyl)-pyrazin-2-yl]-amide To a solution of 5-tert-butyl-4-chloro-2-methyl-2H-pyrazole-3-carboxylic acid [5-bromo-3-(4-methoxy-benzylamino)-pyrazin-2-yl]-amide (87 mg, 0.17 mmol), 2-trifluoromethyl-phenylboronic acid (36 mg, 0.19 mmol), in DMF (0.5 mL), toluene (2 mL) and water (2 mL), $K_2CO_3$ (33 mg, 0.23 mmol) was added. The resulting solution was placed under Ar and (dppf)$PdCl_2$.DCM (14 mg, 0.02 mmol) was added. The resulting mixture was stirred at 100° C. overnight. The organic layer was separated, dried ($Na_2SO_4$) and concentrated. The residue obtained was purified on silica (20:80-100:0 EtOAc: hexane) to yield 5-tert-butyl-4-chloro-2-methyl-2H-pyrazole-3-carboxylic acid [3-(4-methoxy-benzylamino)-5-(2-trifluoromethyl-phenyl)-pyrazin-2-yl]-amide. Mass Spectrum (LCMS, ESI pos.): Calculated for $C_{28}H_{28}ClF_3N_6O$: 573.1 (M+H). Measured: 573.3.

STEP C: 2-(5-tert-butyl-4-chloro-2-methyl-2H-pyrazol-3-yl)-6-(2-trifluoromethyl-phenyl)-1H-imidazo[4,5-b]pyrazine A solution of 5-tert-butyl-4-chloro-2-methyl-2H-pyrazole-3-carboxylic acid [5-bromo-3-(4-methoxy-benzylamino)-pyrazin-2-yl]-amide (28 mg, 0.04 mmol, prepared as described in the previous step) in TFA (3.5 mL) was stirred at 65° C. for 3 h. The resulting mixture was allowed to cool to room temperature, TFA was removed in vacuo and the resulting residue was dissolved in EtOAc (10 mL) and washed with saturated $NaHCO_3$ (20 mL). EtOAc layer was separated, dried ($Na_2SO_4$), and concentrated in vacuo. The resulting residue was dissolved in HOAc (3.5 mL) and stirred at 100° C. overnight. The resulting mixture was allowed to cool to room temperature and the HOAc was removed in vacuo. The resulting residue was dissolved in EtOAc (10 mL) and washed with saturated $NaHCO_3$ (10 mL). EtOAc layer was separated, dried ($Na_2SO_4$), and concentrated in vacuo. The resulting residue was purified on silica 0:100-50:50 EtOAc-hexane to yield 2-(5-tert-butyl-4-chloro-2-methyl-2H-pyrazol-3-yl)-6-(2-trifluoromethyl-phenyl)-1H-imidazo[4,5-b]pyrazine. $^1$H-NMR ($CD_3OD$) δ: 8.53-8.57 (br s, 1H), 7.82-7.86 (m, 1H), 7.68-7.74 (m, 1H), 7.61-7.67 (m, 1H), 7.57-7.60 (m, 1H), 4.19 (s, 3H), 1.43 (s, 9H). Mass Spectrum (LCMS, ESI pos.): Calculated for $C_{20}H_{18}ClF_3N_6$: 435.1 (M+H). Measured: 435.1.

Following the procedures described in Example 8 above, and substituting suitably selected and substituted reagents, starting materials and conditions as would be readily apparent to those skilled in the art, the following representative compounds of the present invention were prepared.

| Cmpd 96 | 2-(5-tert-Butyl-4-chloro-2-methyl-2H-pyrazol-3-yl)-6-(2-fluoro-phenyl)-1H-imidazo[4,5-b]pyrazine<br>$^1$H-NMR (400 MHz, $CD_3OD$) δ: 8.94-8.97 (m, 1H), 8.02-8.08 (m, 1H), 7.46-7.53 (m, 1H), 7.33-7.38 (m, 1H), 7.24-7.30 (m, 1H), 4.22 (s, 3H), 1.47 (s, 9H), 1.28.<br>Mass Spectrum (LCMS, ESI pos.): Calculated for $C_{19}H_{18}ClFN_6$: 385.1 (M + H); Measured: 385.1. |
|---|---|

94

Example 9

2-(5-tert-butyl-4-chloro-2-methyl-2H-pyrazol-3-yl)-7-methoxy-5-(2-trifluoromethyl-phenyl)-1H-imidazo[4,5-b]pyridine (Compound #62)

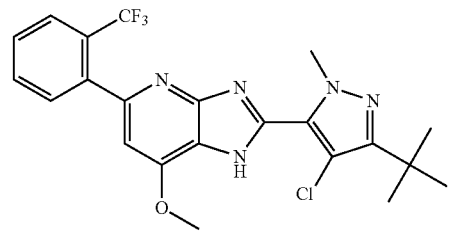 [SMILES: COc1cc(-c2ccccc2C(F)(F)F)nc2nc(-c3c(Cl)c(C(C)(C)C)nn3C)[nH]c12]

STEP A: 4-Methoxy-3-nitro-6-(2-trifluoromethyl-phenyl)-pyridin-2-ylamine

To a solution of 4-chloro-3-nitro-6-(2-trifluoromethyl-phenyl)-pyridin-2-ylamine (317 mg, 0.998 mmol, prepared as described in the Example 1) in MeOH (5 mL) was added NaOMe (1.99 mL, 0.998 mmol, 0.5 M solution in MeOH). The resulting mixture was stirred at 70° C. overnight. The reaction mixture was then diluted with water (20 mL) and extracted with EtOAc (3×10 mL). The organic layers were combined, dried ($MgSO_4$) and concentrated. The resulting residue was purified on silica 0:100-50:50 EtOAc-hexanes to yield 4-methoxy-3-nitro-6-(2-trifluoromethyl-phenyl)-pyridin-2-ylamine. $^1$H-NMR (400 MHz, $CDCl_3$) δ: 7.78 (d, J=7.8 Hz, 1H), 7.61-7.67 (m, 1H), 7.54-7.60 (m, 1H), 7.50 (d, J=7.6 Hz, 1H), 6.46 (s, 1H), 6.27 (br. s., 2H), 3.97 (s, 3H).

STEP B: 2-(5-tert-butyl-4-chloro-2-methyl-2H-pyrazol-3-yl)-7-methoxy-5-(2-trifluoromethyl-phenyl)-1H-imidazo[4,5-b]pyridine Following the procedures described in the Example 1, STEPS C and D, the title compound was prepared from 4-methoxy-3-nitro-6-(2-trifluoromethyl-phenyl)-pyridin-2-ylamine. $^1$H-NMR (400 MHz, $CDCl_3$) δ: $^1$H-NMR ($CD_3OD$) δ: 7.82 (d, J=7.3 Hz, 1H), 7.66-7.73 (m, 1H), 7.56-7.66 (m, 2H), 6.99 (s, 1H), 4.12 (s, 3H), 4.02 (s, 3H), 1.43 (s, 9H). Mass Spectrum (LCMS, ESI pos.) Calculated For $C_{22}H_{21}ClF_3N_5O$: 464.1 (M+H). Measured: 464.3.

Following the procedures described in Example 9 above, and substituting suitably selected and substituted reagents, starting materials and conditions as would be readily apparent to those skilled in the art, the following representative compounds of the present invention were prepared.

| Cmpd 62 | 2-(5-tert-butyl-4-chloro-2-methyl-2H-pyrazol-3-yl)-7-methoxy-5-(2-trifluoromethyl-phenyl)-1H-imidazo[4,5-b]pyridine hydrochloride<br>$^1$H-NMR ($CD_3OD$) δ: 7.98-8.03 (m, 1H), 7.84-7.93 (m, 2H), 7.74-7.81 (m, 1H), 7.51 (s, 1H), 4.32 (s, 3H), 4.10 (s, 3H), 1.46 (s, 9H).<br>Mass Spectrum (LCMS, ESI pos.) Calculated For $C_{22}H_{21}ClF_3N_5O$: 464.1 (M + H), Measured: 464.3. |
|---|---|

Example 10

2-(5-tert-Butyl-4-chloro-2-methyl-2H-pyrazol-3-yl)-5-(2-trifluoromethoxy-phenyl)-1H-imidazo[4,5-b]pyrazine (Compound #94)

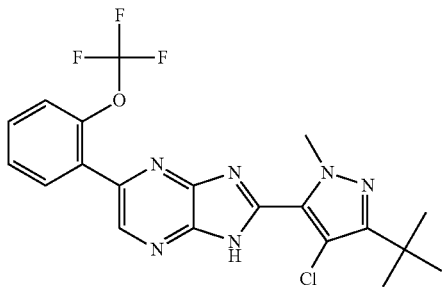 [SMILES: Cn1nc(C(C)(C)C)c(Cl)c1-c1nc2nc(-c3ccccc3OC(F)(F)F)cnc2[nH]1]

STEP A: 5-tert-Butyl-4-chloro-2-methyl-2H-pyrazole-3-carboxylic acid (3-amino-5-bromo-pyrazin-2-yl)-amide To a mixture of 5-bromo-pyrazine-2,3-diamine (250 mg, 1.32 mmol) in 1:1 DMF/DCM (8 mL) was added NaH (159 mg, 3.97 mmol, 60% dispersion in mineral oil) slowly. After stirring at room temperature for 1 h, the resulting mixture was cooled to 0° C. Solid 5-tert-butyl-4-chloro-2-methyl-2H-pyrazole-3-carbonyl chloride (373 mg, 1.59 mmol, prepared as described in Example 1, STEP C) was added slowly. The resulting mixture was warmed to room temperature and then stirred for 18 h. The resulting mixture was treated with 50 mL of EtOAc and washed with aqueous saturated NH$_4$Cl (20 mL), H$_2$O (2×10 mL) and brine (10 mL). After drying with Na$_2$SO$_4$, the resulting solution was concentrated in vacuo and the residue was purified by flash chromatography on silica gel (0:100-20:80 EtOAc/hexanes) to yield 5-tert-butyl-4-chloro-2-methyl-2H-pyrazole-3-carboxylic acid (3-amino-5-bromo-pyrazin-2-yl)-amide as a light brown solid. $^1$H-NMR (400 MHz, CDCl$_3$) δ: 8.88 (s, 1H), 8.12 (s, 1H), 5.34 (br. s., 2H), 4.14 (s, 3H), 1.42 (s, 9H). Mass Spectrum (LCMS, ESI pos.) Calculated For C$_{13}$H$_{16}$BrClN$_6$O: 387.0 (M+H). Measured: 387.0.

STEP B: 2-(5-tert-Butyl-4-chloro-2-methyl-2H-pyrazol-3-yl)-5-(2-trifluoromethoxy-phenyl)-1H-imidazo[4,5-b]pyrazine To a mixture of 5-tert-butyl-4-chloro-2-methyl-2H-pyrazole-3-carboxylic acid (3-amino-5-bromo-pyrazin-2-yl)-amide (45.0 mg, 0.116 mmol, prepared as described in the previous step), 2-trifluoromethoxy-phenyl-boronic acid (28.7 mg, 0.139 mmol), Cs$_2$CO$_3$ (95 mg, 0.29 mmol) and Pd (dppf)$_2$.DCM (9.5 mg, 0.012 mmol) in 1,4-dioxane (3 mL) was added water (1.5 mL). After stirring at 100° C. for 16 h, the resulting mixture was cooled to room temperature and treated with EtOAc (50 mL), washed with H$_2$O (20 mL), brine (20 mL) and then dried with Na$_2$SO$_4$. Removal of the solvent under reduced pressure followed by flash chromatography of the residue on silica gel (0:100-35:65 EtOAc-hexanes) yielded 2-(5-tert-Butyl-4-chloro-2-methyl-2H-pyrazol-3-yl)-5-(2-trifluoromethoxy-phenyl)-1H-imidazo[4,5-b]pyrazine as a light yellow solid. $^1$H-NMR (400 MHz, CD$_3$OD) δ: 8.79 (s, 1H), 7.87-7.94 (m, 1H), 7.45-7.64 (m, 3H), 4.14 (s, 3H), 1.44 (s, 9H). Mass Spectrum (LCMS, ESI pos.) Calculated For C$_{20}$H$_{18}$ClF$_3$N$_6$O: 451.1 (M+H). Measured: 451.1.

Following the procedure described in Example 10, above, and substituting suitably selected and substituted reagents, starting materials and conditions as would be readily apparent to those skilled in the art, the following representative compounds of the present invention were prepared.

| Cmpd | |
|---|---|
| 110 | 2-(5-tert-Butyl-4-chloro-2-methyl-2H-pyrazol-3-yl)-5-(2-chloro-phenyl)-1H-imidazo[4,5-b]pyrazine<br>$^1$H-NMR (400 MHz, CD$_3$OD) δ: 8.76 (s, 1H), 7.68 (m, 1H), 7.59 (m, 1H), 7.45-7.52 (m, 2H), 4.15 (s, 3H), 1.45 (s, 9H)<br>Mass Spectrum (LCMS, ESI pos.) Calculated For C$_{19}$H$_{18}$Cl$_2$N$_6$: 401.1 (M + H), Measured: 401.0 |

Example 11

2-[2-(5-tert-Butyl-4-chloro-2-methyl-2H-pyrazol-3-yl)-6-(2-trifluoromethyl-phenyl)-3H-imidazo[4,5-c]pyridin-4-yloxy]-ethanol (Compound #57)

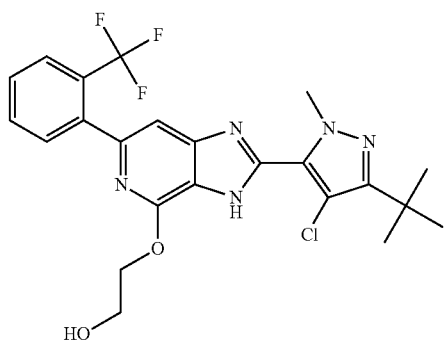 [SMILES: Cn1nc(C(C)(C)C)c(Cl)c1-c1nc2cc(-c3ccccc3C(F)(F)F)nc(OCCO)c2[nH]1]

STEP A: 2-(4-Amino-6-chloro-3-nitro-pyridin-2-yloxy)-ethanol

To a mixture of 60% sodium hydride in mineral oil (769 mg, 19.2 mmol) in ethylene glycol (10 mL) was added 2,6-dichloro-3-nitro-pyridin-4-ylamine (2.00 g, 9.62 mmol) slowly over 5 min. After stirring at room temperature for 16 h, the resulting mixture was treated with saturated NH$_4$Cl (20 mL) and extracted with EtOAc (3×50 mL). The combined organic layers were washed with H$_2$O (2×50 mL), brine (50 mL), and then dried over Na$_2$SO$_4$. The solvent was removed in vacuo and the resulting residue was triturated with hexanes. 2-(4-Amino-6-chloro-3-nitro-pyridin-2-yloxy)-ethanol was obtained as a light yellow solid (by filtration) and washed with hexanes. $^1$H-NMR (400 MHz, CD$_3$OD) δ: 6.50 (s, 1H), 4.37-4.50 (m, 2H), 3.80-3.93 (m, 2H). Mass Spectrum (LCMS, ESI pos.) Calculated For C$_7$H$_8$ClN$_3$O$_4$: 234.0 (M+H). Measured: 234.0.

STEP B: 2-[2-(tert-Butyl-dimethyl-silanyloxy)-ethoxy]-6-chloro-3-nitro-pyridin-4-ylamine To a mixture of 2-(4-amino-6-chloro-3-nitro-pyridin-2-yloxy)-ethanol (4.40 g, 18.8 mmol, prepared as described in the previous step) and tert-butyl-chloro-dimethyl-silane (3.12 g, 20.7 mmol) in DCM (50 mL) was added imidazole (1.80 g, 26.4 mmol). After stirring at room temperature for 2 h, the resulting mixture was treated with saturated NH$_4$Cl (50 mL)

and extracted with EtOAc (3×50 mL). The combined organic layers were washed with H₂O (3×50 mL), brine (50 mL), and dried over Na₂SO₄. The solvent was removed in vacuo and the residue was purified by flash chromatography on silica gel (0:100-20:80 EtOAc/hexane) to yield 2-[2-(tert-butyl-dimethyl-silanyloxy)-ethoxy]-6-chloro-3-nitro-pyridin-4-ylamine as a light yellow solid. ¹H-NMR (400 MHz, CDCl₃) δ: 6.35 (s, 1H), 6.17 (br. s., 2H), 4.49 (t, J=5.1 Hz, 2H), 3.96 (t, J=5.1 Hz, 2H), 0.88 (s, 9H), 0.08 (s, 6H).

STEP C: 2-[2-(tert-Butyl-dimethyl-silanyloxy)-ethoxy]-3-nitro-6-(2-trifluoromethyl-phenyl)-pyridin-4-ylamine To a mixture of 2-[2-(tert-butyl-dimethyl-silanyloxy)-ethoxy]-6-chloro-3-nitro-pyridin-4-ylamine (1.20 g, 3.45 mmol, prepared as described in the previous step), 2-trifluoromethyl-phenyl-boronic acid (786 mg, 4.14 mmol), Cs₂CO₃ (2.81 g, 8.62 mmol) and Pd(dppf)₂.DCM (282 mg, 0.345 mmol) in 1,4-dioxane (12 mL) was added water (5 mL). The resulting mixture was stirred at 110° C. under microwave irradiation for 2 h and then cooled to room temperature. The resulting mixture was treated with of EtOAc (50 mL), then washed with H₂O and brine and was dried (Na₂SO₄). Removal of the solvent under reduced pressure followed by flash chromatography of the residue on silica gel (5:95-40:60 EtOAc-hexanes) yielded 2-[2-(tert-butyl-dimethyl-silanyloxy)-ethoxy]-3-nitro-6-(2-trifluoromethyl-phenyl)-pyridin-4-ylamine as a light brown solid. ¹H-NMR (400 MHz, CDCl₃) δ: 7.76 (d, J=7.8 Hz, 1H), 7.51-7.65 (m, 2H), 7.46 (d, J=7.3 Hz, 1H), 6.41 (s, 1H), 6.08 (br. s., 2H), 4.50 (t, J=5.3 Hz, 2H), 3.95 (t, J=5.3 Hz, 2H), 0.89 (s, 9H), 0.07 (s, 6H). Mass Spectrum (LCMS, ESI pos.) Calculated For $C_{20}H_{26}F_3N_3O_4Si$: 458.1 (M+H). Measured: 458.0.

STEP D: 5-tert-Butyl-4-chloro-2-methyl-2H-pyrazole-3-carboxylic acid [2-[2-(tert-butyl-dimethyl-silanyloxy)-ethoxy]-3-nitro-6-(2-trifluoromethyl-phenyl)-pyridin-4-yl]-amide To a mixture of 60% sodium hydride in mineral oil (120 mg, 3.00 mmol) in THF (10 mL) at 0° C. was added 2-[2-(tert-butyl-dimethyl-silanyloxy)-ethoxy]-3-nitro-6-(2-trifluoromethyl-phenyl)-pyridin-4-ylamine (458 mg, 1.00 mmol, prepared as described in the previous step) slowly. The resulting mixture was warmed to room temperature and then stirred for 1 h under Ar. 5-tert-Butyl-4-chloro-2-methyl-2H-pyrazole-3-carbonyl chloride (259 mg, 1.10 mmol, prepared as described in Example 1, STEP C) was added and the resulting mixture was stirred for 3 h under Ar. After quenching with saturated aqueous NH₄Cl solution (5 mL), the mixture was treated with EtOAc (100 mL) and washed with H₂O, brine and dried with Na₂SO₄. Removal of the solvent under reduced pressure followed by flash chromatography of the residue on silica gel (0:100-10:90 EtOAc/hexanes) yielded 5-tert-butyl-4-chloro-2-methyl-2H-pyrazole-3-carboxylic acid [2-[2-(tert-butyl-dimethyl-silanyloxy)-ethoxy]-3-nitro-6-(2-trifluoromethyl-phenyl)-pyridin-4-yl]-amide as a white solid. ¹H-NMR (400 MHz, CD₃OD) δ: 10.10 (s, 1H), 8.33 (s, 1H), 7.81 (d, J=7.6 Hz, 1H), 7.62-7.70 (m, 1H), 7.52-7.62 (m, 2H), 4.51-4.61 (m, 2H), 4.11 (s, 3H), 3.94-4.01 (m, 2H), 1.42 (s, 9H), 0.89 (s, 9H), 0.07 (s, 6H). Mass Spectrum (LCMS, ESI pos.) Calculated For $C_{29}H_{37}ClF_3N_5O_5Si$: 656.2 (M+H). Measured: 656.2.

STEP E: 2-(5-tert-Butyl-4-chloro-2-methyl-2H-pyrazol-3-yl)-4-[2-(tert-butyl-dimethyl-silanyloxy)-ethoxy]-6-(2-trifluoromethyl-phenyl)-3H-imidazo[4,5-c]pyridine A mixture of 5-tert-butyl-4-chloro-2-methyl-2H-pyrazole-3-carboxylic acid [2-[2-(tert-butyl-dimethyl-silanyloxy)-ethoxy]-3-nitro-6-(2-trifluoromethyl-phenyl)-pyridin-4-yl]-amide (428 mg, 0.650 mmol, prepared as described in the previous step) and iron powder (291 mg, 5.22 mmol) in 1:1 AcOH/EtOH (7 mL) was stirred at 100° C. under Ar for 1 h. After cooling to room temperature, the mixture was treated with EtOAc (20 mL) and filtered through diatomaceous earth. The filtrate was concentrated in vacuo and the residue was purified by flash chromatography on silica gel (0:100-10:90 EtOAc/hexanes) to yield 2-(5-tert-butyl-4-chloro-2-methyl-2H-pyrazol-3-yl)-4-[2-(tert-butyl-dimethyl-silanyloxy)-ethoxy]-6-(2-trifluoromethyl-phenyl)-3H-imidazo[4,5-c]pyridine as a white solid. ¹H-NMR (400 MHz, CD₃OD) δ: 7.81 (d, 1H), 7.65-7.71 (m, 1H), 7.55-7.62 (m, 2H), 7.31 (s, 1H), 4.64 (t, J=4.9 Hz, 2H), 4.02-4.10 (m, 5H), 1.44 (s, 9H), 0.86 (s, 9H), 0.06 (s, 6H). Mass Spectrum (LCMS, ESI pos.) Calculated For $C_{29}H_{37}ClF_3N_5O_2Si$: 608.2 (M+H). Measured: 608.3.

STEP F: 2-[2-(5-tert-Butyl-4-chloro-2-methyl-2H-pyrazol-3-yl)-6-(2-trifluoromethyl-phenyl)-3H-imidazo[4,5-c]pyridin-4-yloxy]-ethanol A mixture of 2-(5-tert-butyl-4-chloro-2-methyl-2H-pyrazol-3-yl)-4-[2-(tert-butyl-dimethyl-silanyloxy)-ethoxy]-6-(2-trifluoromethyl-phenyl)-3H-imidazo[4,5-c]pyridine (390 mg, 0.641 mmol, prepared as described in the previous step) and tetrabutylammonium fluoride hydrate (914 mg, 3.21 mmol) in THF (10 mL) was stirred at 50° C. for 18 h. After cooling to room temperature, the resulting mixture was treated with EtOAc (50 mL) and washed with H₂O (2×20 mL), brine (20 mL). The organic layer was dried with Na₂SO₄ and concentrated in vacuo. The residue was purified by flash chromatography on silica gel (40:60-60:40 EtOAc/heptane) to yield 2-[2-(5-tert-butyl-4-chloro-2-methyl-2H-pyrazol-3-yl)-6-(2-trifluoromethyl-phenyl)-3H-imidazo[4,5-c]pyridin-4-yloxy]-ethanol as a white solid. ¹H-NMR (400 MHz, CD₃OD) δ: 7.67 (dd, J=7.3, 2.0 Hz, 1H), 7.48-7.56 (m, 2H), 7.39 (td, J=6.7, 1.8 Hz, 2H), 4.64-4.68 (m, 2H), 4.05 (s, 3H), 3.97-4.02 (m, 2H), 1.42-1.49 (m, 9H). Mass Spectrum (LCMS, ESI pos.) Calculated For $C_{23}H_{23}ClF_3N_5O_2$: 492.2 (M+H). Measured: 492.4.

Following the procedure described in Example 11, above, and substituting suitably selected and substituted reagents, starting materials and conditions as would be readily apparent to those skilled in the art, the following representative compounds of the present invention were prepared.

| Cmpd 58 | 2-[2-(5-tert-Butyl-4-chloro-2-methyl-2H-pyrazol-3-yl)-6-(2-chloro-phenyl)-3H-imidazo[4,5-c]pyridin-4-yloxy]-ethanol<br>¹H-NMR (400 MHz, CD₃OD) δ: 7.67 (dd, J = 7.3, 2.0 Hz, 1H), 7.48-7.56 (m, 2H), 7.32-7.45 (m, 2H), 4.64-4.68 (m, 2H), 4.05 (s, 3H), 3.97-4.02 (m, 2H), 1.44 (s, 9H).<br>Mass Spectrum (LCMS, ESI pos.) Calculated For $C_{22}H_{23}Cl_2N_5O_2$: 460.1 (M + H), Measured: 460.2. |
|---|---|
| Cmpd 83 | 3-tert-Butyl-5-[6-(2-chloro-phenyl)-4-(2-hydroxy-ethoxy)-3H-imidazo[4,5-c]pyridin-2-yl]-1-methyl-1H-pyrazole-4-carbonitrile<br>¹H-NMR (400 MHz, CD₃OD) δ: 7.64-7.71 (m, 1H), 7.49-7.56 (m, 2H), 7.34-7.44 (m, 2H), 4.64-4.71 (m, 2H), 4.11 (s, 3H), 3.97-4.04 (m, 2H), 1.47 (s, 9H).<br>Mass Spectrum (LCMS, ESI pos.) Calculated For $C_{23}H_{23}ClN_6O_2$: 451.2 (M + H), Measured: 451.1. |
| Cmpd 84 | 3-tert-Butyl-5-[4-(2-hydroxy-ethoxy)-6-(2-trifluoromethyl-phenyl)-3H-imidazo[4,5-c]pyridin-2-yl]-1-methyl-1H-pyrazole-4-carbonitrile<br>¹H-NMR (400 MHz, CDCl₃) δ: 7.82 (d, J = 7.3 Hz, 1H), 7.66-7.74 (m, 1H), 7.56-7.66 (m, 2H), 7.35 (s, 1H), 4.60-4.67 (m, 2H), 4.12 (s, 3H), 3.94-4.01 (m, 2H), 1.48 (s, 9H).<br>Mass Spectrum (LCMS, ESI pos.) Calculated For $C_{24}H_{23}F_3N_6O_2$: 485.2 (M + H), Measured: 485.2. |

Example 12

[2-(5-tert-Butyl-4-chloro-2-methyl-2H-pyrazol-3-yl)-6-(2-trifluoromethyl-phenyl)-3H-imidazo[4,5-c]pyridin-4-yloxy]-acetic acid (Compound #88)

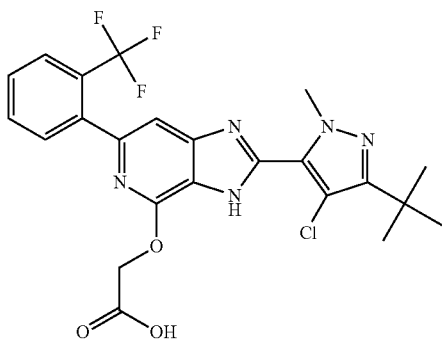 [SMILES: Cn1nc(C(C)(C)C)c(Cl)c1-c1nc2cc(-c3ccccc3C(F)(F)F)nc(OCC(=O)O)c2[nH]1]

STEP A: [2-(5-tert-Butyl-4-chloro-2-methyl-2H-pyrazol-3-yl)-6-(2-trifluoromethyl-phenyl)-3H-imidazo[4,5-c]pyridin-4-yloxy]-acetaldehyde To a suspension of 2-[2-(5-tert-butyl-4-chloro-2-methyl-2H-pyrazol-3-yl)-6-(2-trifluoromethyl-phenyl)-3H-imidazo[4,5-c]pyridin-4-yloxy]-ethanol (230 mg, 0.466 mmol, prepared as described in Example 11, STEP F) in DCM (10 mL) at 0° C. was added Dess-Martin periodinane (395 mg, 0.931 mmol). The resulting mixture was warmed to room temperature and stirred for 2 h. The reaction was then quenched by adding aqueous 10% $Na_2S_2O_3$ solution (20 mL). The resulting mixture was treated with EtOAc (50 mL) and washed with saturated $NaHCO_3$ solution (20 mL), $H_2O$ (20 mL) and brine (20 mL). After drying with $Na_2SO_4$, the resulting solution was concentrated in vacuo and the residue was purified by flash chromatography on silica gel (20:80-50:50 EtOAc/hexanes) to yield [2-(5-tert-butyl-4-chloro-2-methyl-2H-pyrazol-3-yl)-6-(2-trifluoromethyl-phenyl)-3H-imidazo[4,5-c]pyridin-4-yloxy]-acetaldehyde as a yellow solid. $^1$H-NMR (400 MHz, $CDCl_3$) δ: 7.67 (dd, J=7.5, 1.9 Hz, 1H), 7.49-7.54 (m, 2H), 7.35-7.44 (m, J=7.3, 7.3, 7.3, 7.3, 1.6 Hz, 2H), 5.07 (t, J=4.9 Hz, 1H), 4.52 (dd, J=4.8, 1.5 Hz, 2H), 4.04 (s, 3H), 1.45 (s, 9H). Mass Spectrum (LCMS, ESI pos.) Calculated For $C_{23}H_{21}F_3N_5O_2$: 492.1 (M+H). Measured: 492.1.

STEP B: [2-(5-tert-Butyl-4-chloro-2-methyl-2H-pyrazol-3-yl)-6-(2-trifluoromethyl-phenyl)-3H-imidazo[4,5-c]pyridin-4-yloxy]-acetic acid To a mixture of [2-(5-tert-butyl-4-chloro-2-methyl-2H-pyrazol-3-yl)-6-(2-trifluoromethyl-phenyl)-3H-imidazo[4,5-c]pyridin-4-yloxy]-acetaldehyde (30.0 mg, 0.0610 mmol, prepared as described in the previous step) in 5:5:2 tart-BuOH/2-methyl-2-butene/$H_2O$ (1.2 mL) was added sodium chlorite (11.6 mg, 0.128 mmol) followed by sodium dihydrogen phosphate (17.8 mg, 0.183 mmol). After stirring at room temperature for 16 h, the resulting mixture was treated with 1N NaOH (2 mL) and concentrated in vacuo. The resulting residue was treated with $H_2O$ (20 mL) and washed with EtOAc (2×10 mL). The aqueous phase was acidified to pH 5 by adding HOAc and then extracted with EtOAc (3×15 mL). The combined organic layers were washed with $H_2O$ (15 mL), brine (15 mL) and then dried with $Na_2SO_4$. Removal of the solvent in vacuo yielded [2-(5-tert-butyl-4-chloro-2-methyl-2H-pyrazol-3-yl)-6-(2-trifluoromethyl-phenyl)-3H-imidazo[4,5-c]pyridin-4-yloxy]-acetic acid as a light yellow solid. $^1$H-NMR (400 MHz, $CD_3OD$) δ: 7.13-8.04 (m, 5H), 5.10 (s, 2H), 4.06 (s, 3H), 1.43 (s, 9H). Mass Spectrum (LCMS, ESI pos.) Calculated For $C_{23}H_{21}ClF_3N_5O_3$: 508.1 (M+H). Measured: 508.1.

Following the procedure described in Example 12 above, and substituting suitably selected and substituted reagents, starting materials and conditions as would be readily apparent to those skilled in the art, the following representative compounds of the present invention were prepared.

| Cmpd | |
|---|---|
| 85 | [2-(5-tert-Butyl-4-cyano-2-methyl-2H-pyrazol-3-yl)-6-(2-chloro-phenyl)-3H-imidazo[4,5-c]pyridin-4-yloxy]-acetic acid<br>$^1$H-NMR (400 MHz, $CD_3OD$) δ: 7.61-7.66 (m, 1H), 7.58 (s, 1H), 7.45-7.50 (m, 1H), 7.30-7.38 (m, 2H), 5.12 (s, 2H), 4.11 (s, 3H), 2.76-2.96 (m, 4H), 1.45 (s, 9H).<br>Mass Spectrum (LCMS, ESI pos.) Calculated For $C_{23}H_{21}ClN_6O_3$: 465.1 (M + H), Measured: 465.1. |
| 86 | [2-(5-tert-Butyl-4-cyano-2-methyl-2H-pyrazol-3-yl)-6-(2-trifluoromethyl-phenyl)-3H-imidazo[4,5-c]pyridin-4-yloxy]-acetic acid<br>$^1$H-NMR (400 MHz, $CDCl_3$) δ: 7.78-7.83 (m, 1H), 7.64-7.71 (m, 1H), 7.55-7.62 (m, 2H), 7.40 (s, 1H), 5.13 (s, 2H), 4.13 (s, 3H), 2.75-2.96 (m, 4H), 1.48 (s, 9H).<br>Mass Spectrum (LCMS, ESI pos.) Calculated For $C_{24}H_{21}F_3N_6O_3$: 499.2 (M + H), Measured: 499.1. |
| 87 | [2-(5-tert-Butyl-4-chloro-2-methyl-2H-pyrazol-3-yl)-6-(2-chloro-phenyl)-3H-imidazo[4,5-c]pyridin-4-yloxy]-acetic acid<br>$^1$H-NMR (400 MHz, $CD_3OD$) δ: 7.11-8.06 (m, 5H), 5.10 (s, 2H), 4.06 (s, 3H), 1.46 (s, 9H).<br>Mass Spectrum (LCMS, ESI pos.) Calculated For $C_{22}H_{21}Cl_2N_5O_3$: 474.1 (M + H), Measured: 474.1. |

Example 13

{2-[2-(5-tert-Butyl-4-chloro-2-methyl-2H-pyrazol-3-yl)-6-(2-trifluoromethyl-phenyl)-3H-imidazo[4,5-c]pyridin-4-yloxy]-ethyl}-dimethyl-amine (Compound #53)

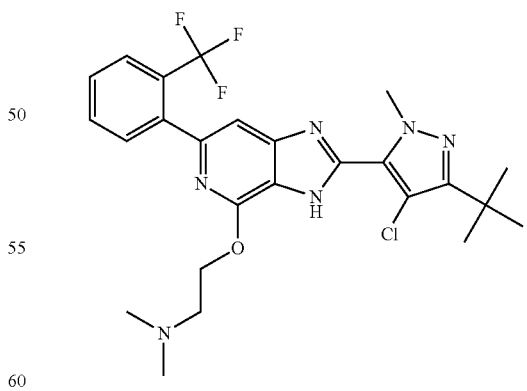

To a mixture of [2-(5-tert-butyl-4-chloro-2-methyl-2H-pyrazol-3-yl)-6-(2-trifluoromethyl-phenyl)-3H-imidazo[4,5-c]pyridin-4-yloxy]-acetaldehyde (40.0 mg, 0.0813 mmol, prepared as described in Example 12, STEP A) in 30:1 MeOH/AcOH (2 mL) was added 2.0 M dimethyl amine in THF (81.3 µL, 0.163 mmol) followed by sodium cyanoborohydride (10.2 mg, 0.163 mmol). After stirring at room temperature for 18 h, the resulting mixture was treated with EtOAc (50 mL) and washed with saturated aqueous NH$_4$Cl (20 mL), H$_2$O (20 mL) and brine (20 mL). The organic layer was dried with Na$_2$SO$_4$ and concentrated in vacuo. The resulting residue was purified by flash chromatography on silica gel (0:100-10:90 MeOH/DCM) to yield {2-[2-(5-tert-Butyl-4-chloro-2-methyl-2H-pyrazol-3-yl)-6-(2-trifluoromethyl-phenyl)-3H-imidazo[4,5-c]pyridin-4-yloxy]-ethyl}-dimethyl-amine as a light yellow solid. $^1$H-NMR (400 MHz, CD$_3$OD) δ: 7.84 (d, J=7.6 Hz, 1H), 7.67-7.75 (m, 1H), 7.58-7.66 (m, 2H), 7.37-7.43 (m, 1H), 4.80-4.86 (m, 2H), 4.03 (s, 3H), 3.47-3.55 (m, 2H), 2.88 (s, 6H), 1.45 (s, 9H). Mass Spectrum (LCMS, ESI pos.) Calculated For C$_{25}$H$_{28}$ClF$_3$N$_6$O: 521.2 (M+H). Measured: 521.2.

Following the procedure described in Example 13 above, and substituting suitably selected and substituted reagents, starting materials and conditions as would be readily apparent to those skilled in the art, the following representative compounds of the present invention were prepared.

Example 14

2-(5-tert-Butyl-4-chloro-2-methyl-2H-pyrazol-3-yl)-6-(2,6-dichloro-phenyl)-4-methoxy-3H-imidazo[4,5-c]pyridine sodium salt (Compound #103)

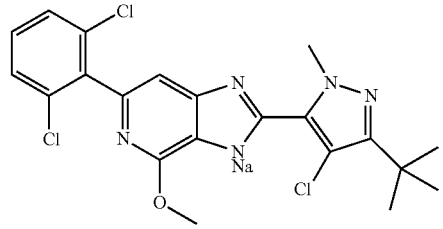

STEP A:
6-(2,6-Dichlorophenyl)-4-hydroxy-1H-pyridin-2-one

NaH (400 mg, 10.0 mmol, 60% mineral oil dispersion) was placed in a 100 mL round bottom flask equipped with a stir

| | |
|---|---|
| Cmpd 49 | 2-(5-tert-Butyl-4-chloro-2-methyl-2H-pyrazol-3-yl)-4-(2-morpholin-4-yl-ethoxy)-6-(2-trifluoromethyl-phenyl)-3H-imidazo[4,5-c]pyridine<br>$^1$H-NMR (400 MHz, CD$_3$OD) δ:: 7.79-7.84 (m, 1H), 7.66-7.72 (m, 1H), 7.57-7.63 (m, 2H), 7.34 (s, 1H), 4.75 (t, J = 5.6 Hz, 2H), 4.04 (s, 3H), 3.67-3.75 (m, 4H), 2.98 (t, J = 5.7 Hz, 2H), 2.60-2.76 (m, 4H), 1.43-1.46 (m, 9H).<br>Mass Spectrum (LCMS, ESI pos.) Calculated For C$_{27}$H$_{30}$ClF$_3$N$_6$O$_2$: 563.2 (M + H), Measured: 563.2. |
| Cmpd 50 | 2-(5-tert-Butyl-4-chloro-2-methyl-2H-pyrazol-3-yl)-4-[2-(4-methyl-piperazin-1-yl)-ethoxy]-6-(2-trifluoromethyl-phenyl)-3H-imidazo[4,5-c]pyridine<br>$^1$H-NMR (400 MHz, CD$_3$OD) δ: 7.80-7.85 (m, 1H), 7.67-7.74 (m, 1H), 7.57-7.64 (m, 2H), 7.34 (s, 1H), 4.75 (t, J = 5.5 Hz, 2H), 4.04 (s, 3H), 3.03 (t, J = 5.5 Hz, 2H), 2.86 (br. s., 8H), 2.61 (s, 3H), 1.45 (s, 9H).<br>Mass Spectrum (LCMS, ESI pos.) Calculated For C$_{28}$H$_{33}$ClF$_3$N$_7$O: 576.2 (M + H), Measured: 576.2. |
| Cmpd 51 | 2-(5-tert-Butyl-4-chloro-2-methyl-2H-pyrazol-3-yl)-6-(2-chloro-phenyl)-4-(2-pyrrolidin-1-yl-ethoxy)-3H-imidazo[4,5-c]pyridine<br>$^1$H-NMR (400 MHz, CD$_3$OD) δ: 7.66-7.71 (m, 1H), 7.56 (s, 1H), 7.51-7.55 (m, 1H), 7.37-7.47 (m, 2H), 4.87-4.91 (m, 2H), 4.04 (s, 3H), 3.70-3.75 (m, 2H), 3.42-3.50 (m, 4H), 2.03-2.11 (m, 4H), 1.45 (s, 9H).<br>Mass Spectrum (LCMS, ESI pos.) Calculated For C$_{26}$H$_{30}$Cl$_2$N$_6$O: 513.2 (M + H), Measured: 513.3. |
| Cmpd 52 | 2-(5-tert-Butyl-4-chloro-2-methyl-2H-pyrazol-3-yl)-4-(2-pyrrolidin-1-yl-ethoxy)-6-(2-trifluoromethyl-phenyl)-3H-imidazo[4,5-c]pyridine<br>$^1$H-NMR (400 MHz, CD$_3$OD) δ: 7.84 (d, J = 7.6 Hz, 1H), 7.69-7.75 (m, 1H), 7.59-7.67 (m, 2H), 7.41 (s, 1H), 4.83-4.87 (m, 2H), 4.04 (s, 3H), 3.68-3.74 (m, 2H), 3.47 (br. s., 4H), 2.06-2.12 (m, 4H), 1.45 (s, 9H).<br>Mass Spectrum (LCMS, ESI pos.) Calculated For C$_{27}$H$_{30}$ClF$_3$N$_6$O: 547.2 (M + H), Measured: 547.3. |
| Cmpd 54 | 2-(5-tert-Butyl-4-chloro-2-methyl-2H-pyrazol-3-yl)-6-(2-chloro-phenyl)-4-(2-morpholin-4-yl-ethoxy)-3H-imidazo[4,5-c]pyridine<br>$^1$H-NMR (400 MHz, CD$_3$OD) δ: 7.61-7.69 (m, 1H), 7.46-7.55 (m, 2H), 7.32-7.45 (m, 2H), 4.74-4.83 (m, 2H), 4.04 (s, 3H), 3.71 (br. s., 4H), 3.05 (br. s., 2H), 2.75 (br. s., 4H), 1.44 (br. s., 9H).<br>Mass Spectrum (LCMS, ESI pos.) Calculated For C$_{26}$H$_{30}$Cl$_2$N$_6$O$_2$: 529.2 (M + H), Measured: 529.3. |
| Cmpd 55 | 2-(5-tert-Butyl-4-chloro-2-methyl-2H-pyrazol-3-yl)-6-(2-chloro-phenyl)-4-[2-(4-methyl-piperazin-1-yl)-ethoxy]-3H-imidazo[4,5-c]pyridine<br>$^1$H-NMR (400 MHz, CD$_3$OD) δ: 7.64-7.69 (m, 1H), 7.50-7.55 (m, 1H), 7.50 (s, 1H), 7.35-7.45 (m, 2H), 4.78 (t, J = 5.6 Hz, 2H), 4.04 (s, 3H), 3.04 (t, J = 5.6 Hz, 2H), 2.83 (br. s., 8H), 2.52 (s, 3H), 1.44 (s, 9H).<br>Mass Spectrum (LCMS, ESI pos.) Calculated For C$_{27}$H$_{33}$Cl$_2$N$_7$O: 542.2 (M + H), Measured: 542.2. |
| Cmpd 56 | {2-[2-(5-tert-Butyl-4-chloro-2-methyl-2H-pyrazol-3-yl)-6-(2-chloro-phenyl)-3H-imidazo[4,5-c]pyridin-4-yloxy]-ethyl}-dimethyl-amine<br>$^1$H-NMR (400 MHz, CD$_3$OD) δ: 7.68 (dd, J = 7.2, 2.1 Hz, 1H), 7.55 (s, 1H), 7.51-7.54 (m, 1H), 7.36-7.45 (m, 2H), 4.82-4.88 (m, 2H), 4.04 (s, 3H), 3.44 (t, J = 5.3 Hz, 2H), 2.81 (s, 6H), 1.42-1.48 (m, 9H). Mass Spectrum (LCMS, ESI pos.) Calculated For C$_{24}$H$_{28}$Cl$_2$N$_6$O: 487.2 (M + H), Measured: 487.1. | bar and then evacuated and backflushed with Ar. Dry THF (30 mL) was added via syringe and methyl acetoacetate (1.08 mL, 10.0 mmol) was added dropwise via syringe to the stirred mixture. Once the solution was homogeneous, the mixture was cooled to −78° C. and n-BuLi (4.20 mL of a 2.5 M solution in hexanes, 10.5 mmol) was added dropwise via syringe at a rate that maintained the internal temperature below −70° C. The resulting mixture was stirred at −78° C. for 30 min and 2,6-dichlorobenzonitrile (1.72 g, 10.0 mmol) was added as a solid in one portion. The resulting solution was stirred at −78° C. allowing the reaction to warm to room temperature slowly overnight (~16 h).

The resulting mixture was then cooled in an ice bath and concentrated HCl was added dropwise at a rate that maintained the internal temperature below 5° C. to give a pH ~4. The resulting mixture was diluted with $H_2O$ (20 mL) and extracted with EtOAc (3×20 mL). The combined extracts were dried over MgSO4 and filtered. The solvent was removed under reduced pressure.

Toluene was added to the residue and the resulting mixture was refluxed for 24 h. The resulting mixture was then cooled to room temperature and the solid was isolated by filtration. The solid was washed with toluene (20 mL) and the residual solvent was removed under reduced pressure to yield 6-(2,6-dichlorophenyl)-4-hydroxy-1H-pyridin-2-one. $^1$H NMR (400 MHz, $CD_3OD$) δ: 7.50-7.56 (m, 2H), 7.43-7.49 (m, 1H), 5.99 (d, J=2.2 Hz, 1H), 5.84 (d, J=2.2 Hz, 1H).

STEP B: 6-(2,6-Dichloro-phenyl)-4-hydroxy-3-nitro-1H-pyridin-2-one 6-(2,6-Dichlorophenyl)-4-hydroxy-1H-pyridin-2-one (253 mg, 0.990 mmol, prepared as described in the previous step) was placed in a 8 mL vial equipped with a stir bar and AcOH (4 mL) was added. Concentrated $HNO_3$ (0.540 mL, 12.0 mmol) was added via syringe and the vial was capped and stirred at 60° C. for 14 hr. The resulting mixture was cooled to room temperature and poured onto crushed ice (20 mL). The precipitate was isolated by filtration and washed with $H_2O$ (10 mL). The solid was air-dried to yield 6-(2,6-Dichloro-phenyl)-4-hydroxy-3-nitro-1H-pyridin-2-one as a yellow powder. The filtrate was extracted with EtOAc (3×10 mL) and the combined extracts were washed with $H_2O$ (20 mL), dried over $MgSO_4$ and filtered. The solvent was removed under reduced pressure to yield an additional crop of 6-(2,6-dichloro-phenyl)-4-hydroxy-3-nitro-1H-pyridin-2-one. $^1$H-NMR (400 MHz, $CD_3OD$) δ: 7.48-7.61 (m, 3H), 6.13 (s, 1H).

STEP C: 2,4-Dichloro-6-(2,6-dichloro-phenyl)-3-nitro-pyridine 6-(2,6-Dichloro-phenyl)-4-hydroxy-3-nitro-1H-pyridin-2-one (208 mg, 0.689 mmol, prepared as described in the previous step) was placed in a 8 mL vial equipped with a stir bar and $POCl_3$ (4 mL) was added. The resulting mixture was stirred at 100° C. for 24 h, cooled to room temperature, and poured onto crushed ice. The solid was isolated by filtration, dissolved in DCM (20 mL), dried over $MgSO_4$, and filtered. The solvent was removed under reduced pressure and the resulting residue was chromatographed on a 24-g $SiO_2$ pre-packed column eluting with 0:1-1:0 EtOAc/heptane to yield 2,4-dichloro-6-(2,6-dichloro-phenyl)-3-nitro-pyridine. $^1$H-NMR (400 MHz, $CDCl_3$) δ: 7.51 (s, 1H), 7.41-7.48 (m, 2H), 7.33-7.41 (m, 1H).

STEP D: 2-Chloro-6-(2,6-dichlorophenyl)-3-nitropyridin-4-ylamine 2,4-Dichloro-6-(2,6-dichloro-phenyl)-3-nitro-pyridine (94.4 mg, 0.279 mmol, prepared as described in the previous step) was placed in a 8 mL vial equipped with a stir bar and dry MeOH (2 mL) was added via syringe. The resulting solution was gently heated with a heat gun to dissolve the solid and 7M $NH_3$ in MeOH (2.00 mL, 14.0 mmol) was added via syringe. The resulting mixture was stirred at room temperature for 16 h and the solvent was removed under reduced pressure. The resulting residue was purified by preparative thin layer chromatography (TLC) on a 2000μ $SiO_2$ plate developed with 1:4 EtOAc/heptane to yield 2-chloro-6-(2,6-dichlorophenyl)-3-nitropyridin-4-ylamine. $^1$H-NMR (400 MHz, $CDCl_3$) δ: 7.33-7.45 (m, 2H), 7.27-7.33 (m, 1H), 6.68 (s, 1H), 5.86 (br. s., 2H). LCMS (ESI): Calculated for $C_{11}H_6ClN_3O_2$: 318.0 (M+H). Measured: 318.0.

STEP E: 6-(2,6-Dichlorophenyl)-2-methoxy-3-nitropyridin-4-ylamine

2-Chloro-6-(2,6-dichlorophenyl)-3-nitropyridin-4-ylamine (28.7 mg, 0.0901 mmol, prepared as described in the previous step) was placed in a 8 mL vial equipped with a stir bar and anhydrous MeOH (1 mL) was added via syringe. NaOMe (0.5 M in MeOH, (0.396 mL, 0.198 mmol) was added to the stirred mixture, which was then stirred at 65° C. for 4 h. The solvent was removed under reduced pressure and the residue was chromatographed on a 12-g $SiO_2$ pre-packed column eluting with 0:1-2:3 EtOAc/heptane to yield 6-(2,6-dichlorophenyl)-2-methoxy-3-nitropyridin-4-ylamine. $^1$H-NMR (400 MHz, $CDCl_3$) δ: 7.37-7.41 (m, 2H), 7.25-7.30 (m, 1H), 6.35 (s, 1H), 6.15 (br. s., 2H), 4.01 (s, 3H).

STEP F: 2-(5-tert-Butyl-4-chloro-2-methyl-2H-pyrazol-3-yl)-6-(2,6-dichloro-phenyl)-4-methoxy-3H-imidazo[4,5-c]pyridine Following the procedure described in Example 25, STEP C, 2-(5-tert-butyl-4-chloro-2-methyl-2H-pyrazol-3-yl)-6-(2,6-dichloro-phenyl)-4-methoxy-3H-imidazo[4,5-c]pyridine was prepared from 6-(2,6-dichlorophenyl)-2-methoxy-3-nitropyridin-4-ylamine (24.2 mg, 0.0770 mmol, prepared as described in the previous step) and 5-tert-butyl-4-chloro-2-methyl-2H-pyrazole-3-carbonyl chloride (18.1 mg, 0.0770 mmol, prepared as described in Example 1, STEP C). $^1$H-NMR (400 MHz, $CD_3OD$) δ: 7.47-7.53 (m, J=8.3 Hz, 2H), 7.39 (dd, J=8.8, 7.3 Hz, 1H), 7.21 (s, 1H), 4.12 (s, 3H), 4.04 (s, 3H), 1.45 (s, 9H). Mass Spectrum (LCMS, ESI pos.): Calculated for $C_{21}H_{20}Cl_3N_5O$: 464.1 (M+H). Measured: 464.0.

STEP G: 2-(5-tert-Butyl-4-chloro-2-methyl-2H-pyrazol-3-yl)-6-(2,6-dichloro-phenyl)-4-methoxy-3H-imidazo[4,5-c]pyridine sodium salt Following the procedure described in Example 1, STEP F, the 2-(5-tert-Butyl-4-chloro-2-methyl-2H-pyrazol-3-yl)-6-(2,6-dichloro-phenyl)-4-methoxy-3H-imidazo[4,5-c]pyridine sodium salt was prepared from 2-(5-tert-butyl-4-chloro-2-methyl-2H-pyrazol-3-yl)-6-(2,6-dichlorophenyl)-4-methoxy-3H-imidazo[4,5-c]pyridine (11.6 mg, 0.0250 mmol, prepared as described in the previous step) and 0.5 M NaOMe in MeOH (50.0 μL, 0.0.0250 mmol) as a white foam. $^1$H-NMR (400 MHz, $d_6$-DMSO) δ: 7.51-7.55 (m, 2H), 7.39 (dd, J=8.7, 7.5 Hz, 1H), 7.00 (s, 1H), 4.02 (s, 3H), 3.89 (s, 3H), 1.39 (s, 9H). Mass Spectrum (LCMS, ESI pos.): Calculated for $C_{21}H_{20}Cl_3N_5O$: 464.1 (M+H). Measured: 464.0.

Example 15

2-(5-tert-Butyl-4-methoxy-2-methyl-2H-pyrazol-3-yl)-4-methoxy-6-(2-trifluoromethyl-phenyl)-3H-imidazo[4,5-c]pyridine methanesulfonic acid salt (Compound #79); and 2-(5-tert-Butyl-2-methyl-2H-pyrazol-3-yl)-4-methoxy-6-(2-trifluoromethyl-phenyl)-3H-imidazo[4,5-c]pyridine methanesulfonic acid salt (Compound #80)

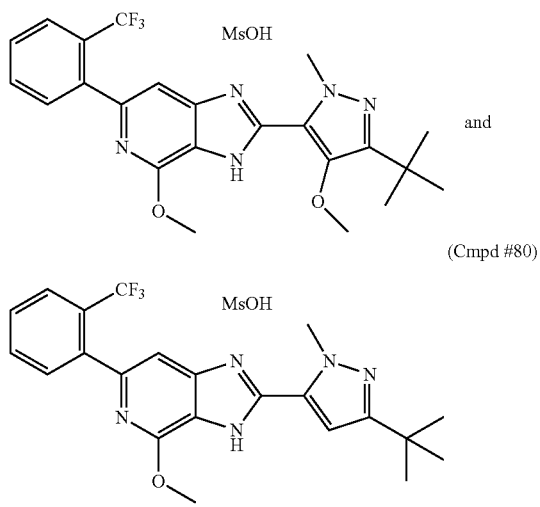

(Cmpd #79)

and (Cmpd #80)

STEP A: 2-(5-tert-butyl-4-methoxy-2-methyl-2H-pyrazol-3-yl)-4-methoxy-6-(2-trifluoromethyl-phenyl)-3H-imidazo[4,5-c]pyridine and 2-(5-tert-Butyl-2-methyl-2H-pyrazol-3-yl)-4-methoxy-6-(2-trifluoromethyl-phenyl)-3H-imidazo[4,5-c]pyridine 5-tert-Butyl-4-methoxy-2-methyl-2H-pyrazole-3-carboxylic acid (49.7 mg, 0.234 mmol, prepared as described in Example E) was dissolved in DCM (2 mL) and DMF (10 µL) was added. Oxalyl chloride (30.6 µL, 0.351 mmol) was added via syringe and the resulting mixture was stirred at room temperature for 1 h. The solvent was removed under reduced pressure and the residue was dissolved in anhydrous THF (3 mL).

A solution of 2-methoxy-3-nitro-6-(2-trifluoromethyl-phenyl)-4-pyridin-4-ylamine (73.3 mg, 0.234 mmol, prepared as described in Example 5, STEP B) in anhydrous THF (3 mL) under Ar was cooled to 0° C. in an ice bath and treated with NaH (28.1 mg of 60% mineral oil dispersion, 0.702 mmol). The THF solution of the acid chloride (prepared as described above) was then added dropwise to the stirred mixture. The resulting mixture was then stirred at 0° C. for 1 h and then poured onto ice (20 mL) and extracted with EtOAc (3×20 mL). The combined extracts were dried over MgSO₄, filtered, and the solvent was removed under reduced pressure.

The resulting residue was dissolved in glacial AcOH (2 mL) and Fe powder (65.3 mg, 1.17 mmol) was added. The resulting mixture was stirred at 100° C. for 1 h and the cooled mixture was poured into ice (20 mL). The resulting aqueous solution was extracted with EtOAc (3×20 mL) and the combined extracts were washed with 1 M LiOH (20 mL) and brine (20 mL). The organic layer was dried over MgSO₄ and filtered. The solvent was removed under reduced pressure and the resulting residue was chromatographed on a 24-g SiO₂ pre-packed column eluting with 0:1-4:1 EtOAc/hexanes to yield 2-(5-tert-butyl-4-methoxy-2-methyl-2H-pyrazol-3-yl)-4-methoxy-6-(2-trifluoro-methyl-phenyl)-3H-imidazo[4,5-c]pyridine. ¹H-NMR (400 MHz, CD₃OD) δ: 7.81 (d, J=7.8 Hz, 1H), 7.65-7.72 (m, 1H), 7.55-7.63 (m, 2H), 7.31 (s, 1H), 4.12 (s, 3H), 4.03 (s, 3H), 3.62 (s, 3H), 1.39 (s, 9H). Mass Spectrum (LCMS, ESI pos.): Calculated for $C_{23}H_{24}F_3N_5O_2$: 460.2 (M+H). Measured: 460.2.

Also isolated was 2-(5-tert-butyl-2-methyl-2H-pyrazol-3-yl)-4-methoxy-6-(2-trifluoromethyl-phenyl)-3H-imidazo[4,5-c]pyridine. ¹H-NMR (400 MHz, CD₃OD) δ: 7.81 (d, J=7.8 Hz, 1H), 7.69 (t, J=7.5 Hz, 1H), 7.54-7.64 (m, 2H), 7.26 (br. s., 1H), 6.79 (br. s., 1H), 4.26 (s, 3H), 4.12 (s, 3H), 1.36 (s, 9H). Mass Spectrum (LCMS, ESI pos.): Calculated for $C_{22}H_{22}F_3N_5O$: 430.2 (M+H). Measured: 430.2.

STEP B: 2-(5-tert-Butyl-4-methoxy-2-methyl-2H-pyrazol-3-yl)-4-methoxy-6-(2-trifluoro-methyl-phenyl)-3H-imidazo[4,5-c]pyridine methanesulfonic acid salt 2-(5-tert-butyl-4-methoxy-2-methyl-2H-pyrazol-3-yl)-4-methoxy-6-(2-trifluoro-methyl-phenyl)-3H-imidazo[4,5-c]pyridine (54.4 mg, 0.118 mmol, prepared in Step A above) was dissolved in EtOAc (1 mL) and 0.5 M MsOH in EtOAc (237 µL, 0.118 mmol) was added. The resulting solution was thoroughly mixed and the solvent was removed under reduced pressure to yield 2-(5-tert-Butyl-4-methoxy-2-methyl-2H-pyrazol-3-yl)-4-methoxy-6-(2-trifluoro-methyl-phenyl)-3H-imidazo[4,5-c]pyridine methanesulfonic acid salt. ¹H-NMR (400 MHz, DMSO-d₆) δ: 7.82-7.90 (m, 1H), 7.72-7.80 (m, 1H), 7.61-7.69 (m, 2H), 7.32 (s, 1H), 4.02 (s, 3H), 4.01 (s, 3H), 3.61 (s, 3H), 2.34 (s, 3H), 1.35 (s, 9H). Mass Spectrum (LCMS, ESI pos.): Calculated for $C_{23}H_{24}F_3N_5O_2$: 460.2 (M+H). Measured: 460.2.

STEP C: 2-(5-tert-Butyl-2-methyl-2H-pyrazol-3-yl)-4-methoxy-6-(2-trifluoromethyl-phenyl)-3H-imidazo[4,5-c]pyridine methanesulfonic acid salt 2-(5-tert-Butyl-2-methyl-2H-pyrazol-3-yl)-4-methoxy-6-(2-trifluoromethyl-phenyl)-3H-imidazo[4,5-c]pyridine (9.2 mg, 0.021 mmol, prepared as in STEP A) was dissolved in EtOAc (1 mL) and 0.5 M MsOH in EtOAc (41 µL, 0.021 mmol) was added. The resulting solution was thoroughly mixed and the solvent was removed under reduced pressure to yield 2-(5-tert-Butyl-2-methyl-2H-pyrazol-3-yl)-4-methoxy-6-(2-trifluoromethyl-phenyl)-3H-imidazo[4,5-c]pyridine methanesulfonic acid salt. ¹H-NMR (400 MHz, acetone-d₆) δ: 7.88 (d, J=8.1 Hz, 1H), 7.74-7.80 (m, 1H), 7.66-7.73 (m, 2H), 7.62 (s, 1H), 7.17 (s, 1H), 4.36 (s, 3H), 4.33 (s, 3H), 2.80 (s, 3H), 1.33 (s, 9H). Mass Spectrum (LCMS, ESI pos.): Calculated for $C_{22}H_{22}F_3N_5O$: 430.2 (M+H). Measured: 430.2.

Example 16

3-tert-Butyl-5-[4-chloro-6-(2-trifluoromethyl-phenyl)-3H-imidazo[4,5-c]pyridin-2-yl]-1-methyl-1H-pyrazole-4-carbonitrile Hydrochloride (Compound #75)

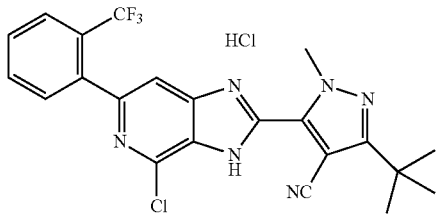 [SMILES: Cn1nc(C(C)(C)C)c(C#N)c1-c1nc2cc(-c3ccccc3C(F)(F)F)nc(Cl)c2[nH]1 ; Cl]

STEP A: 5-Nitro-2-(2-trifluoromethyl-phenyl)-pyridin-4-ylamine

2-Bromo-5-nitropyridin-4-amine (561 mg, 2.57 mmol), $Cs_2CO_3$ (2.52 g, 7.72 mmol), (dppf)PdCl$_2$·DCM (113 mg, 0.154 mmol), and 2-(trifluoromethyl)phenylboronic acid (636 mg, 3.35 mmol) were combined and flushed with Ar and anhydrous DME (24 mL) was added. $H_2O$ (8 mL) was added via syringe and the resulting mixture was stirred at 85° C. for 18 h. The resulting mixture was cooled to room temperature and diluted with EtOAc (30 mL) and the resulting solution was washed with brine (30 mL). The aqueous phase was extracted with EtOAc (3×25 mL) and the combined extracts were dried over $MgSO_4$ and filtered. The solvent was removed under reduced pressure and the residue was chromatographed on a 40-g $SiO_2$ pre-packed column eluting with 0:1-2:3 EtOAc/hexanes to yield 5-nitro-2-(2-trifluoromethyl-phenyl)-pyridin-4-ylamine. $^1$H-NMR (400 MHz, CDCl$_3$) δ: 9.17 (s, 1H), 7.70 (d, J=7.8 Hz, 1H), 7.56 (t, J=7.1 Hz, 1H), 7.49 (t, J=7.5 Hz, 1H), 7.40 (d, J=7.6 Hz, 1H), 7.00 (br. s., 2H), 6.71 (s, 1H). Mass Spectrum (LCMS, ESI pos.): Calculated for $C_{12}H_8F_3N_3O_2$: 284.1 (M+H). Measured: 284.1.

STEP B: 2-Chloro-6-(2-trifluoromethyl-phenyl)-pyridine-3,4-diamine

5-Nitro-2-(2-trifluoromethyl-phenyl)-pyridin-4-ylamine (749 mg, 2.65 mmol, prepared as in the previous step) was dissolved in concentrated HCl (12 mL) and heated to 90° C. $SnCl_2·2H_2O$ (2.98 g, 13.2 mmol) was added to the stirred mixture in small portions and resulting mixture was stirred at 90° C. for 1 h. After completion of addition, the resulting mixture was cooled to 0° C. in an ice bath, treated with 6 M aqueous NaOH (30 mL) and then extracted with DCM (3×40 mL). The combined extracts were dried over $MgSO_4$ and filtered. The solvent was removed under reduced pressure and the residue was chromatographed on a 40-g $SiO_2$ pre-packed column eluting with 0:1-3:2 EtOAc/hexanes to yield 2-chloro-6-(2-trifluoromethyl-phenyl)-pyridine-3,4-diamine. $^1$H-NMR (400 MHz, CDCl$_3$) δ: 7.67 (d, J=7.8 Hz, 1H), 7.47-7.55 (m, 1H), 7.37-7.46 (m, 2H), 6.57 (s, 1H), 4.09 (br s., 2H), 3.74 (br. s., 2H).

STEP C: 3-tert-Butyl-5-[4-chloro-6-(2-trifluoromethyl-phenyl)-3H-imidazo[4,5-c]pyridin-2-yl]-1-methyl-1H-pyrazole-4-carbonitrile 3-tert-butyl-4-cyanopyrazole-5-carboxylic acid (92.6 mg, 0.447 mmol, prepared as in Example C) was dissolved in DCM (2 mL) and DMF (10 μL) and oxalyl chloride (53.1 μL, 0.609 mmol) were added. The resulting mixture was stirred at room temperature for 1 h and the solvent was removed under reduced pressure. The residue was dissolved in DCM (2 mL).

2-Chloro-6-(2-trifluoromethyl-phenyl)-pyridine-3,4-diamine (117 mg, 0.406 mmol, prepared as in STEP B above) was dissolved in DCM (3 mL) and DIEA (141 μL, 0.812 mmol) was added. The acid chloride solution was added dropwise to the stirred mixture, which was then stirred at room temperature for an additional 18 h. The solvent was removed under reduced pressure and the residue was dissolved in POCl$_3$ (1.5 mL). The resulting solution was stirred for 16 h at 100° C. and then cooled to room temperature and poured onto ice (~20 mL). After the POCl$_3$ had been consumed, the resulting precipitate was isolated by filtration and washed with $H_2O$ (2×20 mL). The solid was dissolved in DCM (25 mL) and the solution was dried over $MgSO_4$ and filtered. The solvent was removed under reduced pressure and the crude product was chromatographed on a 40-g $SiO_2$ pre-packed column eluting with 0:1-2:3 EtOAc/hexanes to yield 3-tert-Butyl-5-[4-chloro-6-(2-trifluoromethyl-phenyl)-3H-imidazo[4,5-c]pyridin-2-yl]-1-methyl-1H-pyrazole-4-carbonitrile. $^1$H-NMR (400 MHz, CD$_3$OD) δ: 7.85 (d, J=7.8 Hz, 1H), 7.68-7.76 (m, 2H), 7.62-7.68 (m, 1H), 7.60 (d, J=7.6 Hz, 1H), 4.19 (s, 3H), 1.48 (s, 9H). Mass Spectrum (LCMS, ESI pos.): Calculated for $C_{22}H_{18}ClF_3N_6$: 459.1 (M+H). Measured: 459.2.

STEP D: 3-tert-Butyl-5-[4-chloro-6-(2-trifluoromethyl-phenyl)-3H-imidazo[4,5-c]pyridin-2-yl]-1-methyl-1H-pyrazole-4-carbonitrile hydrochloride A solution of 3-tert-Butyl-5-[4-chloro-6-(2-trifluoromethyl-phenyl)-3H-imidazo[4,5-c]pyridin-2-yl]-1-methyl-1H-pyrazole-4-carbonitrile (111 mg, 0.241 mmol, prepared as in the previous step) in EtOAc (1 mL) was treated with 1 M HCl in Et$_2$O solution (0.241 mL, 0.241 mmol). The resulting mixture was thoroughly mixed and the solvent was removed under reduced pressure to yield 3-tert-butyl-5-[4-chloro-6-(2-trifluoromethyl-phenyl)-3H-imidazo[4,5-c]pyridin-2-yl]-1-methyl-1H-pyrazole-4-carbonitrile hydrochloride. $^1$H-NMR (400 MHz, DMSO-d$_6$) δ: 7.90 (d, J=7.6 Hz, 1H), 7.84 (s, 1H), 7.80 (t, J=7.3 Hz, 1H), 7.71 (t, J=7.6 Hz, 1H), 7.66 (d, J=7.6 Hz, 1H), 4.11 (s, 3H), 1.44 (s, 9H). Mass Spectrum (LCMS, ESI pos.): Calculated for $C_{22}H_{18}ClF_3N_6$: 459.1 (M+H). Measured: 459.2.

Following the procedure described in Example 16, above, and substituting suitably selected and substituted reagents, starting materials and conditions as would be readily apparent to those skilled in the art, the following representative compounds of the present invention were prepared.

| Cmpd | |
|---|---|
| 72 | 3'-{4-Chloro-6-[2-(trifluoromethyl)phenyl]-1H-imidazo[4,5-c]pyridin-2-yl}-2'-methyl-4',5'-dihydro-2'H-spiro[cyclohexane-1,6'-cyclopenta[c]pyrazole] hydrochloride<br>$^1$H-NMR (400 MHz, d$_6$-DMSO) δ: 7.89 (d, J = 7.8 Hz, 1H), 7.76-7.83 (m, 1H), 7.66-7.73 (m, 2H), 7.64 (d, J = 7.6 Hz, 1H), 4.23 (s, 3H), 2.90 (t, J = 6.9 Hz, 2H), 2.25 (t, J = 7.1 Hz, 2H), 1.72-1.87 (m, 2H), 1.61-1.72 (m, 2H), 1.34-1.59 (m, 6H).<br>Mass Spectrum (LCMS, ESI pos.): Calculated for $C_{25}H_{23}ClF_3N_5$: 486.2 (M + H); Measured: 486.2. |
| Cmpd 74 | 2-(5-tert-Butyl-2-methyl-2H-pyrazol-3-yl)-4-chloro-6-(2-trifluoromethyl-phenyl)-3H-imidazo[4,5-c]pyridine hydrochloride<br>$^1$H-NMR (400 MHz, d$_6$-DMSO) δ: 7.89 (d, J = 7.8 Hz, 1H), 7.75-7.83 (m, 1H), 7.67-7.73 (m, 2H), 7.65 (d, J = 7.6 Hz, 1H), 7.04 (s, 1H), 4.30 (s, 3H), 1.32 (s, 9H).<br>Mass Spectrum (LCMS, ESI pos.): Calculated for $C_{21}H_{19}ClF_3N_5$: 434.1 (M + H); Measured: 434.1. |

Example 17

2-(5-tert-Butyl-4-chloro-2-methyl-2H-pyrazol-3-yl)-4-chloro-6-(2-trifluoromethyl-phenyl)-3H-imidazo[4,5-c]pyridine Hydrochloride (Compound #71)

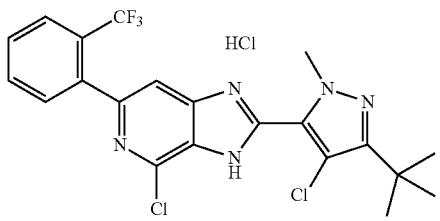 [SMILES: Cn1nc(C(C)(C)C)c(Cl)c1-c1nc2cc(-c3ccccc3C(F)(F)F)nc(Cl)c2[nH]1 ; Cl]

STEP A: 2-(5-tert-Butyl-4-chloro-2-methyl-2H-pyrazol-3-yl)-4-chloro-6-(2-trifluoromethyl-phenyl)-3H-imidazo[4,5-c]pyridine A solution of 2-(5-tert-butyl-2-methyl-2H-pyrazol-3-yl)-4-chloro-6-(2-trifluoromethyl-phenyl)-3H-imidazo[4,5-c]pyridine (101 mg, 0.232 mmol, Compound #74 freebase prepared according to Example 16, STEPS A, B and C) in DCM (2 mL) was treated with $SO_2Cl_2$ (28.3 μL, 0.348 mmol) and the resulting mixture was stirred at room temperature for 14 h. The resulting mixture was then diluted with MeOH (3 mL) and the solvent was removed under reduced pressure. The residue was chromatographed on a 25-g $SiO_2$ pre-packed column eluting with 0:1-3:7 EtOAc/hexanes to yield 2-(5-tert-butyl-4-chloro-2-methyl-2H-pyrazol-3-yl)-4-chloro-6-(2-trifluoromethyl-phenyl)-3H-imidazo[4,5-c]pyridine. $^1$H-NMR (400 MHz, $CD_3OD$) δ: 7.84 (d, J=7.8 Hz, 1H), 7.69-7.76 (m, 1H), 7.68 (s, 1H), 7.62-7.67 (m, 1H), 7.59 (d, J=7.6 Hz, 1H), 4.14 (s, 3H), 1.45 (s, 9H). Mass Spectrum (LCMS, ESI pos.): Calculated for $C_{21}H_{18}Cl_2F_3N_5$: 468.1 (M+H). Measured: 468.1.

STEP B: 2-(5-tert-Butyl-4-chloro-2-methyl-2H-pyrazol-3-yl)-4-chloro-6-(2-trifluoromethyl-phenyl)-3H-imidazo[4,5-c]pyridine hydrochloride Following the procedure described in Example 16, STEP D, 2-(5-tert-butyl-4-chloro-2-methyl-2H-pyrazol-3-yl)-4-chloro-6-(2-trifluoromethyl-phenyl)-3H-imidazo[4,5-c]pyridine hydrochloride was prepared from 2-(5-tert-butyl-4-chloro-2-methyl-2H-pyrazol-3-yl)-4-chloro-6-(2-trifluoromethyl-phenyl)-3H-imidazo[4,5-c]pyridine (62.7 mg, 0.134 mmol) and 1M HCl in $Et_2O$ (0.134 mL, 0.134 mmol). $^1$H-NMR (400 MHz, $d_6$-DMSO) δ: 7.90 (d, J=7.8 Hz, 1H), 7.77-7.83 (m, 1H), 7.76 (s, 1H), 7.68-7.74 (m, 1H), 7.65 (d, J=7.6 Hz, 1H), 4.07 (s, 3H), 1.41 (s, 9H). Mass Spectrum (LCMS, ESI pos.): Calculated for $C_{21}H_{18}Cl_2F_3N_5$: 468.1 (M+H). Measured: 468.1.

Following the procedure described in Example 17 above, and substituting suitably selected and substituted reagents, starting materials and conditions as would be readily apparent to those skilled in the art, the following representative compounds of the present invention were prepared.

Cmpd 62   2-(5-tert-Butyl-4-chloro-2-methyl-2H-pyrazol-3-yl)-7-methoxy-5-(2-trifluoromethyl-phenyl)-1H-imidazo[4,5-b]pyridine hydrochloride
$^1$H-NMR (400 MHz, DMSO-$d_6$) δ: 7.89 (d, J = 7.8 Hz, 1H), 7.79 (t, J = 7.3 Hz, 1H), 7.70 (t, J = 7.6 Hz, 1H), 7.64 (d, J = 7.3 Hz, 1H), 7.04 (s, 1H), 4.11 (s, 3H), 3.96 (s, 3H), 1.40 (s, 9H).
Mass Spectrum (LCMS, ESI pos.): Calculated for $C_{22}H_{21}ClF_3N_5O$: 464.2 (M + H); Measured: 464.2.

Cmpd 76   2-(5-tert-Butyl-4-chloro-2-methyl-2H-pyrazol-3-yl)-7-(2-methoxy-ethoxy)-5-(2-trifluoromethyl-phenyl)-1H-imidazo[4,5-b]pyridine methanesulfonic acid salt
$^1$H-NMR (400 MHz, $d_6$-DMSO) δ: 7.89 (d, J = 7.6 Hz, 1H), 7.79 (t, J = 7.5 Hz, 1H), 7.71 (t, J = 7.6 Hz, 1H), 7.64 (d, J = 7.3 Hz, 1H), 7.07 (s, 1H), 4.55-4.63 (m, 2H), 3.95 (s, 3H), 3.73-3.79 (m, 2H), 3.33 (s, 3H), 2.34 (s, 3H), 1.40 (s, 9H).
Mass Spectrum (LCMS, ESI pos.): Calculated for $C_{24}H_{25}ClF_3N_5O_2$: 508.2 (M + H); Measured: 508.1.

Example 18

3-tert-Butyl-5-[7-methoxy-5-(2-trifluoromethyl-phenyl)-1H-imidazo[4,5-b]pyridin-2-yl]-isoxazole-4-carbonitrile methanesulfonic acid salt (Compound #70)

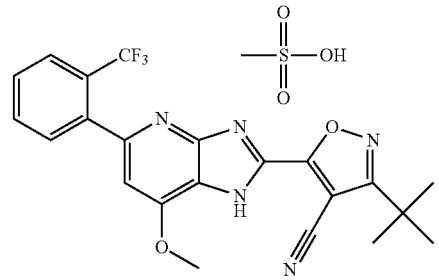

The title compound was prepared by reacting 4-chloro-3-nitro-6-(2-trifluoromethyl-phenyl)-pyridin-2-ylamine (prepared as described in the Example 1) according to the process described in Example 9, STEP A, and then reacting the resulting compound with 3-tert-butyl-4-cyano-isoxazole-5-carboxylic acid (prepared as described in the Example J), according to the processes described in Example 25, STEP C and Example 26. $^1$H-NMR (400 MHz, $d_6$-DMSO) δ: 7.89 (d, J=7.8 Hz, 1H), 7.80 (t, J=7.3 Hz, 1H), 7.71 (t, J=7.6 Hz, 1H), 7.66 (d, J=7.6 Hz, 1H), 7.07 (s, 1H), 4.15 (s, 3H), 2.35 (s, 3H), 1.47 (s, 9H). Mass Spectrum (LCMS, ESI pos.): Calculated for $C_{22}H_{18}F_3N_5O_2$: 442.2 (M+H). Measured: 442.2.

Following the procedure described in Example 18 above, and substituting suitably selected and substituted reagents, starting materials and conditions as would be readily apparent to those skilled in the art, the following representative compounds of the present invention were prepared.

Cmpd 81   2-(5-tert-Butyl-2-methyl-2H-pyrazol-3-yl)-7-methoxy-5-(2-trifluoromethyl-phenyl)-1H-imidazo[4,5-b]pyridine hydrochloride
$^1$H-NMR (400 MHz, $d_6$-DMSO) δ: 7.90 (d, J = 7.8 Hz, 1H), 7.81 (t, J = 7.5 Hz, 1H), 7.72 (t, J = 7.6 Hz, 1H), 7.67 (d, J = 7.6 Hz, 1H), 7.09 (s, 1H), 7.06 (s, 1H), 4.26 (s, 3H), 4.13 (s, 3H), 1.30 (s, 9H).
Mass Spectrum (LCMS, ESI pos.): Calculated for $C_{22}H_{22}F_3N_5O$: 430.2 (M + H); Measured: 430.2.

Cmpd 112  2-(5-tert-Butyl-2-methyl-2H-pyrazol-3-yl)-7-(2-methoxy-ethoxy)-5-(2-trifluoromethyl-phenyl)-1H-imidazo[4,5-b]pyridine methanesulfonic acid salt
¹H-NMR (400 MHz, d₆-DMSO) δ: 7.91 (d, J = 7.8 Hz, 1H), 7.82 (t, J = 7.5 Hz, 1H), 7.74 (t, J = 7.6 Hz, 1H), 7.68 (d, J = 7.6 Hz, 1H), 7.17 (br. s., 1H), 7.10 (s, 1H), 4.59-4.67 (m, 2H), 4.26 (s, 3H), 3.76-3.83 (m, J = 5.1, 3.3 Hz, 2H), 3.34 (s, 3H), 2.36 (s, 3H), 1.30 (s, 9H).
Mass Spectrum (LCMS, ESI pos.): Calculated for C₂₄H₂₆F₃N₅O₂: 474.2 (M + H); Measured: 474.2.

Example 19

2-(3-tert-Butyl-isoxazol-5-yl)-4-chloro-6-(2-trifluoromethyl-phenyl)-3H-imidazo[4,5-c]pyridine hydrochloride (Compound #73)

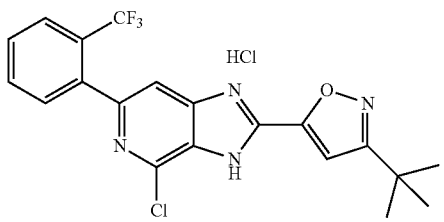 [SMILES: CC(C)(C)c1cc(-c2nc3cc(-c4ccccc4C(F)(F)F)nc(Cl)c3[nH]2)on1 ; Cl]

STEP A: 3-tert-Butyl-isoxazole-5-carboxylic acid [4-amino-2-chloro-6-(2-trifluoromethyl-phenyl)-pyridin-3-yl]-amide and 3-tert-Butyl-isoxazole-5-carboxylic acid [3-amino-2-chloro-6-(2-trifluoromethyl-phenyl)-pyridin-4-yl]-amide 3-tert-butyl-4-isoxazole-5-carboxylic acid (72.8 mg, 0.430 mmol, prepared as in Example I, above) was dissolved in DCM (2 mL) and DMF (10 µL) and oxalyl chloride (51.2 µL, 0.587 mmol) were added. The resulting mixture was stirred at room temperature for 1 h and the solvent was removed under reduced pressure. The resulting residue was dissolved in DCM (2 mL).

2-Chloro-6-(2-trifluoromethyl-phenyl)-pyridine-3,4-diamine (113 mg, 0.391 mmol, prepared as in Example 16, STEP B) was dissolved in DCM (3 mL) and then DIEA (136 µL, 0.782 mmol) was added. The acid chloride solution prepared above was added dropwise to the stirred mixture, which was then stirred at room temperature for 18 h. The solvent was removed under reduced pressure and the resulting residue was chromatographed on a 24-g SiO₂ pre-packed column eluting with 0:1-3:2 EtOAc/hexanes to yield 3-tert-butyl-isoxazole-5-carboxylic acid [4-amino-2-chloro-6-(2-trifluoromethyl-phenyl)-pyridin-3-yl]-amide and 3-tert-butyl-isoxazole-5-carboxylic acid [3-amino-2-chloro-6-(2-trifluoromethyl-phenyl)-pyridin-4-yl]-amide. Mass Spectrum (LCMS, ESI pos.): Calculated for C₂₀H₁₈ClF₃N₄O₂: 439.1 (M+H). Measured: 439.1.

STEP B: 2-(3-tert-Butyl-isoxazol-5-yl)-4-chloro-6-(2-trifluoromethyl-phenyl)-3H-imidazo[4,5-c]pyridine 3-tert-Butyl-isoxazole-5-carboxylic acid [4-amino-2-chloro-6-(2-trifluoromethyl-phenyl)-pyridin-3-yl]-amide (73.9 mg, 0.168 mmol, prepared as in the previous step) was dissolved in AcOH (1 mL) and the resulting solution was heated to 100° C. for 14 h. The resulting mixture was cooled to room temperature and poured into H₂O (20 mL). The aqueous phase was extracted with DCM (3×10 mL) and the combined extracts were washed with sat NaHCO₃ solution (20 mL). The organic layer was dried over MgSO₄, filtered and the solvent was removed under reduced pressure. The residue was dissolved in POCl₃ (1 mL) and heated for 16 h at 100° C. The resulting mixture was cooled to room temperature and poured onto ice (~20 mL). After the POCl₃ had been consumed, the precipitate was isolated by filtration and washed with H₂O (2×20 mL). The solid was dissolved in DCM (25 mL) and the solution was dried over MgSO₄ and filtered. The solvent was removed under reduced pressure and the crude product was chromatographed on a 24-g SiO₂ pre-packed column eluting with 0:1-2:3 EtOAc/hexanes to yield 2-(3-tert-butyl-isoxazol-5-yl)-4-chloro-6-(2-trifluoromethyl-phenyl)-3H-imidazo[4,5-c]pyridine. ¹H-NMR (400 MHz, CD₃OD) δ: 7.84 (d, J=7.8 Hz, 1H), 7.69-7.77 (m, 1H), 7.62-7.68 (m, 2H), 7.59 (d, J=7.6 Hz, 1H), 7.30 (s, 1H), 1.43 (s, 9H). Mass Spectrum (LCMS, ESI pos.): Calculated for C₂₀H₁₆ClF₃N₄O: 421.1 (M+H). Measured: 421.1.

Example 20

2-(5-tert-Butyl-4-chloro-2-methyl-2H-pyrazol-3-yl)-5-(2-chloro-phenyl)-1H-imidazo[4,5-b]pyridine (Compound #23)

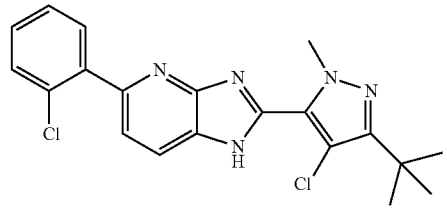 [SMILES: Cn1nc(C(C)(C)C)c(Cl)c1-c1nc2nc(-c3ccccc3Cl)ccc2[nH]1]

STEP A: 5-tert-Butyl-4-chloro-2-methyl-2H-pyrazole-3-carboxylic acid (6-bromo-3-nitro-pyridin-2-yl)-amide A solution of 6-bromo-3-nitro-pyridin-2-ylamine (750 mg, 3.44 mmol) in THF (20 mL) was treated with NaH (413 mg, 10.3 mmol) at room temperature for 1 h. Simultaneously a solution of 5-tert-butyl-4-chloro-2-methyl-2H-pyrazole-3-carboxylic acid (969 mg, 4.47 mmol, prepared as described in Example B) in DCM (20 mL) was treated with oxalyl chloride (390 µL, 4.47 mmol) and DMF (4 drops) at room temperature for 1 h. The acid chloride solution was concentrated to dryness in vacuo, taken up in THF (10 mL), and added to the sodium anilide solution. The resulting mixture was stirred at room temperature for 15 min, quenched with saturated aqueous NH₄Cl (50 mL), and extracted twice with EtOAc (60 mL, 20 mL). The combined extracts were dried over MgSO₄ and concentrated in vacuo. The residue was purified on a 40-g SEPRA Si 50 SPE column (Isco system: Flow rate=25 mL/min; Eluent=EtOAc/hexanes, 1:99 v/v for 1 min, then 1:99 to 3:17 v/v over 40 min) to yield 5-tert-butyl-4-chloro-2-methyl-2H-pyrazole-3-carboxylic acid (6-bromo-3-nitro-pyridin-2-yl)-amide as a pale yellow solid. ¹H-NMR (400 MHz, CDCl₃) δ: 10.48 (br. s., 1H), 8.31 (d, J=8.6 Hz, 1H), 7.46 (d, J=8.6 Hz, 1H), 4.12 (s, 3H), 1.42 (s, 9H). Mass Spectrum (LCMS, APCI pos.): Calculated for $C_{14}H_{15}BrClN_5O_3$: 416.0 (M+H). Measured: 416.1.

STEP B: 5-tert-Butyl-4-chloro-2-methyl-2H-pyrazole-3-carboxylic acid [6-(2-chloro-phenyl)-3-nitro-pyridin-2-yl]-amide A solution of 5-tert-butyl-4-chloro-2-methyl-2H-pyrazole-3-carboxylic acid (6-bromo-3-nitro-pyridin-2-yl)-amide (200 mg, 0.480 mmol, prepared as described in the previous step) in DME (20 mL) and water (5 mL) was treated with 2-chlorophenylboronic acid (78.8 mg, 0.504 mmol) and cesium carbonate (469 mg, 1.44 mmol). The resulting mixture was degassed via sonication, placed under Ar, treated with PdCl$_2$(dppf).DCM (19.6 mg, 0.0240 mmol), and heated to 90° C. for 3 h. The cooled mixture was then diluted with water (40 mL) and extracted twice with EtOAc (50 mL). The combined extracts were dried over MgSO$_4$ and concentrated in vacuo. The residue was purified on a 24-g SEPRA Si 50 SPE column (Isco system: Flow rate=20 mL/min; Eluent=EtOAc/hexanes, 1:99 v/v for 10 min, then 1:99 to 3:17 v/v over 40 min) to yield 5-tert-butyl-4-chloro-2-methyl-2H-pyrazole-3-carboxylic acid [6-(2-chloro-phenyl)-3-nitro-pyridin-2-yl]-amide as a yellow solid. Mass Spectrum (LCMS, APCI pos.): Calculated for $C_{20}H_{19}Cl_2N_5O_3$: 448.1 (M+H). Measured: 448.0.

STEP C: 2-(5-tert-Butyl-4-chloro-2-methyl-2H-pyrazol-3-yl)-5-(2-chloro-phenyl)-1H-imidazo[4,5-b]pyridine A solution of 5-tert-butyl-4-chloro-2-methyl-2H-pyrazole-3-carboxylic acid [6-(2-chloro-phenyl)-3-nitro-pyridin-2-yl]-amide (157 mg, 0.350 mmol, prepared as described in the previous step) in acetic acid (5 mL) was treated with iron powder (97.8 mg, 1.75 mmol) and heated to 100° C. for 3 h. The cooled mixture then was concentrated in vacuo, taken up in water (50 mL) and extracted twice with EtOAc (50 mL). The combined extracts were dried over MgSO$_4$ and concentrated in vacuo. The residue was purified on a 12-g SEPRA Si 50 SPE column (Isco system: Flow rate=15 mL/min; Eluent=EtOAc/hexanes, 1:99 v/v for 10 min, then 1:99 to 3:17 v/v over 40 min) to yield 2-(5-tert-butyl-4-chloro-2-methyl-2H-pyrazol-3-yl)-5-(2-chloro-phenyl)-1H-imidazo[4,5-b]pyridine as a white solid. Mass Spectrum (LCMS, APCI pos.): Calculated for $C_{20}H_{19}Cl_2N_5$: 400.1 (M+H). Measured: 400.2.

Following the procedures described in Example 20 and substituting suitably selected and substituted reagents, starting materials and conditions as would be readily apparent to those skilled in the art, the following representative compounds of the present invention were prepared.

| | |
|---|---|
| Cmpd 23 | 2-(5-tert-Butyl-4-chloro-2-methyl-2H-pyrazol-3-yl)-5-(2-chloro-phenyl)-1H-imidazo[4,5-b]pyridine hydrochloride<br>$^1$H-NMR (400 MHz, CD$_3$OD) δ: 8.06 (d, J = 8.1 Hz, 1H), 7.48-7.55 (m, 2H), 7.42-7.48 (m, 1H), 7.30-7.38 (m, 2H), 4.02 (s, 3H), 1.36 (s, 9H).<br>Mass Spectrum (LCMS, APCI pos.): Calculated for $C_{20}H_{19}Cl_2N_5$: 400.1 (M + H); Measured: 400.2. |
| Cmpd 25 | 2-(5-tert-Butyl-4-chloro-2-methyl-2H-pyrazol-3-yl)-5-(2-trifluoromethoxy-phenyl)-1H-imidazo[4,5-b]pyridine hydrochloride<br>$^1$H-NMR (400 MHz, CD$_3$OD) δ: 7.85 (dd, J = 7.6, 1.8 Hz, 1H), 7.73-7.83 (m, 1H), 7.47-7.70 (m, 4H), 4.17 (br. s., 3H), 1.46 (s, 9H).<br>Mass Spectrum (LCMS, APCI pos.): Calculated for $C_{21}H_{19}ClF_3N_5O$: 450.1 (M + H); Measured: 450.2. |
| Cmpd 32 | 2-(5-tert-Butyl-4-chloro-2-methyl-2H-pyrazol-3-yl)-5-(2-trifluoromethyl-phenyl)-1H-imidazo[4,5-b]pyridine hydrochloride<br>$^1$H-NMR (400 MHz, CD$_3$OD) δ: 8.49 (d, J = 8.3 Hz, 1H), 7.95 (d, J = 7.1 Hz, 1H), 7.75-7.87 (m, 2H), 7.69 (d, J = 8.1 Hz, 2H), 4.19 (s, 3H), 1.47 (s, 9H).<br>Mass Spectrum (LCMS, APCI pos.): Calculated for $C_{21}H_{19}ClF_3N_5$: 434.1 (M + H); Measured: 434.2. |
| Cmpd 33 | 2-(5-tert-Butyl-4-chloro-2-methyl-2H-pyrazol-3-yl)-5-(2-fluoro-phenyl)-1H-imidazo[4,5-b]pyridine hydrochloride<br>$^1$H-NMR (CD$_3$OD) δ: 8.39-8.53 (m, 1H), 7.84-7.98 (m, 2H), 7.53-7.66 (m, 1H), 7.25-7.47 (m, 2H), 4.19 (s, 3H), 1.46 (s, 9H)<br>Mass Spectrum (LCMS, APCI pos.): Calculated for $C_{20}H_{19}ClFN_5$: 384.1 (M + H); Measured: 384.3. |

Example 21

8-(5-tert-Butyl-2-methyl-2H-pyrazol-3-yl)-6-methyl-2-(2-trifluoromethyl-phenyl)-7H-purine trifluoroacetic acid salt (Compound #35)

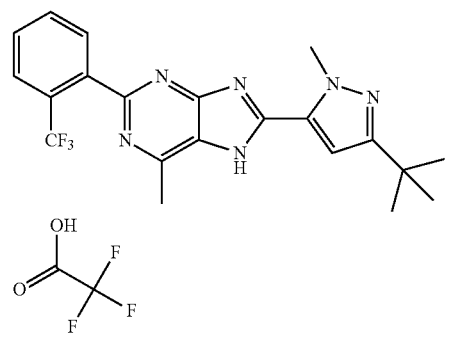

STEP A: 5-tert-Butyl-2-methyl-2H-pyrazole-3-carboxylic acid [6-methyl-5-nitro-2-(2-trifluoromethyl-phenyl)-pyrimidin-4-yl]-amide A solution of 6-methyl-5-nitro-2-(2-trifluoromethyl-phenyl)-pyrimidin-4-ylamine (150 mg, 0.503 mmol, prepared as described in Example 2, STEP A) in THF (10 mL) was treated with NaH (60.4 mg, 1.51 mmol, 60% dispersion in oil), and the resulting mixture was allowed to stir for 30 min at room temperature. 5-tert-Butyl-2-methyl-2H-pyrazole-3-carbonyl chloride (131 mg, 0.654 mmol) was added as a solution in THF (3 mL). After 15 min, the mixture was quenched with saturated aqueous NH$_4$Cl (20 mL) and extracted twice with EtOAc (25 mL). The combined extracts were dried over MgSO$_4$ and concentrated in vacuo. The residue was purified on a 12-g SEPRA Si 50 SPE column (Isco system: Flow rate=15 mL/min; Eluent=EtOAc/hexanes, 1:99 v/v for 10 min, then 1:99 to 1:4 v/v over 40 min) to yield 5-tert-butyl-2-methyl-2H-pyrazole-3-carboxylic acid [6-methyl-5-nitro-2-(2-trifluoromethyl-phenyl)-pyrimidin-4-yl]-amide as a colorless glassy solid. $^1$H-NMR (400 MHz, CDCl$_3$) δ: 9.10 (s, 1H), 7.79-7.86 (m, 2H), 7.60-7.72 (m, 2H), 6.64 (s, 1H), 4.14 (s, 3H), 2.83 (s, 3H), 1.33 (s, 9H). Mass Spectrum (LCMS, APCI pos.): Calculated for C$_{21}$H$_{21}$F$_3$N$_6$O$_3$: 463.2 (M+H). Measured: 463.2.

STEP B: 5-tert-Butyl-2-methyl-2H-pyrazole-3-carboxylic acid [5-amino-6-methyl-2-(2-trifluoromethyl-phenyl)-pyrimidin-4-yl]-amide A solution of 5-tert-butyl-2-methyl-2H-pyrazole-3-carboxylic acid [6-methyl-5-nitro-2-(2-trifluoromethyl-phenyl)-pyrimidin-4-yl]-amide (226 mg, 0.490 mmol, prepared as described in the previous step) in ethanol (10 mL) and water (5 mL) was treated with ammonium chloride (262 mg, 4.90 mmol) and iron powder (137 mg, 2.45 mmol), and the mixture was heated to 50° C. for 4 h. Ethanol was removed in vacuo, and the resulting residue was diluted with water (20 mL) and extracted twice with EtOAc (30 mL). The combined extracts were dried over MgSO$_4$ and concentrated in vacuo. The residue was purified on a 12-g SEPRA Si 50 SPE column (Isco system: Flow rate=20 mL/min; Eluent=EtOAc/hexanes, 1:99 v/v for 10 min, then 1:99 to 1:4 v/v over 40 min) to yield 5-tert-butyl-2-methyl-2H-pyrazole-3-carboxylic acid [5-amino-6-methyl-2-(2-trifluoromethyl-phenyl)-pyrimidin-4-yl]-amide as an off-white solid. Mass Spectrum (LCMS, APCI pos.): Calculated for C$_{21}$H$_{23}$F$_3$N$_6$O: 433.2 (M+H). Measured: 433.2.

STEP C: 8-(5-tert-Butyl-2-methyl-2H-pyrazol-3-yl)-6-methyl-2-(2-trifluoromethyl-phenyl)-7H-purine trifluoroacetic acid salt A solution of 5-tert-butyl-2-methyl-2H-pyrazole-3-carboxylic acid [5-amino-6-methyl-2-(2-trifluoromethyl-phenyl)-pyrimidin-4-yl]-amide (45.8 mg, 0.106 mmol, prepared as described in the previous step) in 1,4-dioxane (10 mL) was treated with CSA (49.2 mg, 0.213 mmol) and heated to 100° C. under a reflux condenser for 3 h. The cooled mixture was then diluted with water (20 mL) and extracted twice with EtOAc (25 mL). The combined extracts were dried over MgSO$_4$ and concentrated in vacuo. The residue was purified by RP-HPLC on a C18 column eluting with a linear gradient of 10-80% CH$_3$CN in 0.1% TFA/H$_2$O over 25 min to 8-(5-tert-butyl-2-methyl-2H-pyrazol-3-yl)-6-methyl-2-(2-trifluoromethyl-phenyl)-7H-purine trifluoroacetic acid salt as an off-white solid. $^1$H-NMR (400 MHz, CD$_3$OD) δ: 7.77 (d, J=7.6 Hz, 1H), 7.57-7.70 (m, 3H), 6.87 (s, 1H), 4.27 (s, 3H), 2.80 (s, 3H), 1.28 (s, 9H). Mass Spectrum (LCMS, APCI pos.): Calculated for C$_{21}$H$_{21}$F$_3$N$_6$: 415.2 (M+H). Measured: 415.2.

Example 22

2-(3-tert-Butyl-isoxazol-5-yl)-5-(2-trifluoromethyl-phenyl)-1H-imidazo[4,5-b]pyridine (Compound #31)

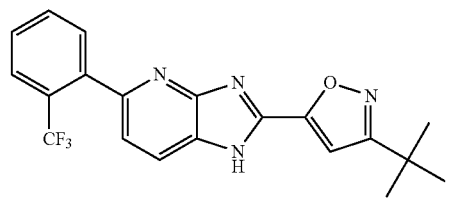 [SMILES: CC(C)(C)c1cc(-c2nc3nc(-c4ccccc4C(F)(F)F)ccc3[nH]2)on1]

STEP A: 3-tert-Butyl-isoxazole-5-carboxylic acid (6-bromo-3-nitro-pyridin-2-yl)-amide A solution of 6-bromo-3-nitro-pyridin-2-ylamine (500 mg, 2.29 mmol) in THF (10 mL) was treated with NaH (275 mg, 6.88 mmol) at room temperature for 1 h. Simultaneously a solution of 3-tert-butyl-isoxazole-5-carboxylic acid (524 mg, 3.10 mmol, prepared as described in Example I) in DCM (10 mL) was treated with oxalyl chloride (270 μL, 3.10 mmol) and DMF (2 drops) at room temperature for 1 h. The acid chloride solution was concentrated to dryness in vacuo, taken up in THF (10 mL), and added to the sodium anilide solution. The resulting mixture was stirred at room temperature for 15 min, quenched with saturated aqueous NH$_4$Cl (50 mL), and extracted twice with EtOAc (50 mL). The combined extracts were dried over MgSO$_4$ and concentrated in vacuo. The residue was purified on a 40-g SEPRA Si 50 SPE column (Isco system: Flow rate=25 mL/min; Eluent=EtOAc/hexanes, 1:99 v/v for 1 min, then 1:99 to 3:17 v/v over 40 min) to yield 3-tert-butyl-isoxazole-5-carboxylic acid (6-bromo-3-nitro-pyridin-2-yl)-amide as a solid. $^1$H-NMR (400 MHz, CDCl$_3$) δ: 10.85 (br. s., 1H), 8.37 (d, J=8.6 Hz, 1H), 7.48 (d, J=8.6 Hz, 1H), 7.03 (s, 1H), 1.39 (s, 9H). Mass Spectrum (LCMS, APCI pos.): Calculated for C$_{13}$H$_{13}$BrN$_4$O$_4$: 369.0 (M+H). Measured: 369.0.

STEP B: 6-(2-Trifluoromethyl-phenyl)-3-nitro-pyridin-2-ylamine

A solution of 3-tert-butyl-isoxazole-5-carboxylic acid (6-bromo-3-nitro-pyridin-2-yl)-amide (139 mg, 0.377 mmol, prepared as described in the previous step) in DME (15 mL) and water (5 mL) was treated with 2-trifluoromethylphenylboronic acid (85.8 mg, 0.452 mmol) and cesium carbonate (245 mg, 0.753 mmol). The resulting mixture was de-gassed via sonication, placed under Ar, treated with PdCl$_2$(dppf).DCM (15.4 mg, 0.019 mmol), and heated to 80° C. for 18 h. The cooled mixture was diluted with water (50 mL) and extracted twice with EtOAc (50 mL, 25 mL). The combined extracts were dried over MgSO$_4$ and concentrated in vacuo. The residue was purified on a 12-g SEPRA Si 50 SPE column (Isco system: Flow rate=15 mL/min; Eluent=EtOAc/hexanes, 1:99 v/v for 10 min, then 1:99 to 3:17 v/v over 40 min) to yield 6-(2-trifluoromethyl-phenyl)-3-nitro-pyridin-2-ylamine as a yellow solid. Mass Spectrum (LCMS, APCI pos.): Calculated for C$_{12}$H$_8$F$_3$N$_3$O$_2$: 284.1 (M+H). Measured: 284.0.

STEP C: 3-tert-Butyl-isoxazole-5-carboxylic acid [3-nitro-6-(2-trifluoromethyl-phenyl)-pyridin-2-yl]-amide A solution of 6-(2-trifluoromethyl-phenyl)-3-nitro-pyridin-2-ylamine (69.0 mg, 0.244 mmol, prepared as described in the previous step) in THF (10 mL) was treated with NaH (29.2 mg, 0.731 mmol, 60% dispersion in oil) at room temperature for 1 h. Simultaneously, a solution of 3-tert-butyl-isoxazole-5-carboxylic acid (49.5 mg, 0.292 mmol, prepared as described in Example L) in DCM (10 mL) was treated with oxalyl chloride (25.5 µL, 0.292 mmol) and DMF (2 drops) at room temperature for 1 h. The resulting mixture was concentrated in vacuo, taken up in THF (10 mL) and added to the sodium anilide solution. The resulting mixture was then allowed to stir at room temperature for 15 min, quenched with saturated aqueous NH$_4$Cl (20 mL), and extracted twice with EtOAc (20 mL). The combined extracts were dried over MgSO$_4$ and concentrated in vacuo. The residue was purified on a 4-g SEPRA Si 50 SPE column (Isco system: Flow rate=10 mL/min; Eluent=EtOAc/hexanes, 1:99 v/v for 5 min, then 1:99 to 1:9 v/v over 40 min) to yield 3-tert-butyl-isoxazole-5-carboxylic acid [3-nitro-6-(2-trifluoromethyl-phenyl)-pyridin-2-yl]amide as a white solid. Mass Spectrum (LCMS, APCI pos.): Calculated for C$_{20}$H$_{17}$F$_3$N$_4$O$_4$: 435.1 (M+H). Measured: 435.1.

STEP D: 2-(3-tert-Butyl-isoxazol-5-yl)-5-(2-trifluoromethyl-phenyl)-1H-imidazo[4,5-b]pyridine A solution of 3-tert-butyl-isoxazole-5-carboxylic acid [3-nitro-6-(2-trifluoromethyl-phenyl)-pyridin-2-yl]-amide (78.0 mg, 0.180 mmol, prepared as described in the previous step) in acetic acid (5 mL) was treated with iron powder (50.1 mg, 0.898 mmol) and heated to 100° C. for 2 h. The volume of acetic acid was reduced to 2 mL by concentrating in vacuo, and saturated aqueous NaHCO$_3$ (50 mL) was added. The resulting mixture was extracted twice with EtOAc (60 mL). The combined extracts were dried over MgSO$_4$ and concentrated in vacuo. The residue was purified on a 4-g SEPRA Si 50 SPE column (Isco system: Flow rate=10 mL/min; Eluent=EtOAc/hexanes, 1:99 v/v for 5 min, then 1:99 to 1:9 v/v over 40 min) to yield 2-(3-tert-butyl-isoxazol-5-yl)-5-(2-trifluoromethyl-phenyl)-1H-imidazo[4,5-b]pyridine as a white solid. $^1$H-NMR (400 MHz, CDCl$_3$) δ: 10.06 (br. s., 1H), 8.16 (d, J=8.3 Hz, 1H), 7.81 (d, J=8.1 Hz, 1H), 7.64 (d, J=7.6 Hz, 1H), 7.52-7.60 (m, 2H), 7.46 (d, J=8.3 Hz, 1H), 7.07 (s, 1H), 1.42 (s, 9H). Mass Spectrum (LCMS, APCI pos.): Calculated for C$_{20}$H$_{17}$F$_3$N$_4$O: 387.1 (M+H). Measured: 387.1.

Following the procedures described in Example 22, and substituting suitably selected and substituted reagents, starting materials and conditions as would be readily apparent to those skilled in the art, the following representative compounds of the present invention were prepared.

| | |
|---|---|
| Cmpd 26 | 2-(3-tert-Butyl-isoxazol-5-yl)-5-(2-chloro-phenyl)-1H-imidazo[4,5-b]pyridine<br>$^1$H-NMR (400 MHz, CDCl$_3$) δ: 10.64 (br. s., 1H), 8.19 (d, J = 8.3 Hz, 1H), 7.68 (d, J = 8.3 Hz, 1H), 7.63 (dd, J = 7.1, 2.3 Hz, 1H), 7.48-7.54 (m, 1H), 7.34-7.39 (m, 2H), 7.05 (s, 1H), 1.42 (s, 9H).<br>Mass Spectrum (LCMS, APCI pos.): Calculated for C$_{19}$H$_{17}$ClN$_4$O: 353.1 (M + H); Measured: 353.1. |
| Cmpd 27 | 2-(5-tert-Butyl-2-methyl-2H-pyrazol-3-yl)-5-(2-chloro-phenyl)-1H-imidazo[4,5-b]pyridine<br>$^1$H-NMR (400 MHz, CDCl$_3$) δ: 8.16 (d, J = 8.3 Hz, 1H), 7.45-7.62 (m, 3H), 7.33-7.42 (m, 2H), 6.61 (s, 1H), 4.37 (s, 3H), 1.37 (s, 9H).<br>Mass Spectrum (LCMS, APCI pos.): Calculated for C$_{20}$H$_{20}$ClN$_5$: 366.1 (M + H); Measured: 366.3. |
| Cmpd 29 | 2-(3-tert-Butyl-isoxazole-5-yl)-5-(2-trifluoromethoxy-phenyl)-1H-imidazo[4,5-b]pyridine<br>$^1$H-NMR (400 MHz, CDCl$_3$) δ: 10.69 (br. s., 1H), 8.19 (d, J = 8.6 Hz, 1H), 7.84 (dd, J = 7.1, 2.3 Hz, 1H), 7.72 (d, J = 8.3 Hz, 1H), 7.41-7.47 (m, 2H), 7.36-7.41 (m, 1H), 7.06 (s, 1H), 1.41 (s, 9H).<br>Mass Spectrum (LCMS, APCI pos.): Calculated for C$_{20}$H$_{17}$F$_3$N$_4$O$_2$: 403.1 (M + H); Measured: 403.2. |
| Cmpd 30 | 2-(3-tert-Butyl-isoxazol-5-yl)-5-(2-fluoro-phenyl)-1H-imidazo[4,5-b]pyridine<br>$^1$H-NMR (400 MHz, CDCl$_3$) δ: 8.17 (d, J = 7.6 Hz, 1H), 7.97 (t, J = 7.2 Hz, 1H), 7.84 (dd, J = 8.6, 2.0 Hz, 1H), 7.34-7.42 (m, 1H), 7.15-7.26 (m, 2H), 7.06 (s, 1H), 1.41 (s, 9H).<br>Mass Spectrum (LCMS, APCI pos.): Calculated for C$_{19}$H$_{17}$FN$_4$O: 337.1 (M + H); Measured: 337.2. |
| Cmpd 36 | 2-(5-tert-Butyl-2-methyl-2H-pyrazol-3-yl)-5-(2-fluoro-phenyl)-1H-imidazo[4,5-b]pyridine<br>$^1$H-NMR (400 MHz, CDCl$_3$) δ: 8.15 (d, J = 8.3 Hz, 1H), 7.89 (td, J = 7.8, 1.8 Hz, 1H), 7.77 (dd, J = 8.3, 2.0 Hz, 1H), 7.34-7.42 (m, 1H), 7.21-7.26 (m, 1H), 7.15-7.21 (m, 1H), 6.50 (s, 1H), 4.35 (s, 3H), 1.34 (s, 9H).<br>Mass Spectrum (LCMS, APCI pos.): Calculated for C$_{20}$H$_{20}$FN$_5$: 350.2 (M + H); Measured: 350.2. |

Example 23

2-(5-tert-Butyl-2-methyl-2H-pyrazol-3-yl)-5-(2-trifluoromethyl-phenyl)-1H-imidazo[4,5-b]pyridine (Compound #34)

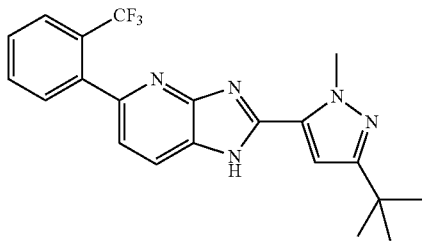 [SMILES: Cn1nc(C(C)(C)C)cc1-c1nc2nc(-c3ccccc3C(F)(F)F)ccc2[nH]1]

Step A: 5-tert-Butyl-2-methyl-2H-pyrazole-3-carboxylic acid (5-tert-butyl-2-methyl-2H-pyrazole-3-carbonyl)-[3-nitro-6-(2-trifluoromethyl-phenyl)-pyridin-2-yl]-amide A solution of 3-nitro-6-(2-trifluoromethyl-phenyl)-pyridin-2-ylamine (200 mg, 0.706 mmol, prepared as described in Example 22, STEP B) in THF (15 mL) was treated with NaH (84.7 mg, 2.12 mmol) at room temperature for 1 h. The resulting mixture was treated with a solution of 5-tert-butyl-2-methyl-2H-pyrazole-3-carbonyl chloride (156 mg, 0.777 mmol) as a solution in THF (6 mL) and allowed to stir at room temperature for 15 min. The mixture was quenched with saturated aqueous NH$_4$Cl (25 mL) and extracted twice with EtOAc (35 mL). The combined extracts were dried over MgSO$_4$ and concentrated in vacuo. The residue was purified on a 24-g SEPRA Si 50 SPE column (Isco system: Flow rate=20 mL/min; Eluent=EtOAc/hexanes, 1:99 v/v for 5 min, then 1:99 to 1:9 v/v over 40 min) to yield 5-tert-butyl-2-methyl-2H-pyrazole-3-carboxylic acid (5-tert-butyl-2-methyl-2H-pyrazole-3-carbonyl)-[3-nitro-6-(2-trifluoromethyl-phenyl)-pyridin-2-yl]-amide as a yellow solid. Mass Spectrum (LCMS, APCI pos.): Calculated for C$_{30}$H$_{32}$F$_3$N$_7$O$_4$: 612.3 (M+H). Measured: 612.1.

Step B: 2-(5-tert-Butyl-2-methyl-2H-pyrazol-3-yl)-5-(2-trifluoromethyl-phenyl)-1H-imidazo[4,5-b]pyridine A solution of 5-tert-butyl-2-methyl-2H-pyrazole-3-carboxylic acid (5-tert-butyl-2-methyl-2H-pyrazole-3-carbonyl)-[3-nitro-6-(2-trifluoromethyl-phenyl)-pyridin-2-yl]-amide (339 mg, 0.554 mmol, prepared as described in the previous step) was taken up in acetic acid (10 mL), treated with iron powder (124 mg, 2.22 mmol), and heated to 90° C. for 15 h. The resulting mixture was concentrated to a volume of 3 mL, treated with saturated aqueous NaHCO$_3$ (75 mL) and extracted twice with EtOAc (75 mL, 40 mL). The combined extracts were dried over MgSO$_4$ and concentrated in vacuo. The residue was purified on a 24-g SEPRA Si 50 SPE column (Isco system: Flow rate=20 mL/min; Eluent=EtOAc/hexanes, 1:19 v/v for 5 min, then 1:19 to 1:4 v/v over 40 min) to yield 2-(5-tert-butyl-2-methyl-2H-pyrazol-3-yl)-5-(2-trifluoromethyl-phenyl)-1H-imidazo[4,5-b]pyridine as a white solid. $^1$H-NMR (400 MHz, CDCl$_3$) δ: 8.13 (d, J=8.3 Hz, 1H), 7.81 (d, J=8.1 Hz, 1H), 7.61-7.68 (m, 1H), 7.52-7.59 (m, 2H), 7.40 (d, J=8.1 Hz, 1H), 6.56 (s, 1H), 4.37 (s, 3H), 1.37 (s, 9H). Mass Spectrum (LCMS, APCI pos.): Calculated for C$_{21}$H$_{20}$F$_3$N$_5$: 400.2 (M+H). Measured: 400.2.

Following the procedures described in Example 23 above, and substituting suitably selected and substituted reagents, starting materials and conditions as would be readily apparent to those skilled in the art, the following representative compounds of the present invention were prepared.

| Cmpd 37 | 2-(5-tert-Butyl-2-methyl-2H-pyrazol-3-yl)-5-(2-trifluoromethoxy-phenyl)-1H-imidazo[4,5-b]pyridine<br>$^1$H-NMR (400 MHz, CDCl$_3$) δ: 8.15 (d, J = 8.3 Hz, 1H), 7.79 (d, J = 6.3 Hz, 1H), 7.62 (d, J = 8.3 Hz, 1H), 7.37-7.49 (m, 3H), 6.59 (s, 1H), 4.38 (s, 3H), 1.34 (s, 9H).<br>Mass Spectrum (LCMS, APCI pos.): Calculated for C$_{21}$H$_{20}$F$_3$N$_5$O: 416.2 (M + H); Measured: 416.2. |
|---|---|

Example 24

2-(5-tert-Butyl-4-chloro-2-methyl-2H-pyrazol-3-yl)-4-(4-methyl-piperazin-1-yl)-6-(2-trifluoromethyl-phenyl)-3H-imidazo[4,5-c]pyridine methanesulfonic acid salt (Compound #28)

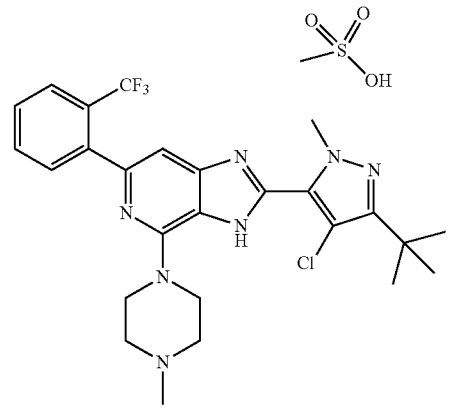

STEP A: 6-Chloro-2-(4-methyl-piperazin-1-yl)-3-nitro-pyridin-4-ylamine

A solution of 2,6-dichloro-3-nitro-pyridin-4-ylamine (0.500 g, 2.40 mmol) in DMF (5 mL) was treated with K$_2$CO$_3$ (1.66 g, 12.0 mmol) and 1-methylpiperazine (0.267 mL, 2.40 mmol) at room temperature for 18 h. The resulting mixture was diluted with water (75 mL) and extracted three times with EtOAc (50 mL). The combined extracts were dried over MgSO$_4$ and concentrated in vacuo. The residue was purified on a 24-g SEPRA Si 50 SPE column (Isco system: Flow rate=15 mL/min; Eluent=EtOAc-hexanes, 3:1 v/v for 5 min, then 3:1 to 1:0 v/v over 40 min) to yield 6-chloro-2-(4-methyl-piperazin-1-yl)-3-nitro-pyridin-4-ylamine as a bright yellow solid. $^1$H-NMR (400 MHz, CD$_3$OD) δ: 6.22 (s, 1H), 3.39-3.45 (m, 4H), 2.49-2.55 (m, 4H), 2.34 (s, 3H). Mass Spectrum (LCMS, APCI pos.): Calculated for C$_{10}$H$_{14}$ClN$_5$O$_2$: 272.1 (M+H). Measured: 272.1.

STEP B: 2-(4-Methyl-piperazin-1-yl)-3-nitro-6-(2-trifluoromethyl-phenyl)-pyridin-4-ylamine A solution of 6-chloro-2-(4-methyl-piperazin-1-yl)-3-nitro-pyridin-4-ylamine (578 mg, 2.13 mmol, prepared as described in the previous step) in 1,4-dioxane (20 mL) was treated with K₃PO₄ (2.03 g, 9.58 mmol), 1,1'-bis(di-tert-butylphosphino)ferrocene (101 mg, 0.213 mmol), and 2-trifluoromethylphenylboronic acid (910 mg, 4.79 mmol). The resulting mixture was degassed via sonication, Pd(OAc)₂ (47.8 mg, 0.213 mmol) was added, and the mixture was heated to 80° C. for 18 h. The cooled mixture was diluted with water (50 mL) and extracted twice with EtOAc (60 mL). The combined extracts were dried over MgSO₄ and concentrated in vacuo. The residue was purified on a 40-g SEPRA Si 50 SPE column (Isco system: Flow rate=20 mL/min; Eluent=EtOAc-hexanes, 3:1 v/v for 5 min, then 3:1 to 1:0 v/v over 40 min) to yield 2-(4-methyl-piperazin-1-yl)-3-nitro-6-(2-trifluoromethyl-phenyl)-pyridin-4-ylamine as an orange solid. $^1$H-NMR (400 MHz, CDCl₃) δ: 7.74 (d, J=7.6 Hz, 1H), 7.55-7.61 (m, 1H), 7.45-7.54 (m, 2H), 6.13 (s, 1H), 6.02 (br. s., 2H), 3.46-3.52 (m, 4H), 2.44-2.50 (m, 4H), 2.32 (s, 3H). Mass Spectrum (LCMS, APCI pos.): Calculated for $C_{17}H_{18}F_3N_5O_2$: 382.1 (M+H). Measured: 382.1.

STEP C: 5-tert-Butyl-4-chloro-2-methyl-2H-pyrazole-3-carboxylic acid [2-(4-methyl-piperazin-1-yl)-3-nitro-6-(2-trifluoromethyl-phenyl)-pyridin-4-yl]-amide A solution of 2-(4-methyl-piperazin-1-yl)-3-nitro-6-(2-trifluoromethyl-phenyl)-pyridin-4-ylamine (240 mg, 0.630 mmol, prepared as described in the previous step) in THF (10 mL) was treated with NaH (75.6 mg, 1.89 mmol, 60% dispersion in mineral oil) at room temperature for 1 h. At the same time, a solution of 5-tert-butyl-4-chloro-2-methyl-2H-pyrazole-3-carboxylic acid (164 mg, 0.756 mmol, prepared as described in Example B) in DCM (10 mL) was treated with oxalyl chloride (66.0 µL, 0.756 mmol) and DMF (2 drops) at room temperature for 1 h. The resulting mixture was concentrated in vacuo, taken up in THF (6 mL), and added to the sodium anilide solution at room temperature. The solution was stirred at room temperature for 30 min, quenched with saturated aqueous NH₄Cl (20 mL), and extracted three times with EtOAc (25 mL). The combined extracts were dried over MgSO₄ and concentrated in vacuo. The residue was purified on a 24-g SEPRA Si 50 SPE column (Isco system: Flow rate=15 mL/min; Eluent=EtOAc-hexanes, 3:2 v/v for 5 min, then 3:2 to 4:1 v/v over 40 min) to yield 5-tert-butyl-4-chloro-2-methyl-2H-pyrazole-3-carboxylic acid [2-(4-methyl-piperazin-1-yl)-3-nitro-6-(2-trifluoromethyl-phenyl)-pyridin-4-yl]-amide as an orange solid. Mass Spectrum (LCMS, APCI pos.): Calculated for $C_{26}H_{29}ClF_3N_7O_3$: 580.2 (M+H). Measured: 580.2.

STEP D: 2-(5-tert-Butyl-4-chloro-2-methyl-2H-pyrazol-3-yl)-4-(4-methyl-piperazin-1-yl)-6-(2-trifluoromethyl-phenyl)-3H-imidazo[4,5-c]pyridine A solution of 5-tert-butyl-4-chloro-2-methyl-2H-pyrazole-3-carboxylic acid [2-(4-methyl-piperazin-1-yl)-3-nitro-6-(2-trifluoromethyl-phenyl)-pyridin-4-yl]-amide (300 mg, 0.517 mmol, prepared as described in the previous step) in AcOH (10 mL) was treated with iron powder (86.7 mg, 1.55 mmol) and heated to 100° C. for 5 h. The mixture was concentrated in vacuo, treated with saturated aqueous NaHCO₃ (25 mL), and extracted three times with EtOAc (30 mL). The combined extracts were dried over MgSO₄ and concentrated in vacuo. The residue was purified on a 12-g SEPRA Si 50 SPE column (Isco system: Flow rate=10 mL/min; Eluent=EtOAc-hexanes, 1:99 v/v for 5 min, then 1:99 to 3:17 v/v over 40 min) to yield 2-(5-tert-butyl-4-chloro-2-methyl-2H-pyrazol-3-yl)-4-(4-methyl-piperazin-1-yl)-6-(2-trifluoromethyl-phenyl)-3H-imidazo[4,5-c]pyridine as a tan solid. $^1$H-NMR (400 MHz, CDCl₃) δ: 9.99 (s, 1H), 7.76 (d, J=7.6 Hz, 1H), 7.56-7.61 (m, 2H), 7.45-7.52 (m, 1H), 6.95 (s, 1H), 4.30 (s, 7H), 2.59 (t, J=4.9 Hz, 4H), 2.36 (s, 3H), 1.45 (s, 9H). Mass Spectrum (LCMS, APCI pos.): Calculated for $C_{26}H_{29}ClF_3N_7$: 532.2 (M+H). Measured: 532.2.

STEP E: 2-(5-tert-Butyl-4-chloro-2-methyl-2H-pyrazol-3-yl)-4-(4-methyl-piperazin-1-yl)-6-(2-trifluoromethyl-phenyl)-3H-imidazo[4,5-c]pyridine methanesulfonic acid salt A solution of 2-(5-tert-butyl-4-chloro-2-methyl-2H-pyrazol-3-yl)-4-(4-methyl-piperazin-1-yl)-6-(2-trifluoromethyl-phenyl)-3H-imidazo[4,5-c]pyridine (158 mg, 0.297 mmol, prepared as described in the previous step) in DCM (10 mL) was treated with methanesulfonic acid (19.2 µL, 0.297 mmol) at room temperature for 1 h. The resulting mixture was concentrated in vacuo, triturated with hexanes, and filtered. The solid was air-dried and placed under high vacuum for 30 min to yield 2-(5-tert-butyl-4-chloro-2-methyl-2H-pyrazol-3-yl)-4-(4-methyl-piperazin-1-yl)-6-(2-trifluoromethyl-phenyl)-3H-imidazo[4,5-c]pyridine methanesulfonic acid salt as a tan solid. $^1$H-NMR (400 MHz, CD₃OD) δ: 7.83 (d, J=8.3 Hz, 1H), 7.68-7.74 (m, 1H), 7.58-7.65 (m, 2H), 7.20 (s, 1H), 5.52 (d, J=13.1 Hz, 2H), 4.12 (s, 3H), 3.64 (d, J=11.6 Hz, 2H), 3.45-3.58 (m, 2H), 3.26 (br. s., 2H), 2.96 (s, 3H), 2.69 (s, 4H), 1.45 (s, 9H). Mass Spectrum (LCMS, APCI pos.): Calculated for $C_{26}H_{29}ClF_3N_7$: 532.2 (M+H). Measured: 532.2.

Following the procedures described in Example 24 above, and substituting suitably selected and substituted reagents, starting materials and conditions as would be readily apparent to those skilled in the art, the following representative compounds of the present invention were prepared.

| | |
|---|---|
| Cmpd 22 | 3-tert-Butyl-1-methyl-5-[4-piperidin-1-yl-6-(2-trifluoromethyl-phenyl)-3H-imidazo[4,5-c]pyridine-2-yl]-1H-pyrazole-4-carbonitrile<br>$^1$H-NMR (400 MHz, CDCl₃) δ: 9.95 (s, 1H), 7.76 (d, J = 7.8 Hz, 1H), 7.56-7.60 (m, 2H), 7.45-7.52 (m, 1H), 6.87 (s, 1H), 4.36 (s, 3H), 4.21 (d, J = 5.1 Hz, 4H), 1.72 (br. s., 6H), 1.47 (s, 9H).<br>Mass Spectrum (LCMS, APCI pos.): Calculated for $C_{27}H_{28}F_3N_7$: 508.2 (M + H); Measured: 508.4. |
| Cmpd 24 | 3-tert-Butyl-1-methyl-5-[4-(4-methyl-piperazin-1-yl)-6-(2-trifluoromethyl-phenyl)-3H-imidazo[4,5-c]pyridin-2-yl]-1H-pyrazole-4-carbonitrile methanesulfonic acid salt<br>$^1$H-NMR (400 MHz, CD₃OD) δ: 7.85 (d, J = 8.1 Hz, 1H), 7.72 (d, J = 7.6 Hz, 1H), 7.61-7.68 (m, 2H), 7.21 (s, 1H), 5.55 (m, 2H), 4.17 (s, 3H), 3.49-3.71 (m, 4H), 3.25-3.31 (m, 2H), 2.97 (s, 3H), 2.69 (s, 3H), 1.48 (s, 9H).<br>Mass Spectrum (LCMS, APCI pos.): Calculated for $C_{27}H_{29}F_3N_8$: 523.3 (M + H); Measured: 523.3. |

Example 25

2-(5-tert-Butyl-4-chloro-2-methyl-2H-pyrazol-3-yl)-6-(2-chloro-phenyl)-4-methoxy-3H-imidazo[4,5-c]pyridine (Compound #11)

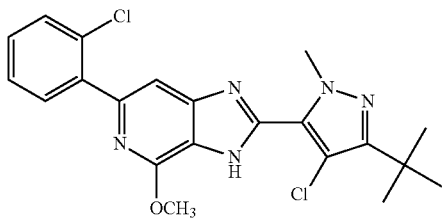 [SMILES: COc1nc(-c2ccccc2Cl)cc2nc(-c3c(Cl)c(C(C)(C)C)nn3C)[nH]c12]

STEP A:
6-Chloro-2-methoxy-3-nitro-pyridin-4-ylamine

To a stirred solution of 2,6-dichloro-3-nitro-pyridin-4-ylamine (20.0 g, 96.1 mmol) in MeOH (100 mL) was added 0.5 M NaOMe in MeOH (423 mL, 211 mmol) dropwise. The resulting mixture was stirred at room temperature for 3 h. The resulting mixture was then concentrated to ca. ⅓ of the volume and slowly poured into saturated NH$_4$Cl solution (200 mL). The resulting mixture was extracted with EtOAc (3×150 mL). The combined EtOAc extracts were dried (Na$_2$SO$_4$), and concentrated in vacuo to yield a tan solid which was suspended in hexane (500 mL) and sonicated for 10 min. The resulting solid was collected by suction filtration and dried under suction to yield 6-chloro-2-methoxy-3-nitro-pyridin-4-ylamine as a powder. $^1$H-NMR (400 MHz, CDCl$_3$) δ: 6.39 (s, 1H), 6.28 (br s, 2H), 4.05 (s, 3H).

STEP B: 6-(2-Chloro-phenyl)-2-methoxy-3-nitro-pyridin-4-ylamine

A solution of 6-chloro-2-methoxy-3-nitro-pyridin-4-ylamine (8.90 g, 43.7 mmol, prepared as described in the previous step) in 1,4-dioxane (200 mL) and water (100 mL) was treated with Cs$_2$CO$_3$ (35.6 g, 109 mmol) and 2-chlorophenylboronic acid (10.2 g, 65.5 mmol) under Ar. To the resulting mixture was added Cl$_2$Pd(dppf).DCM (3.50 g, 4.30 mmol) and the mixture was then heated to 90° C. for 15 h. The cooled mixture was diluted with EtOAc (500 mL) and washed with water (500 mL). The aqueous layer was extracted twice with EtOAc (3×300 mL). The combined extracts were dried over MgSO$_4$ and concentrated in vacuo. The residue was purified on silica (0:100-50:50 EtOAc/hexanes) to yield a yellowish white solid. The solid was dissolved in EtOAc (200 mL) with heating and hexane (150 mL) was added. The resulting solution was concentrated until the solution became turbid and heated to yield a clear solution which was left overnight at room temperature. The crystals formed were collected by suction filtration. This recrystallization procedure was repeated twice to yield 6-(2-chloro-phenyl)-2-methoxy-3-nitro-pyridin-4-ylamine. $^1$H-NMR (400 MHz, CDCl$_3$) δ: 7.59-7.66 (m, 1H), 7.43-7.51 (m, 1H), 7.31-7.39 (m, 2H), 6.69 (s, 1H), 6.11 (br. s., 2H), 4.07 (s, 3H). Mass Spectrum (LCMS, ESI pos.) Calculated for C$_{12}$H$_{10}$N$_3$O$_3$Cl: 280.0 (M+H). Measured: 280.1.

STEP C: 2-(5-tert-Butyl-4-chloro-2-methyl-2H-pyrazol-3-yl)-6-(2-chloro-phenyl)-4-methoxy-3H-imidazo[4,5-c]pyridine A solution of 6-(2-chloro-phenyl)-2-methoxy-3-nitro-pyridin-4-ylamine (8.10 g, 29.0 mmol, prepared as described in the previous step) in THF (200 mL) was treated with NaH (3.47 g, 86.8 mmol, 60% dispersion in oil) at 0° C. for 1 h. Simultaneously a solution of 5-tert-butyl-4-chloro-2-methyl-2H-pyrazole-3-carboxylic acid (6.90 g, 31.8 mmol, prepared as described in Example B) in DCM (200 mL) was treated with oxalyl chloride (3.2 mL, 36 mmol) and DMF (50 μL) at 0° C. and stirred at room temperature for 1 h. The volatile components were removed in vacuo, and the resulting residue was dried in vacuo for 15 min taken up in THF (20 mL) and added to the above sodium anilide solution at 0° C. The resulting mixture was stirred at room temperature for 30 min, quenched with saturated aqueous NH$_4$Cl (20 mL), and extracted with EtOAc (3×100 mL). The combined extracts were dried over MgSO$_4$ and concentrated in vacuo. The resulting solid was suspended in hexane (200 mL) and sonicated for 10 min and collected by suction filtration to yield 5-tert-butyl-4-chloro-2-methyl-2H-pyrazole-3-carboxylic acid [6-(2-chloro-phenyl)-2-methoxy-3-nitro-pyridin-4-yl]-amide as a tan-colored solid.

A solution of 5-tert-butyl-4-chloro-2-methyl-2H-pyrazole-3-carboxylic acid [6-(2-chloro-phenyl)-2-methoxy-3-nitro-pyridin-4-yl]-amide (9.10 g, 32.6 mmol, prepared as described in the previous step above) in AcOH (50 mL) was treated with iron powder (6.80 g, 122 mmol) and heated to 100° C. for 3 h. The resulting mixture was cooled to room temperature and treated with EtOAc (100 mL). The resulting mixture was then filtered through a pad of diatomaceous earth and the filtrate was concentrated in vacuo. The residue was purified on silica (0:100-100:0 EtOAc/hexane) to yield a white solid. The solid obtained was dissolved in Et$_2$O (200 mL) with heating and sonication. Hexanes (50 mL) were added and the resulting mixture was concentrated until a precipitate started to form. The solution was left at room temperature overnight and the solid formed was collected by suction filtration to yield 2-(5-tert-butyl-4-chloro-2-methyl-2H-pyrazol-3-yl)-6-(2-chloro-phenyl)-4-methoxy-3H-imidazo[4,5-c]pyridine. $^1$H-NMR (400 MHz, CD$_3$OD) δ: 7.76-7.58 (m, 1H), 7.49 (m, 2H), 7.39 (m, 2H), 4.16 (s, 3H), 4.04 (s, 3H), 1.44 (s, 9H). Mass Spectrum (LCMS, ESI pos.) Calculated for C$_{21}$H$_{21}$N$_5$OCl$_2$: 430.1 (M+H). Measured: 430.2.

Example 26

2-(5-tert-Butyl-4-chloro-2-methyl-2H-pyrazol-3-yl)-6-(2-chloro-phenyl)-4-methoxy-3H-imidazo[4,5-c]pyridine methanesulfonic acid salt (Compound #11)

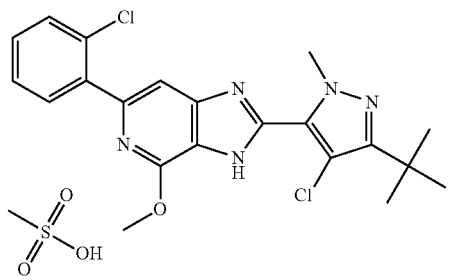

A solution of 2-(5-tert-butyl-4-chloro-2-methyl-2H-pyrazol-3-yl)-6-(2-chloro-phenyl)-4-methoxy-3H-imidazo[4,5-c]pyridine (159 mg, 0.370 mmol, prepared as described in Example 25) in DCM (10 mL) and treated with methanesulfonic acid (35.6 mg, 0.370 mmol) at room temperature for 1 h. The solution was concentrated in vacuo and the resulting solid was triturated with hexanes, filtered, washed with hexanes, air-dried, and placed under high vacuum for 30 min to yield 2-(5-tert-butyl-4-chloro-2-methyl-2H-pyrazol-3-yl)-6-(2-chloro-phenyl)-4-methoxy-3H-imidazo[4,5-c]pyridine methanesulfonic acid salt as a white solid. $^1$H-NMR (400 MHz, CD$_3$OD) δ: 7.64-7.69 (m, 2H), 7.62-7.64 (m, 1H), 7.50-7.61 (m, 2H), 4.75-4.81 (m, 3H), 4.16 (s, 3H), 2.70 (s, 3H), 1.46 (s, 9H). Mass Spectrum (LCMS, APCI pos.) Calculated for $C_{21}H_{21}N_5OCl_2$: 430.1 (M+H). Measured: 430.2.

Example 27

2-(5-tert-Butyl-4-chloro-2-methyl-2H-pyrazol-3-yl)-6-(2-chloro-phenyl)-4-methoxy-3H-imidazo[4,5-c]pyridine trifluoroacetic acid salt (Compound #11)

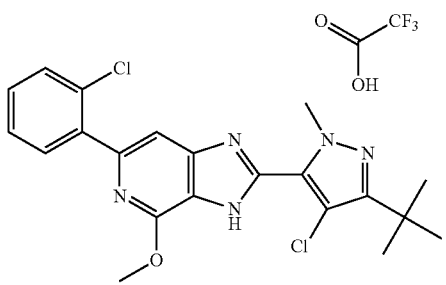

To a solution of 5-tert-butyl-4-chloro-2-methyl-2H-pyrazole-3-carboxylic acid [6-(2-chloro-phenyl)-2-methoxy-3-nitro-pyridin-4-yl]amide (96.3 mg, 0.201 mmol, prepared as described in Example 25, STEP C) in HOAc (10 mL), was added iron powder (56.2 mg, 1.01 mmol) and the resulting mixture was heated to 100° C. for 5 h. The HOAc was then removed in vacuo. The resulting residue was partitioned between EtOAc (30 mL) and saturated aqueous NaHCO$_3$ (20 mL). The organic layer was dried over MgSO$_4$ and concentrated in vacuo. The resulting residue was purified on a 12-g SEPRA Si 50 SPE column (Isco system: Flow rate=20 mL/min; Eluent=EtOAc/hexanes, 1:99 v/v for 10 min, then 1:99 to 1:4 v/v over 40 min). The resulting residue was further purified by RP-HPLC on a C18 column eluting with a linear gradient of 40-100% CH$_3$CN in 0.1% TFA/H$_2$O over 20 min to yield 2-(5-tert-butyl-4-chloro-2-methyl-2H-pyrazol-3-yl)-6-(2-chloro-phenyl)-4-methoxy-3H-imidazo[4,5-c]pyridine trifluoroacetic acid salt as a white solid. $^1$H-NMR (CD$_3$OD) δ: 7.69 (dd, J=7.2, 2.1 Hz, 1H), 7.50-7.56 (m, 2H), 7.37-7.46 (m, 2H), 4.25 (s, 3H), 4.05 (s, 3H), 1.45 (s, 9H). Mass Spectrum (LCMS, ESI pos.) Calculated for $C_{21}H_{21}N_5OCl_2$: 430.1 (M+H). Measured: 430.2.

Example 28

2-(5-tert-Butyl-4-chloro-2-methyl-2H-pyrazol-3-yl)-6-(2-chloro-phenyl)-4-methoxy-3H-imidazo[4,5-c]pyridine potassium salt (Compound #11)

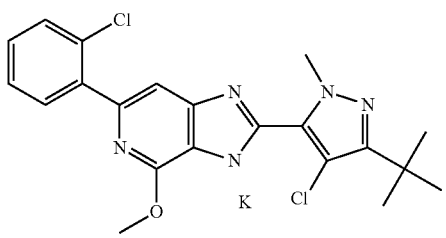

To a solution of 2-(5-tert-butyl-4-chloro-2-methyl-2H-pyrazol-3-yl)-6-(2-chloro-phenyl)-4-methoxy-3H-imidazo[4,5-c]pyridine (11.0 g, 25.7 mmol, prepared as described in Example 25) in THF (20 mL) and MeOH (20 mL) at 0° C., a solution of KOMe (1.90 g, 25.7 mmol) in MeOH (20 mL) was added dropwise. The resulting mixture was stirred at room temperature for 1 h and concentrated. The resulting thick syrup was dried in vacuo at 80° C. overnight to yield 2-(5-tert-butyl-4-chloro-2-methyl-2H-pyrazol-3-yl)-6-(2-chloro-phenyl)-4-methoxy-3H-imidazo[4,5-c]pyridine potassium salt as a white foam. $^1$H-NMR (400 MHz, CD$_3$OD) δ: 7.66-7.69 (m, 1H), 7.46-7.50 (m, 1H), 7.43 (s, 1H), 7.28-7.39 (m, 2H), 4.12 (s, 3H), 3.90 (s, 3H), 1.44 (s, 9H). Mass Spectrum (LCMS, ESI pos.) Calculated for $C_{21}H_{21}N_5OCl_2$: 430.1 (M+H). Measured: 430.2.

Example 29

2-(5-tert-Butyl-4-chloro-2-methyl-2H-pyrazol-3-yl)-6-(2-chloro-phenyl)-4-methoxy-3H-imidazo[4,5-c]pyridine hydrochloride (Compound #11)

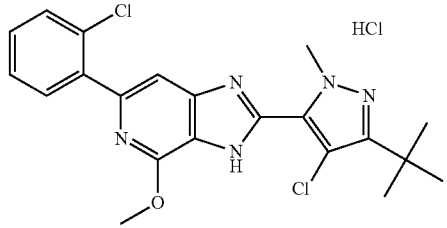 [SMILES: COc1nc(-c2ccccc2Cl)cc2nc(-c3c(Cl)c(C(C)(C)C)nn3C)[nH]c12 ; Cl]

2-(5-tert-Butyl-4-chloro-2-methyl-2H-pyrazol-3-yl)-6-(2-chloro-phenyl)-4-methoxy-3H-imidazo[4,5-c]pyridine hydrochloride was prepared from 2-(5-tert-butyl-4-chloro-2-methyl-2H-pyrazol-3-yl)-6-(2-chloro-phenyl)-4-methoxy-3H-imidazo[4,5-c]pyridine prepared as described in Example 25) according to the procedure described in Example 2, STEP C substituting 6M HCl in IPA with 2M HCl in Et$_2$O. $^1$H-NMR (CD$_3$OD) δ: 7.69-7.65 (m, 1H), 7.53-7.60 (m, 2H), 7.42-7.49 (m, 2H), 4.40 (s, 3H), 4.10 (s, 3H), 1.47 (s, 9H). Mass Spectrum (LCMS, ESI pos.) Calculated for $C_{21}H_{21}N_5OCl_2$: 430.1 (M+H). Measured: 430.2.

Example 30

2-(5-tert-Butyl-4-chloro-2-methyl-2H-pyrazol-3-yl)-6-(2-chloro-phenyl)-4-methoxy-3H-imidazo[4,5-c]pyridine sodium salt (Compound #11)

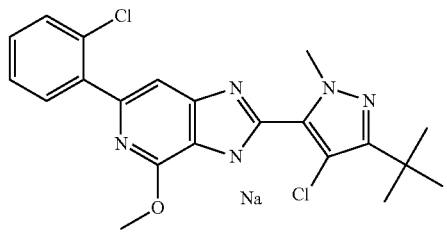

2-(5-tert-Butyl-4-chloro-2-methyl-2H-pyrazol-3-yl)-6-(2-chloro-phenyl)-4-methoxy-3H-imidazo[4,5-c]pyridine sodium salt was prepared from 2-(5-tert-butyl-4-chloro-2-methyl-2H-pyrazol-3-yl)-6-(2-chloro-phenyl)-4-methoxy-3H-imidazo[4,5-c]pyridine prepared as described in Example 25) according to the procedure described in Example 5, STEP E. $^1$H-NMR (CD$_3$OD) δ: 7.67 (d, J=7.8 Hz, 1H), 7.48 (d, J=8.2 Hz, 1H), 7.41 (s, 1H), 7.26-7.39 (m, 2H), 4.11 (s, 3H), 3.87 (s, 3H), 1.44 (s, 9H). Mass Spectrum (LCMS, ESI pos.) Calculated for C$_{21}$H$_{21}$N$_5$OCl$_2$: 430.1 (M+H). Measured: 430.2.

Following the procedures described in Examples 25-30 above, and substituting suitably selected and substituted reagents, starting materials and conditions as would be readily apparent to those skilled in the art, the following representative compounds of the present invention were prepared.

| Cmpd | |
|---|---|
| Cmpd 2 | 2-(5-tert-Butyl-4-chloro-2-methyl-2H-pyrazol-3-yl)-4-methoxy-6-(2-trifluoromethoxy-phenyl)-3H-imidazo[4,5-c]pyridine sodium salt<br>$^1$H-NMR (CD$_3$OD) δ: 7.96-8.04 (m, 1H), 7.61 (s, 1H), 7.47-7.54 (m, 2H), 7.41-7.47 (m, 1H), 4.21 (s, 3H), 4.06 (s, 3H), 1.46 (s, 9H).<br>Mass Spectrum (LCMS, APCI pos.) Calculated For C$_{22}$H$_{21}$ClF$_3$N$_5$O$_2$: 480.1 (M + H), Measured: 480.3. |
| Cmpd 12 | 2-(5-tert-Butyl-2-methyl-2H-pyrazol-3-yl)-6-(2-chloro-phenyl)-4-methoxy-3H-imidazo[4,5-c]pyridine<br>$^1$H-NMR (CD$_3$OD) δ: 7.68 (dd, J = 7.2, 1.9 Hz, 1H), 7.48-7.54 (m, 1H), 7.32-7.45 (m, 3H), 6.76 (br. s., 1H), 4.26 (s, 3H), 4.15 (s, 3H), 1.36 (s, 9H).<br>Mass Spectrum (LCMS, APCI pos.) Calculated For C$_{21}$H$_{22}$ClN$_5$O: 396.2 (M + H), Measured: 396.2. |
| Cmpd 13 | 3-tert-Butyl-5-[4-methoxy-6-(2-trifluoromethyl-phenyl)-1H-imidazo[4,5-c]pyridine-2-yl]-isoxazole-4-carbonitrile methanesulfonic acid salt<br>$^1$H-NMR (DMSO-d$_6$) δ: 7.87 (d, J = 7.8 Hz, 1H), 7.74-7.81 (m, 1H), 7.64-7.71 (m, 2H), 7.35 (s, 1H), 4.05 (s, 3H), 2.33 (s, 3H), 1.48 (s, 9H).<br>Mass Spectrum (LCMS, ESI pos.) Calculated For C$_{22}$H$_{18}$F$_3$N$_5$O$_2$: 442.2 (M + H), Measured: 442.1. |
| Cmpd 14 | 3-tert-Butyl-5-[4-isopropoxy-6-(2-trifluoromethyl-phenyl)-3H-imidazo[4,5-c]pyridin-2-yl]-1-methyl-1H-pyrazole-4-carbonitrile benzenesulfonic acid salt<br>$^1$H-NMR (CD$_3$OD) δ: 7.92-8.00 (m, 1H), 7.80-7.86 (m, 4H), 7.68-7.75 (m, 1H), 7.56 (s, 1H), 7.36-7.48 (m, 3H), 6.43 (spt, J = 6.1 Hz, 1H), 4.18 (s, 3H), 1.63 (d, J = 6.1 Hz, 6H), 1.46 (s, 9H).<br>Mass Spectrum (LCMS, ESI pos.) Calculated For C$_{25}$H$_{25}$F$_3$N$_6$O: 483.2 (M + H), Measured: 483.1. |
| Cmpd 15 | 3-tert-Butyl-1-methyl-5-[4-(2,2,2-trifluoro-ethoxy)-6-(2-trifluoromethyl-phenyl)-3H-imidazo[4,5-c]pyridine-2-yl]-1H-pyrazole-4-carbonitrile methanesulfonic acid salt<br>$^1$H-NMR (CD$_3$OD) δ: 7.85 (d, J = 8.1 Hz, 1H), 7.69-7.76 (m, 1H), 7.60-7.68 (m, 2H), 7.48-7.52 (m, 1H), 5.09-5.21 (m, 2H), 4.14 (s, 3H), 2.70 (s, 3H), 1.48 (s, 9H).<br>Mass Spectrum (LCMS, APCI pos.) Calculated For C$_{24}$H$_{20}$F$_6$N$_6$O: 523.2 (M + H), Measured: 523.2. |
| Cmpd 16 | 2-(5-tert-Butyl-4-chloro-2-methyl-2H-pyrazol-3-yl)-4-isopropoxy-6-(2-trifluoromethyl-phenyl)-3H-imidazo[4,5-c]pyridine benzenesulfonic acid salt<br>$^1$H-NMR (CD$_3$OD) δ: 7.93-7.98 (m, 1H), 7.76-7.88 (m, 4H), 7.68-7.74 (m, 1H), 7.55 (s, 1H), 7.40-7.47 (m, 3H), 6.33 (spt, J = 6.0 Hz, 1H), 4.20 (s, 3H), 1.62 (d, J = 6.1 Hz, 6H), 1.51 (s, 9H).<br>Mass Spectrum (LCMS, APCI pos.) Calculated For C$_{25}$H$_{26}$ClN$_5$O: 492.2 (M + H), Measured: 492.0. |
| Cmpd 17 | 3-tert-Butyl-5-[6-(2-chloro-phenyl)-4-methoxy-3H-imidazo[4,5-c]pyridine-2-yl]-1-methyl-1H-pyrazole-4-carbonitrile methanesulfonic acid salt<br>$^1$H-NMR (CD$_3$OD) δ: 7.63-7.70 (m, 3H), 7.50-7.61 (m, 2H), 4.76 (s, 3H), 4.19 (s, 3H), 2.70 (s, 3H), 1.49 (s, 9H).<br>Mass Spectrum (LCMS, APCI pos.) Calculated For C$_{22}$H$_{21}$ClN$_6$O: 421.2 (M + H), Measured: 421.3. |
| Cmpd 18 | 2-(2-methyl-6,6-spirocyclohexyl-2,4,5,6-tetrahydro-cyclopenta-2H-pyrazol-3-yl)-4-methoxy-6-(2-chloro-phenyl)-3H-imidazo[4,5-c]pyridine<br>$^1$H-NMR (CD$_3$OD) δ: 7.66-7.71 (m, 1H), 7.55 (br. s., 2H), 7.29-7.41 (m, 2H), 4.23 (s, 3H), 4.18 (s, 3H), 2.82-2.89 (m, 2H), 2.34 (t, J = 6.9 Hz, 2H), 1.68-1.82 (m, 4H), 1.46-1.63 (m, 6H).<br>Mass Spectrum (LCMS, ESI pos.) Calculated For C$_{25}$H$_{26}$ClN$_5$O: 448.2 (M + H), Measured: 448.3. |
| Cmpd 19 | 2-(5-tert-Butyl-4-chloro-2-methyl-2H-pyrazol-3-yl)-4-(2,2,2-trifluoroethoxy)-6-(2-trifluoromethyl-phenyl)-3H-imidazo[4,5-c]pyridine methanesulfonic acid salt<br>$^1$H-NMR (CD$_3$OD) δ: 7.86 (d, J = 7.6 Hz, 1H), 7.70-7.78 (m, 1H), 7.62-7.70 (m, 2H), 7.53 (s, 1H), 5.22 (q, J = 8.8 Hz, 2H), 4.07 (s, 3H), 2.70 (s, 3H), 1.45 (s, 9H).<br>Mass Spectrum (LCMS, APCI pos.) Calculated For C$_{23}$H$_{20}$ClF$_6$N$_5$O: 532.1 (M + H), Measured: 532.2. |

-continued

| | |
|---|---|
| Cmpd 20 | 2-(5-tert-Butyl-4-chloro-2-methyl-2H-pyrazol-3-yl)-4-(2-methoxy-ethoxy)-6-(2-trifluoromethyl-phenyl)-3H-imidazo[4,5-c]pyridine benzenesulfonic acid salt<br>$^1$H-NMR (CD$_3$OD) δ: 7.93 (d, J = 7.1 Hz, 1H), 7.73-7.85 (m, 4H), 7.69 (d, J = 7.1 Hz, 1H), 7.56 (s, 1H), 7.34-7.44 (m, 3H), 5.26-5.34 (m, 2H), 4.14 (s, 3H), 3.86-3.94 (m, 2H), 3.41 (s, 3H), 1.45 (s, 9H).<br>Mass Spectrum (LCMS, ESI pos.) Calculated For C$_{24}$H$_{25}$ClF$_3$N$_5$O$_2$: 508.2 (M + H), Measured: 508.2. |
| Cmpd 21 | 3-tert-Butyl-5-[4-(2-methoxy-ethoxy)-6-(2-trifluoromethyl-phenyl)-3H-imidazo[4,5-c]pyridine-2-yl]-1-methyl-1H-pyrazole-4-carbonitrile benzenesulfonic acid salt<br>$^1$H-NMR (CD$_3$OD) δ: 7.92-7.97 (m, 1H), 7.77-7.84 (m, 4H), 7.71 (dd, J = 6.9, 1.6 Hz, 1H), 7.60 (s, 1H), 7.36-7.45 (m, 3H), 5.42 (dt, J = 4.0, 2.3 Hz, 2H), 4.19 (s, 3H), 3.89-3.95 (m, 2H), 3.41 (s, 3H), 1.49 (s, 9H).<br>Mass Spectrum (LCMS, ESI pos.) Calculated For C$_{25}$H$_{25}$F$_3$N$_6$O$_2$: 499.2 (M + H), Measured: 499.1. |
| Cmpd 43 | 2-(5-tert-Butyl-4-chloro-2-methyl-2H-pyrazol-3-yl)-6-(2-fluoro-phenyl)-3H-imidazo[4,5-c]pyridine hydrochloride<br>$^1$H-NMR (400 MHz, CD$_3$OD) δ: 9.45 (s, 1H), 8.20 (s, 1H), 7.95-8.01 (m, 1H), 7.81-7.89 (m, 2H), 7.69-7.76 (m, 1H), 4.21 (s, 3H), 1.46 (s, 9H).<br>Mass Spectrum (LCMS, ESI pos.) Calculated For C$_{20}$H$_{19}$ClFN$_5$: 384.1 (M + H), Measured: 384.3. |
| Cmpd 46 | 2-(5-tert-Butyl-4-chloro-2-methyl-2H-pyrazol-3-yl)-6-(2-trifluoromethyl-phenyl)-3H-imidazo[4,5-c]pyridine hydrochloride<br>$^1$H-NMR (400 MHz, CD$_3$OD) δ: 9.34 (s, 1H), 8.29 (s, 1H), 7.79 (td, J = 7.7, 1.8 Hz, 1H), 7.63-7.73 (m, 1H), 7.36-7.51 (m, 2H), 4.20 (s, 3H), 1.43 (s, 9H).<br>Mass Spectrum (LCMS, ESI pos.) Calculated For C$_{21}$H$_{19}$ClF$_3$N$_5$: 434.1 (M + H), Measured: 434.2. |
| Cmpd 48 | 2-(5-tert-Butyl-4-chloro-2-methyl-2H-pyrazol-3-yl)-6-(2-fluoro-phenyl)-3H-imidazo[4,5-c]pyridine hydrochloride<br>$^1$H-NMR (400 MHz, CD$_3$OD) δ: 9.47 (s, 1H), 8.37 (s, 1H), 7.84 (td, J = 7.6, 1.6 Hz, 1H), 7.68-7.78 (m, 1H), 7.42-7.55 (m, 2H), 4.39 (s, 3H).<br>Mass Spectrum (LCMS, ESI pos.) Calculated For C$_{17}$H$_{10}$ClF$_4$N$_5$: 396.1 (M + H), Measured: 396.3. |
| Cmpd 77 | 2-(5-tert-Butyl-4-chloro-2-methyl-2H-pyrazol-3-yl)-6-(2-fluorophenyl)-4-methoxy-3H-imidazo[4,5-c]pyridine sodium salt<br>$^1$H-NMR (400 MHz, d$_6$-DMSO) δ: 8.11-8.23 (m, 1H), 7.58 (d, J = 2.2 Hz, 1H), 7.16-7.36 (m, 3H), 4.01 (s, 3H), 4.03 (s, 3H), 1.38 (s, 9H).<br>Mass Spectrum (LCMS, ESI pos.): Calculated for C$_{21}$H$_{21}$ClFN$_5$O: 414.2 (M + H); Measured: 414.0. |
| Cmpd 78 | 2-(5-tert-Butyl-4-fluoro-2-methyl-2H-pyrazol-3-yl)-4-methoxy-6-(2-trifluoromethyl-phenyl)-3H-imidazo[4,5-c]pyridine methanesulfonic acid salt<br>$^1$H-NMR (400 MHz, d$_6$-DMSO) δ: 7.86 (d, J = 7.8 Hz, 1H), 7.76 (t, J = 7.3 Hz, 1H), 7.61-7.70 (m, J = 7.1, 4.5 Hz, 2H), 7.31 (s, 1H), 4.12 (s, 3H), 4.02 (s, 3H), 2.36 (s, 3H), 1.35 (s, 9H).<br>Mass Spectrum (LCMS, ESI pos.): Calculated for C$_{22}$H$_{21}$F$_4$N$_5$O: 448.2 (M + H); Measured: 448.2. |
| Cmpd 89 | 2-(5-tert-Butyl-4-chloro-2-methyl-2H-pyrazol-3-yl)-6-(2-chlorophenyl)-4-(2,2,2-trifluoro-ethoxy)-3H-imidazo[4,5-c]pyridine sodium salt<br>$^1$H-NMR (400 MHz, d$_6$-DMSO) δ: 7.70 (dd, J = 7.6, 1.7 Hz, 1H), 7.51 (dd, J = 8.1, 1.2 Hz, 1H), 7.44 (s, 1H), 7.40 (td, J = 7.5, 1.3 Hz, 1H), 7.29-7.35 (m, 1H), 5.14 (q, J = 9.5 Hz, 2H), 4.00 (s, 3H), 1.39 (s, 9H).<br>Mass Spectrum (LCMS, ESI pos.): Calculated for C$_{22}$H$_{20}$Cl$_2$F$_3$N$_5$O: 498.1 (M + H); Measured: 498.1. |
| Cmpd 90 | 2-(5-tert-Butyl-4-chloro-2-methyl-2H-pyrazol-3-yl)-4-(2,2,2-trifluoro-ethoxy)-6-(2-trifluoromethoxyphenyl)-3H-imidazo[4,5-c]pyridine sodium salt<br>$^1$H-NMR (400 MHz, d$_6$-DMSO) δ: 7.95 (d, J = 7.6 Hz, 1H), 7.51 (s, 1H), 7.37-7.50 (m, 3H), 5.17 (q, J = 9.5 Hz, 2H), 4.01 (s, 3H), 1.39 (s, 9H).<br>Mass Spectrum (LCMS, ESI pos.): Calculated for C$_{23}$H$_{20}$ClF$_6$N$_5$O$_2$: 548.1 (M + H); Measured: 548.1. |
| Cmpd 91 | 2-(5-tert-Butyl-4-chloro-2-methyl-2H-pyrazol-3-yl)-6-(2-fluorophenyl)-4-(2,2,2-trifluoroethoxy)-3H-imidazo[4,5-c]pyridine sodium salt<br>$^1$H-NMR (400 MHz, d$_6$-DMSO) δ: 8.07-8.19 (m, 1H), 7.66 (d, J = 2.2 Hz, 1H), 7.19-7.37 (m, 3H), 5.21 (q, J = 9.3 Hz, 2H), 4.02 (s, 3H), 1.39 (s, 9H).<br>Mass Spectrum (LCMS, ESI pos.): Calculated for C$_{22}$H$_{20}$ClF$_4$N$_5$O: 482.1 (M + H); Measured: 482.1. |

| | |
|---|---|
| Cmpd 92 | 2-(5-tert-Butyl-4-chloro-2-methyl-2H-pyrazol-3-yl)-6-(2-fluorophenyl)-4-isopropoxy-3H-imidazo[4,5-c]pyridine sodium salt<br>$^1$H-NMR (400 MHz, d$_6$-DMSO) δ: 8.04-8.16 (m, 1H), 7.56 (d, J = 2.0 Hz, 1H), 7.17-7.35 (m, 3H), 5.60 (spt, J = 6.2 Hz, 1H), 4.00 (s, 3H), 1.41 (d, J = 6.4 Hz, 6H), 1.39 (s, 9H).<br>Mass Spectrum (LCMS, ESI pos.): Calculated for C$_{23}$H$_{25}$ClFN$_5$O: 442.2 (M + H); Measured: 442.1. |
| Cmpd 93 | 2-(5-tert-Butyl-4-chloro-2-methyl-2H-pyrazol-3-yl)-4-isopropoxy-6-(2-trifluoromethoxyphenyl)-3H-imidazo[4,5-c]pyridine sodium salt<br>$^1$H-NMR (400 MHz, d$_6$-DMSO) δ: 7.92 (d, J = 7.6 Hz, 1H), 7.42-7.50 (m, 1H), 7.35-7.42 (m, 3H), 5.57 (spt, J = 6.2 Hz, 1H), 3.99 (s, 3H), 1.39 (s, 9H), 1.38 (d, J = 6.1 Hz, 6H).<br>Mass Spectrum (LCMS, ESI pos.): Calculated for C$_{24}$H$_{25}$ClF$_3$N$_5$O$_2$: 508.2 (M + H); Measured: 508.1. |
| Cmpd 97 | 2-[4-Chloro-5-(2-fluoro-1,1-dimethyl-ethyl)-2-methyl-2H-pyrazol-3-yl]-6-(2-chloro-phenyl)-4-methoxy-3H-imidazo[4,5-c]pyridine sodium salt<br>$^1$H-NMR (400 MHz, d$_6$-DMSO) δ: 7.71 (dd, J = 7.7, 1.8 Hz, 1H), 7.49 (dd, J = 7.9, 1.3 Hz, 1H), 7.36-7.42 (m, 1H), 7.35 (s, 1H), 7.25-7.33 (m, 1H), 4.63 (d, J = 47.9 Hz, 2H), 4.05 (s, 3H), 3.96 (s, 3H), 1.41 (d, J = 1.7 Hz, 6H). Mass Spectrum (LCMS, ESI pos.): Calculated for C$_{21}$H$_{20}$Cl$_2$FN$_5$O: 448.1 (M + H); Measured: 448.1. |
| Cmpd 98 | 6-(2-Chloro-phenyl)-2-(5-isopropyl-thiophen-3-yl)-4-methoxy-3H-imidazo[4,5-c]pyridine<br>$^1$H-NMR (400 MHz, CD$_3$OD) δ: 7.88-7.98 (m, 1H), 7.62-7.70 (m, 1H), 7.50-7.55 (m, 1H), 7.44-7.50 (m, 1H), 7.28-7.42 (m, 3H), 4.12-4.17 (m, 3H), 3.17-3.28 (m, 1H), 1.36-1.40 (m, 6H).<br>Mass Spectrum (LCMS, ESI pos.) Calculated for C$_{20}$H$_{18}$ClN$_3$OS: 384.0 (M + H), Measured: 384.1 |
| Cmpd 99 | 2-(4-tert-Butyl-furan-2-yl)-6-(2-chloro-phenyl)-4-methoxy-3H-imidazo[4,5-c]pyridine sodium salt<br>$^1$H-NMR (400 MHz, d$_6$-DMSO) δ: 7.70 (dd, J = 7.6, 1.7 Hz, 1H), 7.48 (dd, J = 7.8, 1.2 Hz, 1H), 7.37 (td, J = 7.5, 1.3 Hz, 1H), 7.32 (d, J = 1.0 Hz, 1H), 7.29 (dd, J = 7.8, 1.7 Hz, 1H), 7.26 (s, 1H), 6.77 (d, J = 1.0 Hz, 1H), 3.93 (s, 3H), 1.25 (s, 9H).<br>Mass Spectrum (LCMS, ESI pos.): Calculated for C$_{21}$H$_{20}$ClN$_3$O$_2$: 382.1 (M + H); Measured: 382.1. |
| Cmpd 100 | 2-(1-tert-Butyl-5-methyl-1H-pyrazol-4-yl)-6-(2-chloro-phenyl)-4-methoxy-3H-imidazo[4,5-c]pyridine sodium salt<br>$^1$H-NMR (400 MHz, d$_6$-DMSO) δ: 7.76 (s, 1H), 7.72 (dd, J = 7.8, 1.7 Hz, 1H), 7.47 (dd, J = 7.8, 1.2 Hz, 1H), 7.36 (td, J = 7.5, 1.3 Hz, 1H), 7.23-7.30 (m, 2H), 3.16 (s, 3H), 2.98 (s, 3H), 1.62 (s, 9H).<br>Mass Spectrum (LCMS, ESI pos.): Calculated for C$_{21}$H$_{22}$ClN$_5$O: 396.2 (M + H); Measured: 396.1. |
| Cmpd 101 | 2-(5-Bromo-4-tert-butyl-furan-2-yl)-6-(2-chloro-phenyl)-4-methoxy-3H-imidazo[4,5-c]pyridine sodium salt<br>$^1$H-NMR (400 MHz, d$_6$-DMSO) δ: 7.69 (dd, J = 7.6, 1.7 Hz, 1H), 7.48 (dd, J = 7.8, 1.2 Hz, 1H), 7.37 (td, J = 7.5, 1.5 Hz, 1H), 7.26-7.32 (m, 1H), 7.26 (s, 1H), 6.80 (s, 1H), 3.93 (s, 3H), 1.34 (s, 9H).<br>Mass Spectrum (LCMS, ESI pos.): Calculated for C$_{21}$H$_{19}$BrClN$_3$O$_2$: 460.0 (M + H); Measured: 460.0. |
| Cmpd 102 | 2-(1-tert-Butyl-1H-pyrazol-4-yl)-6-(2-chloro-phenyl)-4-methoxy-3H-imidazo[4,5-c]pyridine sodium salt<br>$^1$H-NMR (400 MHz, d$_6$-DMSO) δ: 8.15 (s, 1H), 7.89 (s, 1H), 7.70 (d, J = 7.6 Hz, 1H), 7.48 (d, J = 7.6 Hz, 1H), 7.37 (t, J = 7.3 Hz, 1H), 7.29 (t, J = 7.8 Hz, 1H), 7.26 (s, 1H), 3.93 (s, 3H), 1.56 (s, 9H).<br>Mass Spectrum (LCMS, ESI pos.): Calculated for C$_{20}$H$_{20}$ClN$_5$O: 382.1 (M + H); Measured: 382.1. |
| Cmpd 105 | 6-(2-Chloro-phenyl)-2-(4-isopropyl-thiophen-2-yl)-4-methoxy-3H-imidazo[4,5-c]pyridine<br>$^1$H-NMR (400 MHz, CD$_3$OD) δ: 7.73-7.79 (m, 1H), 7.67 (dd, J = 7.4, 2.0 Hz, 1H), 7.48-7.51 (m, 1H), 7.32-7.41 (m, 3H), 7.28 (s, 1H), 4.13 (s, 3H), 3.02 (sept., J = 7.04 Hz, 1H), 1.31 (d, J = 7.04 Hz, 6H).<br>Mass Spectrum (LCMS, ESI pos.) Calculated for C$_{20}$H$_{18}$ClN$_3$OS: 384.0 (M + H), Measured: 384.1 |
| Cmpd 106 | 2-(5-Bromo-4-tert-butyl-furan-2-yl)-6-(2-chloro-phenyl)-3H-imidazo[4,5-b]pyridine sodium salt<br>$^1$H-NMR (400 MHz, d$_6$-DMSO) δ: 7.99 (d, J = 2.2 Hz, 1H), 7.61 (d, J = 2.2 Hz, 1H), 7.55 (dd, J = 7.8, 1.2 Hz, 1H), 7.44-7.49 (m, 1H), 7.41 (td, J = 7.4, 1.3 Hz, 1H), 7.29-7.37 (m, 1H), 6.86 (s, 1H), 1.35 (s, 9H).<br>Mass Spectrum (LCMS, ESI pos.): Calculated for C$_{20}$H$_{17}$BrClN$_3$O: 430.0 (M + H); Measured: 430.0. |

-continued

Cmpd 107  2-(1-tert-Butyl-5-methyl-1H-pyrazol-4-yl)-6-(2-chloro-phenyl)-3H-imidazo[4,5-b]pyridine sodium salt
$^1$H-NMR (400 MHz, $d_6$-DMSO) δ: 7.90 (d, J = 2.0 Hz, 1H), 7.81 (s, 1H), 7.56 (d, J = 2.0 Hz, 1H), 7.54 (d, J = 7.8 Hz, 1H), 7.43-7.48 (m, 1H), 7.39 (t, J = 7.5 Hz, 1H), 7.28-7.35 (m, 1H), 3.01 (s, 3H), 1.63 (s, 9H).
Mass Spectrum (LCMS, ESI pos.): Calculated for $C_{20}H_{20}ClN_5$: 366.2 (M + H); Measured: 366.1.

Cmpd 108  2-(5-tert-Butyl-4-chloro-2-methyl-2H-pyrazol-3-yl)-6-(2-chloro-phenyl)-3H-imidazo[4,5-b]pyridine
$^1$H-NMR (400 MHz, $CD_3OD$) δ: 8.50 (d, J = 2.0 Hz, 1H), 8.15 (d, J = 2.0 Hz, 1H), 7.57-7.62 (m, 1H), 7.41-7.54 (m, 3H), 4.13 (s, 3H), 1.46 (s, 9H).
Mass Spectrum (LCMS, ESI pos.) Calculated For $C_{20}H_{19}Cl_2N_5$: 400.1 (M + H), Measured: 400.1.

Cmpd 109  2-(5-tert-Butyl-4-chloro-2-methyl-2H-pyrazol-3-yl)-6-(2-chloro-phenyl)-4-ethoxy-3H-imidazo[4,5-c]pyridine
$^1$H-NMR (400 MHz, $CD_3OD$) δ: 7.67 (dd, J = 7.4, 2.0 Hz, 1H), 7.50-7.54 (m, 1H), 7.47 (s, 1H), 7.34-7.44 (m, 2H), 4.65 (d, J = 7.0 Hz, 2H), 4.04 (s, 3H), 1.51 (t, J = 7.0 Hz, 3H), 1.45 (s, 9H).
Mass Spectrum (LCMS, ESI pos.) Calculated For $C_{22}H_{23}Cl_2N_5O$: 444.1 (M + H), Measured: 444.1.

Cmpd 111  2-(4-tert-Butyl-1-methyl-1H-imidazol-2-yl)-6-(2-chloro-phenyl)-4-methoxy-3H-imidazo[4,5-c]pyridine
$^1$H-NMR (400 MHz, $CDCl_3$) δ: 7.67 (dd, J = 7.5, 1.8 Hz, 1H), 7.49-7.53 (m, 1H), 7.44 (s, 1H), 7.33-7.42 (m, 2H), 7.06 (s, 1H), 4.16 (s, 3H), 4.12 (s, 3H), 1.34 (s, 9H).
Mass Spectrum (LCMS, ESI pos.) Calculated For $C_{21}H_{22}ClN_5O$: 396.2 (M + H), Measured: 396.1.

Example 31

2-(5-tert-butyl-4-chloro-2-methyl-2H-pyrazol-3-yl)-4-morpholin-4-yl-6-(2-trifluoromethyl-phenyl)-3H-imidazo[4,5-c]pyridine (Compound #59)

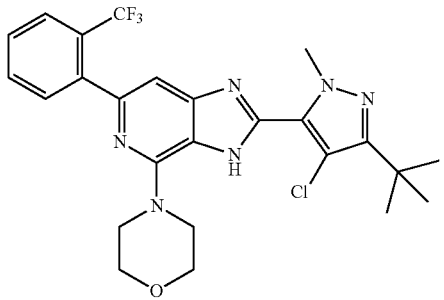 [SMILES: Cn1nc(C(C)(C)C)c(Cl)c1-c1nc2cc(-c3ccccc3C(F)(F)F)nc(N3CCOCC3)c2[nH]1]

STEP A: 6-Chloro-2-morpholin-4-yl-3-nitro-pyridin-4-ylamine

To a solution of 2,6-dichloro-3-nitro-pyridin-4-ylamine (970 mg, 4.66 mmol) in DMF (5 mL), $K_2CO_3$ (3.20 g, 23.0 mmol) was added, followed by addition of morpholine (0.410 mL, 4.60 mmol). The resulting mixture was stirred at room temperature for 2 h. The resulting mixture was diluted with water and extracted with EtOAc (3×10 mL). The organic layers were combined, dried ($Na_2SO_4$) and concentrated. The resulting residue was purified on silica (0:100-50:50 EtOAc-hexanes) to yield 6-chloro-2-morpholin-4-yl-3-nitro-pyridin-4-ylamine. $^1$H-NMR (400 MHz, $CDCl_3$) δ: 5.99-6.20 (m, 3H), 3.72-3.82 (m, 4H), 3.40-3.50 (m, 4H).

STEP B: 2-Morpholin-4-yl-3-nitro-6-(2-trifluoromethyl-phenyl)-pyridin-4-ylamine

Following the procedure described in the Example 24, STEP B and substituting suitably selected and substituted reagents, starting materials and conditions as would be readily apparent to those skilled in the art, 2-Morpholin-4-yl-3-nitro-6-(2-trifluoromethyl-phenyl)-pyridin-4-ylamine was prepared from 6-chloro-2-morpholin-4-yl-3-nitro-pyridin-4-ylamine (prepared as described in the previous step). $^1$H-NMR (400 MHz, $CDCl_3$) δ: 7.76 (d, J=7.8 Hz, 1H), 7.56-7.64 (m, 1H), 7.45-7.56 (m, 2H), 6.18 (s, 1H), 6.05 (br. s., 2H), 3.73-3.81 (m, 4H), 3.44-3.52 (m, 4H).

STEP C: 2-(5-tert-butyl-4-chloro-2-methyl-2H-pyrazol-3-yl)-4-morpholin-4-yl-6-(2-trifluoromethyl-phenyl)-3H-imidazo[4,5-c]pyridine Following the procedure described in the Example 25, STEP C, and substituting suitably selected and substituted reagents, starting materials and conditions as would be readily apparent to those skilled in the art, 2-(5-tert-butyl-4-chloro-2-methyl-2H-pyrazol-3-yl)-4-morpholin-4-yl-6-(2-trifluoromethyl-phenyl)-3H-imidazo[4,5-c]pyridine was prepared. $^1$H-NMR (400 MHz, $CD_3OD$) δ: 7.76-7.80 (m, 1H), 7.63-7.69 (m, 1H), 7.52-7.61 (m, 3H), 4.15-4.21 (m, 4H), 4.10 (s, 3H), 3.81-3.87 (m, 4H), 1.44 (s, 9H). Mass Spectrum (LCMS, ESI pos.) Calculated For $C_{25}H_{26}ClF_3N_5O$: 419.2 (M+H). Measured: 419.4.

Example 32

2-(5-tert-butyl-4-chloro-2-methyl-2H-pyrazol-3-yl)-6-(2-trifluoromethyl-phenyl)-3H-imidazo[4,5-c]pyridine-4-carbonitrile (Compound #60)

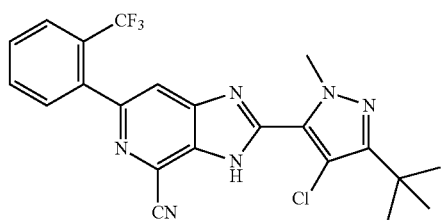 [SMILES: Cn1nc(C(C)(C)C)c(Cl)c1-c1nc2cc(-c3ccccc3C(F)(F)F)nc(C#N)c2[nH]1]

STEP A: 4-Amino-3-nitro-6-(2-trifluoromethyl-phenyl)-pyridine-2-carbonitrile A solution of 4-amino-6-chloro-3-nitro-pyridine-2-carbonitrile (186 mg, 0.937 mmol) in 1,4-dioxane (5 mL) was treated with $K_3PO_4$ (1.00 g, 5.10 mmol), 2-trifluoromethylphenylboronic acid (178 mg, 0.937 mmol), 1,1'-bis(di-tert-butylphosphino)ferrocene (60.5 mg, 0.128 mmol) and $Pd(OAc)_2$ (28.6 mg, 0.128 mmol). The resulting mixture was stirred 80° C. overnight. The cooled mixture was diluted with EtOAc (50 mL) and washed with water (50 mL). The aqueous layer was extracted twice with EtOAc (30 mL) and the combined extracts were dried over $MgSO_4$ and concentrated in vacuo. The resulting residue was purified on silica (0:100-100:0 EtOAc-hexanes) to yield 4-amino-3-nitro-6-(2-trifluoromethyl-phenyl)-pyridine-2-carbonitrile. $^1$H-NMR (400 MHz, $CDCl_3$) δ: 7.79 (m, 1H), 7.67 (m, 4H), 7.52 (m, 1H), 7.04 (s, 1H).

STEP B: 2-(5-tert-butyl-4-chloro-2-methyl-2H-pyrazol-3-yl)-6-(2-trifluoromethyl-phenyl)-3H-imidazo[4,5-c]pyridine-4-carbonitrile 2-(5-tert-butyl-4-chloro-2-methyl-2H-pyrazol-3-yl)-6-(2-trifluoromethyl-phenyl)-3H-imidazo[4,5-c]pyridine-4-carbonitrile was prepared from 4-amino-3-nitro-6-(2-trifluoromethyl-phenyl)-pyridine-2-carbonitrile (prepared as described in the previous step) following the procedure described in Example 25, STEP C. $^1$H-NMR (400 MHz, $CD_3OD$) δ: 7.94-7.97 (m, 1H), 7.85-7.90 (m, 1H), 7.73-7.79 (m, 1H), 7.66-7.71 (m, 1H), 7.59-7.64 (m, 1H), 4.61 (s, 3H), 1.46 (s, 9H). Mass Spectrum (LCMS, ESI pos.) Calculated For $C_{22}H_{18}ClF_3N_6$: 459.1 (M+H). Measured: 459.2.

Following the procedures described in Example 32 above, and substituting suitably selected and substituted reagents, starting materials and conditions as would be readily apparent to those skilled in the art, the following representative compounds of the present invention were prepared.

| | |
|---|---|
| Cmpd 59 | 2-(5-tert-butyl-4-chloro-2-methyl-2H-pyrazol-3-yl)-7-morpholin-4-yl-5-(2-trifluoromethyl-phenyl)-1H-imidazo[4,5-c]pyridine hydrochloride<br>$^1$H-NMR (400 MHz, $CD_3OD$) δ: 7.95 (s, 1H), 7.87 (d, J = 7.3 Hz, 1H), 7.73-7.79 (m, 1H), 7.66-7.72 (m, 1H), 7.61 (d, J = 7.6 Hz, 1H), 4.23 (s, 3H), 1.46 (s, 9H).<br>Mass Spectrum (LCMS, ESI pos.) Calculated For $C_{25}H_{26}ClF_3N_5O$: 419.2 (M + H), Measured: 419.4. |
| Cmpd 60 | 2-(5-tert-butyl-4-chloro-2-methyl-2H-pyrazol-3-yl)-6-(2-trifluoromethyl-phenyl)-3H-imidazo[4,5-c]pyridine-4-carbonitrile benzenesulfonic acid salt<br>$^1$H-NMR (400 MHz, $CD_3OD$) δ: 7.94 (s, 1H), 7.81-7.87 (m, 4H), 7.70-7.77 (m, 1H), 7.63-7.70 (m, 1H), 7.58 (d, J = 7.3 Hz, 1H), 7.37-7.44 (m, 2H), 4.23-4.27 (m, 3H), 1.45 (s, 9H).<br>Mass Spectrum (LCMS, ESI pos.) Calculated For $C_{22}H_{18}ClF_3N_6$: 459.1 (M + H), Measured: 459.2. |

Example 33

2-(5-tert-butyl-4-chloro-2-methyl-2H-pyrazol-3-yl)-7-morpholin-4-yl-5-(2-trifluoromethyl-phenyl)-1H-imidazo[4,5-b]pyridine (Compound #61)

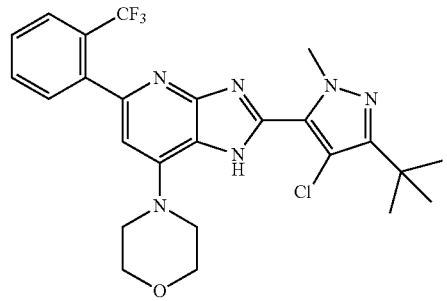 [SMILES: Cn1nc(C(C)(C)C)c(Cl)c1-c1nc2nc(-c3ccccc3C(F)(F)F)cc(N3CCOCC3)c2[nH]1]

STEP A: 4-Morpholin-4-yl-3-nitro-6-(2-trifluoromethyl-phenyl)-pyridin-2-ylamine To a solution of 4-chloro-3-nitro-6-(2-trifluoromethyl-phenyl)-pyridin-2-ylamine (900 mg, 2.83 mmol, prepared as described in the Example 1) in DMF (5 mL), $K_2CO_3$ (1.90 g, 14.0 mmol) was added followed by addition of morpholine (0.240 mL, 2.80 mmol). The resulting mixture was stirred at 80° C. overnight. The resulting mixture was diluted with water (20 mL) and extracted with EtOAc (3×10 mL). The organic layers were combined, dried ($MgSO_4$) and concentrated. The resulting residue was purified on silica 0:100-50:50 EtOAc/hexanes to yield 4-morpholin-4-yl-3-nitro-6-(2-trifluoromethyl-phenyl)-pyridin-2-ylamine. Mass Spectrum (LCMS, ESI pos.) Calculated For Mass Spectrum (LCMS, ESI pos.) Calculated For $C_{16}H_{15}F_3N_4O_3$: 369.1 (M+H). Measured: 369.1.

STEP B: 2-(5-tert-butyl-4-chloro-2-methyl-2H-pyrazol-3-yl)-7-morpholin-4-yl-5-(2-trifluoromethyl-phenyl)-1H-imidazo[4,5-b]pyridine Following the procedure described in the Example 1, 2-(5-tert-butyl-4-chloro-2-methyl-2H-pyrazol-3-yl)-7-morpholin-4-yl-5-(2-trifluoromethyl-phenyl)-1 H-imidazo[4,5-b]pyridine was prepared from 4-morpholin-4-yl-3-nitro-6-(2-trifluoromethyl-phenyl)-pyridin-2-ylamine. $^1$H-NMR (400

MHz, CDCl$_3$) δ: 7.76-7.81 (m, 1H), 7.59-7.66 (m, 1H), 7.51-7.58 (m, 2H), 6.57 (s, 1H), 4.27 (s, 3H), 3.98-4.05 (m, 4H), 3.90-3.97 (m, 4H), 1.45 (s, 9H) Mass Spectrum (LCMS, APCI pos.) Calculated For C$_{25}$H$_{26}$ClF$_3$N$_6$O: 519.3 (M+H). Measured: 519.3.

Following the procedures described in Example 33 above, and substituting suitably selected and substituted reagents, starting materials and conditions as would be readily apparent to those skilled in the art, the following representative compounds of the present invention were prepared.

| | |
|---|---|
| Cmpd 61 | 2-(5-tert-Butyl-4-chloro-2-methyl-2H-pyrazol-3-yl)-7-morpholin-4-yl-5-(2-trifluoromethyl-phenyl)-1H-imidazo[4,5-b]pyridine hydrochloride<br>$^1$H-NMR (400 MHz, CD$_3$OD) δ: 7.93-7.98 (m, 1H), 7.78-7.88 (m, 1H), 7.71 (d, J = 6.8 Hz, 1H), 6.99 (s, 1H), 4.13-4.33 (m, 4H), 4.02-4.07 (m, 3H), 3.87-3.95 (m, 4H), 1.45 (s, 9H).<br>Mass Spectrum (LCMS, ESI pos.) Calculated For C$_{25}$H$_{26}$ClF$_3$N$_6$O: 519.3 (M + H), Measured: 519.3. |
| Cmpd 63 | 2-(5-tert-butyl-4-chloro-2-methyl-2H-pyrazol-3-yl)-4-piperidin-1-yl-6-(2-trifluoromethyl-phenyl)-3H-imidazo[4,5-c]pyridine<br>$^1$H-NMR (400 MHz, CD$_3$OD) δ: 7.74 (d, J = 7.8 Hz, 1H), 7.46-7.63 (m, 3H), 6.93 (s, 1H), 4.13 (br. s., 4H), 4.10 (s, 3H), 1.67 (br. s., 6H), 1.42 (s, 9H).<br>Mass Spectrum (LCMS, ESI pos.) Calculated For C$_{26}$H$_{28}$ClF$_3$N$_6$: 517.2 (M + H), Measured: 517.3. |
| Cmpd 63 | 2-(5-tert-butyl-4-chloro-2-methyl-2H-pyrazol-3-yl)-7-piperidin-1-yl-5-(2-trifluoromethyl-phenyl)-1H-imidazo[4,5-b]pyridine benzenesulfonic acid salt<br>$^1$H-NMR (400 MHz, CD$_3$OD) δ: $^1$H-NMR (MeOH) δ: 7.93-7.98 (m, 1H), 7.77-7.88 (m, 4H), 7.74 (d, J = 7.1 Hz, 1H), 7.37-7.45 (m, 3H), 7.14 (s, 1H), 4.25-4.33 (m, 4H), 4.13-4.18 (m, 3H), 1.82-1.92 (m, 6H), 1.45 (s, 9H)<br>Mass Spectrum (LCMS, ESI pos.) Calculated For C$_{26}$H$_{28}$ClF$_3$N$_6$: 517.2 (M + H), Measured: 517.3. |
| Cmpd 64 | 3-tert-butyl-5-[4-morpholin-4-yl-6-(2-trifluoromethyl-phenyl)-3H-imidazo[4,5-c]pyridin-2-yl]-isoxazole-4-carbonitrile<br>$^1$H-NMR (400 MHz, CD$_3$OD) δ: 7.75 (d, J = 8.1 Hz, 1H), 7.60-7.66 (m, 1H), 7.50-7.59 (m, 2H), 6.90 (s, 1H), 4.26 (t, J = 4.3 Hz, 4H), 3.80 (t, J = 4.4 Hz, 4H), 1.49 (s, 9H).<br>Mass Spectrum (LCMS, ESI pos.) Calculated For C$_{25}$H$_{23}$F$_3$N$_6$O$_2$: 497.2 (M + H), Measured: 497.1. |
| Cmpd 64 | 3-tert-butyl-5-[4-morpholin-4-yl-6-(2-trifluoromethyl-phenyl)-3H-imidazo[4,5-c]pyridin-2-yl]-isoxazole-4-carbonitrile benzenesulfonic acid salt<br>$^1$H-NMR (400 MHz, CD$_3$OD) 7.93-7.99 (m, 1H), 7.73-7.89 (m, 5H), 7.38-7.46 (m, 3H), 7.18 (s, 1H), 4.37-4.44 (m, 4H), 3.91-3.99 (m, 4H), 1.50-1.57 (m, 9H).<br>Mass Spectrum (LCMS, ESI pos.) Calculated For C$_{25}$H$_{23}$F$_3$N$_6$O$_2$: 497.2 (M + H), Measured: 497.1. |
| Cmpd 65 | 3-tert-Butyl-1-methyl-5-[4-morpholin-4-yl-6-(2-trifloromethyl-phenyl)-3H-imidazo[4,5-c]pyridin-2-yl]-1H-pyrazole-4-carbonitrile<br>$^1$H-NMR (400 MHz, CD$_3$OD) 7.75 (d, J = 7.8 Hz, 1H), 7.60-7.66 (m, 1H), 7.49-7.60 (m, 2H), 7.02 (s, 1H), 4.21 (d, J = 4.5 Hz, 4H), 4.16 (s, 3H), 3.81-3.88 (m, 4H), 1.46 (s, 9H).<br>Mass Spectrum (LCMS, ESI pos.) Calculated For C$_{26}$H$_{26}$F$_3$N$_7$O: 510.2 (M + H), Measured: 510.3. |
| Cmpd 65 | 3-tert-butyl-1-methyl-5-[7-morpholin-4-yl-5-(2-trifluoromethyl-phenyl)-1H-imidazo[4,5-b]pyridin-2-yl]-1H-pyrazole-4-carbonitrile benzenesulfonic acid salt<br>$^1$H-NMR (400 MHz, CD$_3$OD) δ: 7.93-7.98 (m, 1H), 7.74-7.88 (m, 5H), 7.36-7.45 (m, 3H), 7.22 (s, 1H), 4.32-4.39 (m, 4H), 4.16 (s, 3H), 3.90-3.97 (m, 4H), 1.48 (s, 9H).<br>Mass Spectrum (LCMS, ESI pos.) Calculated For C$_{26}$H$_{26}$F$_3$N$_7$O: 510.2 (M + H), Measured: 510.3. |
| Cmpd 66 | 2-(5-tert-butyl-4-chloro-2-methyl-2H-pyrazol-3-yl)-4-pyrrolidin-1-yl-6-(2-trifluoromethyl-phenyl)-3H-imidazo[4,5-c]pyridine<br>$^1$H-NMR (400 MHz, CD$_3$OD) δ: 7.76 (d, J = 7.8 Hz, 1H), 7.50-7.65 (m, 3H), 6.85 (s, 1H), 4.10 (s, 3H), 3.98 (s, 4H), 1.98-2.02 (m, 4H), 1.42 (s, 9H).<br>Mass Spectrum (LCMS, ESI pos.) Calculated For C$_{25}$H$_{26}$ClF$_3$N$_6$: 505.2 (M + H), Measured: 505.3. |
| Cmpd 66 | 2-(5-tert-butyl-4-chloro-2-methyl-2H-pyrazol-3-yl)-4-pyrrolidin-1-yl-6-(2-trifluoromethyl-phenyl)-3H-imidazo[4,5-c]pyridine benzenesulfonic acid salt<br>$^1$H-NMR (400 MHz, CD$_3$OD) δ: 7.92-7.97 (m, 1H), 7.70-7.87 (m, 5H), 7.37-7.45 (m, 3H), 7.05 (s, 1H), 4.05-4.32 (m, 7H), 2.15-2.24 (m, 4H), 1.45 (s, 9H).<br>Mass Spectrum (LCMS, ESI pos.) Calculated For C$_{25}$H$_{26}$ClF$_3$N$_6$: 505.2 (M + H), Measured: 505.3. |

Example 34

2-(5-tert-Butyl-2-methyl-2H-pyrazol-3-yl)-6-(2-chloro-phenyl)-3H-imidazo[4,5-c]pyridine hydrochloride (Compound #41)

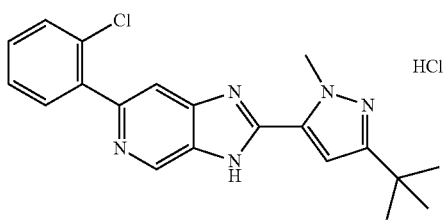 [SMILES: Cn1nc(C(C)(C)C)cc1-c1nc2cc(-c3ccccc3Cl)ncc2[nH]1 ; Cl]

STEP A: 5-tert-Butyl-2-methyl-2H-pyrazole-3-carboxylic acid (2-bromo-5-nitro-pyridin-4-yl)-amide A solution of 2-bromo-5-nitro-pyridin-4-ylamine (62 mg, 0.28 mmol) in THF (5 mL), was treated with NaH (34 mg, 0.85 mmol) under Ar. The resulting solution was stirred for 10 min and then treated with 5-tert-butyl-2-methyl-2H-pyrazole-3-carbonyl chloride (62 mg, 0.31 mmol) in THF (1 mL). The resulting mixture was stirred at room temperature for 1 h. The resulting mixture was purified by direct application to silica preparative TLC plates (2000 micron) and eluted with 3:7 EtOAc-hexanes to yield 5-tert-butyl-2-methyl-2H-pyrazole-3-carboxylic acid (2-bromo-5-nitro-pyridin-4-yl)-amide. $^1$H-NMR (400 MHz, CDCl$_3$) δ: 11.2 (s, 1H), 9.18 (s, 1H), 9.11 (s, 1H), 6.65 (s, 1H). 4.18 (s, 1H), 1.34 (s, 9H).

STEP B: 6-Bromo-2-(5-tert-butyl-2-methyl-2H-pyrazol-3-yl)-3H-imidazo[4,5-c]pyridine A solution of 5-tert-butyl-2-methyl-2H-pyrazole-3-carboxylic acid (2-bromo-5-nitro-pyridin-4-yl)-amide (79.8 mg, 0.183 mmol, prepared as described in the previous step) in acetic acid (1 mL) was treated with Fe powder (102 mg, 1.82 mmol). The resulting mixture was stirred at 110° C. for 1 h, cooled to room temperature, and treated with EtOAc (10 mL) and saturated NaHCO$_3$ (10 mL). The organic layer was separated, washed with saturated NaHCO$_3$ (10 mL), H$_2$O (10 mL), concentrated, and the resulting residue dried in vacuo to yield 6-bromo-2-(5-tert-butyl-2-methyl-2H-pyrazol-3-yl)-3H-imidazo[4,5-c]pyridine. $^1$H-NMR (400 MHz, CDCl$_3$) δ: 10.0 (br s, 1H), 8.80 (br s, 1H), 7.60 (br s, 1H), 6.60 (m, 1H), 4.40 (s, 3H), 1.30 (s, 9H).

STEP C: 2-(5-tert-Butyl-2-methyl-2H-pyrazol-3-yl)-6-(2-chloro-phenyl)-3H-imidazo[4,5-c]pyridine hydrochloride A solution of 6-bromo-2-(5-tert-butyl-2-methyl-2H-pyrazol-3-yl)-3H-imidazo[4,5-c]pyridine (50 mg, 0.15 mmol, prepared as described in the previous step), 2-chlorophenylboronic acid (47 mg, 0.30 mmol), 2M Na$_2$CO$_3$ (0.60 mL, 1.2 mmol) and DME (1 mL) was stirred at 90° C. for 18 h. The resulting mixture was allowed to cool to room temperature and organic layer was separated. The organic layer was purified by direct application to silica preparative TLC plates (2000 micron) and eluted with 3:7 EtOAc-hexanes to yield 2-(5-tert-butyl-2-methyl-2H-pyrazol-3-yl)-6-(2-chloro-phenyl)-3H-imidazo[4,5-c]pyridine.

A solution of 2-(5-tert-butyl-2-methyl-2H-pyrazol-3-yl)-6-(2-chloro-phenyl)-3H-imidazo[4,5-c]pyridine (22.6 mg, 0.061 mmol, as prepared above) in Et$_2$O (1 mL) was treated with 1 M HCl in Et$_2$O (0.068 mL, 0.068 mmol). The resulting mixture was stirred at room temperature for 10 min and concentrated. The residue was dried in vacuo to yield 2-(5-tert-butyl-2-methyl-2H-pyrazol-3-yl)-6-(2-chloro-phenyl)-3H-imidazo[4,5-c]pyridine hydrochloride. $^1$H-NMR (400 MHz, CD$_3$OD) δ: 9.28 (s, 1H), 8.13 (s, 1H), 7.66-7.71 (m, 2H), 7.63 (td, J=7.7, 1.8 Hz, 1H), 7.53-7.60 (m, 1H), 7.02 (s, 1H), 4.36 (s, 3H), 1.35 (s, 9H). Mass Spectrum (LCMS, ESI pos.) Calculated For C$_{20}$H$_{20}$ClN$_5$: 366.1 (M+H). Measured: 366.2.

Following the procedures described in Example 34 above, and substituting suitably selected and substituted reagents, starting materials and conditions as would be readily apparent to those skilled in the art, the following representative compounds of the present invention were prepared.

| | |
|---|---|
| Cmpd 39 | 2-(5-tert-Butyl-2-methyl-2H-pyrazol-3-yl)-6-(2-trifluoromethoxy-phenyl)-3H-imidazo[4,5-c]pyridine hydrochloride<br>$^1$H-NMR (400 MHz, CD$_3$OD) δ: 9.31 (s, 1H), 8.18 (s, 1H), 7.73-7.85 (m, 2H), 7.58-7.68 (m, 2H), 7.02 (s, 1H), 4.36 (s, 3H), 1.35 (s, 9H).<br>Mass Spectrum (LCMS, ESI pos.) Calculated For C$_{21}$H$_{20}$F$_3$N$_5$O: 416.2 (M + H), Measured: 416.3 |
| Cmpd 40 | 2-(5-tert-Butyl-2-methyl-2H-pyrazol-3-yl)-6-(2-trifluoromethyl-phenyl)-3H-imidazo[4,5c]pyridine hydrochloride<br>$^1$H-NMR (400 MHz, CD$_3$OD) δ: 9.28 (s, 1H), 8.13 (s, 1H), 7.66-7.72 (m, 2H), 7.63 (td, J = 7.6, 1.6 Hz, 1H), 7.53-7.60 (m, 1H), 7.02 (s, 1H), 4.36 (s, 3H), 1.35 (s, 9H).<br>Mass Spectrum (LCMS, ESI pos.) Calculated For C$_{21}$H$_{20}$F$_3$N$_5$: 400.2 (M + H), Measured: 400.3. |
| Cmpd 42 | 2-(5-tert-Butyl-2-methyl-2H-pyrazol-3-yl)-6-(2-fluoro-phenyl)-3H-imidazo[4,5-c]pyridine hydrochloride<br>$^1$H-NMR (400 MHz, CD$_3$OD) δ: 9.27 (s, 1H), 8.22 (s, 1H), 7.78 (td, J = 7.6, 1.8 Hz, 1H), 7.64-7.73 (m, 1H), 7.38-7.51 (m, 2H), 7.04 (s, 1H), 4.36 (s, 3H), 1.35 (s, 9H).<br>Mass Spectrum (LCMS, ESI pos.) Calculated For C$_{20}$H$_{20}$FN$_5$: 350.2 (M + H), Measured: 350.3 |
| Cmpd 44 | 3-tert-Butyl-5-[6-(2-fluoro-phenyl)-3H-imidazo[4,5-c]pyridin-2-yl]-1-methyl-1H-pyrazole-4-carbonitrile hydrochloride<br>$^1$H-NMR (400 MHz, CD$_3$OD) δ: 9.43 (s, 1H), 8.33 (s, 1H), 7.80 (td, J = 7.6, 1.6 Hz, 1H), 7.63-7.73 (m, 1H), 7.35-7.51 (m, 2H), 4.21 (s, 3H), 1.46 (s, 9H). |

|  | Mass Spectrum (LCMS, ESI pos.) Calculated For $C_{21}H_{19}FN_6$: 375.2 (M + H), Measured: 375.4 |
|---|---|
| Cmpd 45 | 3-tert-Butyl-1-methyl-5-[6-(2-trifluoromethyl-phenyl)-3H-imidazo[4,5-c]pyridin-2-yl]1H-pyrazole-4-carbonitrile hydrochloride<br>$^1$H-NMR (400 MHz, CD$_3$OD) δ: 9.35 (s, 1H), 8.12 (s, 1H), 7.94-8.01 (m, 1H), 7.81-7.88 (m, 2H), 7.68-7.76 (m, 1H), 4.20 (s, 3H), 1.43 (s, 9H).<br>Mass Spectrum (LCMS, ESI pos.) Calculated For $C_{22}H_{19}F_3N_6$: 425.2 (M + H), Measured: 425.2 |
| Cmpd 47 | 3-tert-Butyl-1-methyl-5-(6-phenyl-3H-imidazo[4,5-c]pyridin-2-yl)-1H-pyrazole-4-carbonitrile hydrochloride<br>$^1$H-NMR (400 MHz, CD$_3$OD) δ: 9.35 (s, 1H), 8.35 (s, 1H), 7.85-7.95 (m, J = 6.7, 2.9 Hz, 2H), 7.61-7.70 (m, 3H), 4.20 (s, 3H), 1.46 (s, 9H).<br>Mass Spectrum (LCMS, ESI pos.) Calculated For $C_{21}H_{20}N_6$: 357.2 (M + H), Measured: 357.4 |

Example 35

2-(5-tert-Butyl-4-chloro-2-methyl-2H-pyrazol-3-yl)-6-(2-chloro-phenyl)-4-methoxy-3H-imidazo[4,5-c]pyridine (Compound #11)

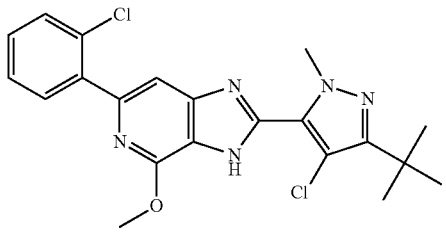 [SMILES: COc1nc(-c2ccccc2Cl)cc2nc(-c3c(Cl)c(C(C)(C)C)nn3C)[nH]c12]

Step A: Ethyl 3-tert-butyl-4-chloro-1-methyl-1H-pyrazole-5-carboxylate

A 5-L, four neck round bottom flask equipped with overhead air stirrer, positive pressure nitrogen inlet, thermocouple, and addition funnel was charged with ethyl 3-tert-butyl-1-methyl-1H-pyrazole-5-carboxylate (250 g, 1.19 mol) in dichloromethane (2.5 L). The resulting solution was cooled to 10° C. with a wet-ice bath. Sulfuryl chloride (149 mL, 1.49 mol) was added via addition funnel at such which maintained the temperature between 21-31° C. The resulting mixture was then stirred for 2 h at room temperature. A separate 12-L, four neck flask equipped with overhead air stirrer and thermocouple was charged H$_2$O (3.75 L) and cooled to 10° C. This mixture was then added via addition funnel, while maintaining the temperature below 32° C. and the resulting mixture was stirred for 30 min. The layers were separated, the aqueous layer was extracted with dichloromethane (2×1 L). The organic layer was carefully washed with NaHCO$_3$ (saturated, 2×2 L), brine (1.25 L), dried over Na$_2$SO$_4$, filtered, and evaporated to yield ethyl 3-tert-butyl-4-chloro-1-methyl-1H-pyrazole-5-carboxylate as a white solid. $^1$H NMR (CHLOROFORM-d) δ: 4.39 (q, J=7.1 Hz, 2H), 4.07 (s, 3H), 1.29-1.49 (m, 12H)

Step B: 3-tert-Butyl-4-chloro-1-methyl-1H-pyrazole-5-carboxylic acid

A 12-L, four neck round bottom flask equipped with overhead air stirrer, positive pressure nitrogen inlet, thermocouple, and addition funnel was charged with ethyl 3-tert-butyl-4-chloro-1-methyl-1H-pyrazole-5-carboxylate (282 g, 1.15 mol) and EtOH (4.3 L). 3M NaOH (960 mL, 2.87 mol) was added in one portion and the resulting slurry began to clarify immediately. The resulting mixture was stirred at room temperature for 2 h and yielded a turbid solution. The turbid solution was evaporated and the resulting aqueous slurry was diluted with H$_2$O (2 L). The basic solution was acidified to pH ~2 using concentrated HCl. The aqueous layer was extracted with dichloromethane (2×800 mL), dried over MgSO$_4$, filtered, and evaporated to yield 3-tert-butyl-4-chloro-1-methyl-1H-pyrazole-5-carboxylic acid as an off-white solid. $^1$H NMR (CHLOROFORM-d) δ: 4.11 (s, 3H), 1.41 (s, 9H)

Step C: 3-tert-butyl-4-chloro-1-methyl-1H-pyrazole-5-carboxyl chloride

A 3-L, four neck round bottom flask equipped with magnetic stirrer, positive pressure nitrogen inlet, gas outlet into a sodium bicarbonate scrubber, thermocouple, and addition funnel was charged with tert-butyl-4-chloro-1-methyl-1H-pyrazole-5-carboxylic acid (99.68 g, 0.460 mol), toluene (1.50 L), and dimethylformamide (1.78 mL). Oxalyl chloride (41.50 mL, 60.71 g, 0.469 mol) was added via addition funnel over 15 min, and a temperature increase to 23° C. was observed, with significant but controlled off-gassing. The resulting mixture was initially turbid but turned clear after 30 min. The mixture was concentrated to yield 3-tert-butyl-4-chloro-1-methyl-1H-pyrazole-5-carboxyl chloride as a yellow solid. $^1$H NMR (400 MHz, CHLOROFORM-d) δ 1.40 (s, 9H), 4.04 (s, 3H)

Step D: 6-Chloro-2-methoxy-3-nitropyridin-4-amine

A 5-L, four neck round bottom flask equipped with overhead stirrer, positive pressure nitrogen inlet, 500-mL addition funnel with nitrogen outlet and a thermocouple was charged with 2,6-dichloro-3-nitropyridin-4-amine (150.0 g, 0.72 mol) and MeOH (1.50 L) and the resulting brown suspension was stirred at room temperature. NaOCH$_3$ (25% solution in MeOH, 260 mL, 1.155 mol) was charged to the addition funnel and added over 30 min (the temperature did not exceed 32° C.). The resulting red suspension was stirred for 1 h, then transferred to a 3-L round bottom flask (with MeOH) and evaporated to near dryness on a rotary evaporator. The resulting red sludge was diluted with aqueous ammonium chloride (1.75 L) and extracted with EtOAc (2×900 mL). The combined organics were washed with water (150 mL), the water layer was diluted with brine (100 mL) and back-extracted with EtOAc (100 mL). The combined organics were dried (MgSO$_4$) and concentrated under reduced pressure at 60° C. to yield 6-chloro-2-methoxy-3-nitropyridin-4-amine as a yellow solid. $^1$H NMR (CHLOROFORM-d) δ: 6.36 (s, 1H), 6.14 (br. s., 2H), 4.04 (s, 3H)

Step E: 6-(2-Chlorophenyl)-2-methoxy-3-nitropyridin-4-amine

A 5 L, four neck round bottom flask equipped with mechanical stirrer, water condenser with nitrogen inlet, thermocouple, and stopper was charged with 6-chloro-2-methoxy-3-nitro-4-pyridinamine (125.30 g, 0.615 mol), 2-chlorophenylboronic acid (116.36 g, 0.744 mol), sodium carbonate (164.97 g, 1.54 mol), toluene (1.80 L), water (0.8 L), and ethanol (0.625 L) and the resulting mixture stirred to achieve a red slurry. The slurry was heated to a mild reflux for 15 min to degas solution and then the temperature was lowered to 60° C. The resulting mixture was treated with (1,1'-bis-(di-tert-butylphosphino)ferrocenepalladium(II) chloride (40.8 g, 61 mmol) and the temperature increased to 69° C., generating a mild reflux. The temperature to 60° C. and stirring was continued for 17 h. The resulting mixture was diluted into water (2 L) and ethyl acetate (1 L), then filtered through CELITE, washing with ethyl acetate (1 L). The layers of filtrate were partitioned and the aqueous further extracted with ethyl acetate (3×500 mL). The combined organics were dried (MgSO$_4$) and concentrated to yield a dark oil. The dark oil was dissolved in dichloromethane and slurried with silica gel (325 g). The slurry was loaded onto a BIOTAGE 150M (2.5 kg silica) and eluted with dichloromethane (3 L) and ethyl acetate-dichloromethane 1:19 (9 L). Fractions of suitable purity were concentrated, lastly from heptane (500 mL) to yield the title compound as a residue. The residue (282 g) was triturated with MTBE (0.50 L), heated in water bath at 40° C. for 30 min, transferred to a mechanically stirred 5 L round bottom flask then diluted with heptane (2 L). The resulting slurry was stirred for 1 h at room temperature and the solids collected by filtration. The filter cake washed with MTBE-heptane (1:9, 500 mL) and heptane (500 mL), then dried in vacuum oven at 50° C. for 45 min to yield 6-(2-chlorophenyl)-2-methoxy-3-nitropyridin-4-amine as a yellow solid. $^1$H NMR (400 MHz, CHLOROFORM-d) δ 3.62 (s, 1H), 4.07 (s, 3H), 6.14 (br. s., 2H), 6.69 (s, 1H), 7.30-7.40 (m, 2H), 7.42-7.52 (m, 1H), 7.59-7.66 (m, 1H)

Step F: 3-tert-Butyl-4-chloro-N-(6-(2-chlorophenyl)-2-methoxy-3-nitropyridin-4-yl)-1-methyl-1H-pyrazole-5-carboxamide A 5 L, four neck round bottom flask equipped with mechanical stirrer, nitrogen inlet, addition funnel with stopper, and thermocouple was charged 6-(2-chlorophenyl)-2-methoxy-3-nitropyridin-4-amine (111.40 g, 0.398 mol) and tetrahydrofuran (1.90 L). The resulting mixture was cooled to 3° C. in ice-water bath and then treated with sodium hydride (31.85 g, 0.796 mol) carefully in one portion with an exotherm to 7° C. observed, to yield a deep-red slurry. This slurry was chilled to 1° C. and a solution of 3-tert-butyl-1-methyl-1H-pyrazole-4-carbonyl chloride (113.05 g, 0.438 mol) in tetrahydrofuran (0.275 L) was added dropwise via addition funnel over 30 min, with an exotherm to 10° C. observed. The ice bath was drained and the resulting mixture reached 8° C. over 30 min. The resulting mixture was then poured into saturated ammonium chloride (2.5 L) and extracted with ethyl acetate (2 L, 2×1 L). The combined organics were washed with brine (1 L) and dried (MgSO$_4$) overnight, protecting from light. The organic phases were concentrated to yield a the title compound as a residue. The residue was triturated with heptane (2.25 L) at 60° C. for 30 min, and the resulting mixture cooled to room temperature while protecting from light. The resulting solids were collected by filtration, washed with heptane (250 mL), and dried in a vacuum oven (50° C.) for 5 h to yield 3-tert-butyl-4-chloro-N-(6-(2-chlorophenyl)-2-methoxy-3-nitropyridin-4-yl)-1-methyl-1H-pyrazole-5-carboxamide as a yellow solid. $^1$H NMR (400 MHz, CHLOROFORM-d) δ 1.41 (s, 9H), 4.10 (s, 3H), 4.12 (s, 3H), 7.34-7.43 (m, 2H), 7.47-7.55 (m, 1H), 7.60-7.68 (m, 1H), 8.49 (s, 1H), 10.13 (br. s., 1H)

Step G: N-(3-amino-6-(2-chlorophenyl)-2-methoxypyridin-4-yl)-3-tert-butyl-4-chloro-1-methyl-1H-pyrazole-5-carboxamide A 2.25 L plastic coated Parr bottle was charged with 3-tert-butyl-4-chloro-N-(6-(2-chlorophenyl)-2-methoxy-3-nitropyridin-4-yl)-1-methyl-1H-pyrazole-5-carboxamide (55.30 g, 0.115 mol) and ethyl acetate (0.55 L). To the resulting slurry was added a slurry of 5% Pt(Sulfided)/C (2.80 g) in ethyl acetate (~20 mL). The resulting mixture was agitated under 35-40 psi hydrogen gas, recharging with hydrogen gas as needed. After 3 h, hydrogen uptake ceased. The resulting mixture was filtered through CELITE to remove catalyst and the filter cake washed with ethyl acetate. The filtrate was concentrated to yield N-(3-amino-6-(2-chlorophenyl)-2-methoxypyridin-4-yl)-3-tert-butyl-4-chloro-1-methyl-1H-pyrazole-5-carboxamide as a off-white solid. $^1$H NMR (400 MHz, CHLOROFORM-d) δ 1.42 (s, 9H), 3.98 (br. s., 2H), 4.06 (s, 3H), 4.15 (s, 3H), 7.27-7.35 (m, 2H), 7.44 (dd, J=7.83, 1.22 Hz, 1H), 7.55 (s, 1H), 7.63 (dd, J=7.58, 1.71 Hz, 1H), 8.54 (br. s., 1H)

Step H: 2-(3-tert-Butyl-4-chloro-1-methyl-1H-pyrazol-5-yl)-6-(2-chlorophenyl)-4-methoxy-3H-imidazo[4,5-c]pyridine A 2-L four neck round bottom flask equipped with mechanical stirrer, reflux condenser with nitrogen outlet, positive pressure nitrogen inlet and thermocouple was charged with N-(3-amino-6-(2-chlorophenyl)-2-methoxypyridin-4-yl)-3-tert-butyl-4-chloro-1-methyl-1H-pyrazole-5-carboxamide (156.2 g, 0.346 mol) and AcOH (glacial, 780 mL). The resulting mixture was heated to 90° C. for 2 h. The resulting mixture was then was cooled to 50° C., transferred to a one-neck round bottom flask and concentrated on a rotary evaporator (bath at 50° C.). The resulting orange pasty solid was dissolved in EtOAc (1.5 L) and added to a separatory funnel containing saturated aqueous sodium bicarbonate (2 L) and EtOAc (1.5 L). The pH of the aqueous was still acidic, and was adjusted with 50% wt/wt NaOH (~10 mL) to pH 8-9, then back to neutral with aqueous HCl (2 M, 120 mL) to a final pH of 6-8. The turbid organic layer was separated and the aqueous layer extracted with EtOAc (2×500 mL). The combined turbid organic layers were warmed in a 50° C. bath with gentle stirring and within 1-2 min, a clear orange solution resulted. The warm organic layer was quickly washed with brine (500 mL), dried (MgSO$_4$) with occasional warming throughout the drying process, filtered and the volatiles removed under reduced pressure. The resulting residue crystallized on standing and then redissolved with dichloromethane to yield a turbid mixture. The resulting concentrate was loaded onto BIOTAGE 150M (2.5 kg silica, prewetted with 4 L heptane) and eluted with heptane (4 L), 10% EtOAc in heptane (12 L), and finally 20% EtOAc in heptane (16 L), whereby fractions of suitable purity were collected and concentrated to yield the title compound.

Final purification was affected using a 3-L one neck round bottom flask, to which was added 2-(3-tert-butyl-4-chloro-1-methyl-1H-pyrazol-5-yl)-6-(2-chlorophenyl)-4-methoxy-3H-imidazo[4,5-c]pyridine (166 g), along with heptane (1.66 L). The flask was swirled on a rotovap bath at 45-48° C. for 15 min, the sides of the flask were scraped and the swirling continued for an additional 15 min. The heat was turned off, ice was added to the bath and the contents swirled until room temperature was achieved. The solid was collected by filtration, washed with heptane (100 mL), and dried in a vacuum oven (50° C.) for 16 h to yield 2-(3-tert-butyl-4-chloro-1-methyl-1H-pyrazol-5-yl)-6-(2-chlorophenyl)-4-methoxy-3H-imidazo[4,5-c]pyridine as a off-white solid. $^1$H NMR (CHLOROFORM-d) δ: 10.25 (br. s., 1H), 7.75 (dd, J=7.6, 1.7 Hz, 1H), 7.64-7.72 (m, 1H), 7.47-7.54 (m, 2H), 7.28-7.43 (m, 2H), 4.37 (s, 3H), 4.20 (s, 3H), 1.45 (s, 9H). NMR Note: Multiple signals observed for some resonances due to either tautomerization of imidazole ring or restricted single-bond rotation.

The product prepared as described above was determined by powder X-ray diffraction to be crystalline form. More particularly, the pXRD of a sample of the off-white product, prepared as described above, was packed onto a zero background holder and scanned under ambient conditions of temperature and humidity. The sample was scanned from 3 to 35° in 2θ with a step size of 0.0165° in 2θ with a continuous scan and a counting time of 10.16 sec. The effective scan speed was 0.2067°/s. Instrument voltage and current settings were 45 kV and 40 mA.

The crystalline form of 2-(3-tert-butyl-4-chloro-1-methyl-1H-pyrazol-5-yl)-6-(2-chlorophenyl)-4-methoxy-3H-imidazo[4,5-c]pyridine, prepared as described above, was characterized by its powder X-ray diffraction pattern, comprising the peaks, listed in Table XRD-1, below.

TABLE XRD-1

| PXRD Peaks | | |
|---|---|---|
| Pos. [°2θ] | d-spacing [Å] | Rel. Int. [%] |
| 8.54 | 10.352 | 100 |
| 11.19 | 7.909 | 19 |
| 12.88 | 6.872 | 27 |
| 15.27 | 5.804 | 8 |
| 15.94 | 5.559 | 88 |
| 18.42 | 4.816 | 5 |
| 20.31 | 4.372 | 9 |
| 22.25 | 3.995 | 23 |
| 23.43 | 3.797 | 28 |
| 24.19 | 3.680 | 12 |
| 25.71 | 3.465 | 17 |
| 28.24 | 3.160 | 9 |
| 29.78 | 3.000 | 9 |

Preferably, the crystalline form of 2-(3-tert-butyl-4-chloro-1-methyl-1H-pyrazol-5-yl)-6-(2-chlorophenyl)-4-methoxy-3H-imidazo[4,5-c]pyridine, prepared as described above, is characterized by its pXRD pattern which comprises peaks having a relative intensity greater than or equal to about 10%, more preferably peaks having a relative intensity greater than or equal to about 20%.

Example 36

2-(5-tert-Butyl-4-chloro-2-methyl-2H-pyrazol-3-yl)-6-(2-chloro-phenyl)-4-methoxy-3H-imidazo[4,5-c]pyridine potassium salt (Compound #11)

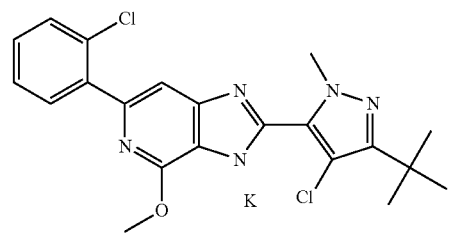

A 50 mL, single neck round bottom flask was charged with 2-(3-tert-butyl-4-chloro-1-methyl-1H-pyrazol-5-yl)-6-(2-chlorophenyl)-4-methoxy-3H-imidazo[4,5-c]pyridine (1.99 g, 4.27 mmol, prepared as described in Example 35 above), tetrahydrofuran (4.00 mL), and methanol (4.00 mL) to yield a solution. The solution was treated with potassium methoxide (~25% w/w in methanol, 1.20 mL, 4.28 mmol). The resulting solution was then concentrated to yield potassium 2-(3-tert-butyl-4-chloro-1-methyl-1H-pyrazol-5-yl)-6-(2-chlorophenyl)-4-methoxyimidazo[4,5-c]pyridin-3-ide as a yellow foam. $^1$H NMR (DMSO-$d_6$) δ: 7.71 (dd, J=7.6, 1.7 Hz, 1H), 7.50 (dd, J=7.9, 1.3 Hz, 1H), 7.39 (td, J=7.5, 1.2 Hz, 1H), 7.35 (s, 1H), 7.27-7.34 (m, 1H), 4.03 (s, 3H), 3.97 (s, 3H), 1.39 (s, 9H)

Biological Example 1

In Vitro Canine TRPM8 Functional Assay

The functional activity of representative compounds of the formula (I) of the present invention was quantified by measuring changes in intracellular calcium concentration using a $Ca^{2+}$-sensitive fluorescent dye. The changes in fluorescent signal were monitored by a fluorescence plate reader, either a FLIPR™ (Molecular Devices) or FDSS (Hamamatsu). Increases in intracellular $Ca^{2+}$ concentration were readily detected upon activation with icilin.

HEK293 cells stably expressing canine TRPM8 were routinely grown as monolayers in Dulbecco's minimum essential medium supplemented with 10% FBS, 2 mM L-glutamine, 100 units/mL penicillin, 100 ug/mL streptomycin and 400 µg/mL G418. Cells were maintained in 5% $CO_2$ at 37° C. At 24 hr prior to assay, cells were seeded in black wall, clear-base poly-D-lysine coated 384-well plates (BD Biosciences, NJ, USA) at a density of 5,000 cells per well in culture medium and grown overnight in 5% $CO_2$ at 37° C. On assay day, growth media was removed, and cells were loaded with Calcium 3 Dye (Molecular Devices) for 35 min at 37° C., under 5% $CO_2$ and then incubated for 25 min at room temperature and atmosphere. Subsequently, cells were tested for agonist-induced increases in intracellular $Ca^{2+}$ levels using FLIPR™ or FDSS. Cells were treated with compounds of the formula (I) at varying concentrations and intracellular $Ca^{2+}$ was measured for 5 min prior to the addition of icilin to each well to achieve a final concentration that produces an approximately 80% maximal response. $EC_{50}$ or $IC_{50}$ values for compounds of the present invention were determined from eight-point concentration-response studies and represent the concentration of compound required to elicit or inhibit 50% of the maximal response, respectively.

Maximal fluorescence intensity (FI) achieved upon addition of icilin was exported from the FLIPR™ or FDSS software and further analyzed using GraphPad Prism 3.02 (Graph Pad Software Inc., CA, U.S.A.). Basal FI was subtracted prior to normalizing data to percent of maximal response. Curves were generated using the average of quadruplicate wells for each data point using nonlinear regression of either sigmoidal dose response or sigmoidal dose response (variable slope). Finally, the $EC_{50}$ and $IC_{50}$ values were calculated with the best-fit curve determined by GraphPad Prism Representative compounds of the present invention were tested according to the procedures as described in Biological Example 1 above, with results as listed in Table 2, below.

TABLE 2 in vitro TRP M8 Activity

| Cmpd No. | % Inh @ 0.2 µM | $IC_{50}$ (nM) |
|---|---|---|
| 1 | 99 | 27 |
| 2 | 100 | 13 |
| 3 | 100 | 17 |
| 4 | 37 | |
| 5 | 99 | 16 |
| 6 | 65 | 69 |
| 7 | 99 | 38 |
| 8 | 99 | 6.0 |
| 9[A] | 100 | 5.6 |
| 10 | 101 | 16 |
| 11[A] | 100 | 3.5 |
| 12 | 101 | 11 |
| 13 | 94 | 46 |
| 14 | 99 | 1.2 |
| 15 | 100 | 1.8 |
| 16 | 99 | 0.59 |
| 17 | 99 | 1.7 |
| 18 | 99 | 8.2 |
| 19 | 100 | 0.84 |
| 20 | 99 | 0.95 |
| 21 | 99 | 0.69 |
| 22 | 99 | 1.4 |
| 23[A] | 96 | 26 |
| 24 | 99 | 7.4 |
| 25 | 100 | 12 |
| 26 | 100 | 35 |
| 27 | 73 | 124 |
| 28 | 99 | 11 |
| 29 | 99 | 33 |
| 30 | 87 | 87 |
| 31 | 100 | 18 |
| 32 | 100 | 7.6 |
| 33 | 98 | 40 |
| 34 | 89 | 77 |
| 35 | 67 | |
| 36 | 26 | |
| 37 | 61 | |
| 39 | 69 | 75 |
| 40 | 86 | 59 |
| 41 | 94 | 51 |
| 42 | 75 | 59 |
| 43 | 100 | 22 |
| 44 | 98 | 37 |
| 45 | 98 | 27 |
| 46 | 99 | 19 |
| 47 | 56 | |
| 48 | 59 | |
| 49 | 100 | 6.4 |
| 50 | 91 | 56 |
| 51 | 88 | 72 |
| 52 | 80 | 79 |
| 53 | 99 | 27 |
| 54 | 99 | 4.2 |

TABLE 2-continued in vitro TRP M8 Activity

| Cmpd No. | % Inh @ 0.2 µM | $IC_{50}$ (nM) |
|---|---|---|
| 55 | 95 | 54 |
| 56 | 99 | 24 |
| 57 | 101 | 1.6 |
| 58 | 101 | 2.0 |
| 59[A] | 99 | 1.1 |
| 60 | 99 | 25 |
| 61[A] | 100 | 5.3 |
| 62[A] | 99 | 30 |
| 63[A] | 99 | 3.1 |
| 64[A] | 97 | 14 |
| 65[A] | 99 | 3.2 |
| 66[A] | 100 | 6.5 |
| 67 | 4 | |
| 68 | 8 | |
| 70 | 36 | |
| 71 | 100 | 8.8 |
| 72 | 95 | 63 |
| 73 | 100 | 28 |
| 74 | 93 | 96 |
| 75 | 100 | 24 |
| 76 | 98 | 5.8 |
| 77 | 102 | 20 |
| 78 | 100 | 16 |
| 79 | 101 | 20 |
| 80 | 100 | 42 |
| 81 | 67 | 120 |
| 83 | 99 | 1.8 |
| 84 | 100 | 1.9 |
| 85 | 32 | |
| 86 | 49 | |
| 87 | 72 | 131 |
| 88 | 36 | |
| 89 | 100 | 0.53 |
| 90 | 99 | 0.73 |
| 91 | 99 | 3.8 |
| 92 | 99 | 2.8 |
| 93 | 99 | 1.2 |
| 94 | 99 | 22.5 |
| 95 | 100 | 27 |
| 96 | 48 | |
| 97 | 101 | 4.9 |
| 98[A] | 100 | 14 |
| 99 | 97 | 31.8 |
| 100 | 94 | 61.3 |
| 101 | 88 | 33.9 |
| 102 | 70 | 120 |
| 103 | 101 | 5.4 |
| 105 | 97 | 28 |
| 106 | not tested | |
| 107 | not tested | |
| 108 | not tested | |
| 109 | not tested | |
| 110[A] | 99 | 24 |
| 111 | 62 | |
| 112 | 98 | 19 |

[A]The noted compounds were prepared and tested as multiple batches, as the free base and/or as different corresponding salt forms. For said compounds, the biological activity listed in Table 2 above is an average of the measured values.

Biological Example 2

Inhibition of Icilin-Induced "Wet-Dog" Shakes in Rats

Icilin was initially developed as a "super-cooling" compound by Delmar Chemicals Ltd. Subsequently it was shown to be one of the most potent known agonists of TRPM8 (MCKEMY, D. D., et al "Identification of a cold receptor reveals a general role for TRP channels in thermosensation", Nature, pp 52-58, Vol. 416 (6876)), having an $EC_{50}$ value of 0.2 µM in stimulating calcium ion influx into TRPM8 transfected cells (BEHRENDT, H-J., et al., "Characterization of the mouse cold menthol receptor TRPM8 and vanilloid receptor type-1 VR1 using a fluorometric imaging plate reader (FLIPR) assay", *Brit J Pharmacol*, 2004, pp 737-745, Vol. 141(4)). Initial in vivo testing of icilin showed it to cause "wet-dog" shakes in rats. Similar shaking or jumping behavior was also evident in mice, rabbits, cats, dogs and monkeys. In humans, icilin produced a sensation of coolness on contact with mucous membranes, cold prickling when 0.1 mg was dropped on the tongue and coldness in the mouth, pharynx and chest lasting 30-60 min when 5-10 mg was ingested orally (WEI, E. T., et al., "AG-3-5: a chemical producing sensations of cold", *J Pharm Pharmacol.*, 1983, pp 110-112, Vol. 35). The inhibition or reversal of icilin-induced shaking behaviors in rodents provides evidence for the engagement and functional blockade of the TRPM8 channel and thereby for the utility of TRPM8 antagonists in treating or preventing a disease or condition in a mammal in which the disease or condition is affected by the modulation of TRPM8 receptors.

Male Sprague Dawley rats (220-450 g, Charles River Labs, n=6-9/treatment) were used to evaluate the ability of test compounds to block icilin-induced "wet-dog" shakes (WDS). The test compound was administered in 10% hydroxypropyl-β-cyclodextrin (HP-β-CD), p.o., 60 min before icilin. Icilin was then administered in 10% solutol/$H_2O$, at 3.0 mg/kg, i.p., and spontaneous "wet-dog" shakes were counted 10 min following the icilin injection over a 10-min period. Results for representative compounds of the present invention are presented in Table 3 below as a percent inhibition of shakes, which was calculated as follows:

% Inhibition=[1−(test compound WDS count/vehicle WDS count)]×100.

Biological Example 3

Chronic Constriction Injury (CCI)-Induced Model of Neuropathic Pain-Acetone-Induced Hypersensitivity Male Sprague-Dawley rats (225-450 g; n=5-8/treatment) were used to evaluate the ability of test compounds to reverse CCI-induced cold hypersensitivity. Four loose ligatures of 4-0 chromic gut were surgically placed around the left sciatic nerve under inhalation anesthesia as described by Bennett et al. (BENNETT, G. J., et al., "A peripheral mononeuropathy in rat that produces disorder of pain sensation like those seen in man", *Pain*, 1988, pp 87-107, Vol. 33(1)). Fourteen to 35 days following CCI surgery, subjects were placed in elevated observation chambers containing wire mesh floors, and five applications of acetone (0.05 mL/application separated by approximately 5 min) were spritzed onto the plantar surface of the paw using a multidose syringe. An abrupt withdrawal or lifting of the paw was considered a positive response. The number of positive responses was recorded for each rat over the five trials. Following baseline withdrawal determinations, test compounds were administered in 10% hydroxypropyl-β-cyclodextrin (HP-β-CD), p.o. The number of withdrawals was re-determined at 2 hr after compound administration. Representative compounds of the present invention were administered at 10 mg/kg in 10% HP-β-CD and tested according to this procedure. Results are presented below as a percent inhibition of shakes, which was calculated for each subject and then averaged by treatment as follows:

% Inhibition=[1−(test compound withdrawals/pre-test withdrawals)]×100.

Representative compounds of the present invention were tested according to the procedures as described in Biological Example 2 and Biological Example 3 above, with results as listed in Table 3, below.

TABLE 3

| Icilin and CCI Inhibition - Compounds of Formula (I) | | | | |
|---|---|---|---|---|
| | Icilin % Inhibition @ 1.5 h | | | |
| Cmpd No. | 10 mg/kg | 5.6 mg/kg | 3 mg/kg | CCI % Inhibition @ 2 h |
| 3 | | | 21.3 | |
| 5 | 20.3 | | | |
| 9 | 91.3 | | 41.8 | 52 |
| 11 | 98 | 97.6 | 85.3 | 82 |
| 17 | 38 | | | |

Formulation Example 1

Oral Solid Dosage Formulation—Prophetic Example

As a specific embodiment of an oral composition, 100 mg of the Compound #11, prepared as in Example 28, above is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed:

1. A compound of formula (I)

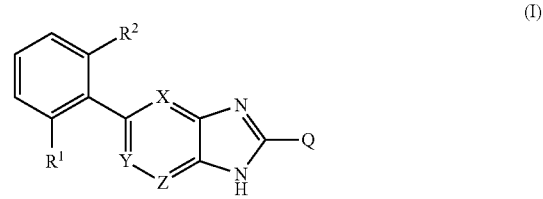

wherein
R$^1$ is selected from the group consisting of hydrogen, fluoro, chloro, fluorinated $C_{1-4}$alkyl and fluorinated $C_{1-4}$alkoxy;
R$^2$ is hydrogen;

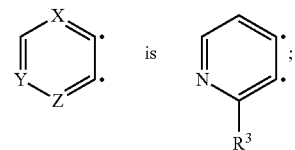

wherein R$^3$ is selected from the group consisting of hydrogen, chloro, cyano, $C_{1-4}$alkyl, fluorinated $C_{1-4}$alkyl, $C_{1-4}$alkoxy, fluorinated $C_{1-4}$alkoxy, —O—$(CH_2)_2$—OH, —O—$CH_2$—$CO_2H$, —O—$(CH_2)_2$—O—($C_{1-4}$alkyl), —O—$CH_2$-(fluorinated $C_{1-2}$alkyl), —O—$(CH_2)_2$—NR$^A$R$^B$ and —NR$^A$R$^B$;
wherein R$^A$ and R$^B$ are each independently selected from the group consisting of hydrogen and $C_{1-4}$alkyl;
alternatively R$^A$ and R$^B$ are taken together with the nitrogen atom to which they are bound to form a ring structure selected form the group consisting of pyrrolidin-1-yl, piperidin-1-yl, piperazin-1-yl, 4-methyl-piperidin-1-yl, 4-methyl-piperazin-1-yl and morpholin-4-yl;

Q is an optionally substituted ring structure selected from the group consisting of formulas (a) through (h)

(f)

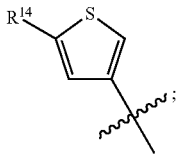

wherein $R^{14}$ is $C_{1-4}$alkyl;

(g)

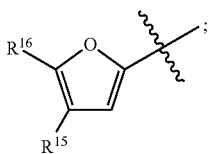

wherein $R^{15}$ is $C_{1-4}$alkyl; and $R^{16}$ is selected from the group consisting of hydrogen, chloro and bromo; and (h)

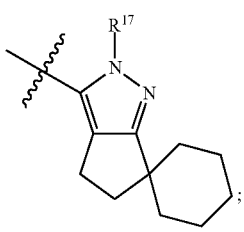

wherein $R^{17}$ is $C_{1-4}$alkyl;

or a solvate, hydrate, tautomer or pharmaceutically acceptable salt thereof.

2. A compound as in claim 1, wherein $R^1$ is selected from the group consisting of hydrogen, fluoro, chloro, fluorinated $C_{1-2}$alkyl and fluorinated $C_{1-2}$alkoxy;

$R^2$ is hydrogen:

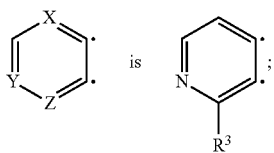

(a)

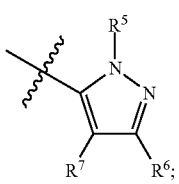

(b)

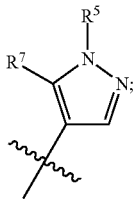

wherein $R^5$ is $C_{1-4}$alkyl; $R^6$ is selected from the group consisting of $C_{1-4}$alkyl and fluorinated $C_{1-4}$alkyl; and $R^7$ is selected from the group consisting of hydrogen, chloro, fluoro, cyano, $C_{1-4}$alkyl and $C_{1-4}$alkoxy;

(c)

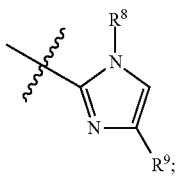

wherein $R^8$ and $R^9$ are each independently selected from the group consisting of $C_{1-4}$alkyl;

(d)

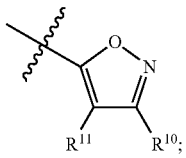

wherein $R^{10}$ is $C_{1-4}$alkyl; and $R^{11}$ is selected from the group consisting of hydrogen and cyano;

(e)

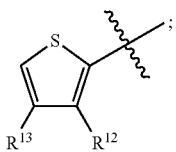

wherein $R^{12}$ and $R^{13}$ are each independently selected from the group consisting of hydrogen and $C_{1-4}$alkyl;

wherein $R^3$ is selected from the group consisting of hydrogen, chloro, cyano, $C_{1-2}$alkyl, fluorinated $C_{1-2}$alkyl, $C_{1-4}$alkoxy, fluorinated $C_{1-2}$alkoxy, —O—$(CH_2)_2$—OH, —O—$CH_2$—$CO_2H$, —O—$(CH_2)_2$—O—($C_{1-4}$alkyl), —O—$CH_2$-(fluorinated $C_{1-2}$alkyl), —O—$(CH_2)_2$—$NR^A R^B$ and —$NR^A R^B$;

wherein $R^A$ and $R^B$ are each independently selected from the group consisting of hydrogen and $C_{1-2}$alkyl; alternatively $R^A$ and $R^B$ are taken together with the nitrogen atom to which they are bound to form a ring structure selected from the group consisting of pyrrolidin-1-yl, piperidin-1-yl, piperazin-1-yl, 4-methyl-piperazin-1-yl and morpholin-4-yl;

Q is an optionally substituted ring structure selected from the group consisting of formulas (a) through (h)

(a)

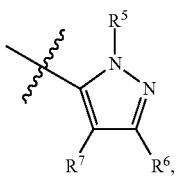

(b)

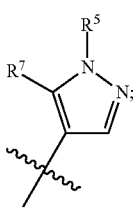

wherein $R^5$ is $C_{1-4}$alkyl; $R^6$ is selected from the group consisting of $C_{1-4}$alkyl and fluorinated $C_{1-4}$alkyl; and $R^7$ is selected from the group consisting of hydrogen, chloro, fluoro, cyano, $C_{1-2}$alkyl and $C_{1-2}$alkoxy;

(c)

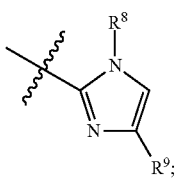

wherein $R^8$ and $R^9$ are each independently selected from the group consisting of $C_{1-4}$alkyl;

(d)

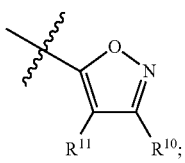

wherein $R^{10}$ is $C_{1-4}$alkyl; and $R^{11}$ is selected from the group consisting of hydrogen and cyano;

(e)

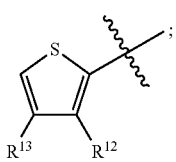

wherein $R^{12}$ and $R^{13}$ are each independently selected from the group consisting of hydrogen and $C_{1-4}$alkyl;

(f)

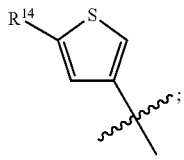

wherein $R^{14}$ is selected from the group consisting of $C_{1-4}$alkyl;

(g)

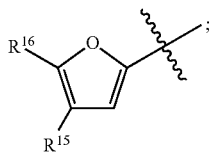

wherein $R^{15}$ is $C_{1-4}$alkyl; and $R^{16}$ is selected from the group consisting of hydrogen, chloro and bromo; and (h)

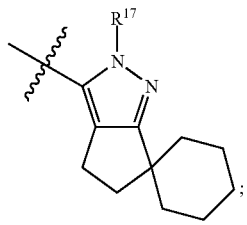

wherein $R^{17}$ is $C_{1-2}$alkyl;

or a solvate, hydrate, tautomer or pharmaceutically acceptable salt thereof.

3. A compound as in claim 2, wherein
$R^1$ is selected from the group consisting of hydrogen, chloro, fluoro, trifluoromethyl and trifluoromethoxy;
$R^2$ is hydrogen;

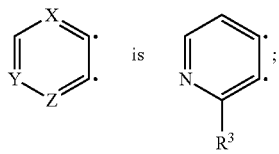

wherein $R^3$ is selected form the group consisting of hydrogen, chloro, cyano, $C_{1-2}$alkyl, trifluoromethyl, $C_{1-4}$alkoxy, —O—$(CH_2)_2$—OH, —O—$CH_2$—$CO_2H$, —O—$(CH_2)_2$—O—$(C_{1-2}$alkyl), O—$CH_2$-(fluorinated $C_{1-2}$alkyl), —O—$(CH_2)_2$—$NR^AR^B$, pyrrolidin-1-yl, piperidin-1-yl, piperazin-1-yl, 4-methyl-piperazin-1-yl and morpholin-4-yl;

and wherein $R^A$ and $R^B$ are each an independently selected $C_{1-2}$alkyl; alternatively $R^A$ and $R^B$ are taken together with the nitrogen atom to which they are bound to form a ring structure selected from the group consisting of pyrrolidin-1-yl, piperidin-1-yl, piperazin-1-yl, 4-methyl-piperazin-1-yl and morpholin-4-yl;

Q is an optionally substituted ring structure selected from the group consisting of formulas (a) through (h)

(a)

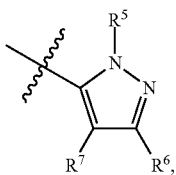

(b)

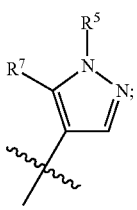

wherein $R^5$ is $C_{1-4}$alkyl; $R^6$ is selected from the group consisting of $C_{1-4}$alkyl and fluorinated $C_{1-4}$alkyl; and $R^7$ is selected from the group consisting of hydrogen, chloro, fluoro, cyano, $C_{1-2}$alkyl and $C_{1-2}$alkoxy;

(c)

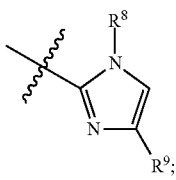

wherein $R^8$ and $R^9$ are each independently selected from the group consisting of $C_{1-4}$alkyl;

(d)

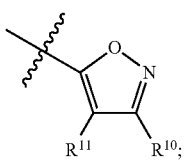

wherein $R^{10}$ is $C_{1-4}$alkyl; and $R^{11}$ is selected from the group consisting of hydrogen and cyano;

(e)

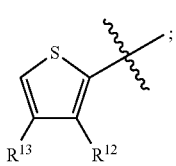

wherein $R^{12}$ is hydrogen and $R^{13}$ is selected from the group consisting of $C_{1-4}$alkyl;

(f)

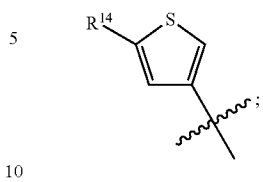

wherein $R^{14}$ is selected from the group consisting of $C_{1-4}$alkyl;

(g)

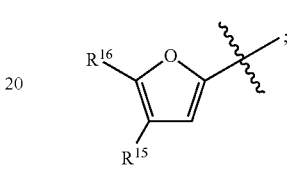

wherein $R^{15}$ is $C_{1-4}$alkyl; and $R^{16}$ is selected from the group consisting of hydrogen and bromo; and (h)

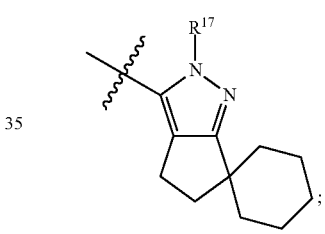

wherein $R^{17}$ is $C_{1-2}$alkyl;

or a solvate, hydrate, tautomer or pharmaceutically acceptable salt thereof.

4. A compound as in claim 3, wherein $R^1$ is selected from the group consisting of hydrogen, chloro, fluoro, trifluoromethyl and trifluoromethoxy;

$R^2$ is hydrogen;

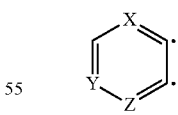

is selected from the group consisting of

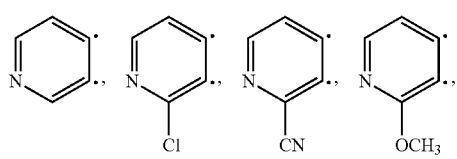

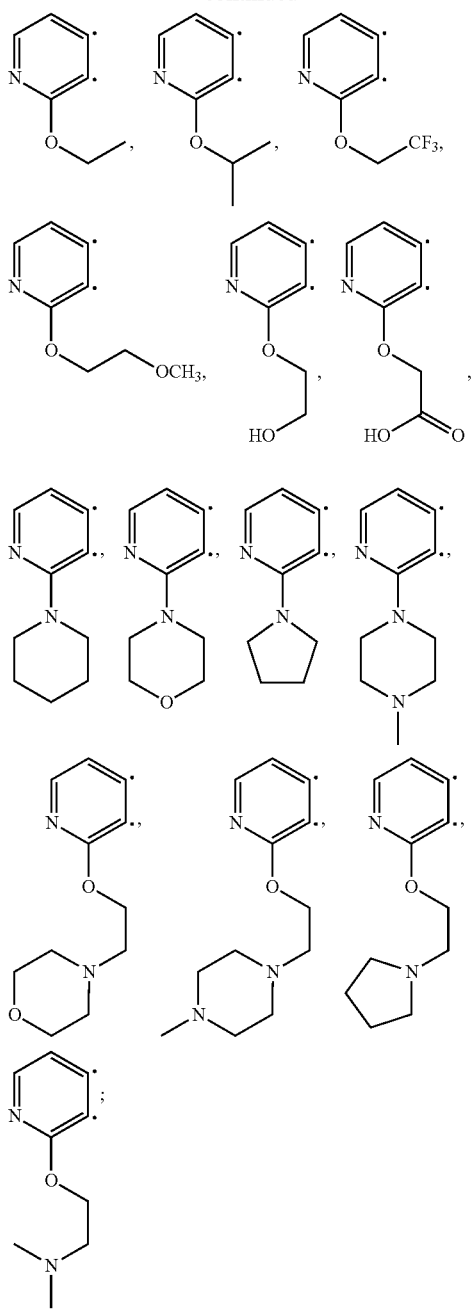

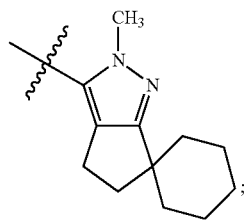 [SMILES: *c1c2c(nn1C)C1(CCCCC1)CC2 ; ";"]

or a solvate, hydrate, tautomer or pharmaceutically acceptable salt thereof.

5. A compound as in claim 4, wherein
R$^1$ is selected from the group consisting of chloro, fluoro, trifluoromethyl and trifluoromethoxy;
R$^2$ is hydrogen;

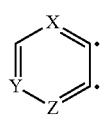

is selected from the group consisting of

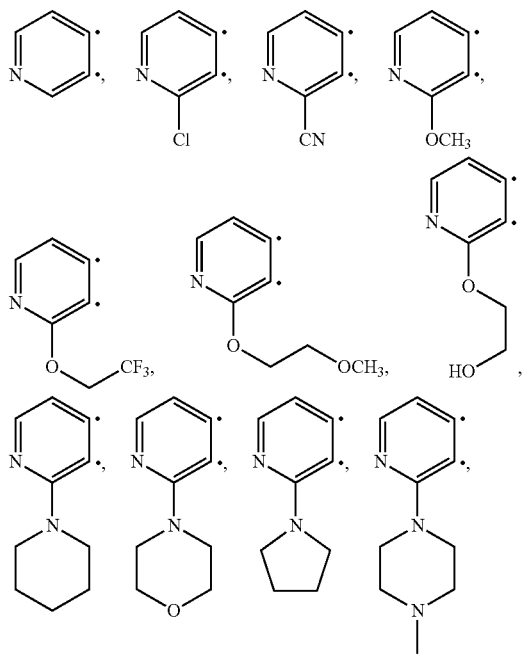

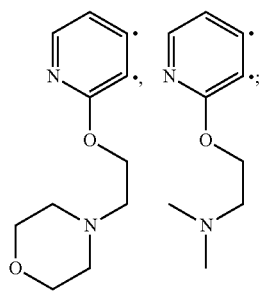

Q is selected from the group consisting of 1-methyl-3-tert-butyl-pyrazol-5-yl, 1-methyl-3-tert-butyl-4-chloro-pyrazol-5-yl, 1-methyl-3-tert-butyl-4-fluoro-pyrazol-5-yl, 1-methyl-3-tert-butyl-4-cyano-pyrazol-5-yl, 1-methyl-3-trifluoromethyl-4-chloro-pyrazol-5-yl, 1-methyl-3-tert-butyl-4-methoxy-pyrazol-5-yl, 1-methyl-3-(1,1-dimethyl-2-fluoro-ethyl)-4-chloro-pyrazol-5-yl, 1-tert-butyl-pyrazol-4-yl, 1-tert-butyl-5-methyl-pyrazol-4-yl, 1-methyl-3-tert-butyl-imidazol-2-yl, 3-tert-butyl-isoxazol-5-yl, 3-tert-butyl-4-cyano-isoxazol-5-yl, 4-isopropyl-thien-2-yl, 5-isopropyl-thien-3-yl, 4-tert-butyl-fur-2-yl, 4-tert-butyl-5-bromo-fur-2-yl, and Q is selected from the group consisting of 1-methyl-3-tert-butyl-pyrazol-5-yl, 1-methyl-3-tert-butyl-4-chloro-pyrazol-5-yl, 1-methyl-3-tert-butyl-4-fluoro-pyrazol-5- yl, 1-methyl-3-tert-butyl-4-cyano-pyrazol-5-yl, 1-methyl-3-tert-butyl-4-methoxy-pyrazol-5-yl, 1-methyl-3-(1,1-dimethyl-2-fluoro-ethyl)-4-chloro-pyrazol-5-yl, 3-tert-butyl-isoxazol-5-yl, 3-tert-butyl-4-cyano-isoxazol-5-yl, 4-isopropyl-thien-2-yl, 5-isopropyl-thien-3-yl, 4-tert-butyl-fur-2-yl, 4-tert-butyl-5-bromo-fur-2-yl and

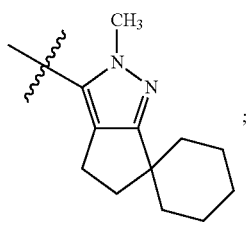 [SMILES: *c1c2c(nn1C)C1(CCCCC1)CC2]
;

or a solvate, hydrate, tautomer or pharmaceutically acceptable salt thereof.

6. A compound as in claim 4, wherein
R¹ is selected from the group consisting of chloro, fluoro, trifluoromethyl and trifluoromethoxy;
R² is hydrogen;

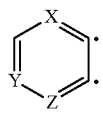

is selected from the group consisting of

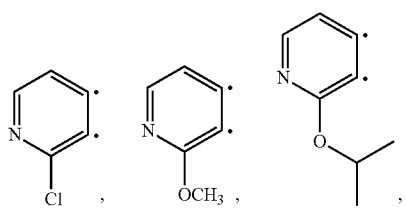

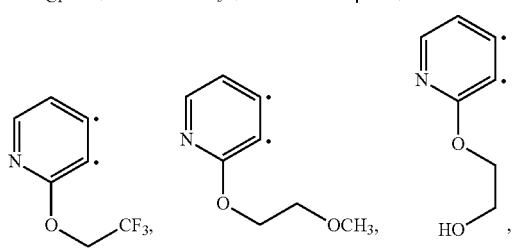

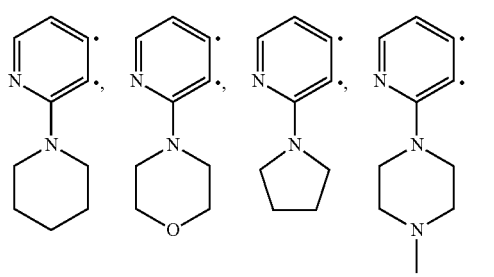
and

-continued

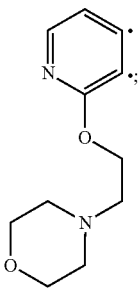
;

Q is selected from the group consisting of 1-methyl-3-tert-butyl-4-chloro-pyrazol-5-yl, 1-methyl-3-tert-butyl-4-cyano-pyrazol-5-yl, 1-methyl-3-(1,1-dimethyl-2-fluoro-ethyl)-4-chloro-pyrazol-5-yl, 3-tert-butyl-isoxazol-5-yl and

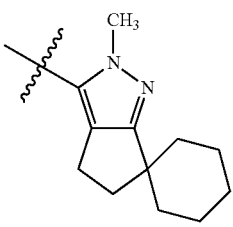
;

or a solvate, hydrate, tautomer or pharmaceutically acceptable salt thereof.

7. A compound as in claim 4, wherein
R¹ is selected from the group consisting of chloro, fluoro, trifluoromethyl and trifluoromethoxy;
R² is hydrogen;

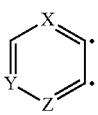

is selected from the group consisting of

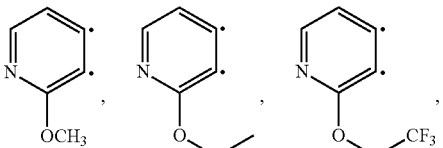

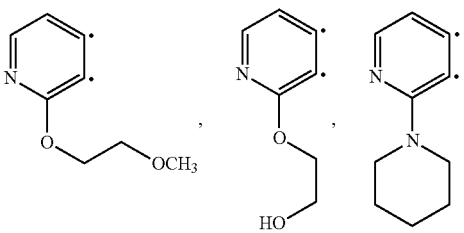

-continued

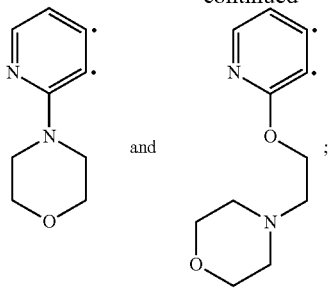

and

Q is selected from the group consisting of 1-methyl-3-tert-butyl-4-chloro-pyrazol-5-yl, 1-methyl-3-tert-butyl-4-cyano-pyrazol-5-yl and 1-methyl-3-(1,1-dimethyl-2-fluoro-ethyl)-4-chloro-pyrazol-5-y;

or a solvate, hydrate, tautomer or pharmaceutically acceptable salt thereof.

8. A compound as in claim 4, wherein
$R^1$ is selected from the group consisting of chloro and trifluoromethyl;
$R^2$ is hydrogen;

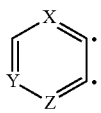

is selected from the group consisting of

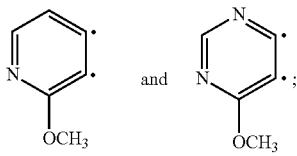

and;

Q is selected from the group consisting of 1-methyl-3-tert-butyl-4-chloro-pyrazol-5-yl and 1-methyl-3-tert-butyl-4-cyano-pyrazol-5-yl;

or a solvate, hydrate, tautomer or pharmaceutically acceptable salt thereof.

9. A compound as in claim 4, wherein $R^1$ is chloro; $R^2$ is hydrogen;

and Q is 1-methyl-3-tert-butyl-4-chloro-pyrazol-5-yl; or a solvate, hydrate, tautomer or pharmaceutically acceptable salt thereof.

10. A compound as in claim 8, wherein the pharmaceutically acceptable salt thereof is selected from the group consisting of sodium salt, potassium salt and methanesulfonic acid salt.

11. A pharmaceutical composition comprising a pharmaceutically acceptable carrier and a compound of claim 1.

12. A process for making a pharmaceutical composition comprising mixing a compound of claim 1 and a pharmaceutically acceptable carrier.

13. A method for inhibiting Icilin and CCI comprising administering to a mammal an effective amount of a compound as in claim 1.

14. A compound as in claim 4, wherein
$R^1$ is selected from the group consisting of chloro and trifluoromethyl; $R^2$ is hydrogen; $R^3$ is —OCH$_3$; Q is selected from the group consisting of 1-methyl-3-tert-butyl-4-chloro-pyrazol-5-yl and 1-methyl-3-tert-butyl-4-cyano-pyrazol-5-yl;

or a solvate, hydrate, tautomer or pharmaceutically acceptable salt thereof.

* * * * *